US007842405B2

(12) United States Patent
Cho et al.

(10) Patent No.: US 7,842,405 B2
(45) Date of Patent: *Nov. 30, 2010

(54) COMPOUND AND ORGANIC LIGHT EMITTING DEVICE USING THE SAME

(75) Inventors: Wook Dong Cho, Daejeon Metropolitan (KR); Ji Eun Kim, Daejeon Metropolitan (KR); Byung Sun Jeon, Seoul (KR); Jun Gi Jang, Daejeon Metropolitan (KR); Seok Hee Yoon, Daejeon Metropolitan (KR); Jae Min Moon, Daejeon Metropolitan (KR)

(73) Assignee: LG Chem, Ltd., Seoul (KR)

( * ) Notice: Subject to any disclaimer, the term of this patent is extended or adjusted under 35 U.S.C. 154(b) by 672 days.

This patent is subject to a terminal disclaimer.

(21) Appl. No.: 11/660,785

(22) PCT Filed: Sep. 23, 2005

(86) PCT No.: PCT/KR2005/003177

§ 371 (c)(1), (2), (4) Date: Feb. 22, 2007

(87) PCT Pub. No.: WO2006/080644

PCT Pub. Date: Aug. 3, 2006

(65) Prior Publication Data

US 2008/0093982 A1 Apr. 24, 2008

(30) Foreign Application Priority Data

Sep. 24, 2004 (KR) ...................... 10-2004-0077245

(51) Int. Cl.
*H01L 51/54* (2006.01)

(52) U.S. Cl. ....................... 428/690; 428/917; 313/504; 313/506; 252/301.16; 257/40; 257/E51.032; 546/15; 546/16; 546/18; 556/408

(58) Field of Classification Search .................. 556/408
See application file for complete search history.

(56) References Cited

U.S. PATENT DOCUMENTS

| | | | |
|---|---|---|---|
| 6,605,373 | B2 | 8/2003 | Woo et al. |
| 6,613,454 | B2 | 9/2003 | Ara et al. |
| 6,630,254 | B2 | 10/2003 | Leclerc et al. |
| 2004/0219386 | A1 | 11/2004 | Thoms |

FOREIGN PATENT DOCUMENTS

| | | |
|---|---|---|
| EP | 1 310 539 B1 | 3/2005 |
| JP | 2008-510800 | 4/2008 |
| JP | 2008-511157 | 4/2008 |
| JP | 2008-511158 | 4/2008 |
| JP | 2008-511159 | 4/2008 |
| WO | WO 93/09074 A2 | 5/1993 |
| WO | WO 2004/020371 A1 | 3/2004 |
| WO | WO 2006/080640 | 8/2006 |
| WO | WO 2006/080641 | 8/2006 |
| WO | WO 2006/080642 | 8/2006 |
| WO | WO 2006/080643 | 8/2006 |
| WO | WO 2006/080644 | 8/2006 |

OTHER PUBLICATIONS

Tritschler, Wolfgang et al., "Synthese and Konformation von Spiroacridanen", Chem. Ber. 117, 2703-2713 (1984).
Patrick Keller, "Photo-Cross-Linkable Liquid-Crystalline Side-Chain Polysiloxanes", Chemistry of Materials, vol. 2, pp. 3-4, 1990.
Geselowitz et al., "Quantitation of Triple-Helix Formation Using a Photo-Cross-Linkable Aryl Azide/Biotin/Oligonucleotide Conjugate", Bioconjugate Chem., vol. 6, pp. 502-506, 1995.

*Primary Examiner*—D. Lawrence Tarazano
*Assistant Examiner*—Michael Wilson
(74) *Attorney, Agent, or Firm*—McKenna Long & Aldridge LLP

(57) ABSTRACT

Disclosed is an organic light emitting device. The organic light emitting device comprises a first electrode, organic material layer(s) comprising a light emitting layer, and a second electrode. The first electrode, the organic material layer(s), and the second electrode form layered structure and at least one layer of the organic material layer(s) include the compound of Formula 1 or the compound of Formula 1 into which a thermosetting or photo-crosslinkable functional group is introduced.

7 Claims, 1 Drawing Sheet

[Fig. 1]
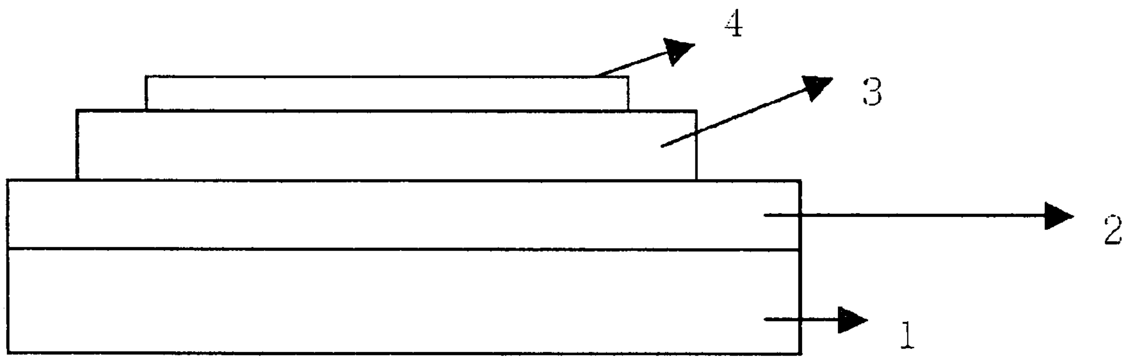
[Fig. 2]
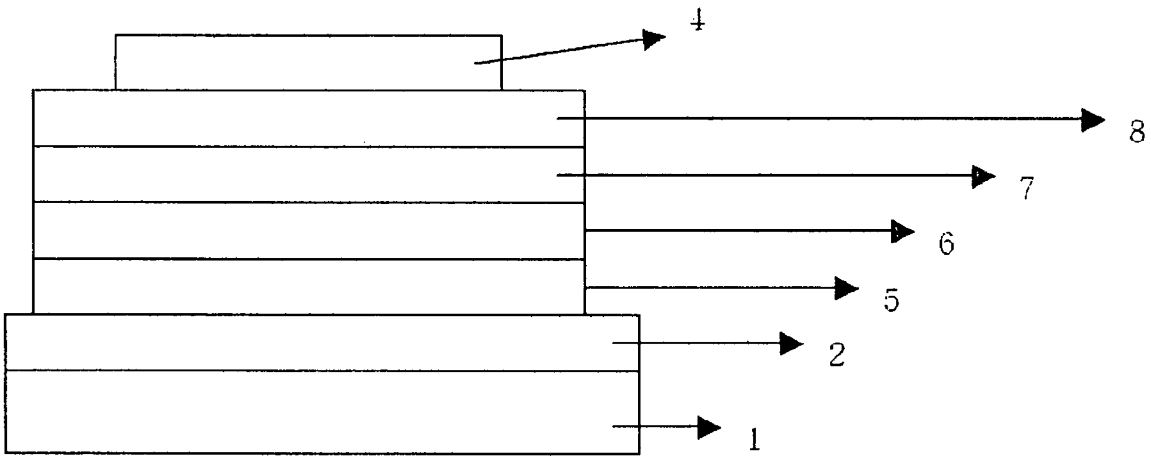

COMPOUND AND ORGANIC LIGHT EMITTING DEVICE USING THE SAME

This application claims priority to International application No. PCT/KR2005/003177 filed on Sep. 23, 2005, and Korean Application No. 10-2004-0077245 filed on Sep. 24, 2004, both of which are incorporated by reference, as if fully set forth herein.

TECHNICAL FIELD

The present invention relates to an organic light emitting device which comprises a fluorene derivative capable of significantly improving a lifespan, efficiency, and electrochemical and thermal stabilities thereof.

BACKGROUND ART

An organic light emission phenomenon is an example of a conversion of current into visible rays through an internal process of a specific organic molecule. The organic light emission phenomenon is based on the following mechanism. When organic material layers are interposed between an anode and a cathode, if voltage is applied between the two electrodes, electrons and holes are injected from the cathode and the anode into the organic material layer. The electrons and the holes which are injected into the organic material layer are recombined to form an exciton, and the exciton is reduced to a bottom state to emit light. An organic light emitting device which is based on the above mechanism typically comprises a cathode, an anode, and organic material layer(s), for example, organic material layers including a hole injection layer, a hole transport layer, a light emitting layer, and an electron transport layer, interposed therebetween.

The materials used in the organic light emitting device are mostly pure organic materials or complexes of organic material and metal. The material used in the organic light emitting device may be classified as a hole injection material, a hole transport material, a light emitting material, an electron transport material, or an electron injection material, according to its use. In connection with this, an organic material having a p-type property, which is easily oxidized and is electrochemically stable when it is oxidized, is mostly used as the hole injection material or the hole transport material. Meanwhile, an organic material having an n-type property, which is easily reduced and is electrochemically stable when it is reduced, is used as the electron injection material or the electron transport material. As the light emitting layer material, an organic material having both p-type and n-type properties is preferable, which is stable when it is oxidized and when it is reduced. Also a material having high light emission efficiency for conversion of the exciton into light when the exciton is formed is preferable.

In addition, it is preferable that the material used in the organic light emitting device further have the following properties.

First, it is preferable that the material used in the organic light emitting device have excellent thermal stability. The reason is that joule heat is generated by movement of electric charges in the organic light emitting device. NPB, which has recently been used as the hole transport layer material, has a glass transition temperature of 100° C. or lower, thus it is difficult to apply to an organic light emitting device requiring a high current.

Second, in order to produce an organic light emitting device that is capable of being actuated at low voltage and has high efficiency, holes and electrons which are injected into the organic light emitting device must be smoothly transported to a light emitting layer, and must not be released out of the light emitting layer. To achieve this, a material used in the organic light emitting device must have a proper band gap and a proper HOMO and LUMO energy levels. A LUMO energy level of PEDOT:PSS, which is currently used as a hole transport material of an organic light emitting device produced using a solution coating method, is lower than that of an organic material used as a light emitting layer material, thus it is difficult to produce an organic light emitting device having high efficiency and a long lifespan.

Moreover, the material used in the organic light emitting device must have excellent chemical stability, electric charge mobility, and interfacial characteristic with an electrode or an adjacent layer. That is to say, the material used in the organic light emitting device must be little deformed by moisture or oxygen. Furthermore, proper hole or electron mobility must be assured so as to balance densities of the holes and of the electrons in the light emitting layer of the organic light emitting device to maximize the formation of excitons. Additionally, it has to be able to have a good interface with an electrode including metal or metal oxides so as to assure stability of the device.

Accordingly, there is a need to develop an organic light emitting device including an organic material having the above-mentioned requirements in the art.

DISCLOSURE OF INVENTION

Technical Problem

Therefore, the object of the present inventions is to provide an organic light emitting device which is capable of satisfying conditions required of a material usable for an organic light emitting device, for example, a proper energy level, electrochemical stability, and thermal stability, and which includes a fluorene derivative having a chemical structure capable of playing various roles required in the organic light emitting device, depending on a substituent group.

Technical Solution

The present invention provides an organic light emitting device which comprises a first electrode, organic material layer(s) comprising a light emitting layer, and a second electrode, wherein the first electrode, the organic material layer(s), and the second electrode form a layered structure and at least one layer of the organic material layer(s) includes a compound of the following Formula 1 or a compound of Formula 1 into which a thermosetting or photo-crosslinkable functional group is introduced:

[Formula 1]

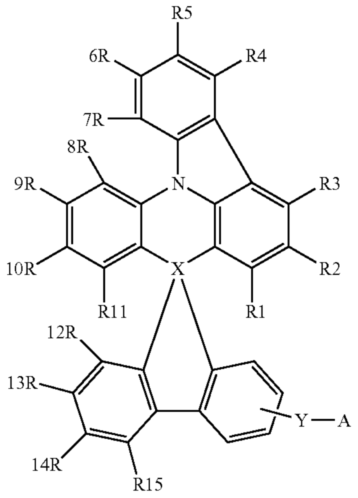

In Formula 1, X is C or Si,

-continued

A is

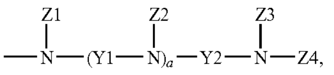

and a is zero or positive integer.

Y is a bond; bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups.

Y1 and Y2 are each bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups.

Z1 to Z4 are each independently hydrogen; aliphatic hydrocarbons having a carbon number of 1-20; aromatic hydrocarbons; aromatic hydrocarbons which are substituted with at least one substituent group selected from the group consisting of the nitro, nitrile, halogen, alkyl, alkoxy, amino, aromatic hydrocarbon, and heterocyclic groups; a silicon group substituted with aromatic hydrocarbons; a heterocyclic group; a heterocyclic group which is substituted with at least one substituent group selected from the group consisting of the nitro, nitrile, halogen, alkyl, alkoxy, amino, aromatic hydrocarbon, and heterocyclic groups; a thiophenyl group which is substituted with hydrocarbons having a carbon number of 1-20 or aromatic hydrocarbons having a carbon number of 6-20; or a boron group which is substituted with aromatic hydrocarbons.

R1 to R11 are each independently hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, an amino group, a nitrile group, a nitro group, a halogen group, an amide group, or an ester group. R1 to R11 may form aliphatic or hetero condensation rings along with adjacent groups.

R12 to R15 are each independently hydrogen, a substituted or unsubstituted alkyl group, a substituted or unsubstituted alkoxy group, a substituted or unsubstituted alkenyl group, a substituted or unsubstituted aryl group, a substituted or unsubstituted heterocyclic group, an amino group, a nitrile group, a nitro group, a halogen group, an amide group, or an ester group. R12 to R15 may form aliphatic or hetero condensation rings along with adjacent groups.

R7 and R8 may be directly connected to each other, or may form a condensation ring along with a group selected from the group consisting of O, S, NR, PR, C=O, CRR', and SiRR', R and R' independently or collectively being hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a nitrile group, an amide group, or an ester group. R7 and R8 may form a condensation ring to form a spiro compound.

A detailed description will be given of the substituent groups of Formula 1.

In Z1 to Z4 as the substituent groups of Formula 1, the aromatic hydrocarbons are exemplified by monocyclic aromatic rings, such as phenyl, biphenyl, and terphenyl, and multicyclic aromatic rings, such as naphthyl, anthracenyl, pyrenyl, and perylenyl. The heterocyclic group is exemplified by thiophene, furan, pyrrole, imidazole, thiazole, oxazole, oxadiazole, thiadiazole, triazole, pyridyl, pyridazyl, pyrazine, quinoline, and isoquinoline.

Examples of aliphatic hydrocarbons having a carbon number of 1-20 include straight chain aliphatic hydrocarbons, branched chain aliphatic hydrocarbons, saturated aliphatic hydrocarbons, and unsaturated aliphatic hydrocarbons. They are exemplified by an alkyl group, such as a methyl group, an ethyl group, an n-propyl group, an iso-propyl group, an n-butyl group, a sec-butyl group, an iso-butyl group, a ter-butyl group, a pentyl group, and a hexyl group; an alkenyl group having a double bond, such as styryl; and an alkynyl group having a triple bond, such as an acetylene group.

The carbon number of the alkyl, alkoxy, and alkenyl groups of R1 to R15 of Formula 1 is not limited, but is preferably 1-20.

The length of the alkyl group contained in the compound does not affect the conjugate length of the compound, but may affect the method of applying the compound to the organic light emitting device, for example, a vacuum deposition method or a solution coating method.

Illustrative, but non-limiting, examples of the aryl group of R1 to R15 of Formula 1 include monocyclic aromatic rings, such as a phenyl group, a biphenyl group, a terphenyl group, and a stilbene group, and multicyclic aromatic rings, such as a naphthyl group, an anthracenyl group, a phenanthrene group, a pyrenyl group, and a perylenyl group.

Illustrative, but non-limiting, examples of the arylamine group of R1 to R11 of Formula 1 include a diphenylamine group, a dinaphthylamine group, a dibiphenylamine group, a phenylnaphthylamine group, a phenyldiphetylamine group, a ditolylamine group, a phenyltolylamine group, a carbazolyl group, and a triphenylamine group.

Illustrative, but non-limiting, examples of the heterocyclic group of R1 to R15 of Formula 1 include a thiophenyl group, a furan group, a pyrrolyl group, an imidazolyl group, a thiazolyl group, an oxazolyl group, an oxadiazolyl group, a triazolyl group, a pyridyl group, a pyradazine group, a quinolinyl group, an isoquinoline group, and an acridyl group.

In addition, illustrative, but non-limiting, examples of the alkenyl, aryl, arylamine, and heterocyclic groups of R1 to R15 of Formula 1 include compounds shown in the following Formulae.

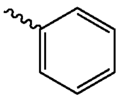

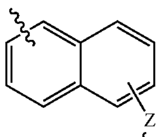

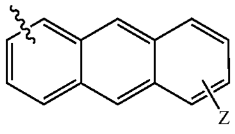

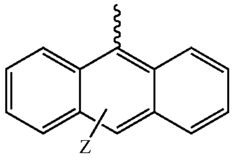

-continued

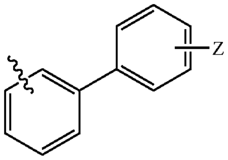
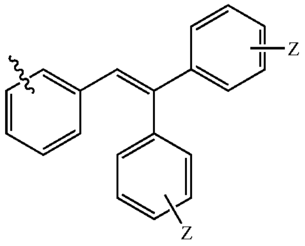
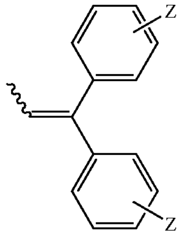
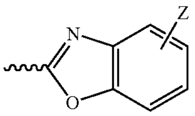
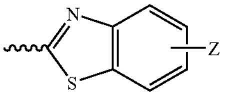
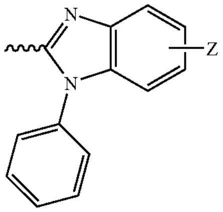
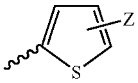
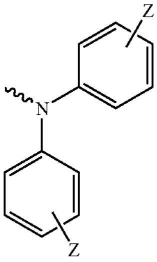
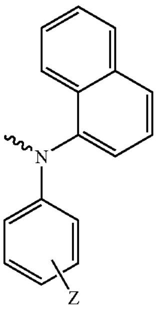
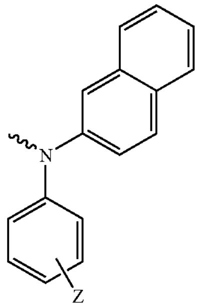
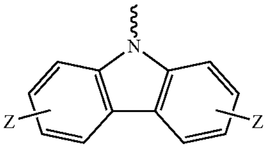
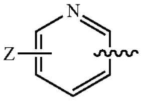
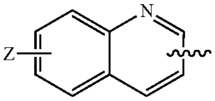
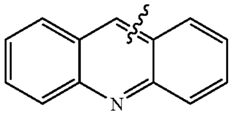
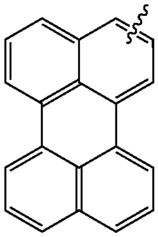

-continued

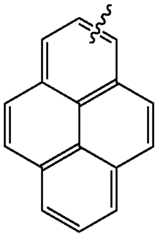
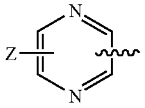
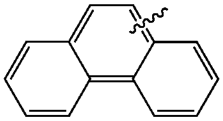
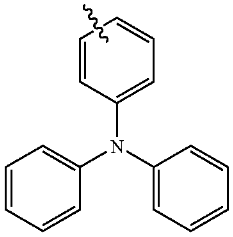

In the above Formulae, Z is a group selected from the group consisting of hydrogen, aliphatic hydrocarbons having a carbon number of 1-20, an alkoxy group, an arylamine group, an aryl group, a heterocyclic group, a nitrile group, and an acetylene group. Examples of the arylamine, aryl, and heterocyclic groups of Z are as shown in the above-mentioned substituent groups of R1 to R15.

According to a preferred embodiment of the present invention, X of Formula 1 is C, and R7 and R8 are directly connected to each other, or form a condensation ring along with a group selected from the group consisting of O, S, NR, PR, C═O, CRR', and SiRR' (R and R' are as defined in Formula 1).

According to another preferred embodiment of the present invention, X of Formula 1 is Si, and R7 and R8 may be directly connected to each other, or form a condensation ring along with a group selected from the group consisting of O, S, NR, PR, CRR', and SiRR' (R and R' are as defined in Formula 1).

According to still another preferred embodiment of the present invention, the compound of Formula 1 is any one of compounds of the following Formulae 2 to 5.

[Formula 2]

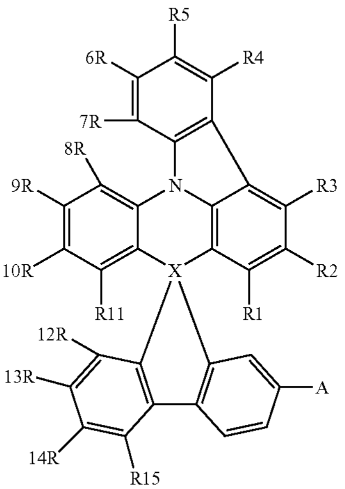

-continued
[Formula 3]
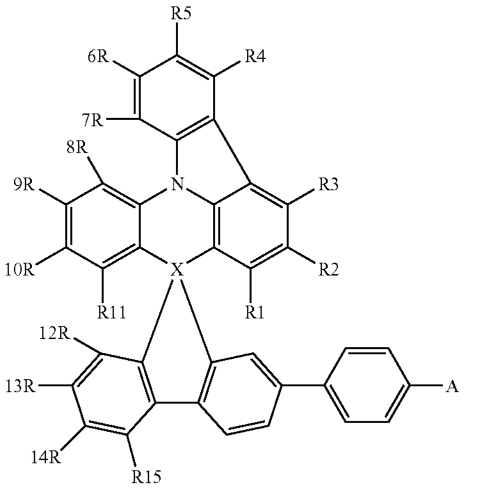
[Formula 4]
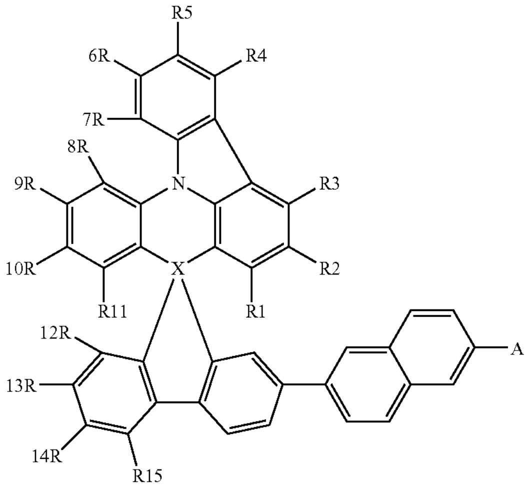
[Formula 5]
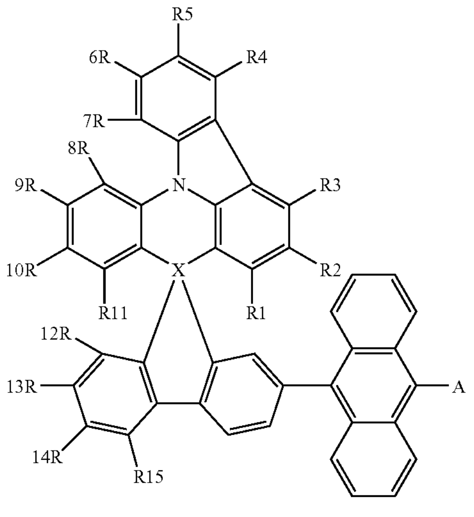
In the above Formulae, A is as defined in Formula 1.
Illustrative, but non-limiting, examples of a group A of Formula 1 are as follows.
1
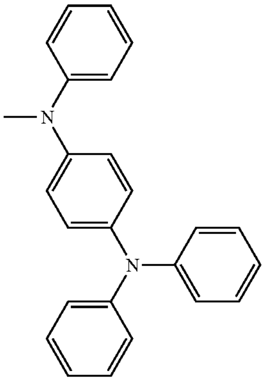
2
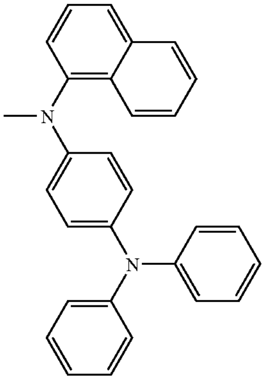
3
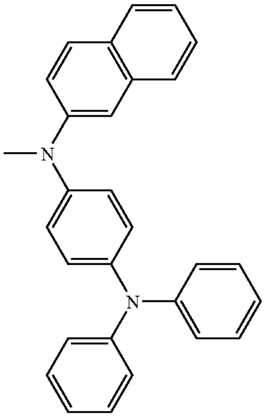

-continued
4
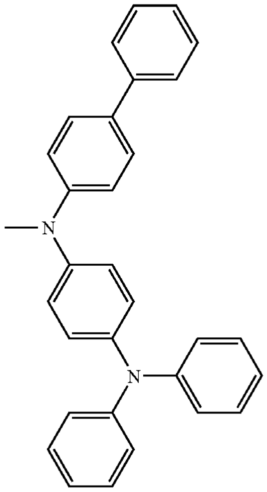
5
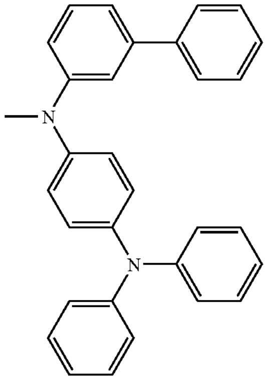
6
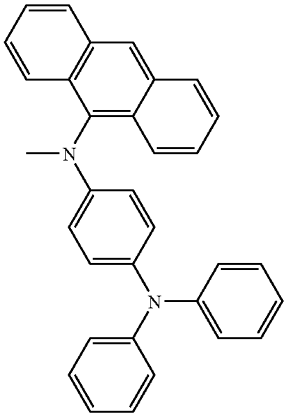
-continued
7
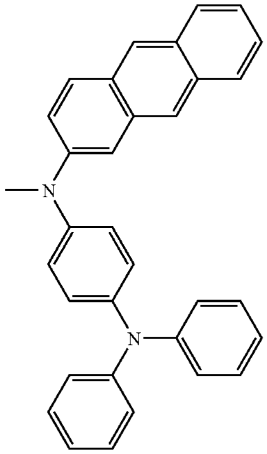
8
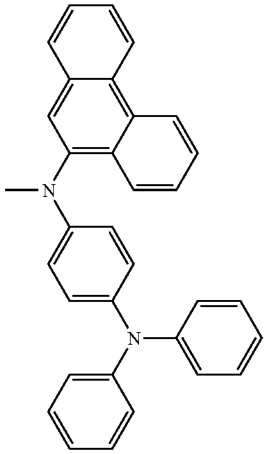
9
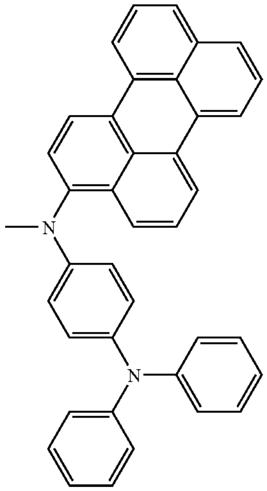

-continued
10
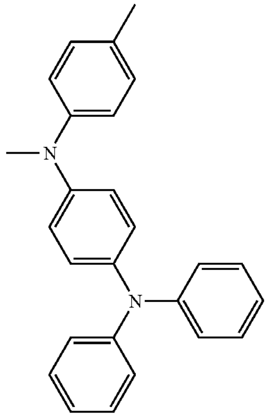
11
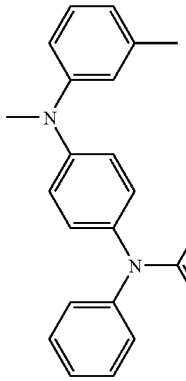
12
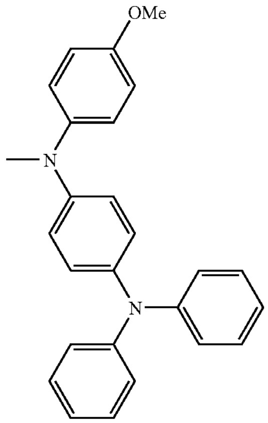
13
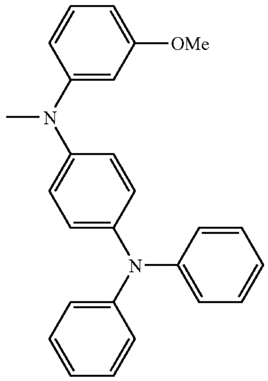
-continued
14
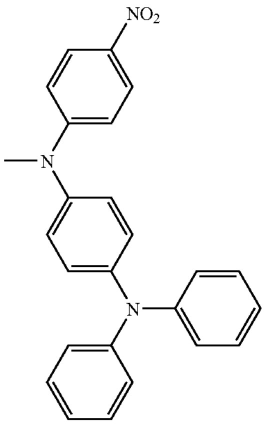
15
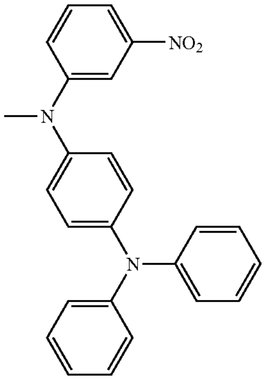
16
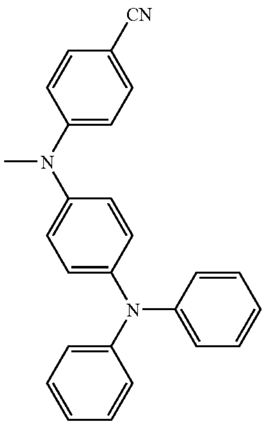
17
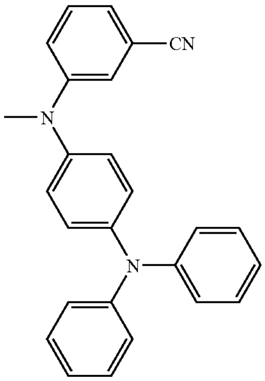

-continued
18
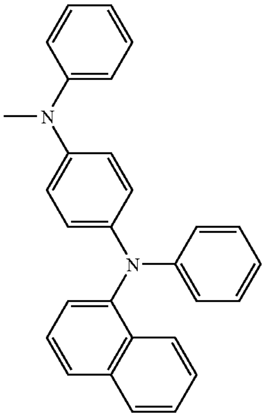
19
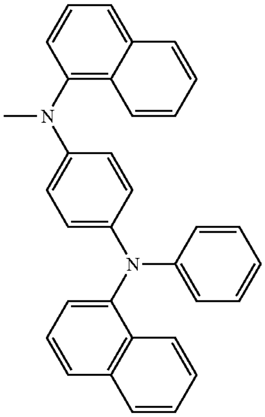
20
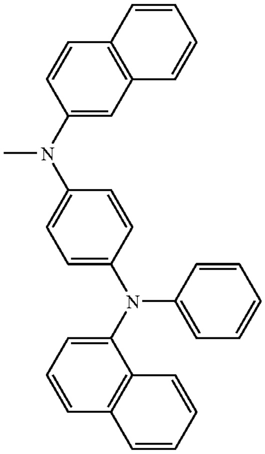
-continued
21
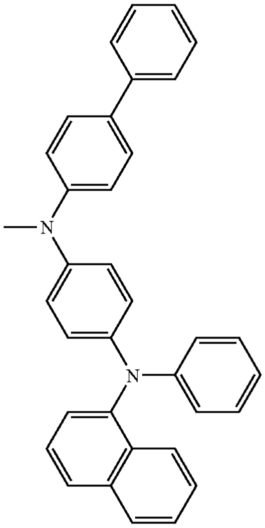
22
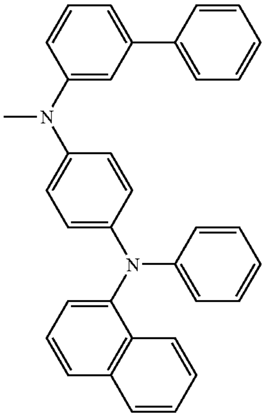
23
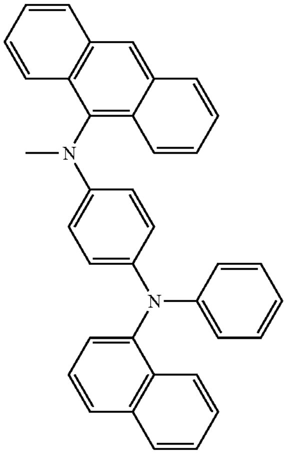

-continued
24
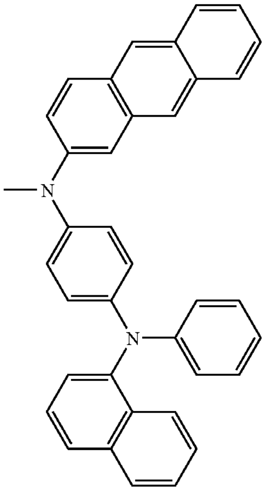
25
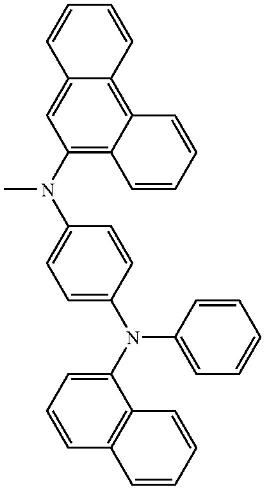
26
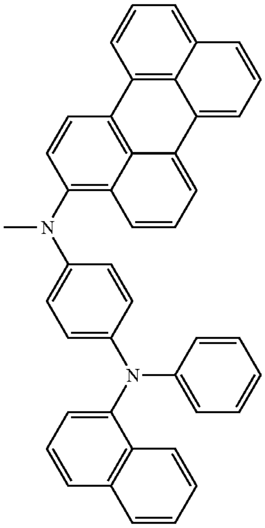
-continued
27
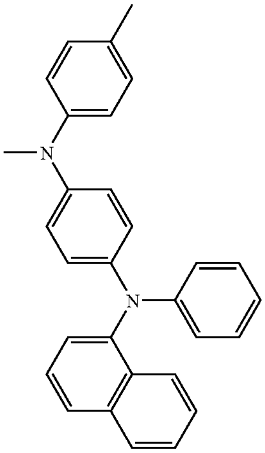
28
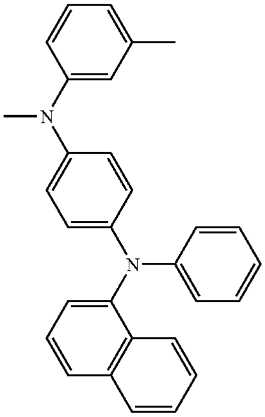
29
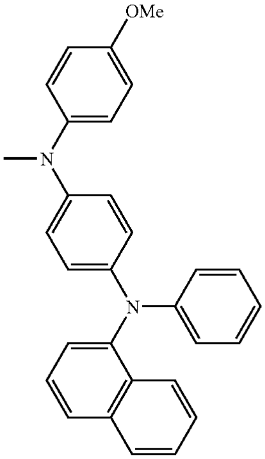

-continued
30
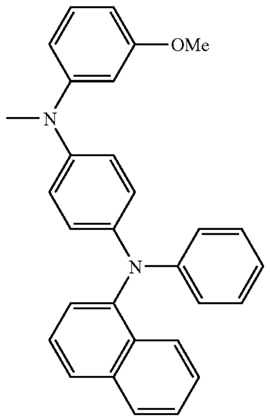
31
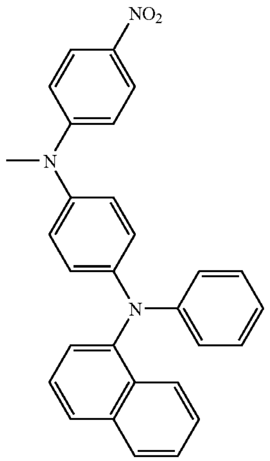
32
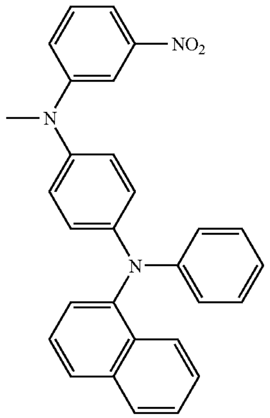
-continued
33
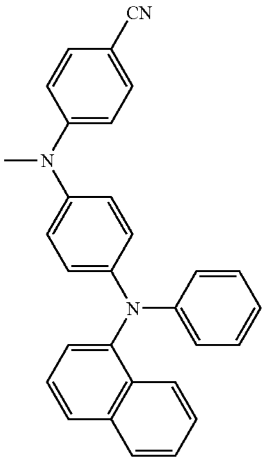
34
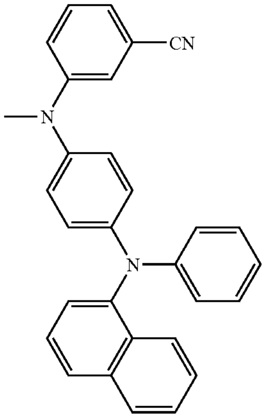
35
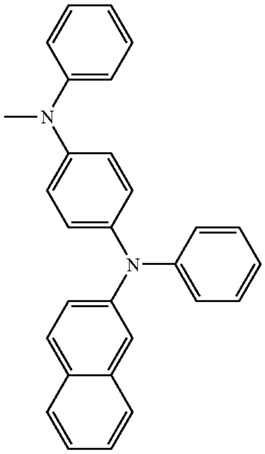

-continued
36
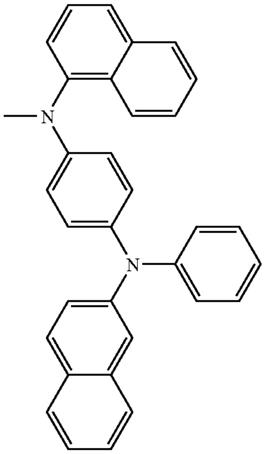
37
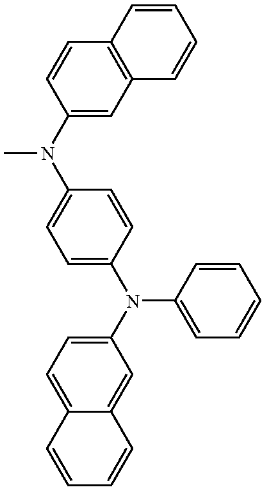
38
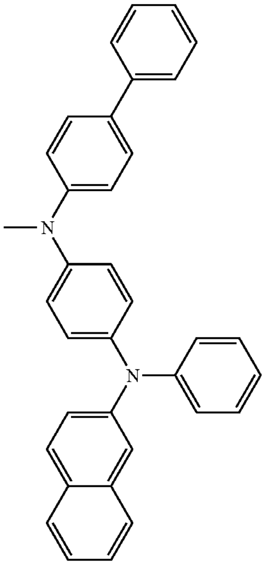
-continued
39
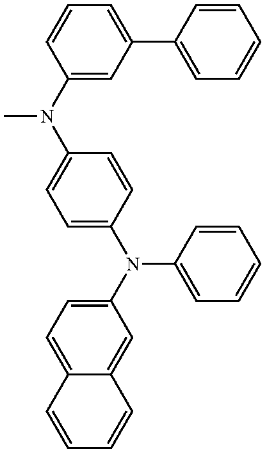
40
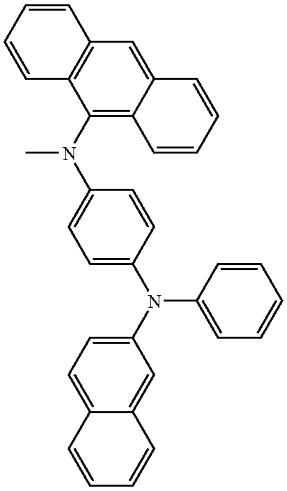
41
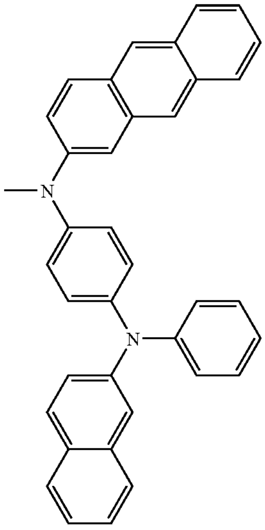

-continued
42
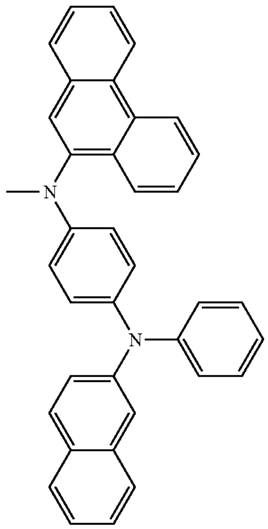
43
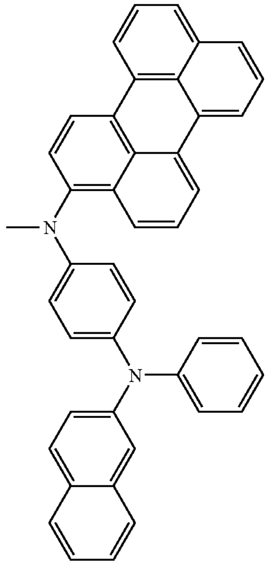
44
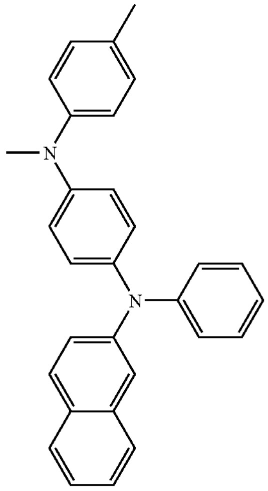
-continued
45
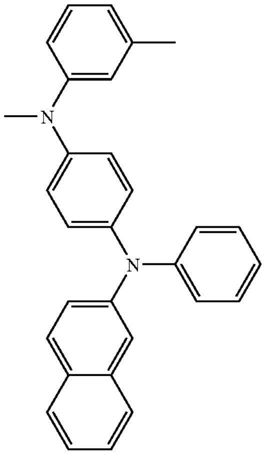
46
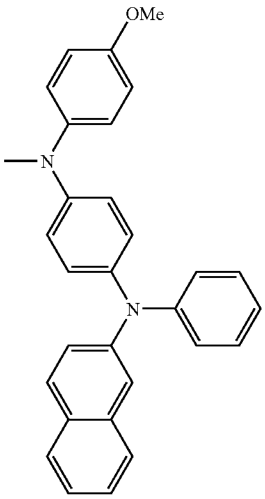
47
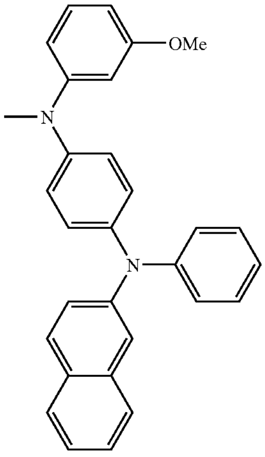

-continued
48
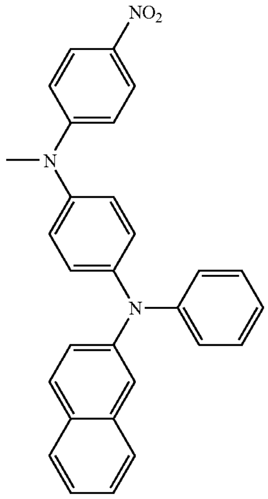
49
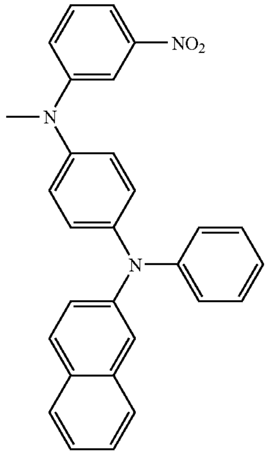
50
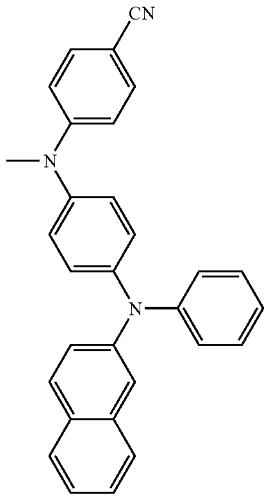
-continued
51
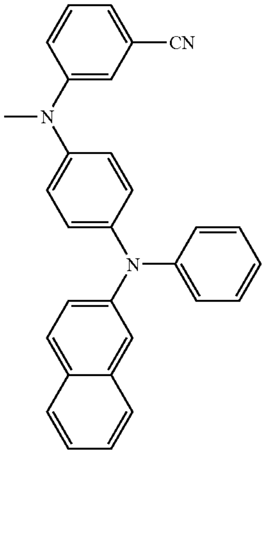
52
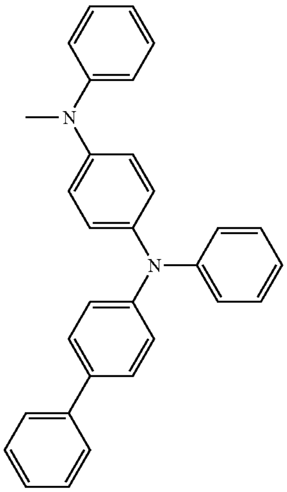
53
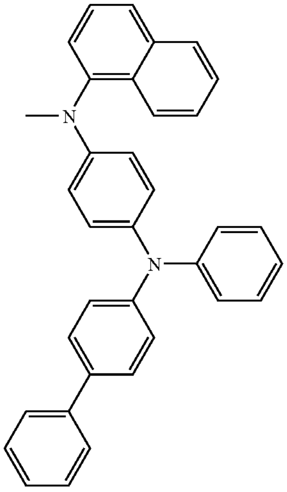

-continued
54
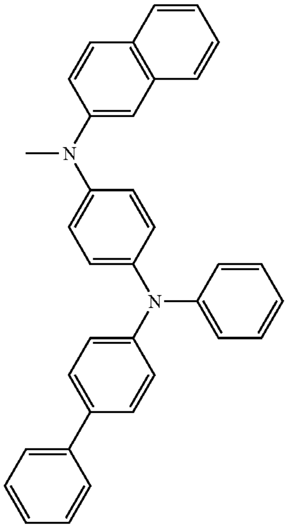
55
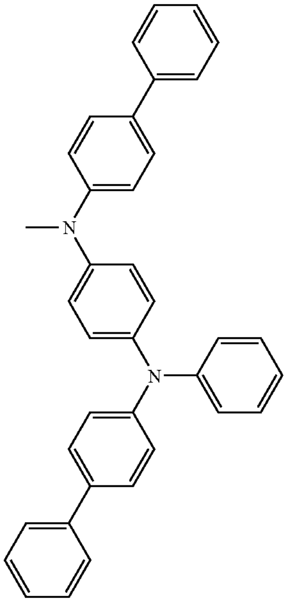
56
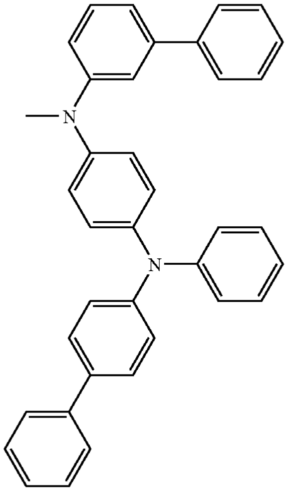
-continued
57
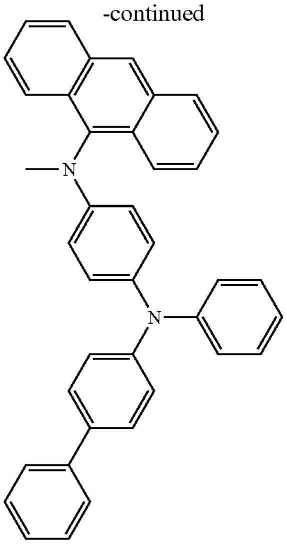
58
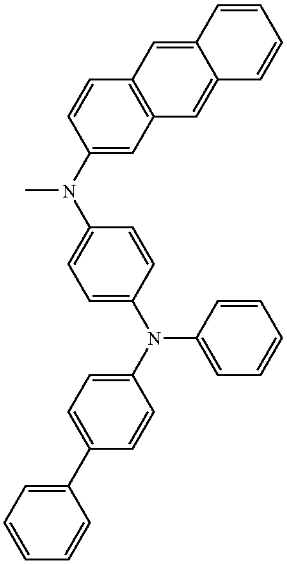
59
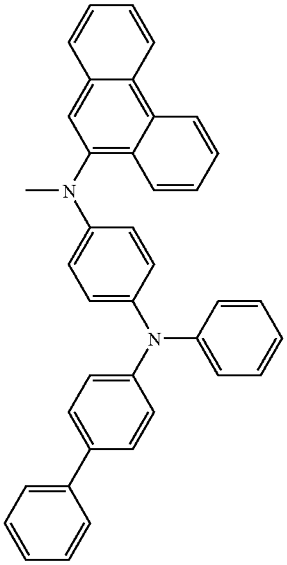

-continued
60
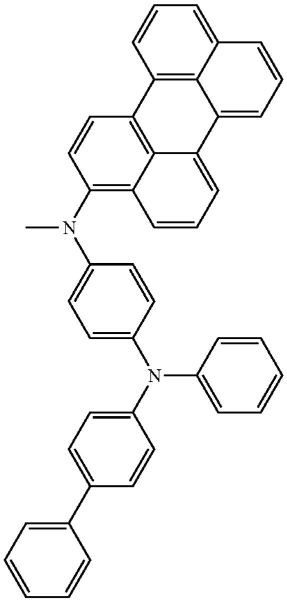
61
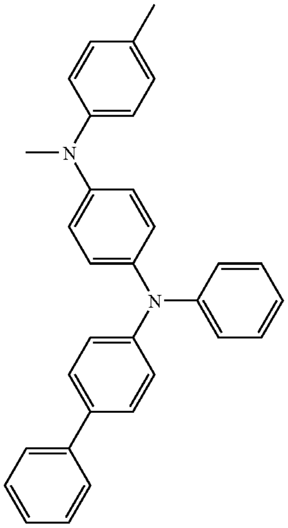
62
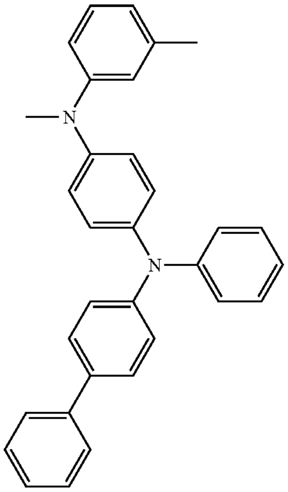
-continued
63
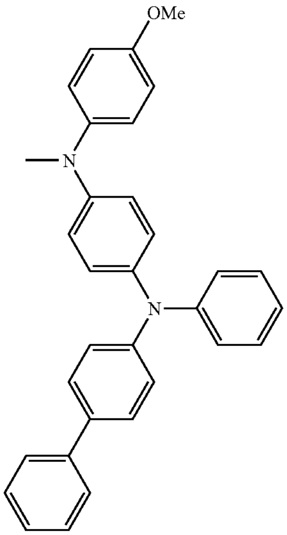
64
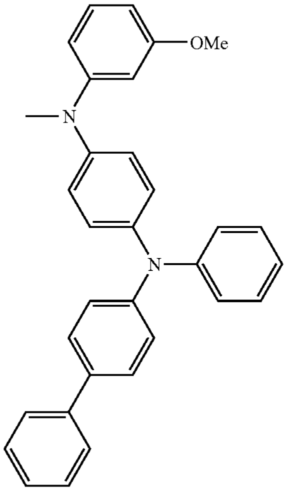
65
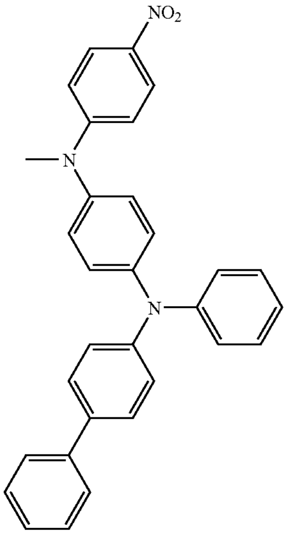

-continued
66
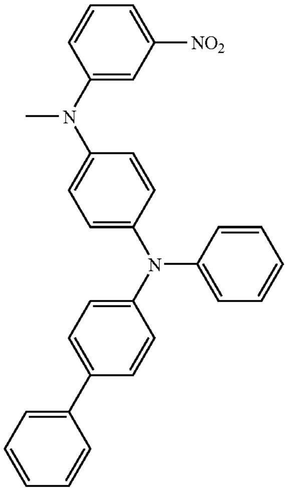
67
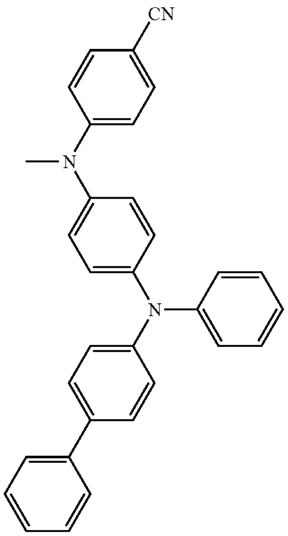
68
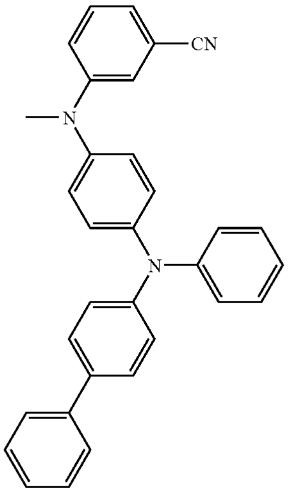
-continued
69
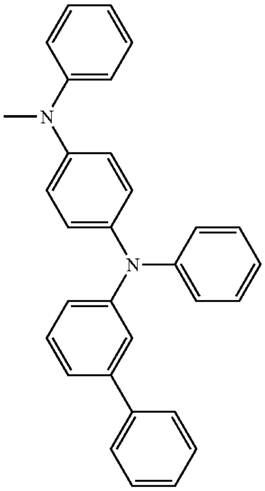
70
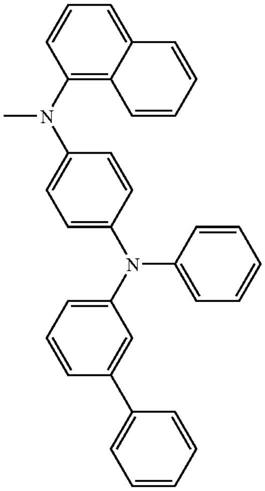
71
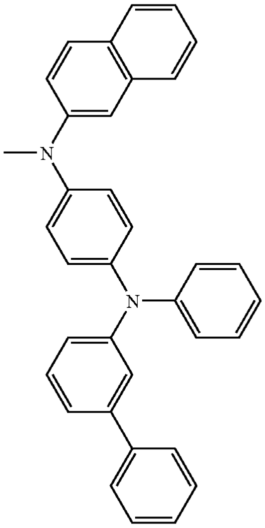

-continued
72
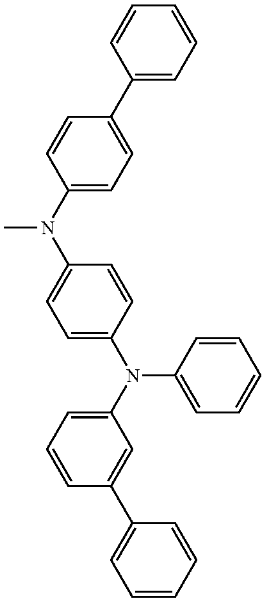
73
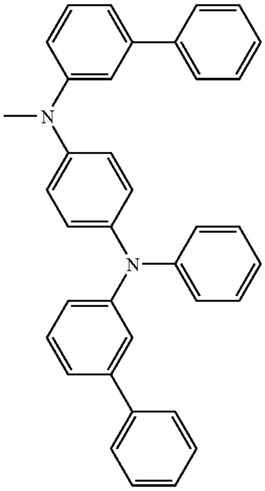
74
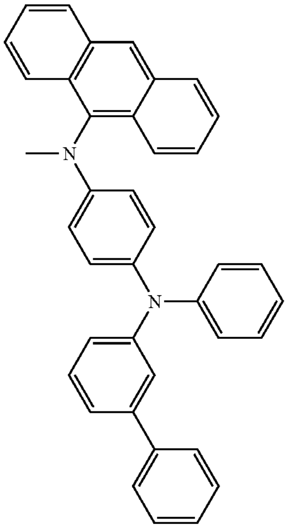
-continued
75
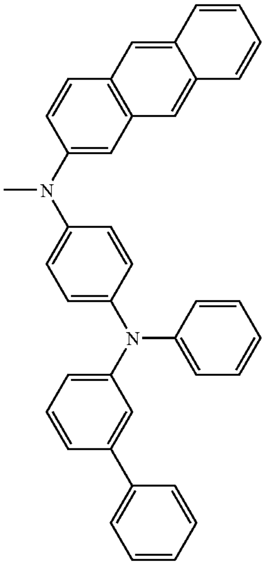
76
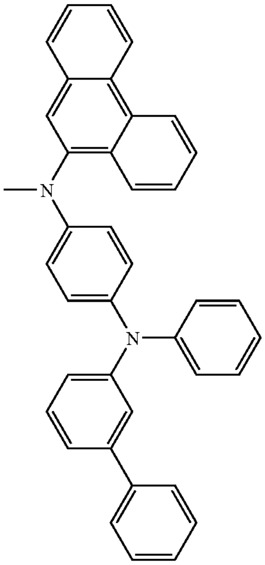

-continued
77
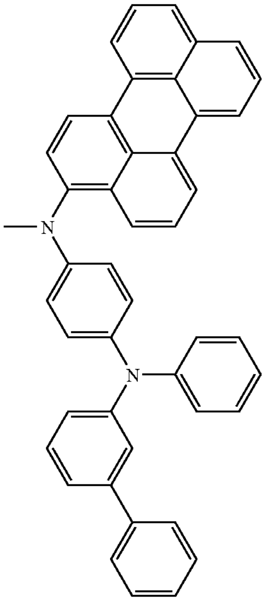
78
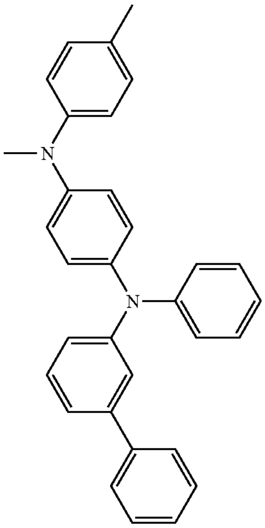
79
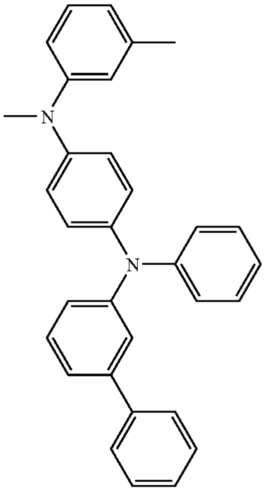
-continued
80
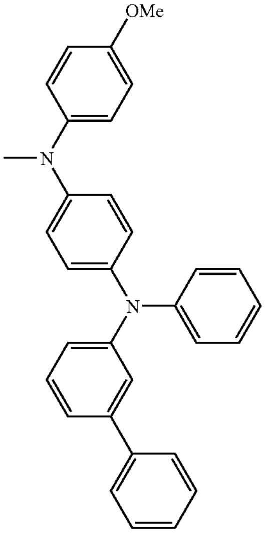
81
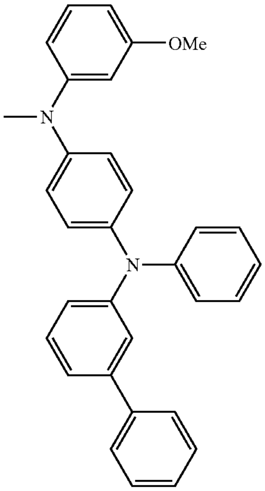
82
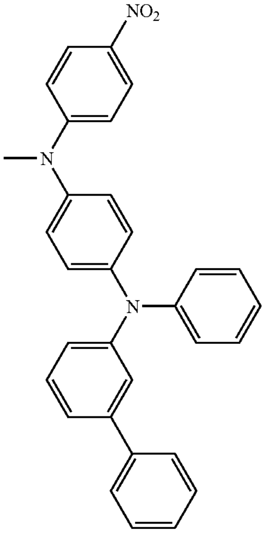

-continued
83
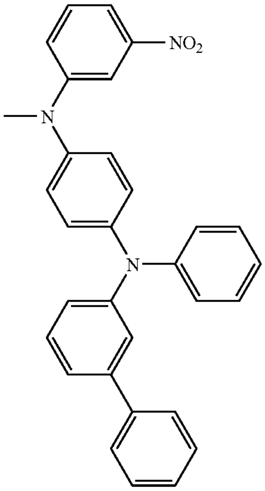
84
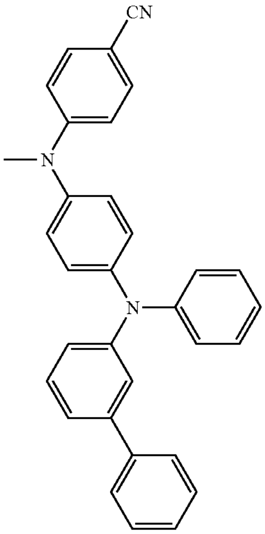
85
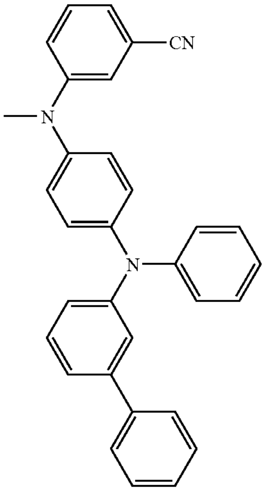
-continued
86
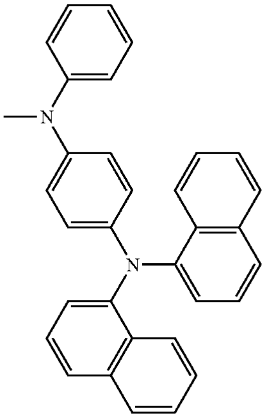
87
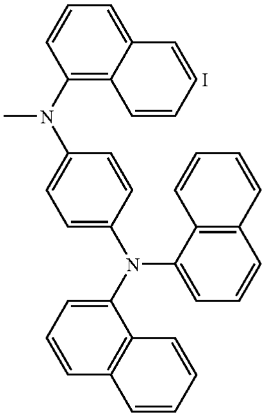
88
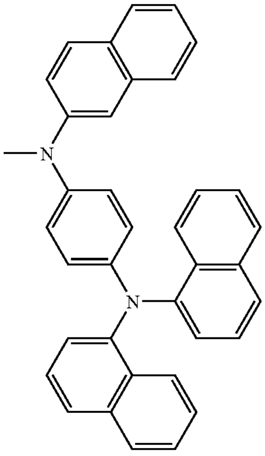

-continued
89
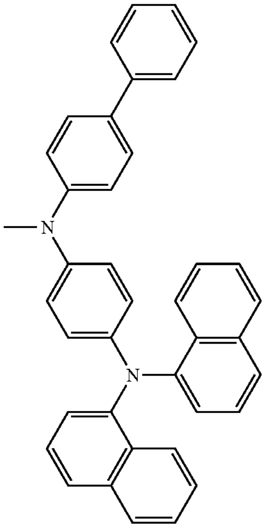
90
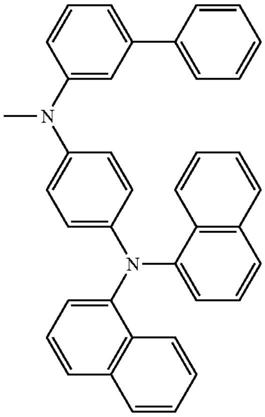
91
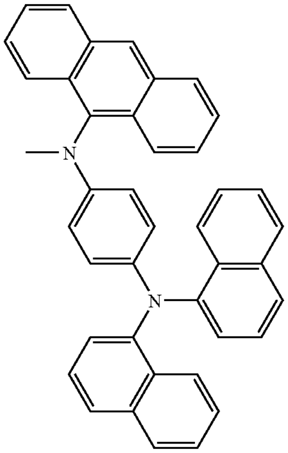
-continued
92
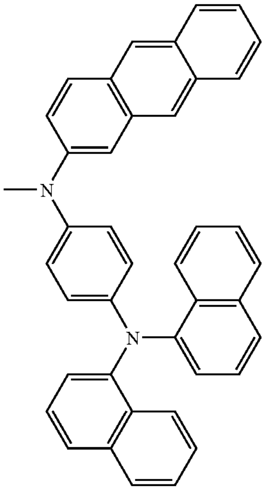
93
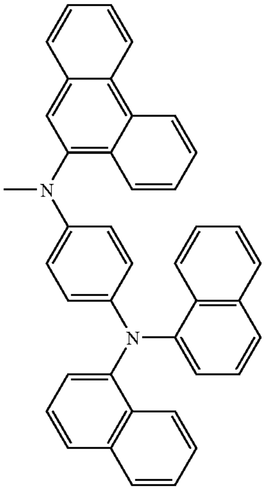
94
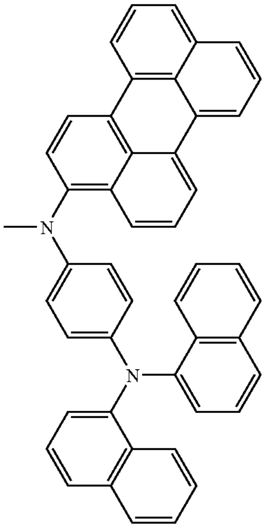

-continued
95
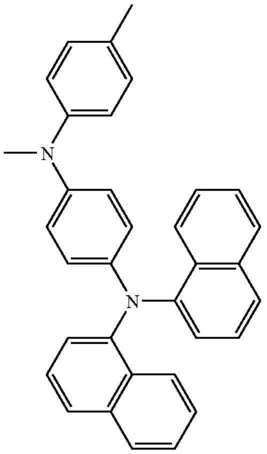
96
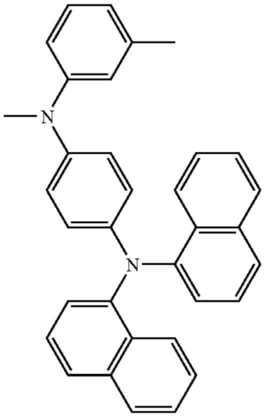
97
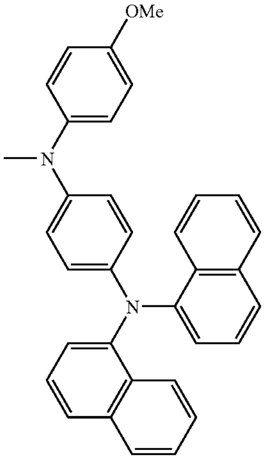
-continued
98
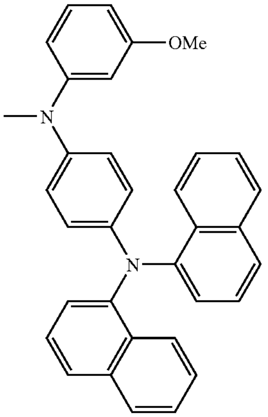
99
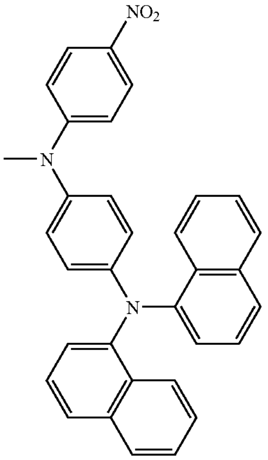
100
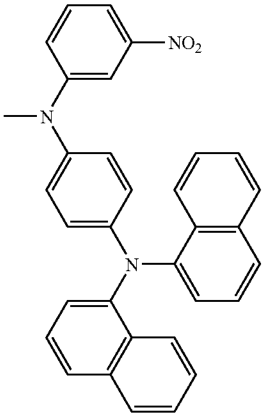

-continued
101
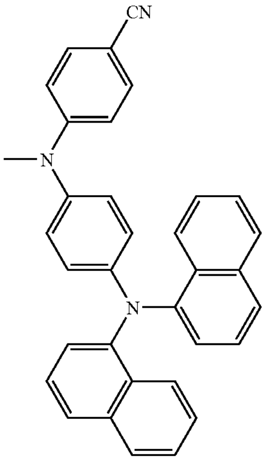
102
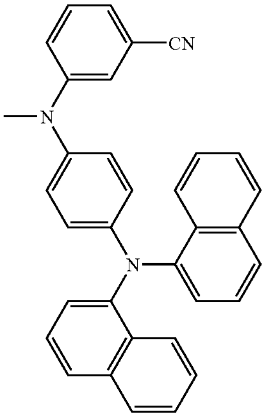
103
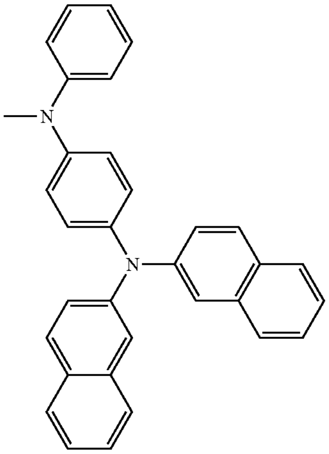
-continued
104
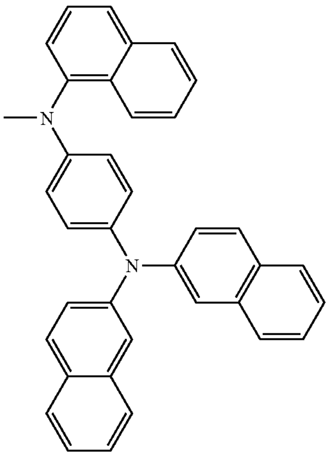
105
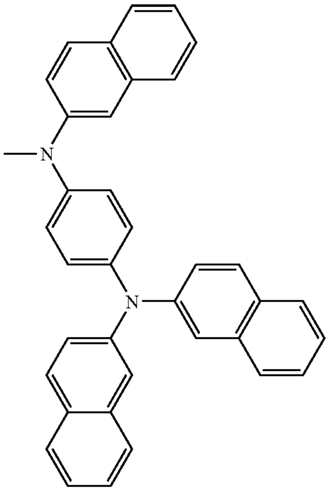
106
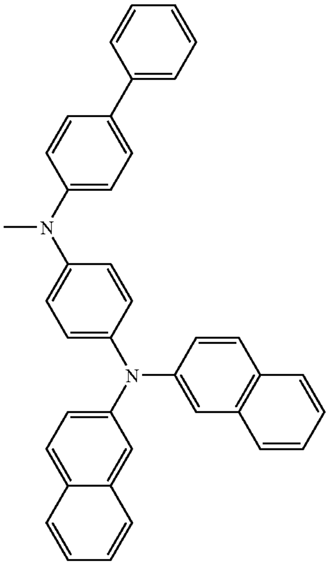

-continued
107
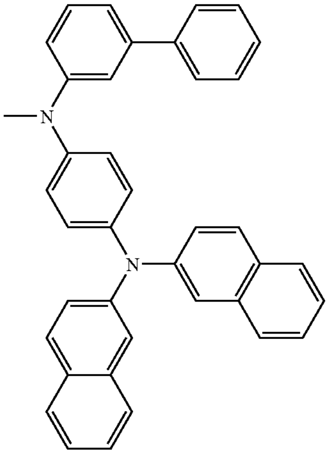
108
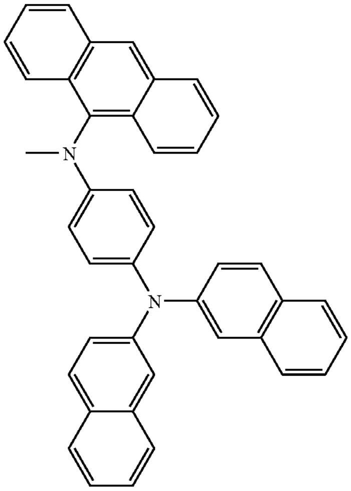
109
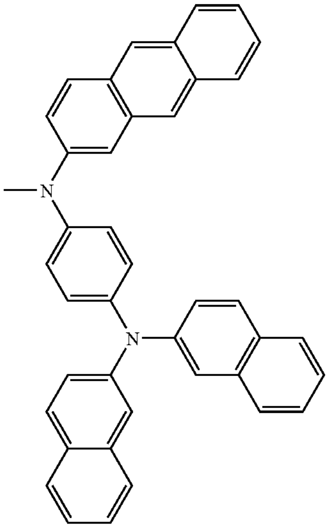
-continued
110
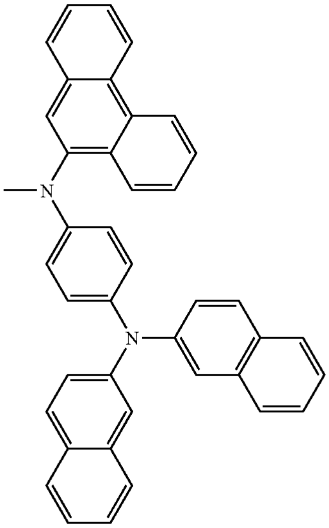
111
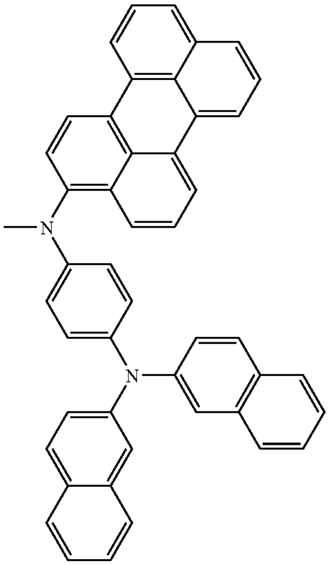
112
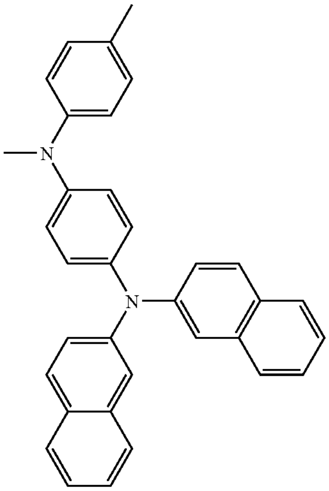

-continued
113
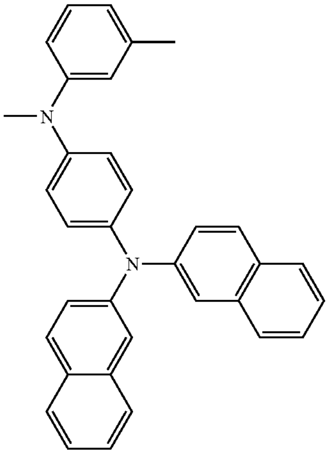
114
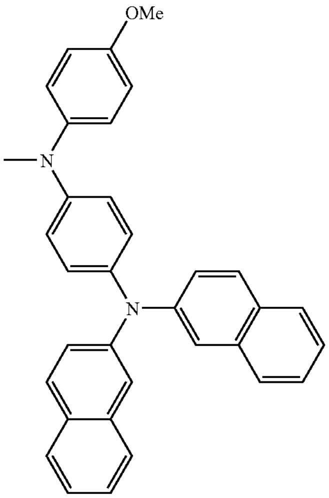
115
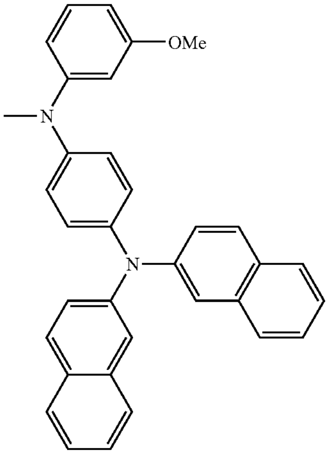
-continued
116
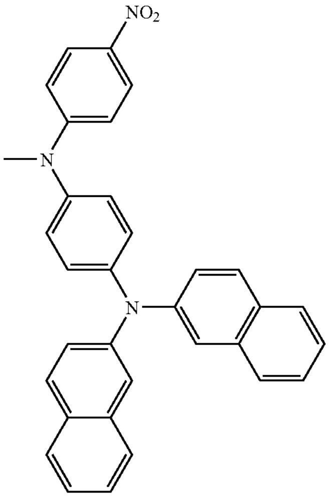
117
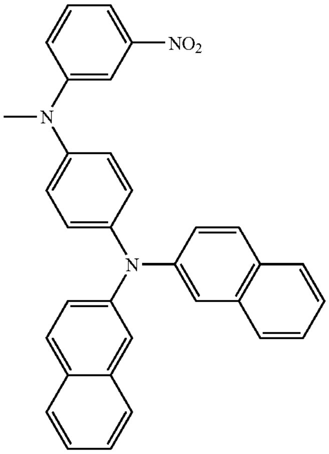
118
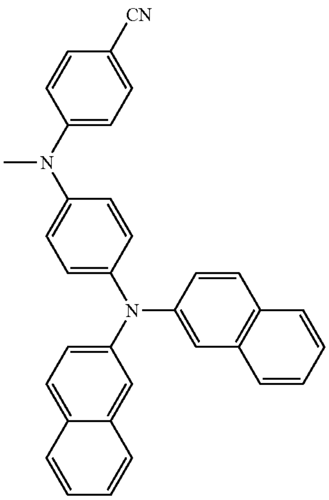

-continued
119
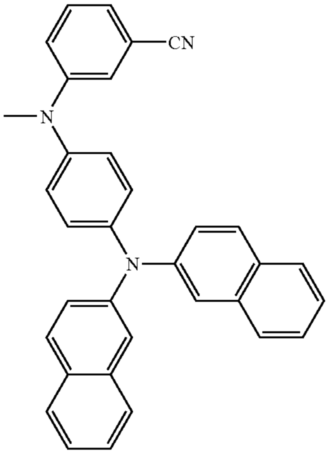
120
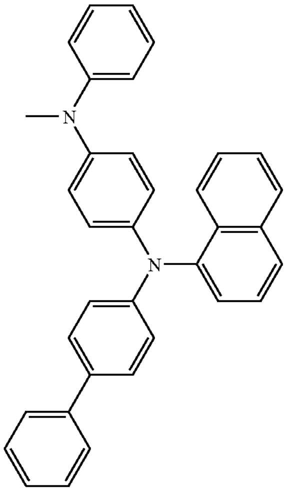
121
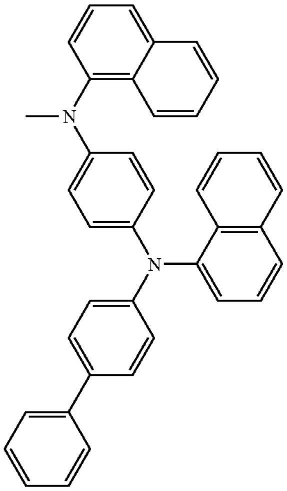
-continued
122
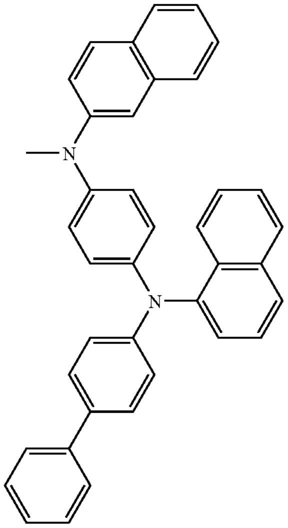
123
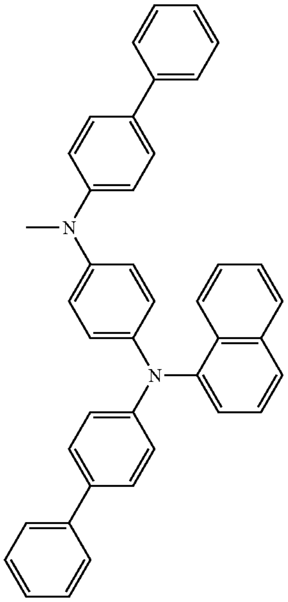
124
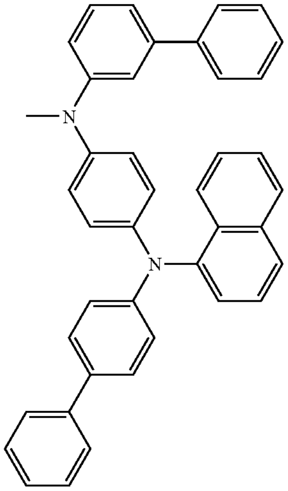

-continued
125
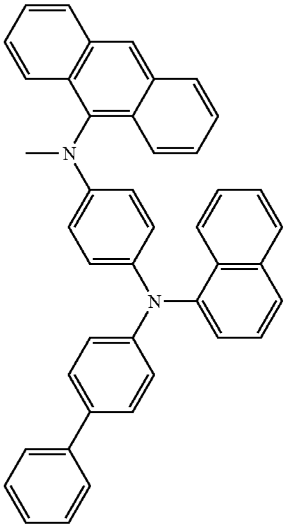
126
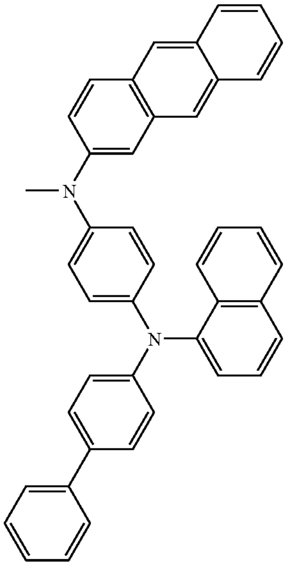
127
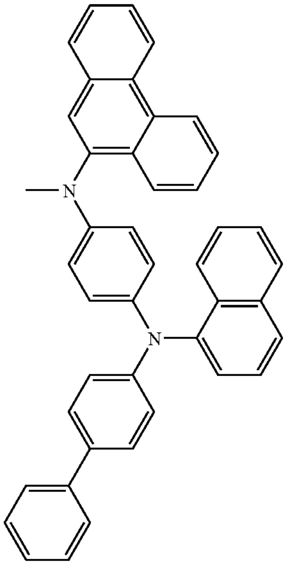
-continued
128
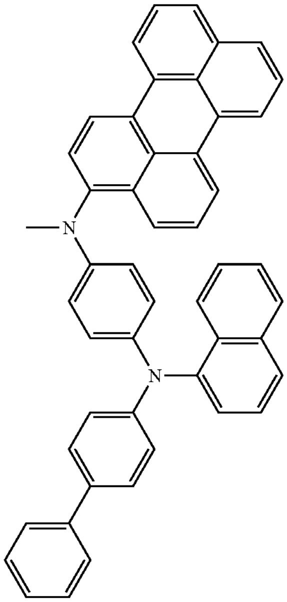
129
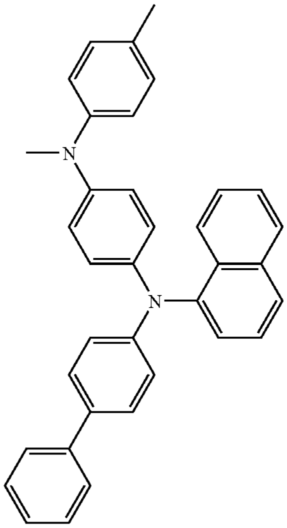
130
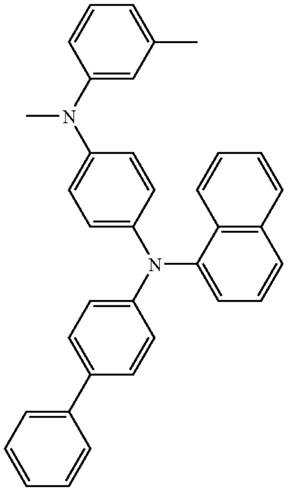

-continued
131
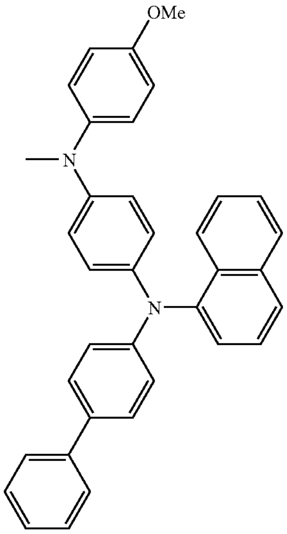
132
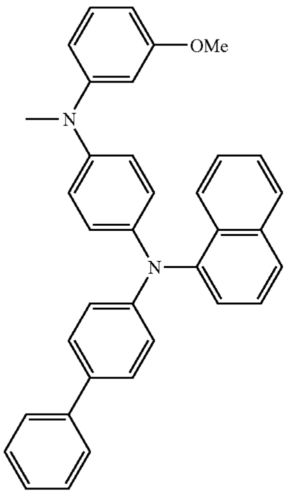
133
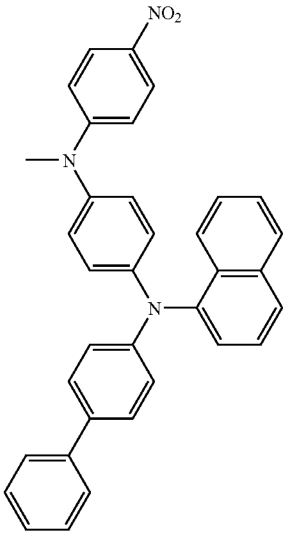
-continued
134
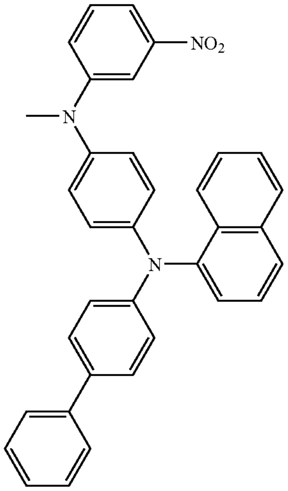
135
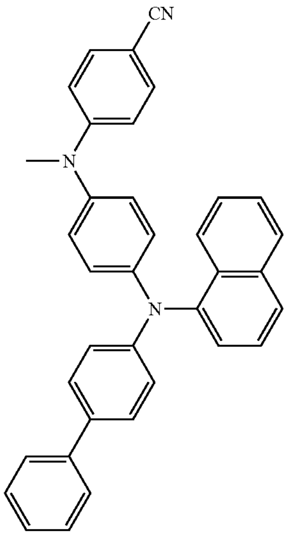
136
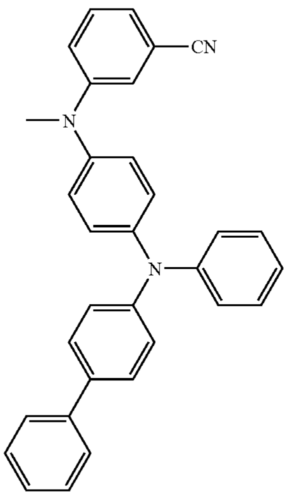

-continued
137
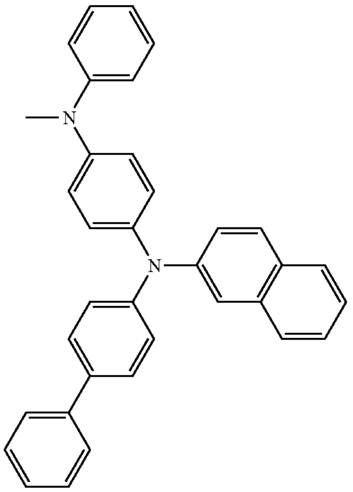
138
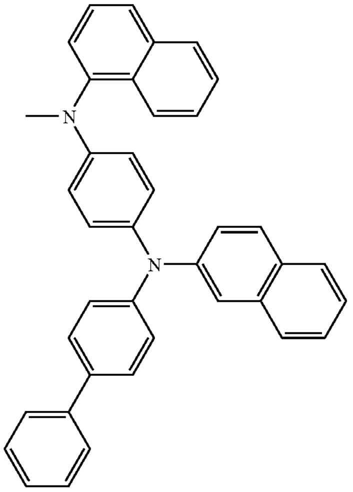
139
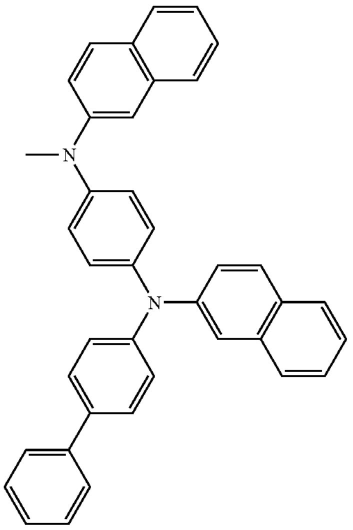
-continued
140
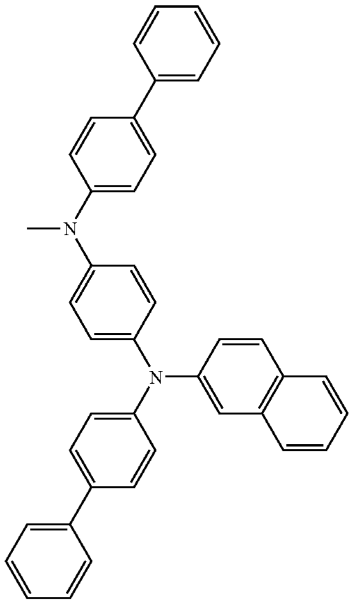
141
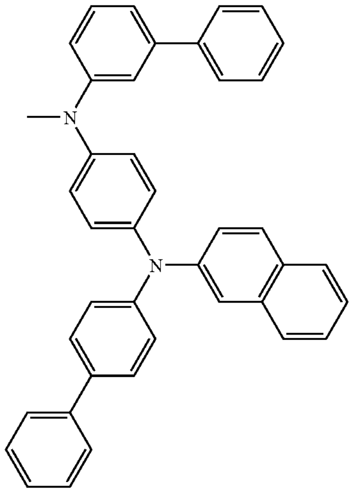
142
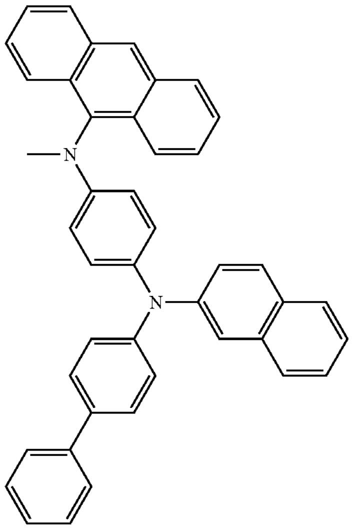

-continued
143
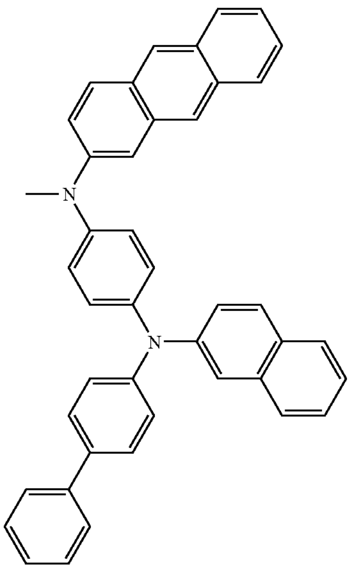
144
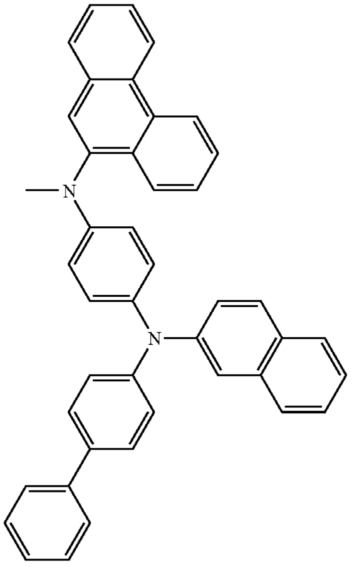
-continued
145
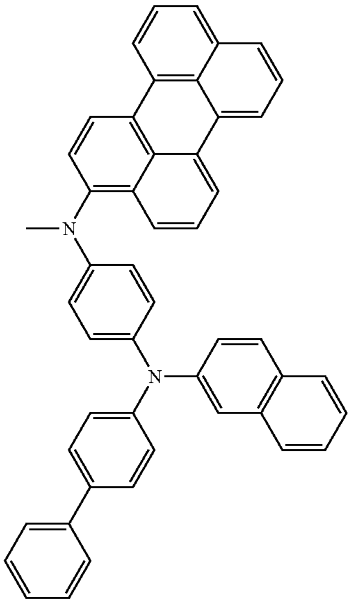
146
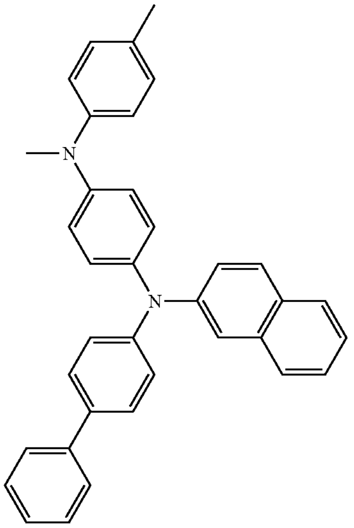
147
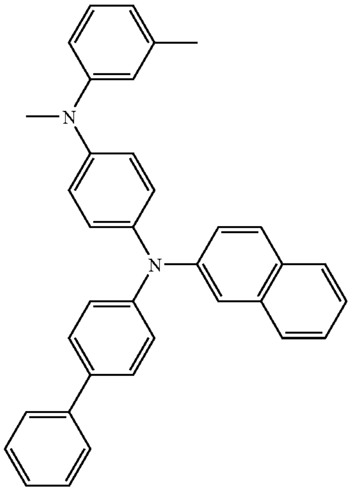

-continued
148
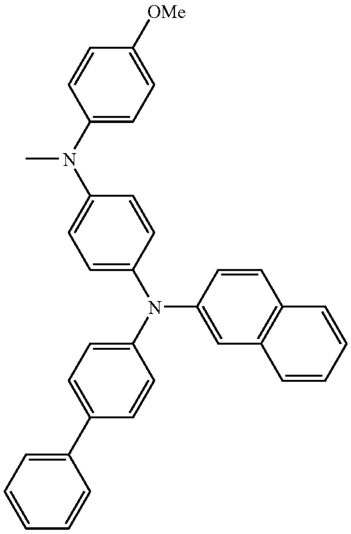
149
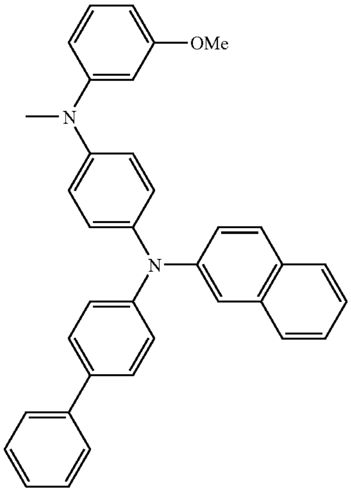
150
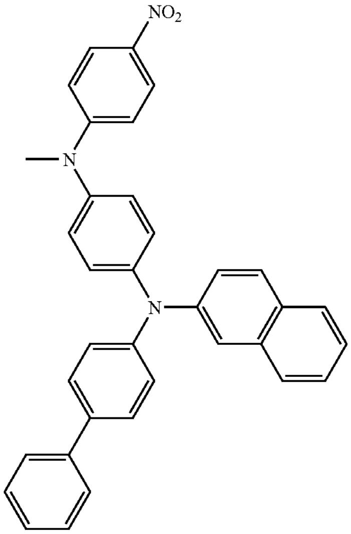
-continued
151
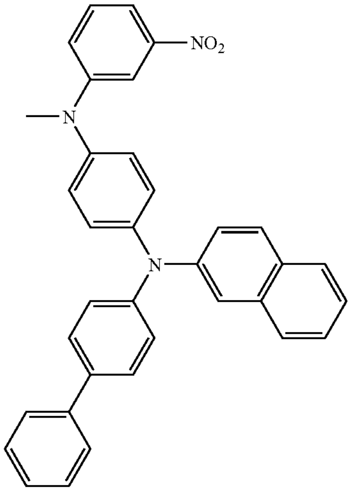
152
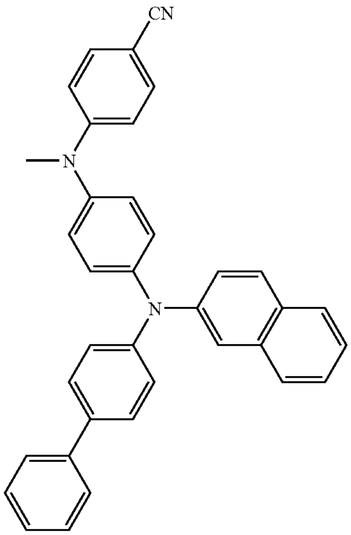
153
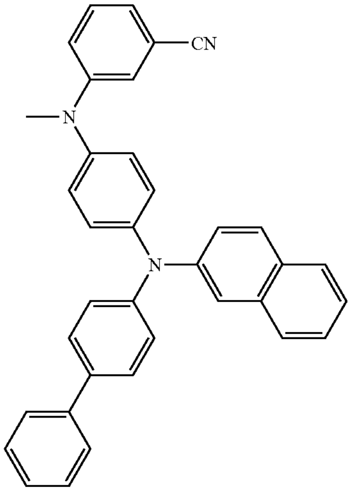

-continued
154
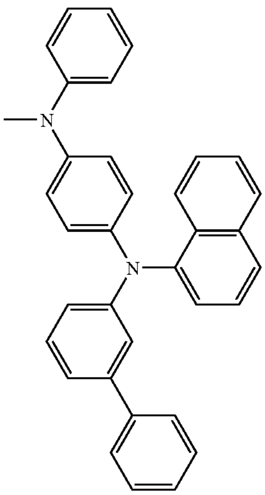
155
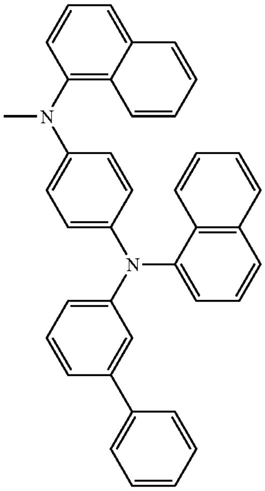
156
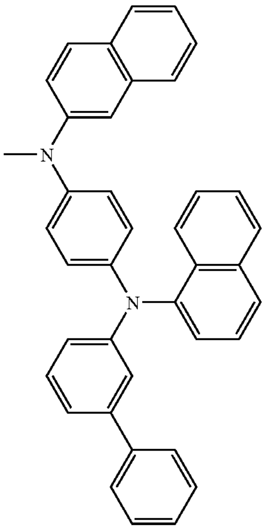
-continued
157
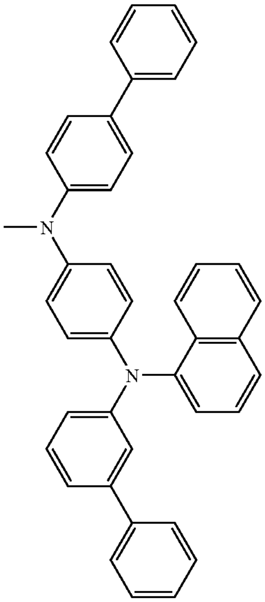
158
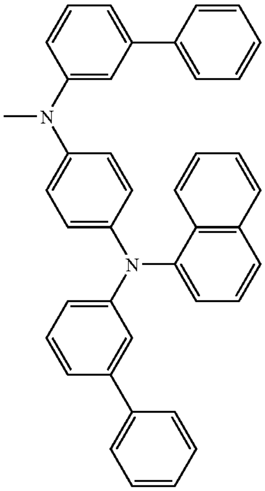
159
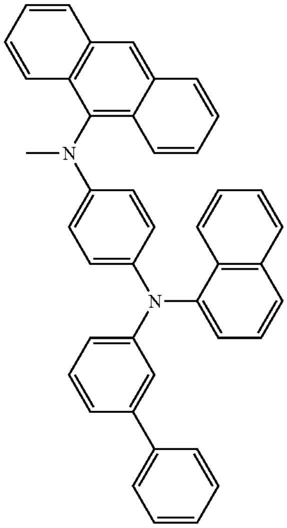

-continued
160
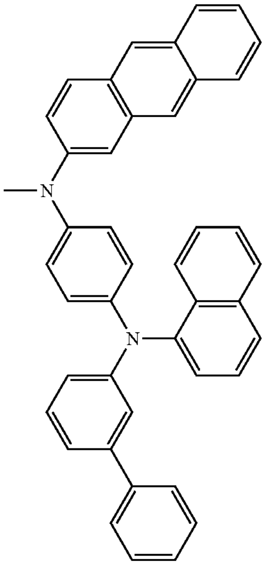
161
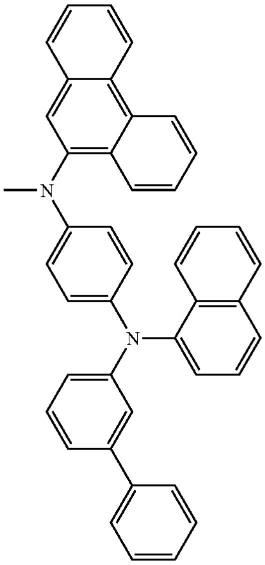
-continued
162
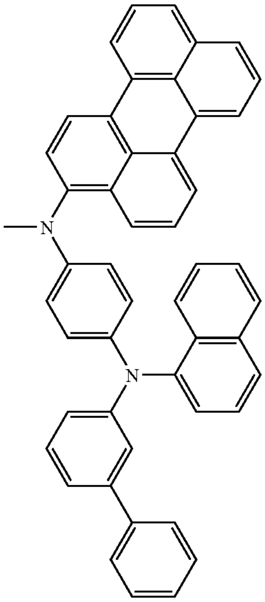
163
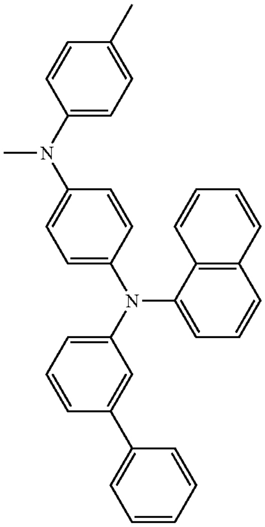
164
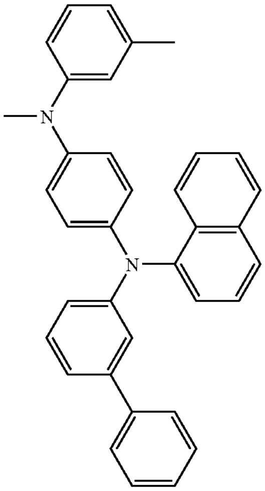

-continued
165
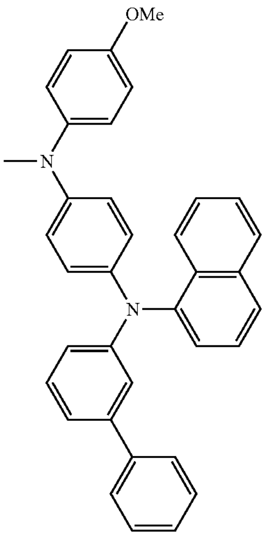
166
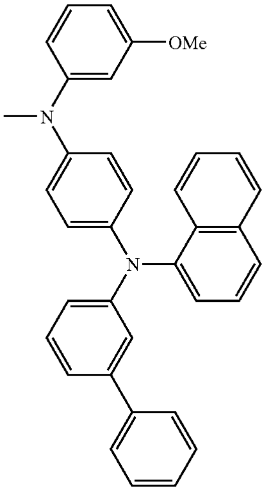
167
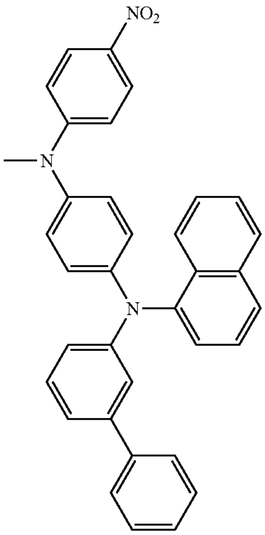
-continued
168
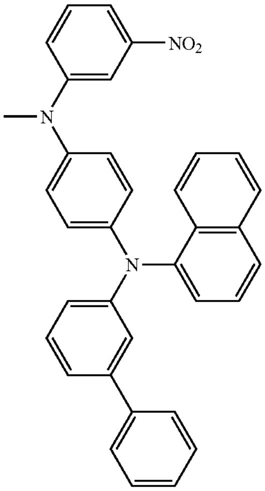
169
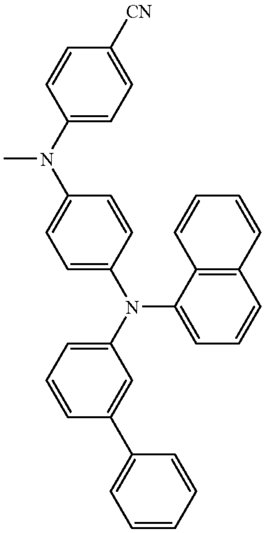
170
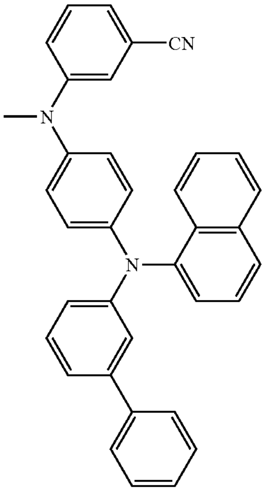

-continued
171
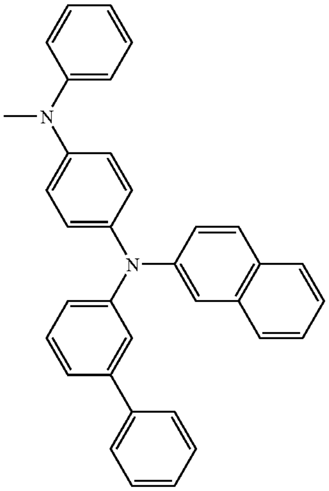
172
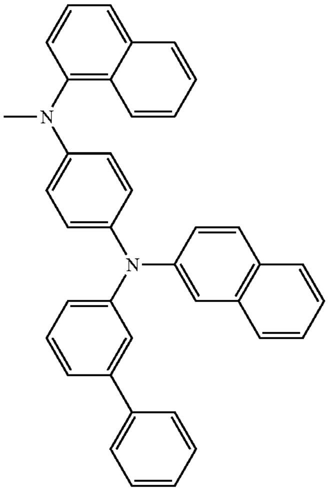
173
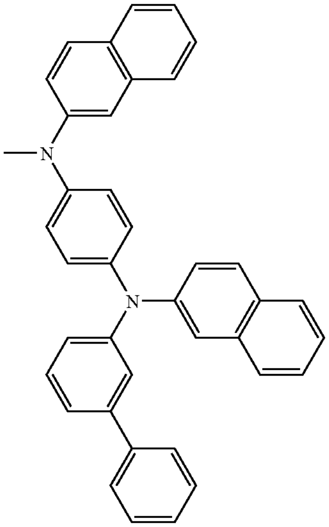
-continued
174
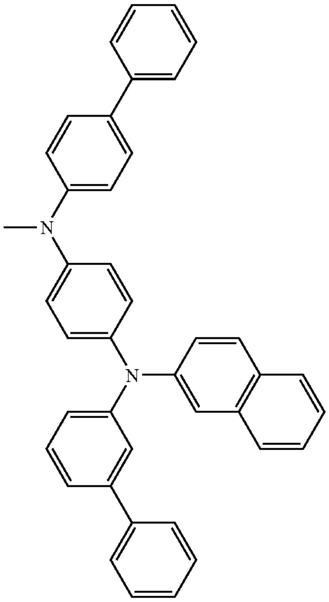
175
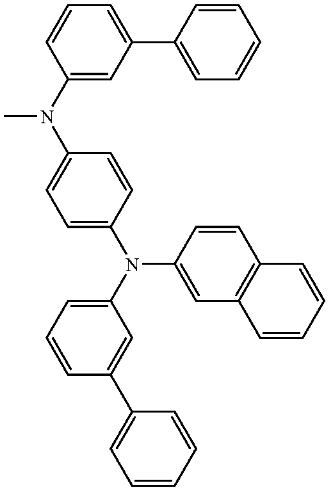
176
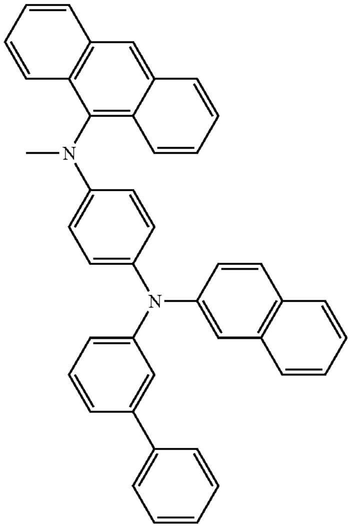

-continued
177
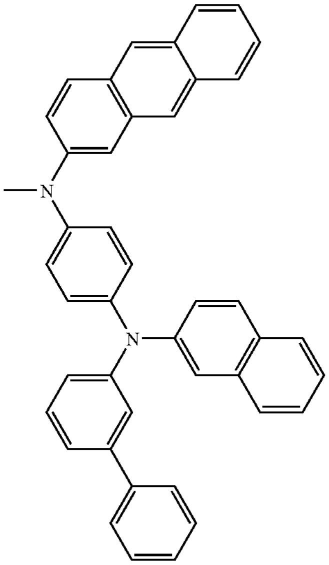
178
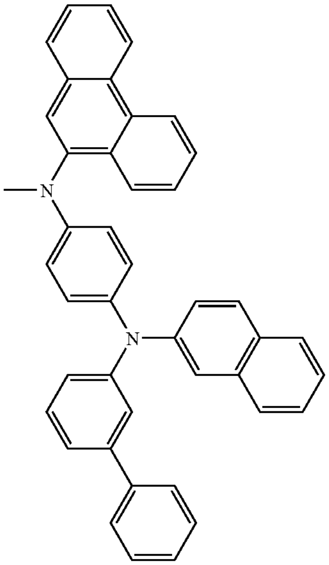
-continued
179
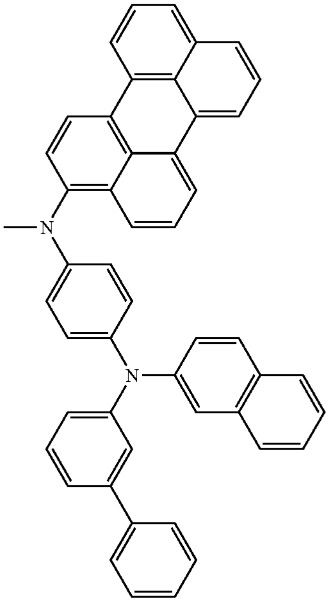
180
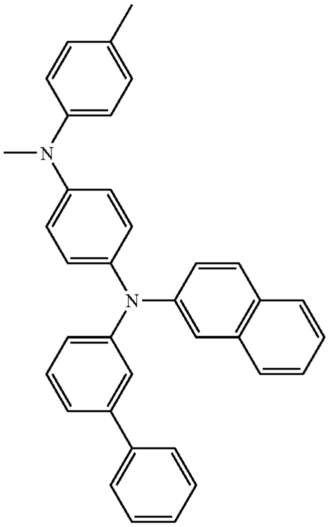
181
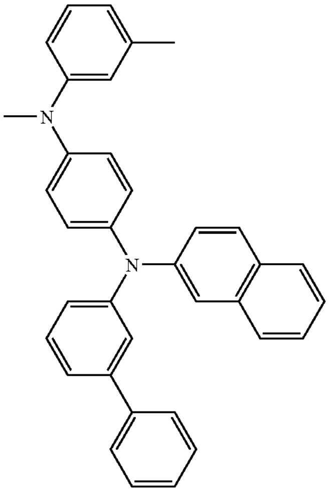

-continued
182
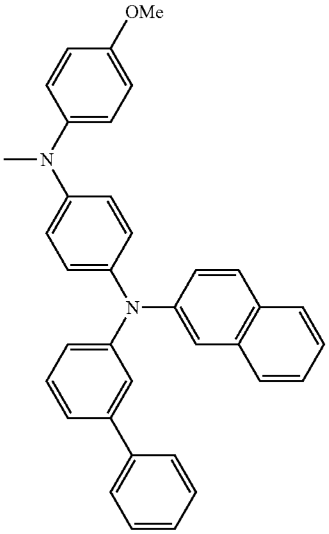
183
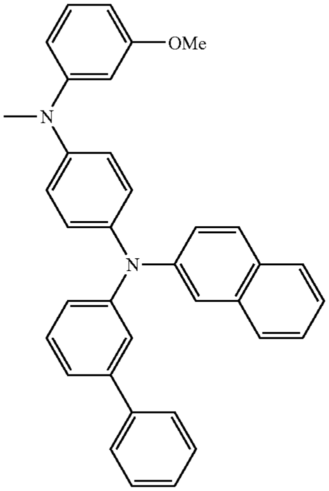
184
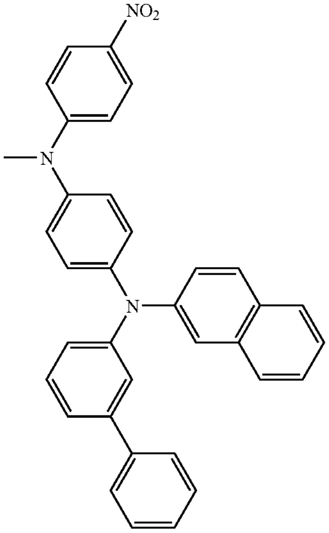
-continued
185
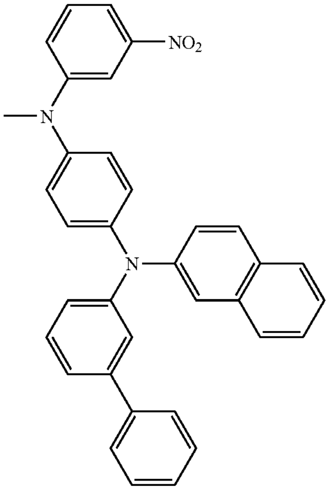
186
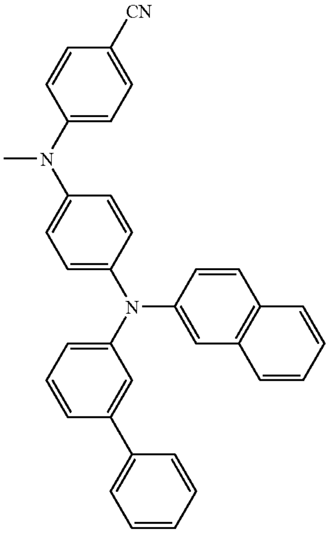
187
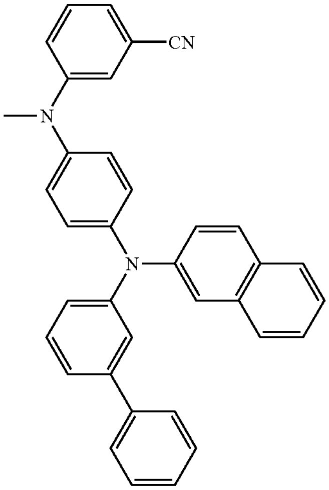

-continued
188
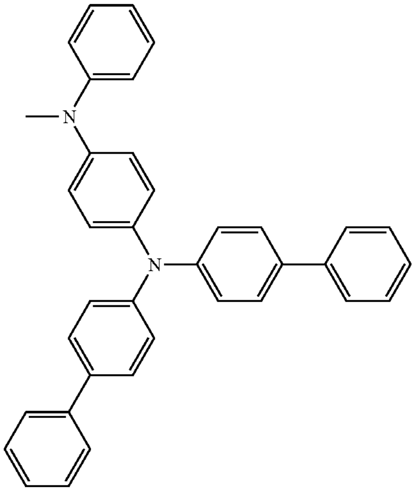
189
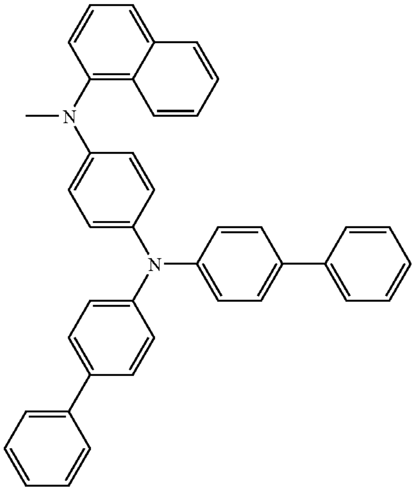
190
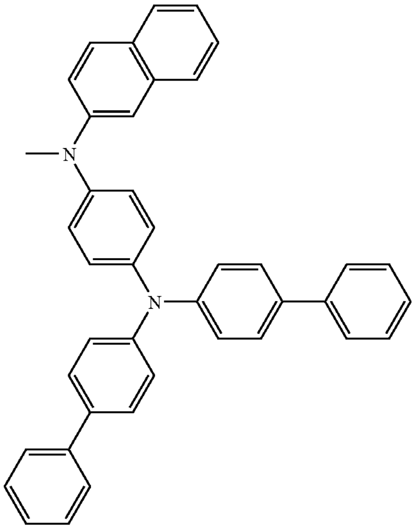
-continued
191
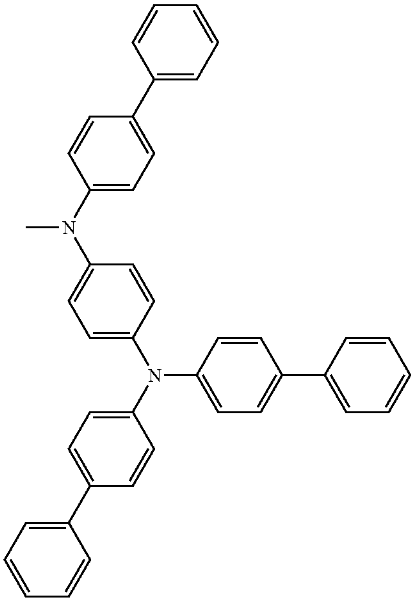
192
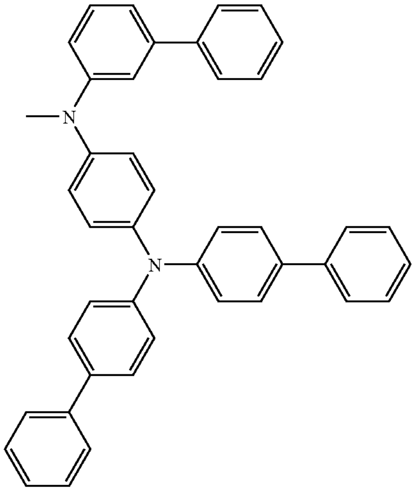
193
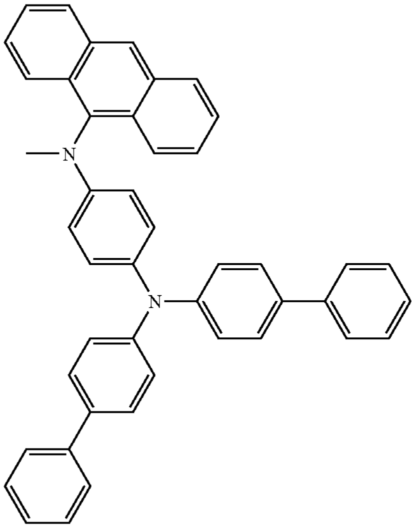

-continued
194
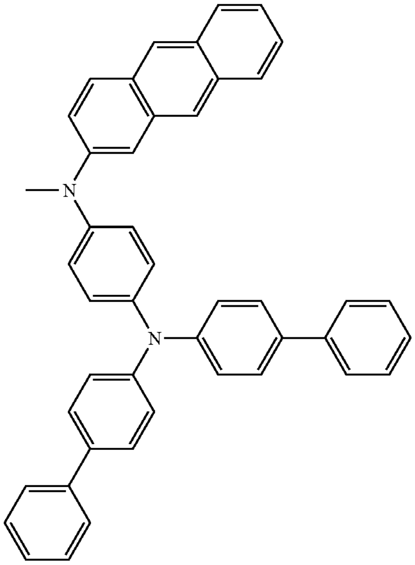
195
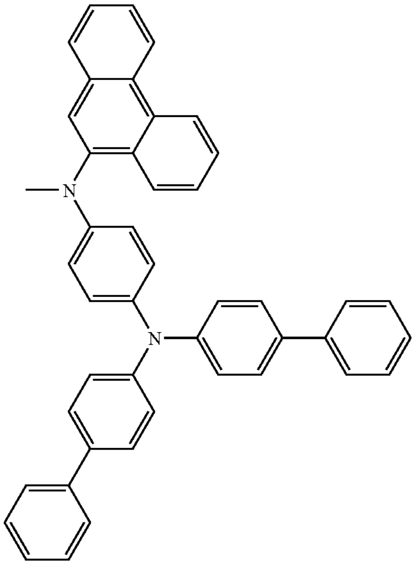
-continued
196
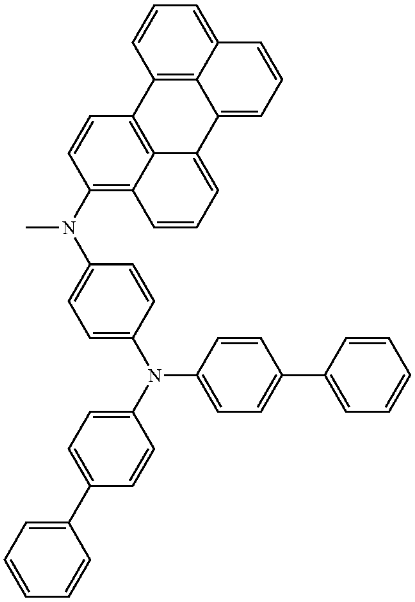
197
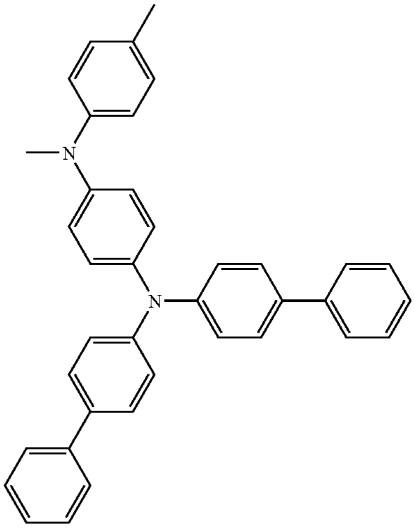
198
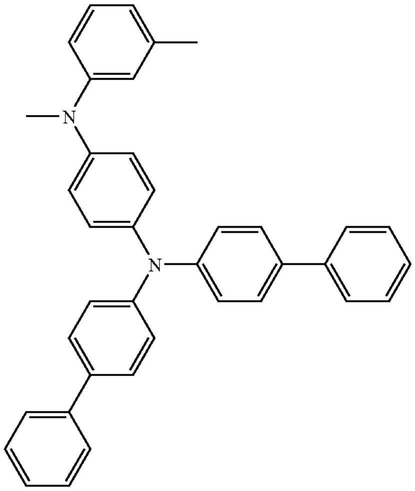

-continued
199
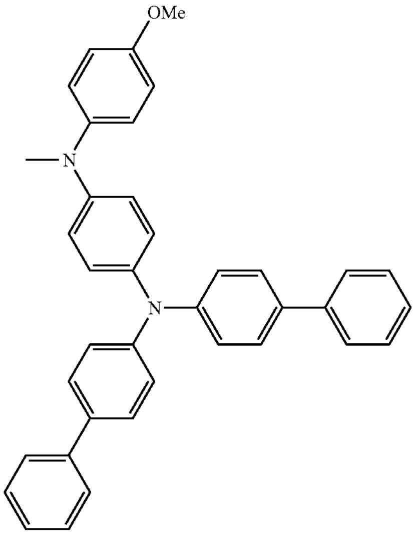
200
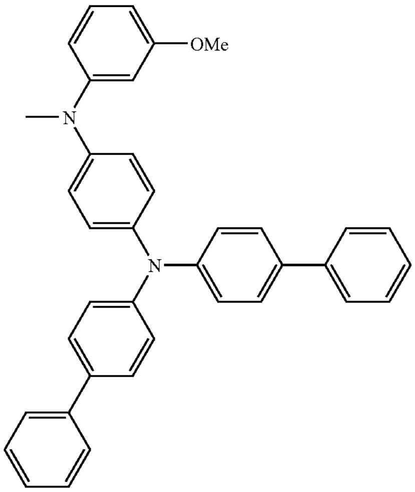
201
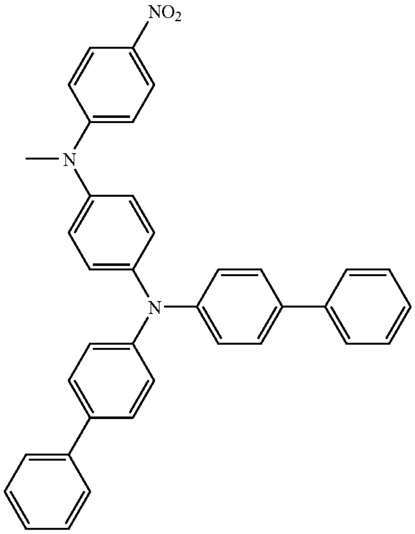
-continued
202
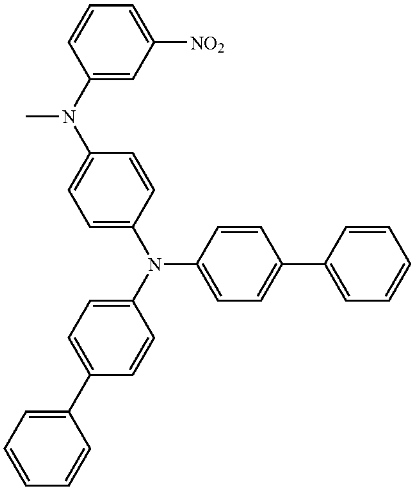
203
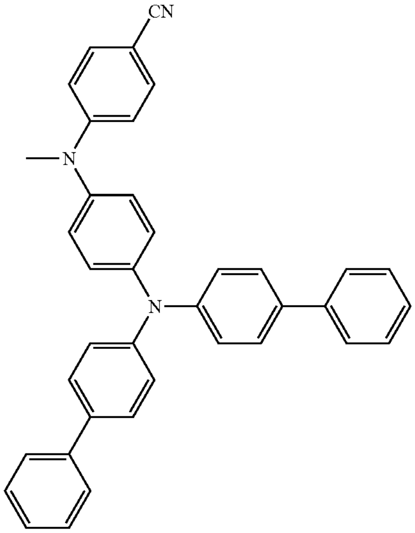
204
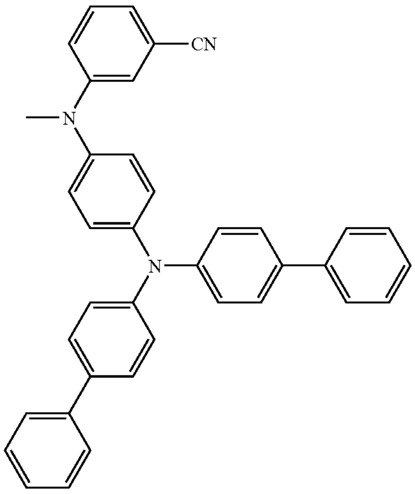

-continued
205
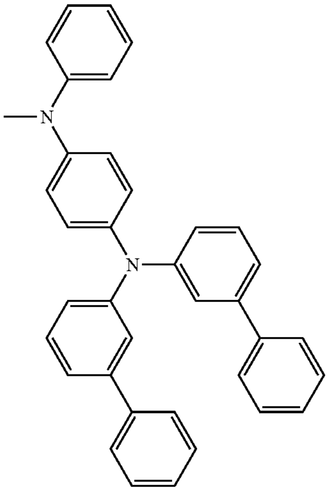
206
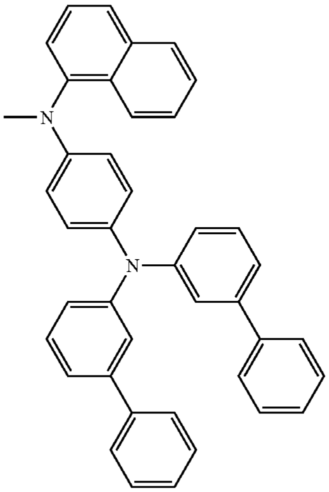
207
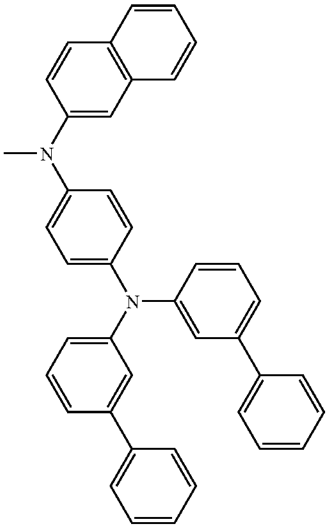
-continued
208
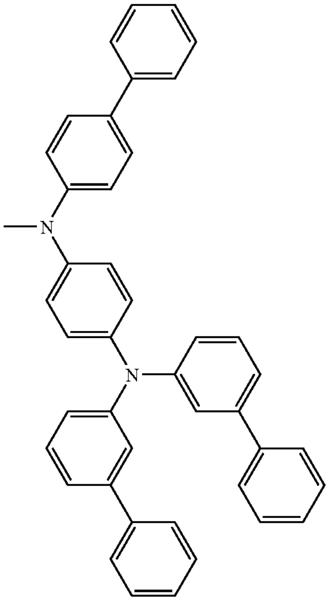
209
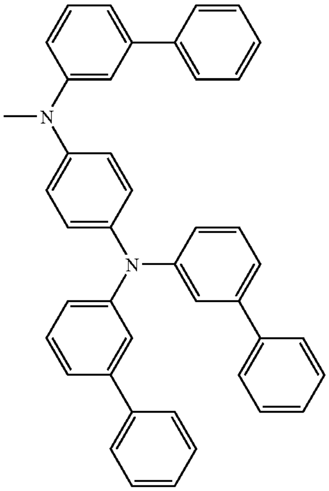
210
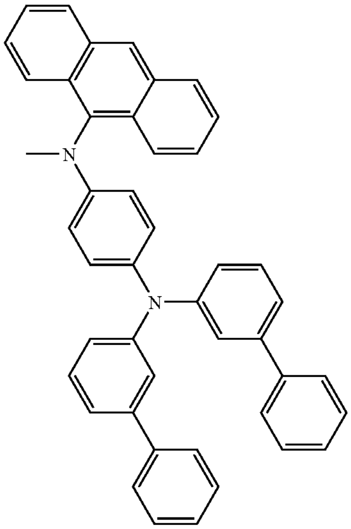

-continued
211
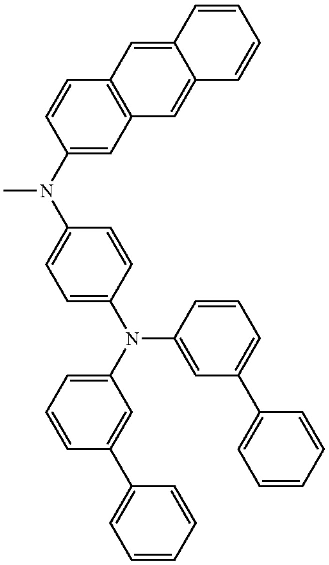
212
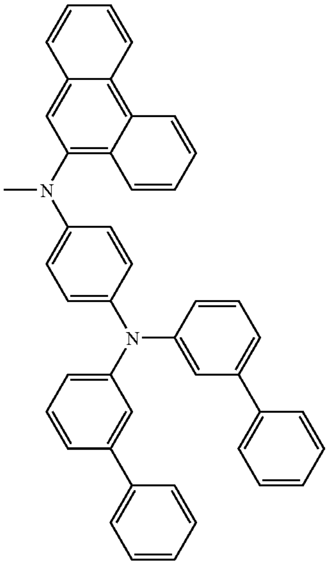
-continued
213
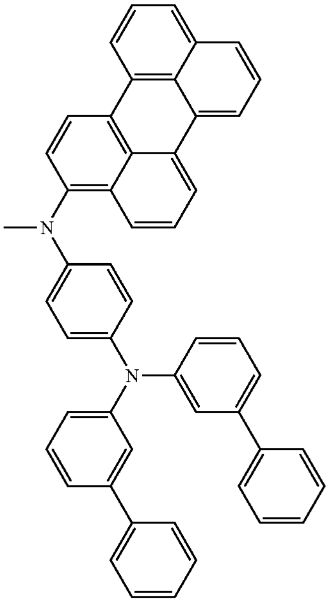
214
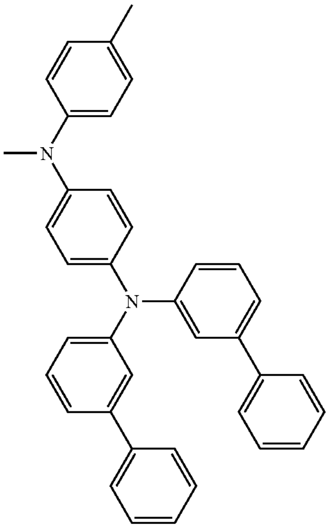
215
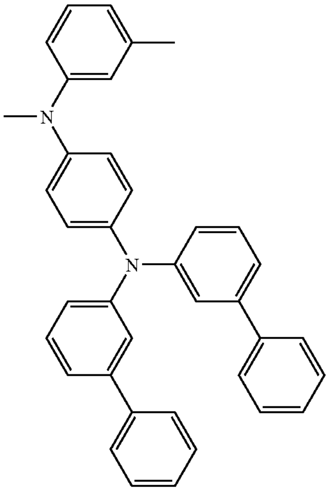

-continued
216
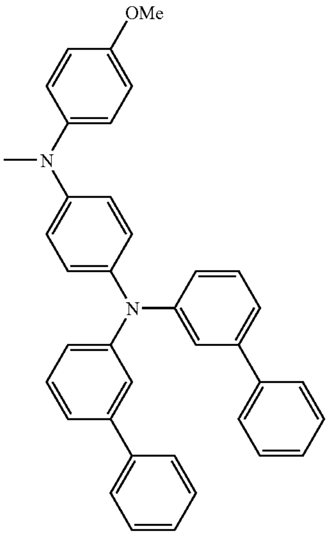
217
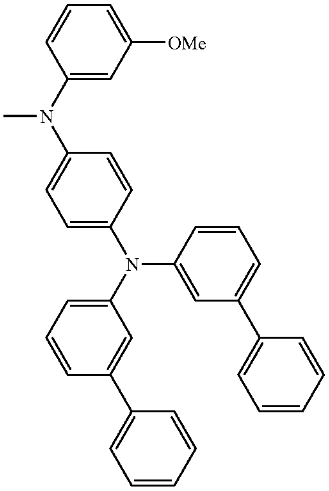
218
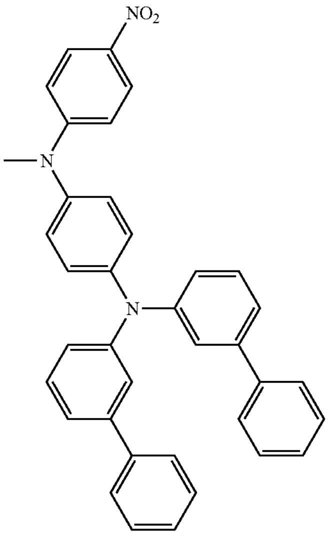
-continued
219
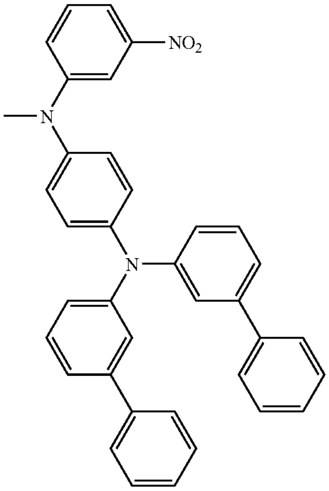
220
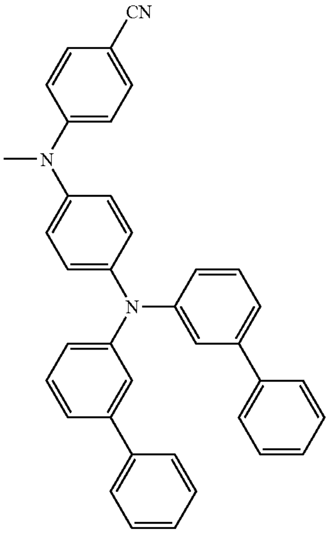
221
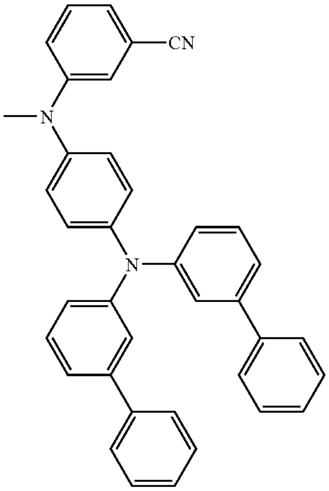

-continued
222
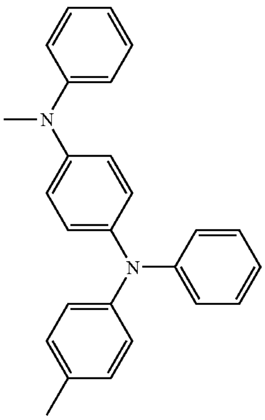
223
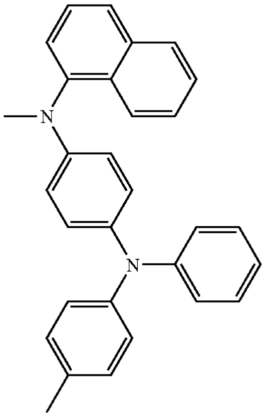
224
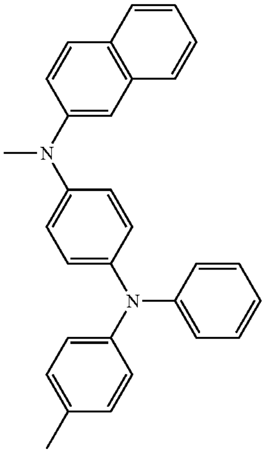
-continued
225
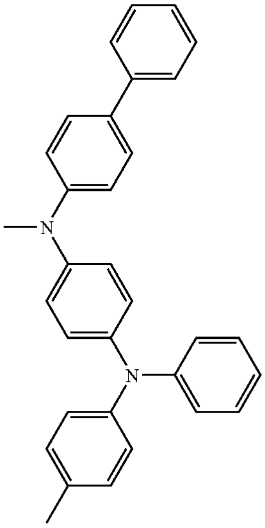
226
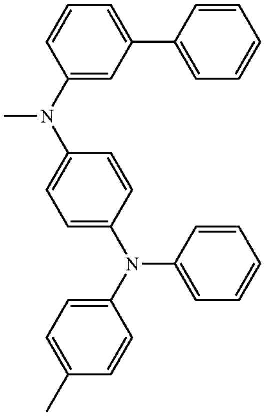
227
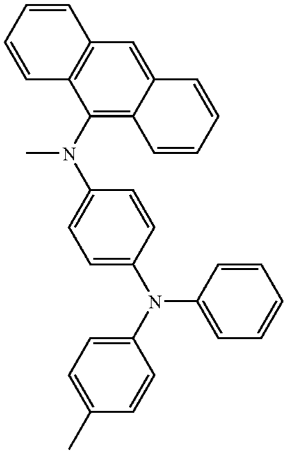

-continued
228
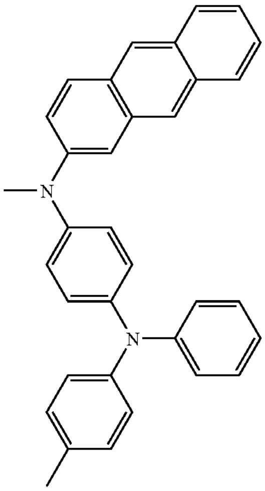
229
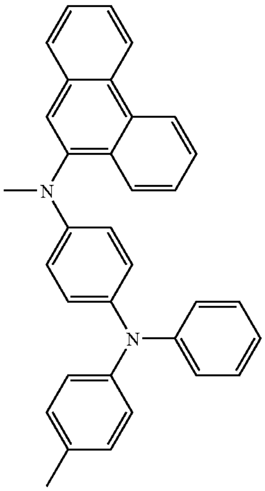
230
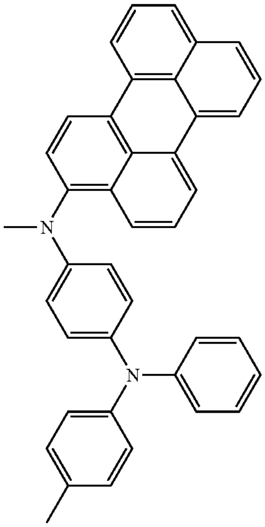
-continued
231
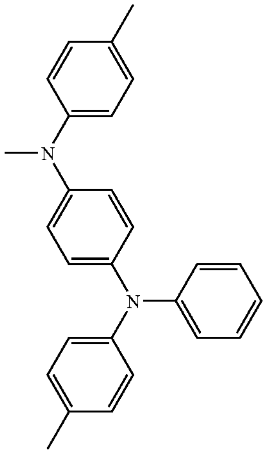
232
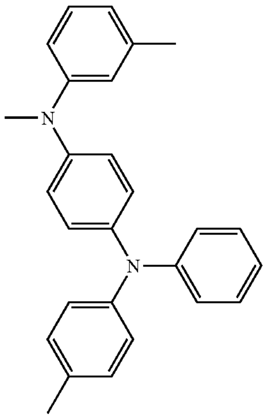
233
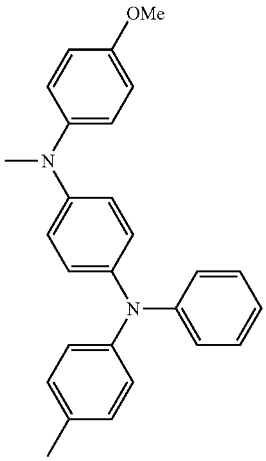

-continued
234
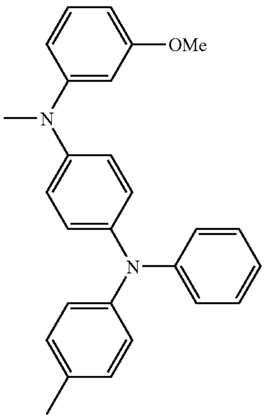
235
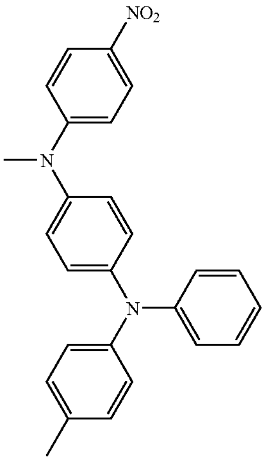
236
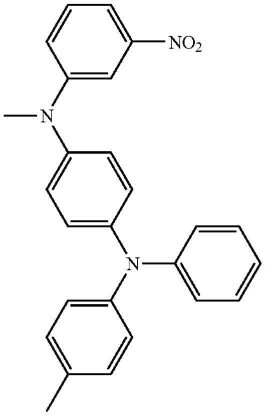
-continued
237
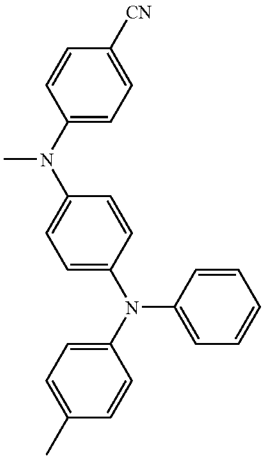
238
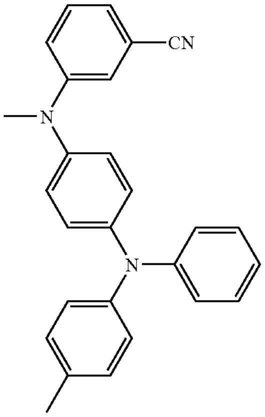
239
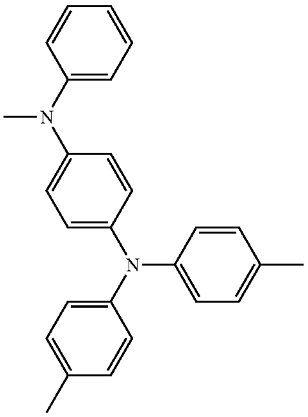

-continued
240
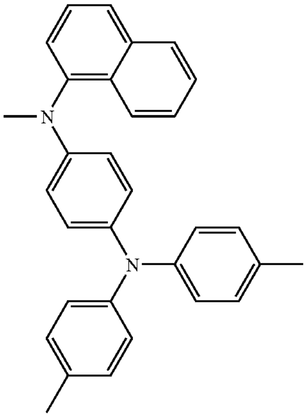
241
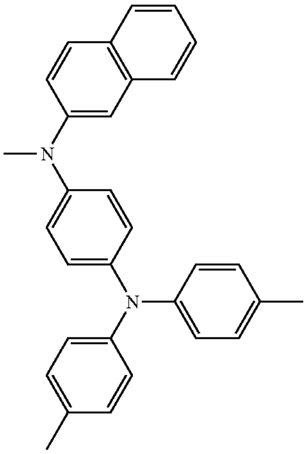
242
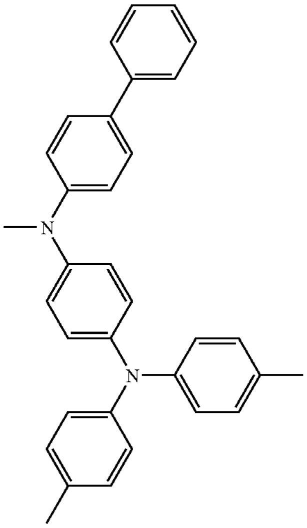
-continued
243
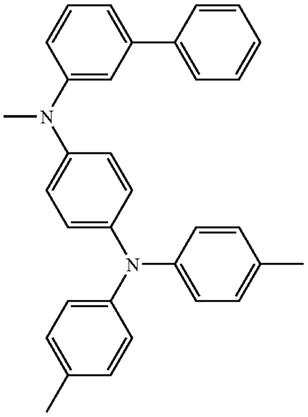
244
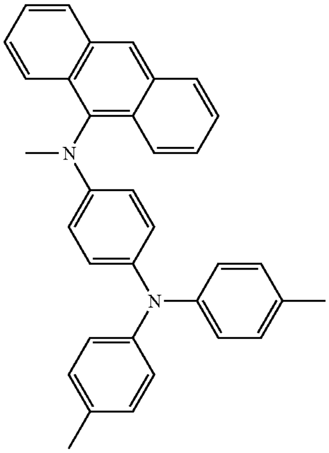
245
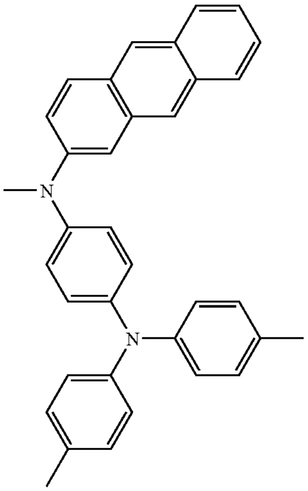

-continued
246
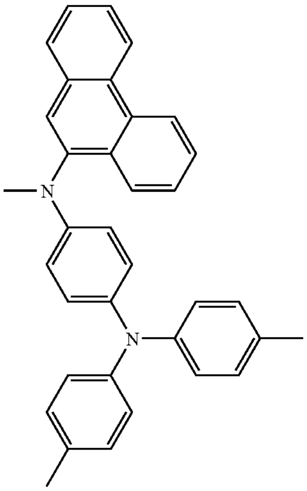
247
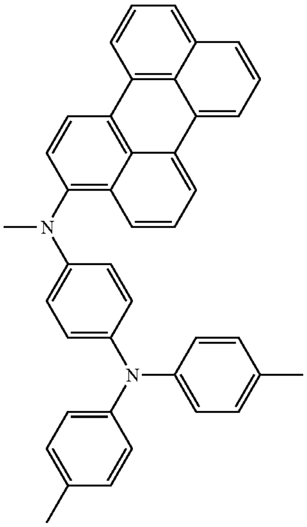
248
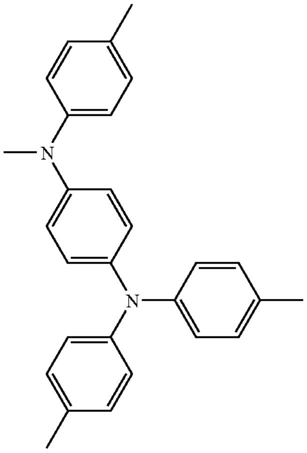
-continued
249
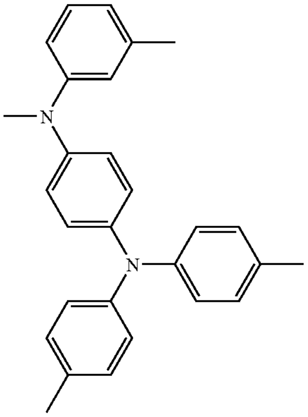
250
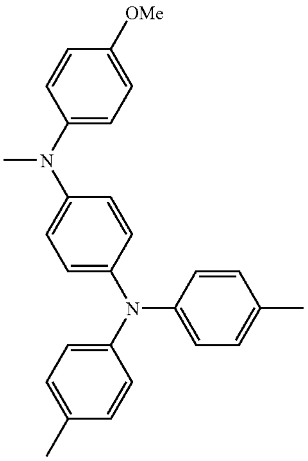
251
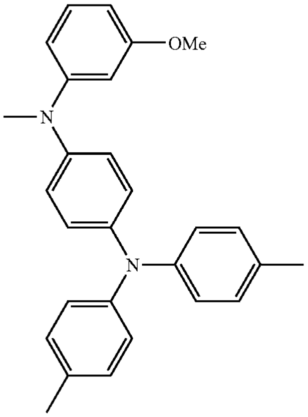

-continued
252
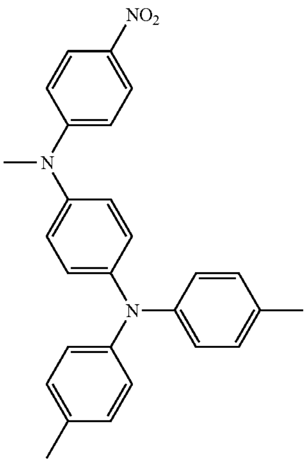
253
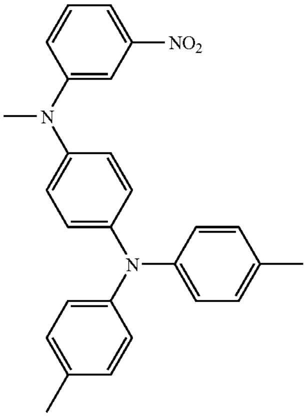
254
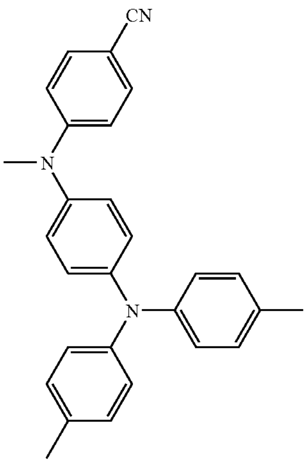
-continued
255
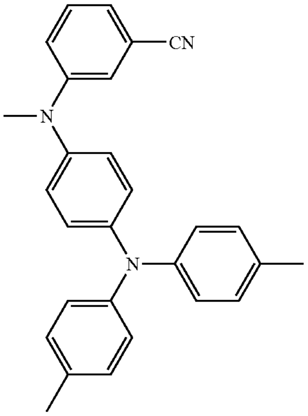
256
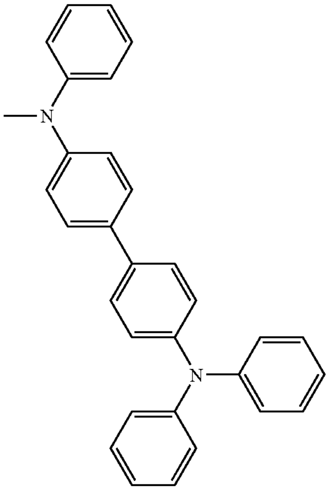
257
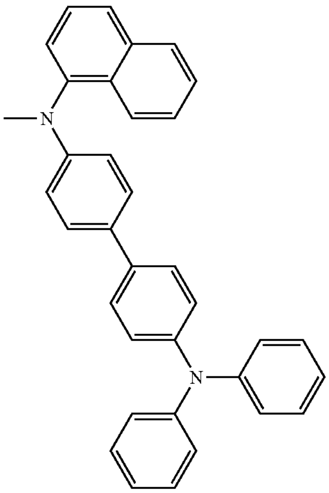

-continued
258
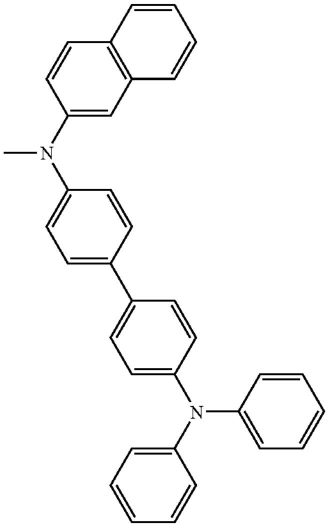
259
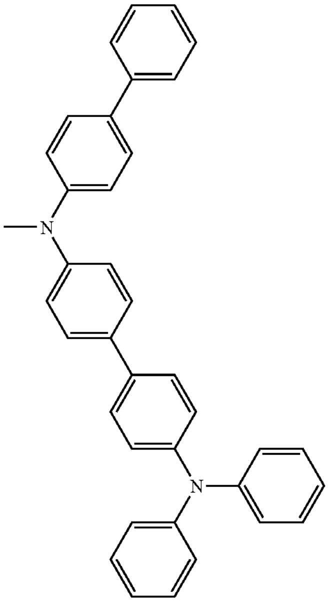
260
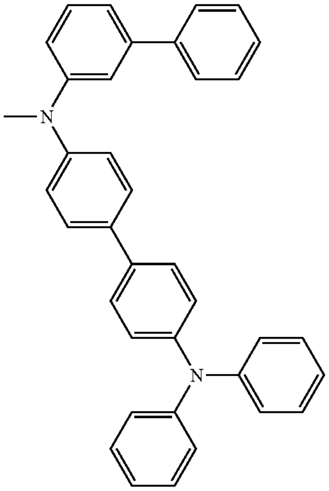
-continued
261
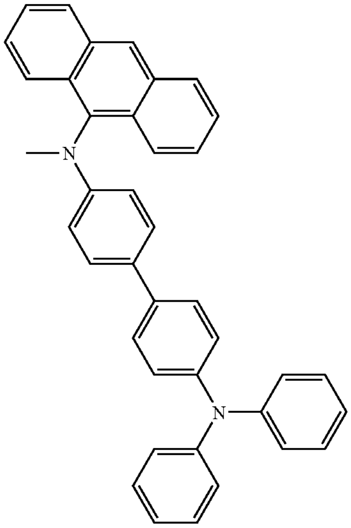
262
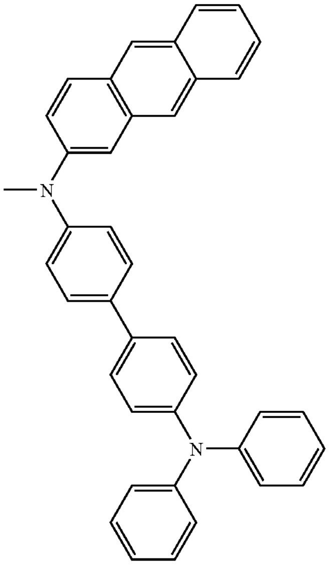
263
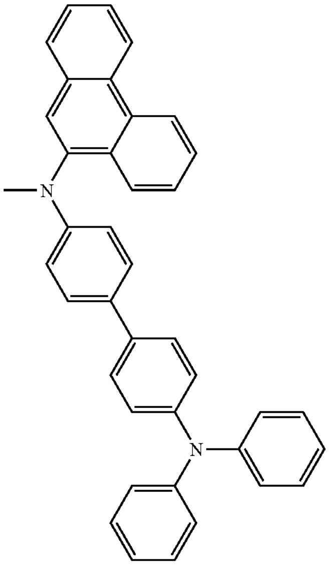

-continued
264
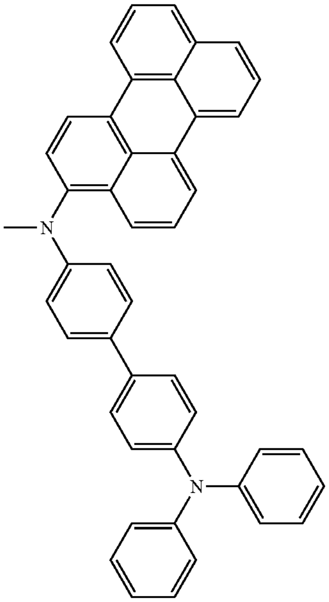
265
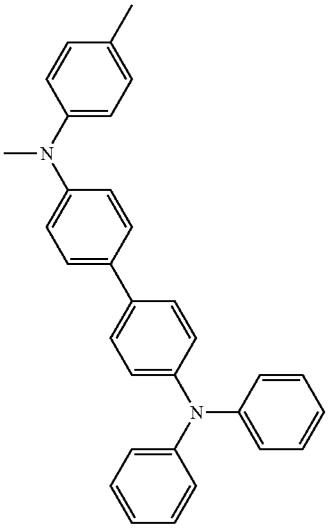
266
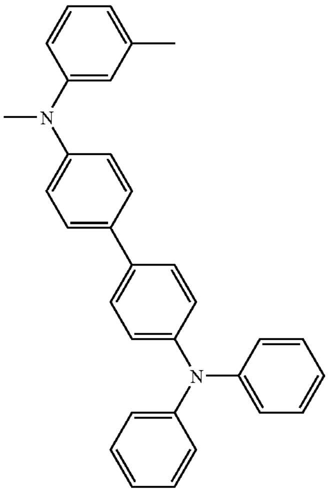
-continued
267
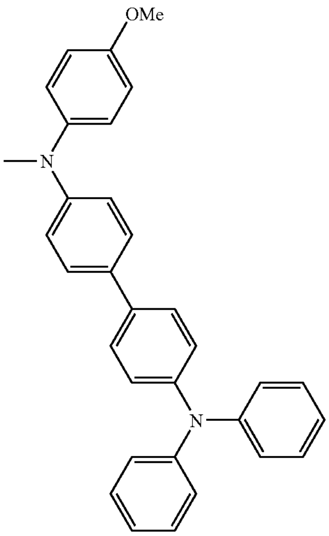
268
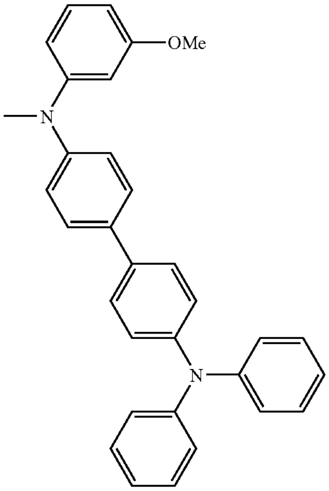
269
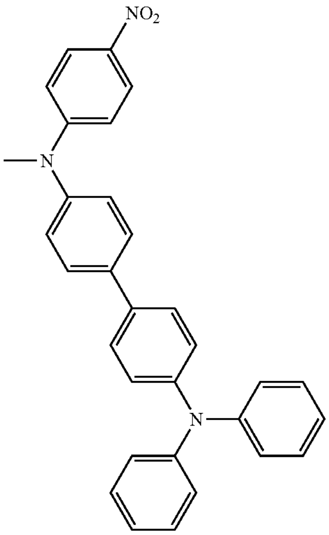

-continued
270
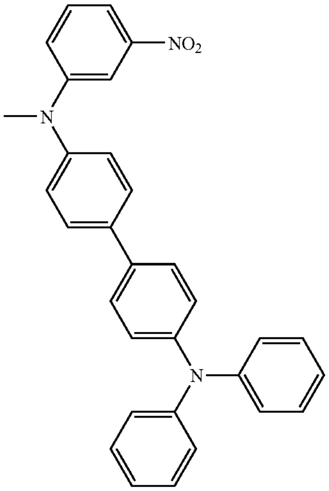
271
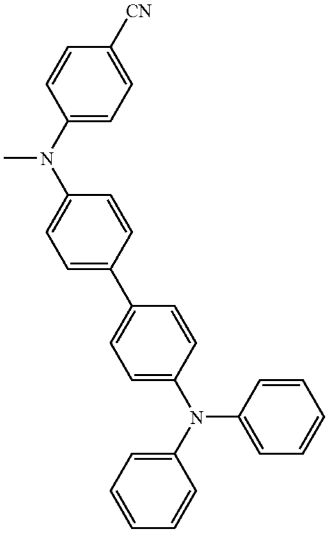
272
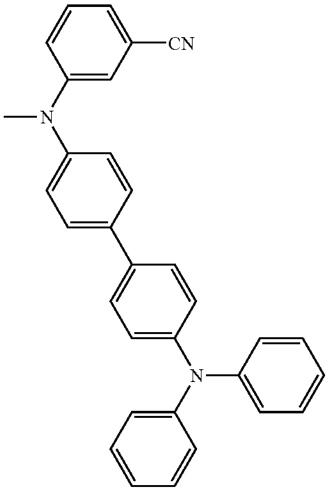
-continued
273
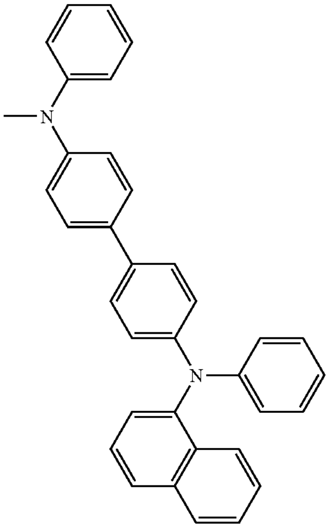
274
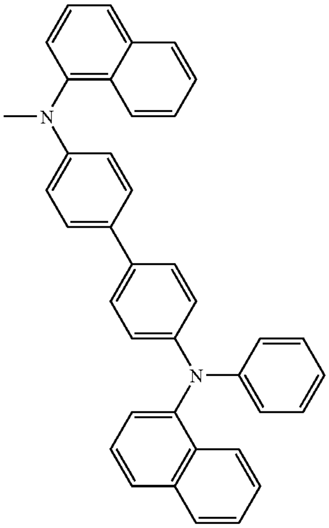
275
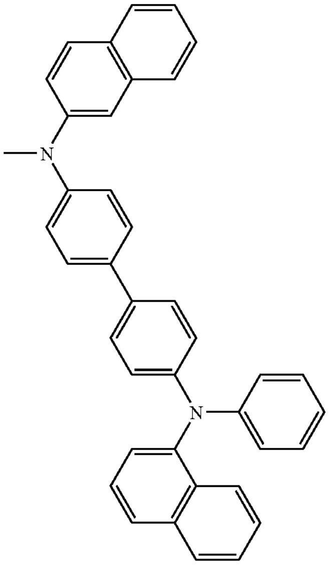

-continued
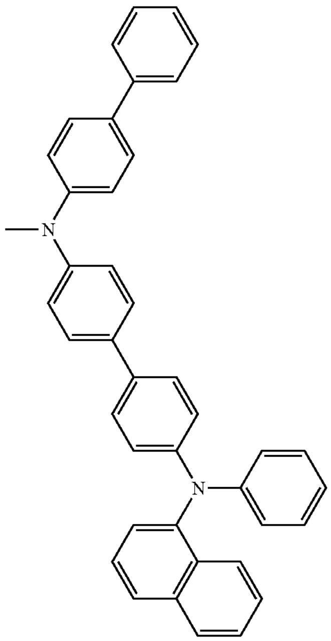
276
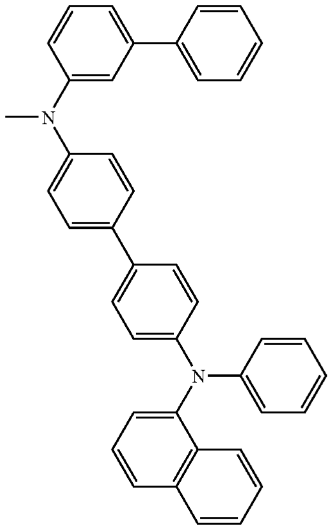
277
-continued
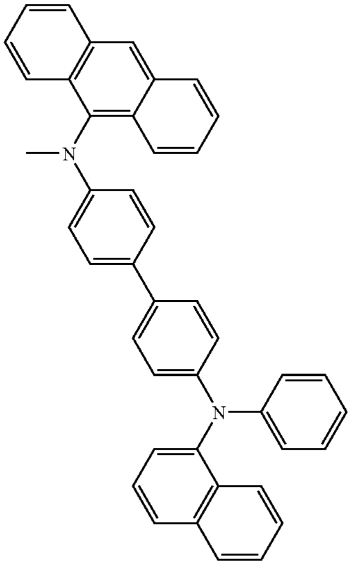
278
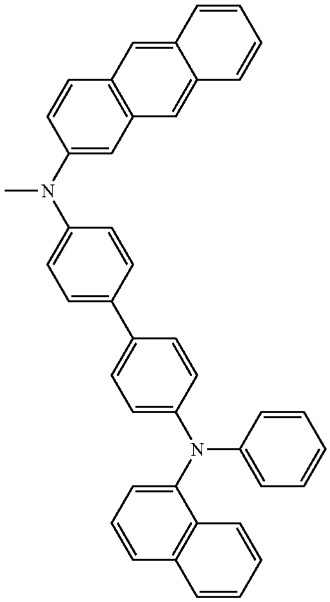
279

-continued
280
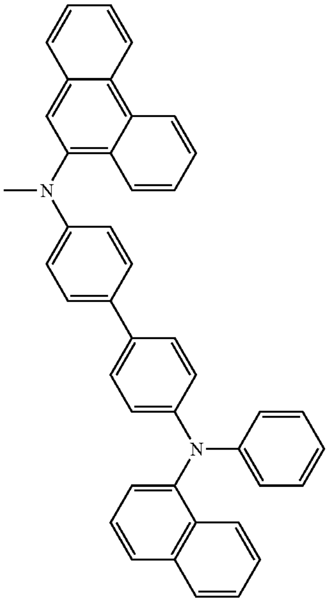
281
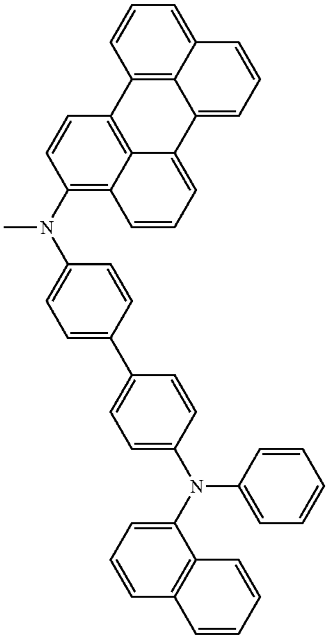
-continued
282
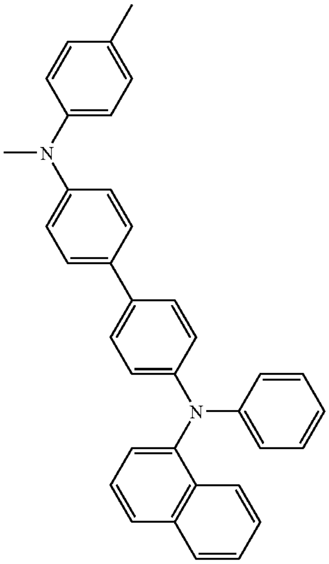
283
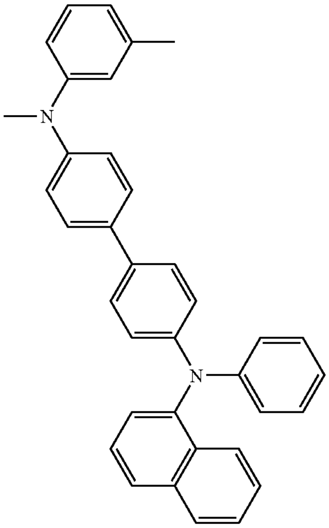

-continued
284
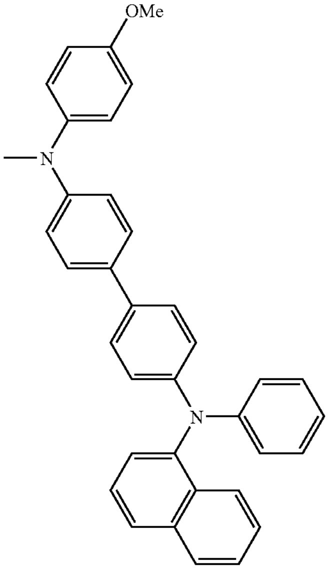
285
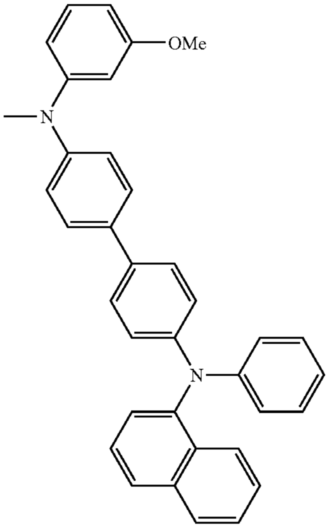
286
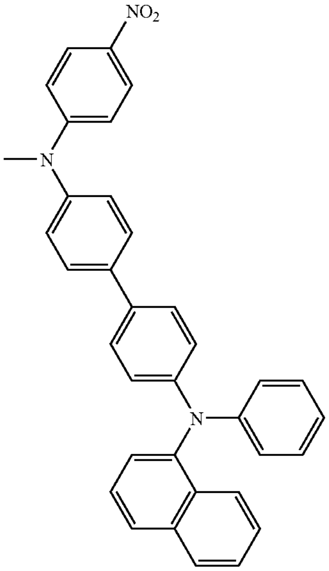
-continued
287
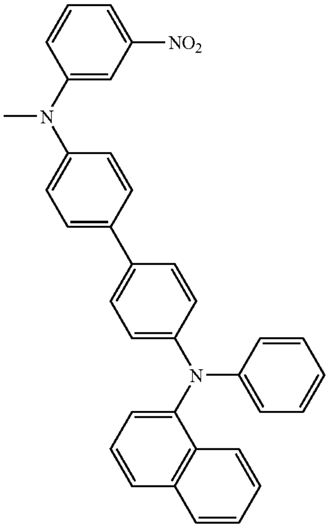
288
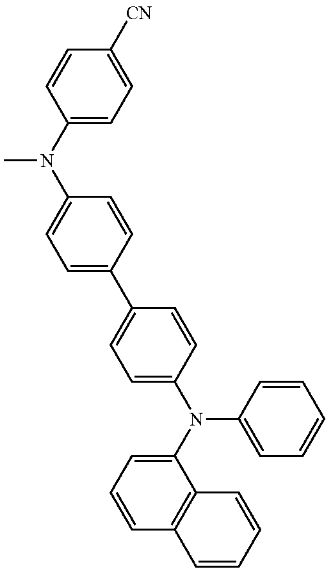
289
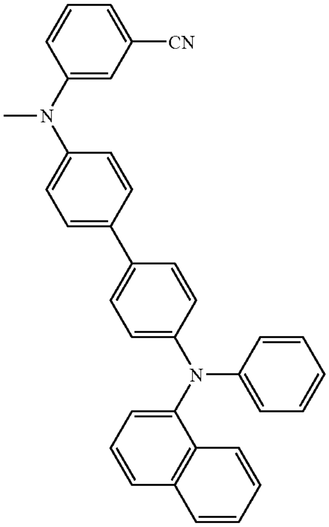

-continued
290
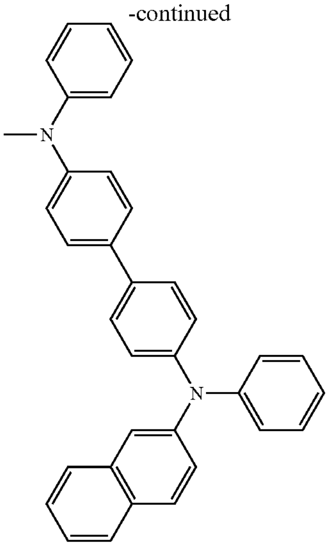
291
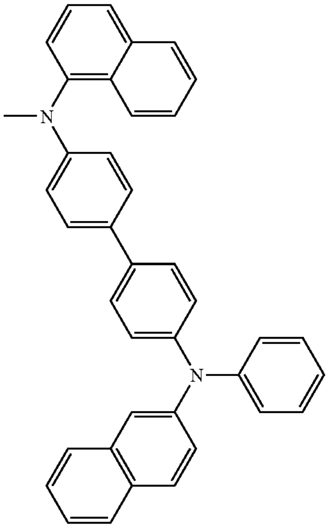
292
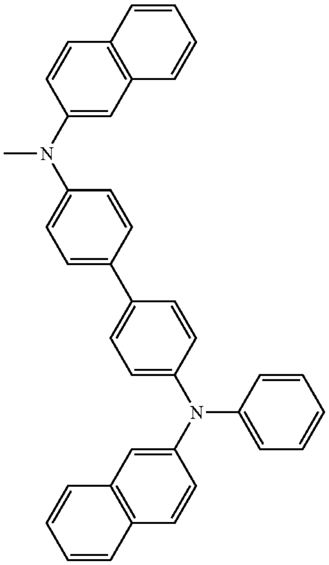
-continued
293
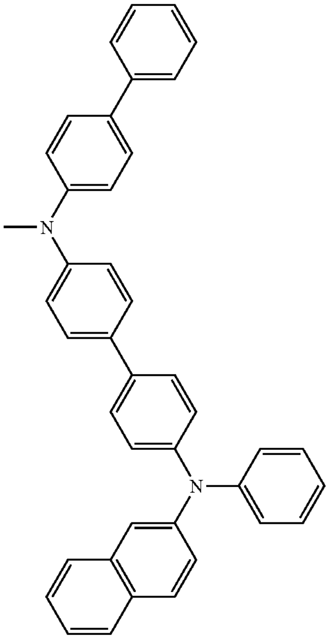
294
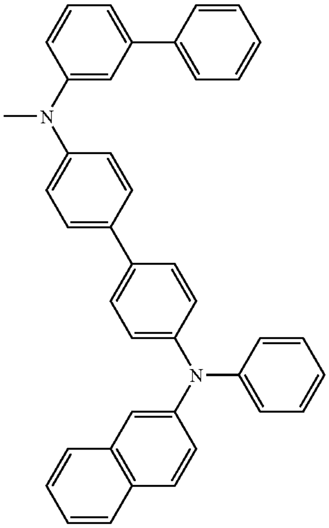

-continued
295
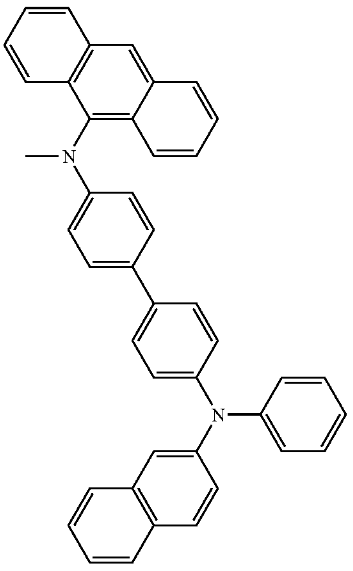
296
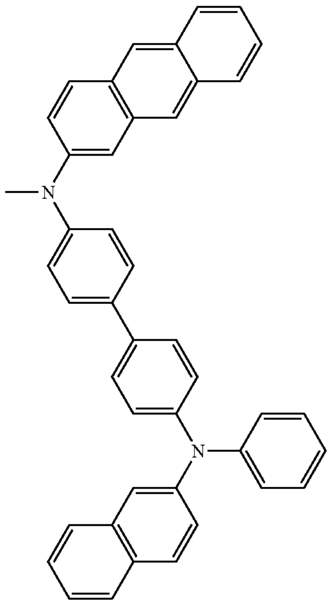
-continued
297
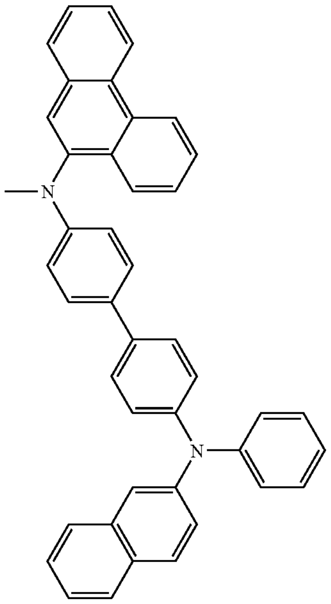
298
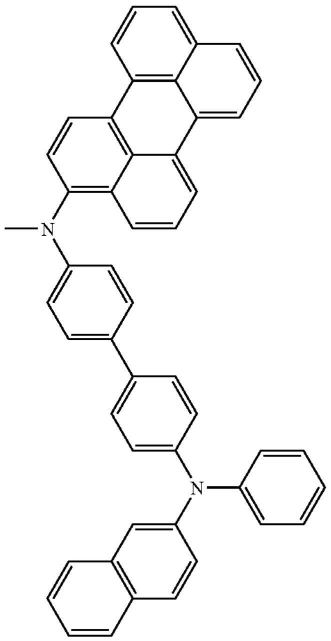

-continued
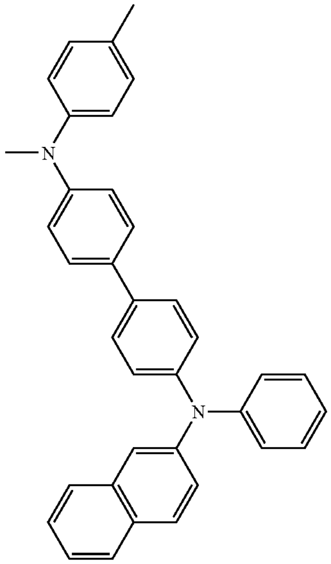
299
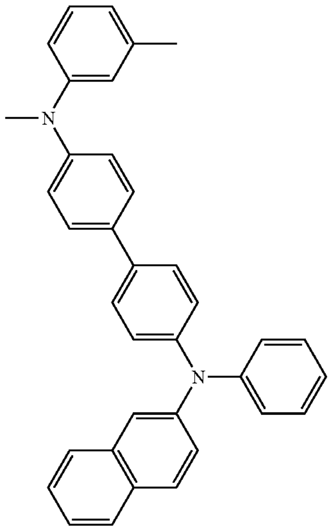
300
-continued
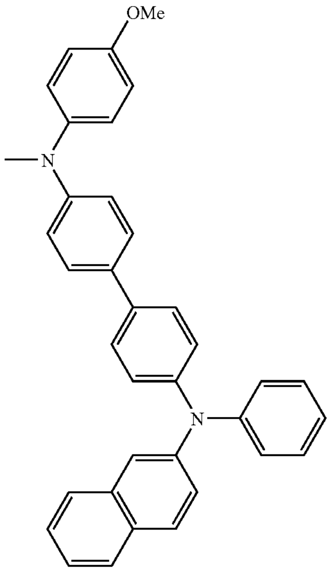
301
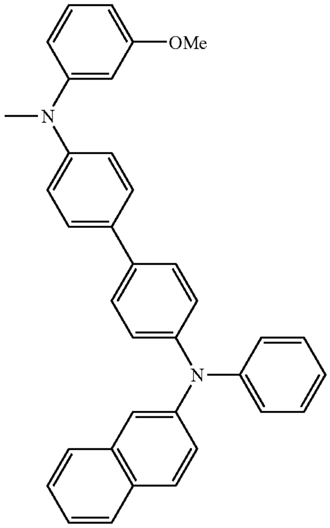
302

-continued
303
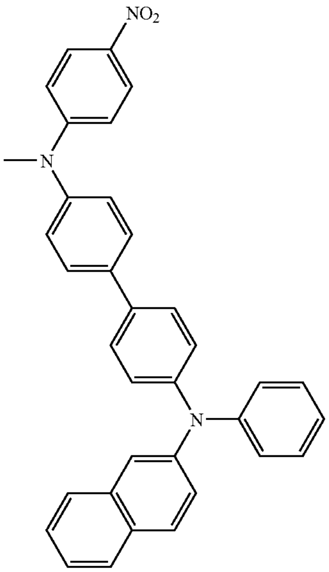
304
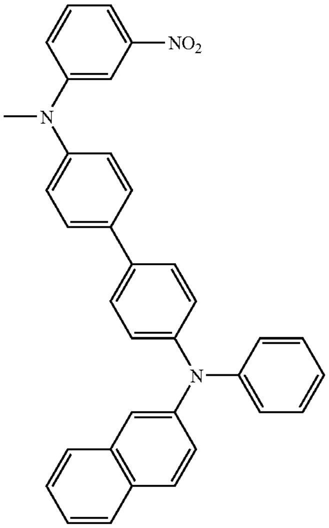
-continued
305
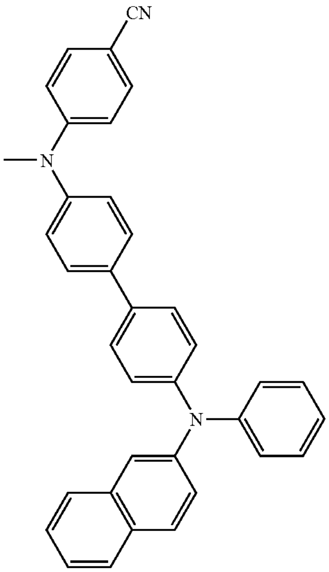
306
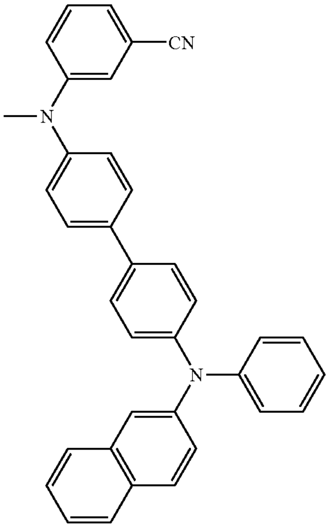

-continued
307
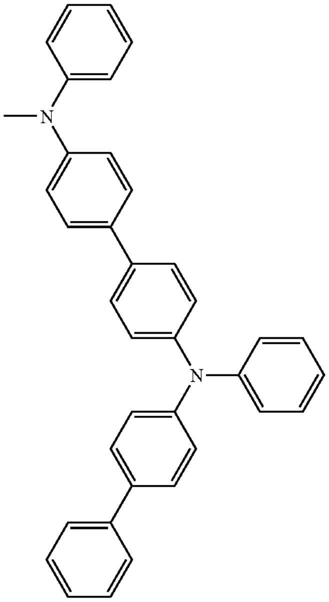
309
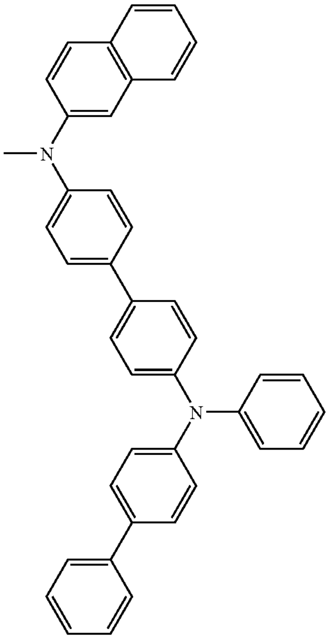
308
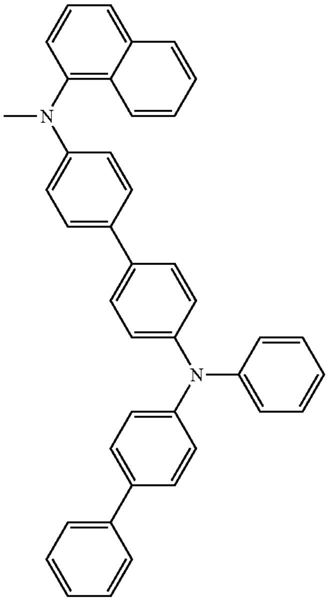
310
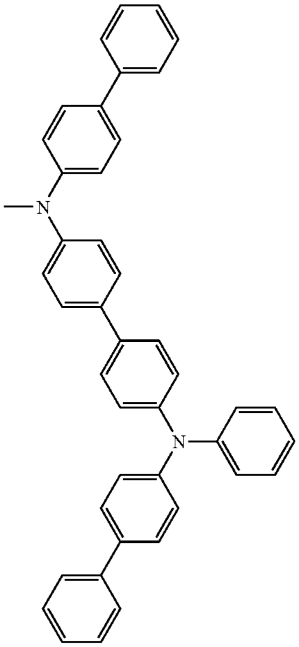

-continued
311
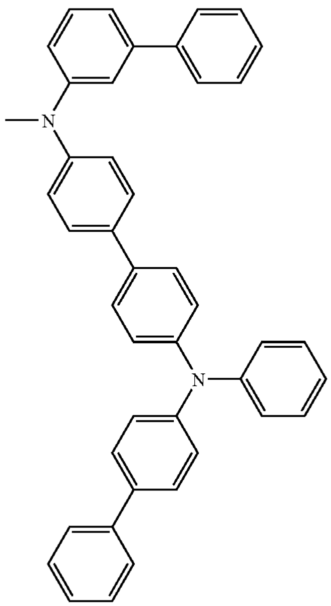
312
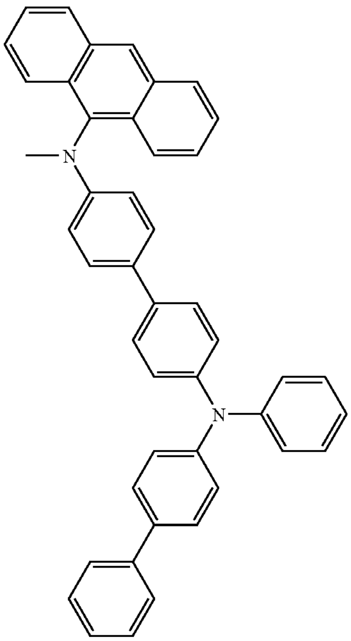
-continued
313
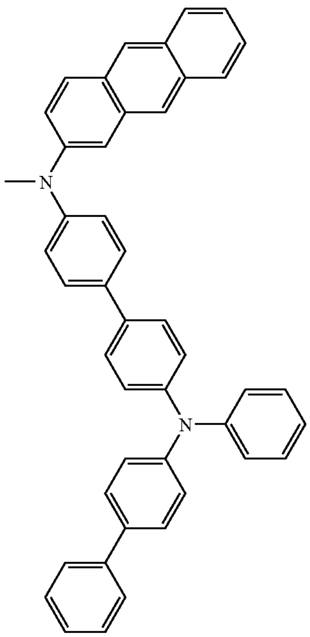
314
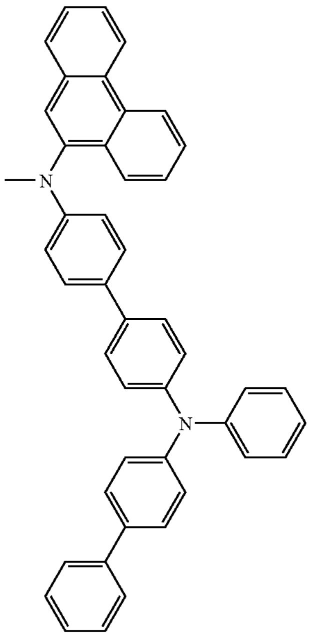

-continued
315
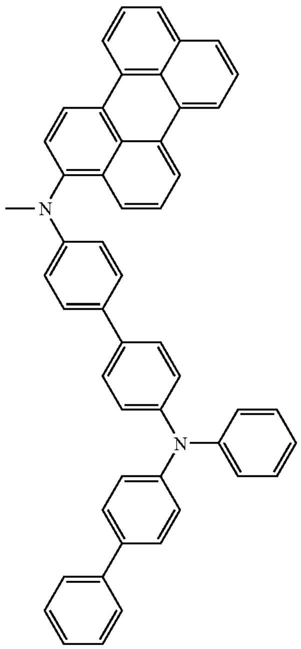
316
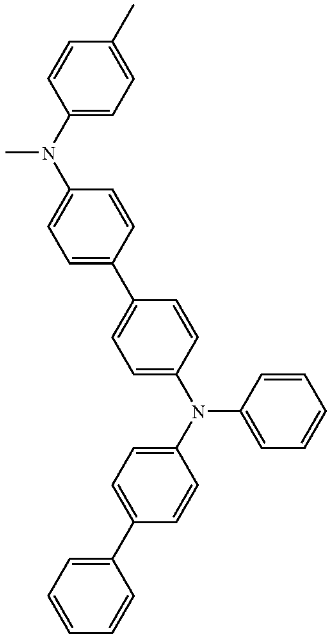
-continued
317
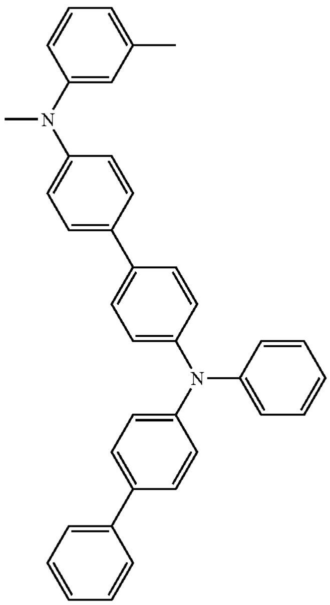
318
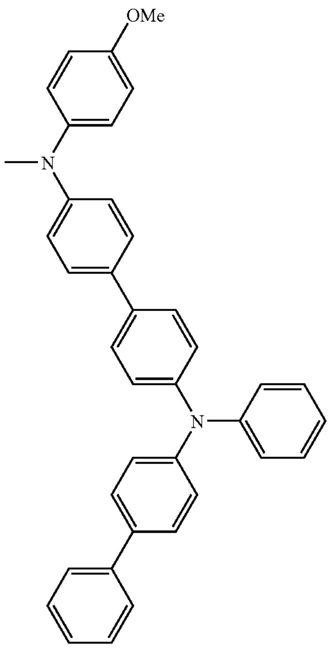

-continued
319
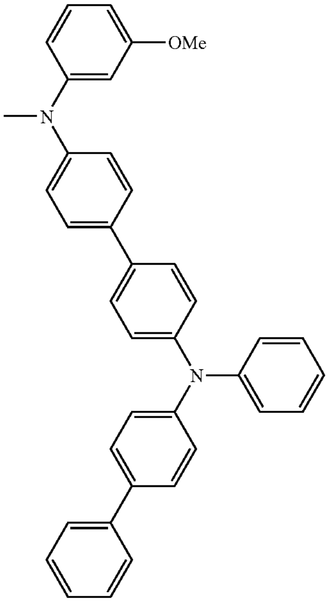
320
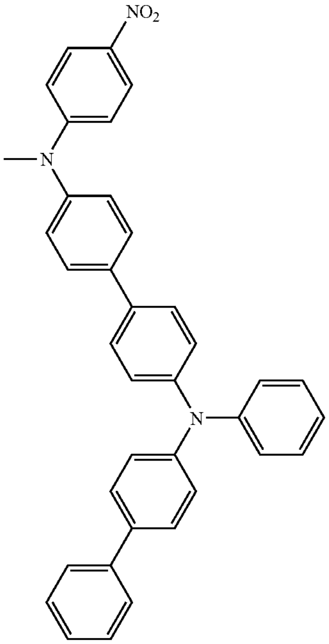
-continued
321
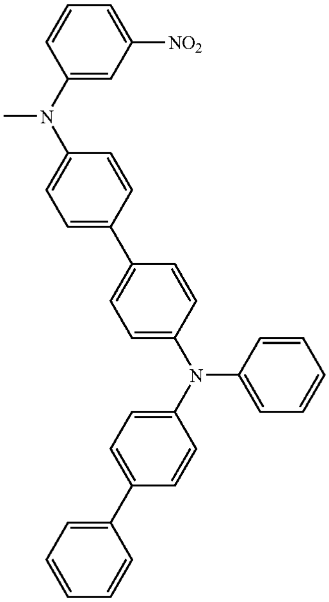
322
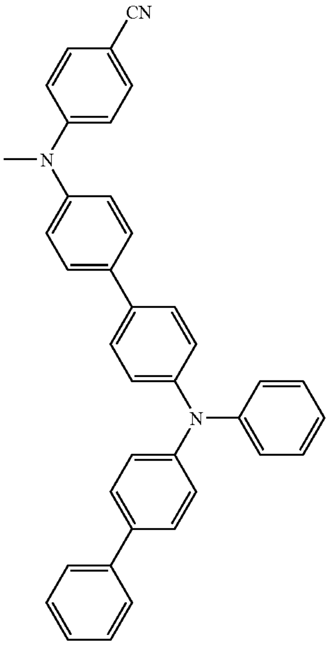

-continued
323
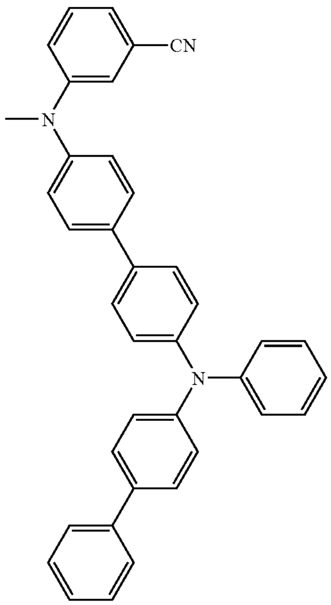
324
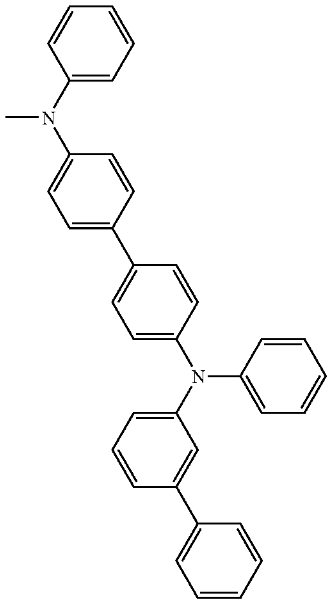
-continued
325
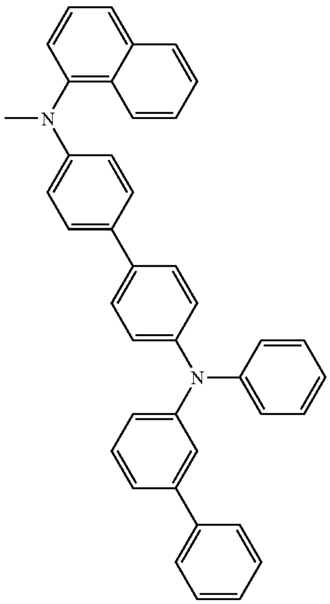
326
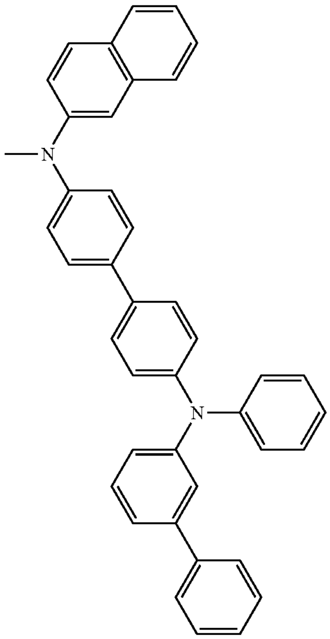

-continued
327
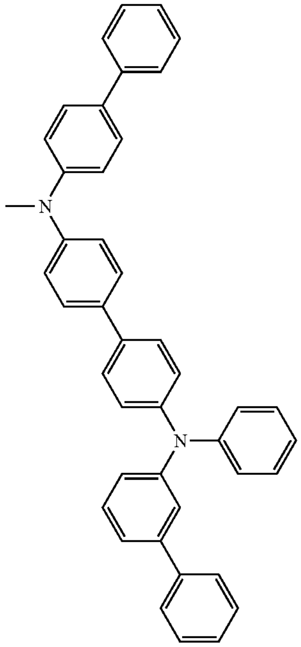
328
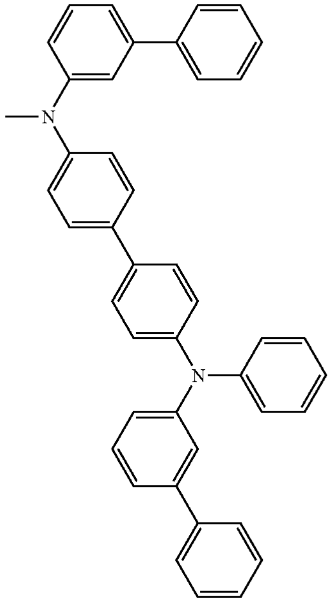
-continued
329
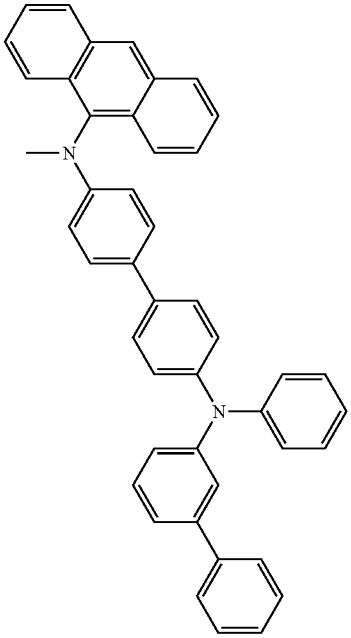
330
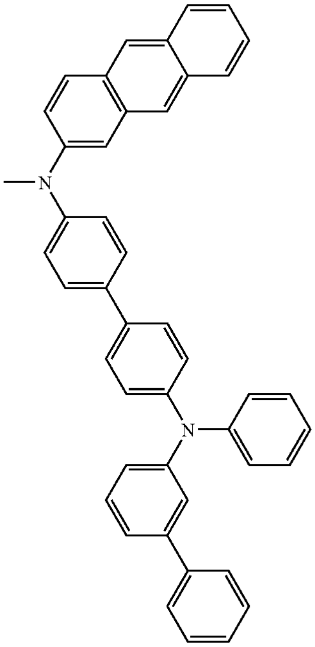

-continued
331
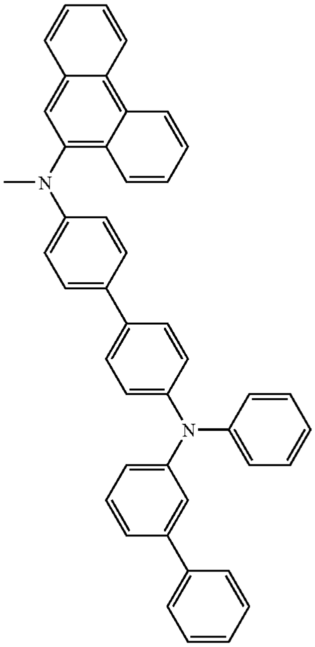
332
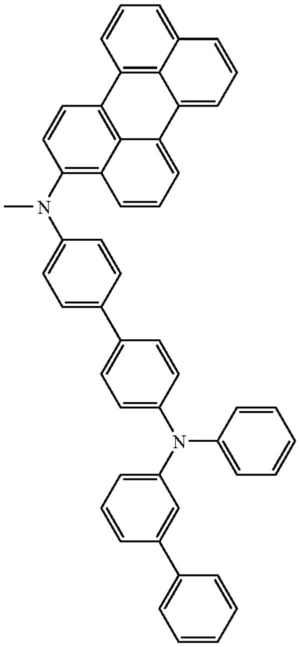
-continued
333
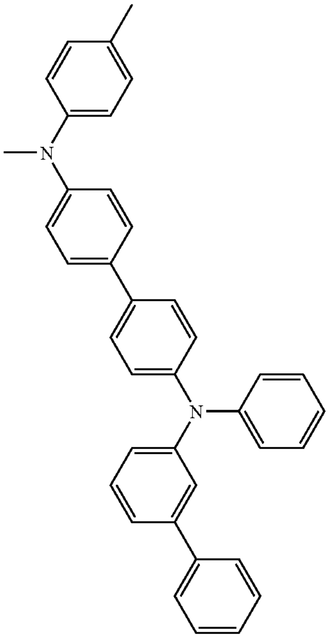
334
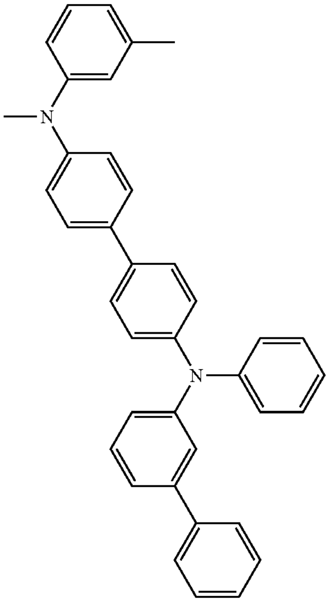

-continued
335
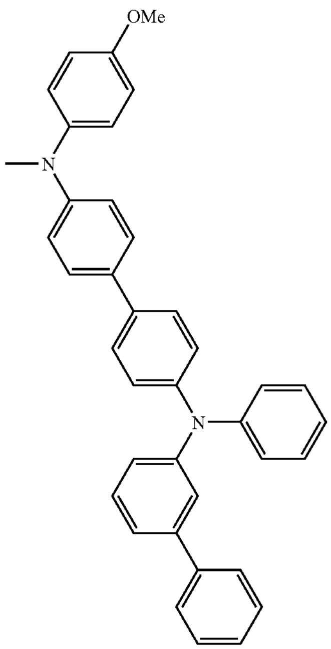
336
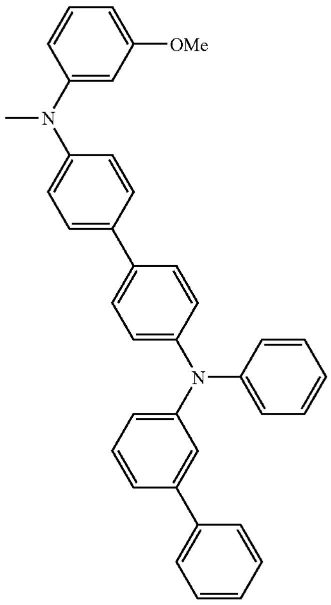
-continued
337
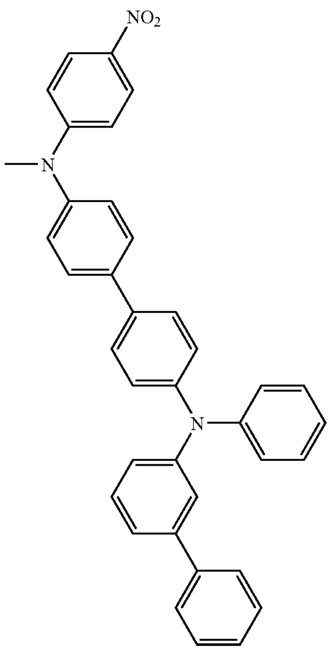
338
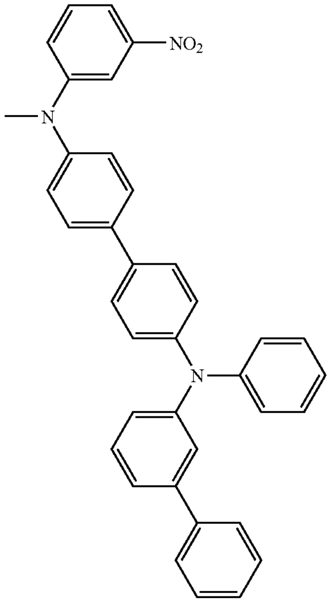

-continued
339
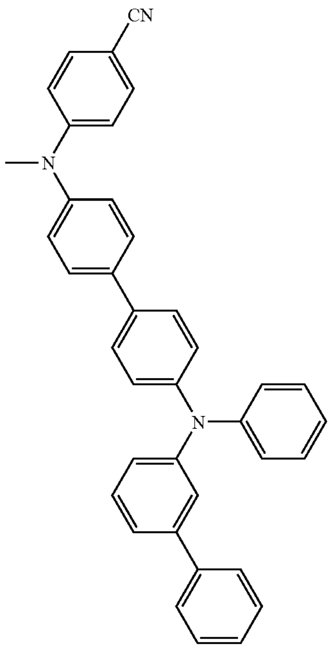
340
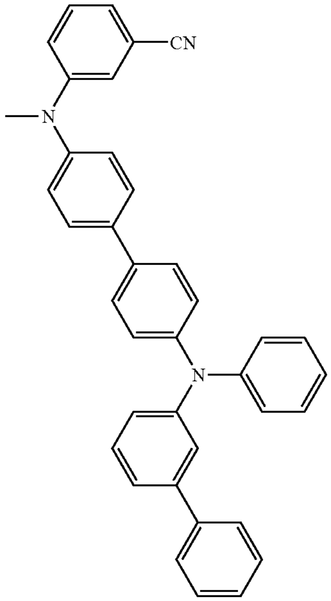
-continued
341
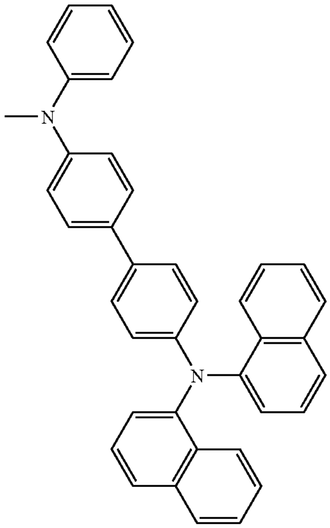
342
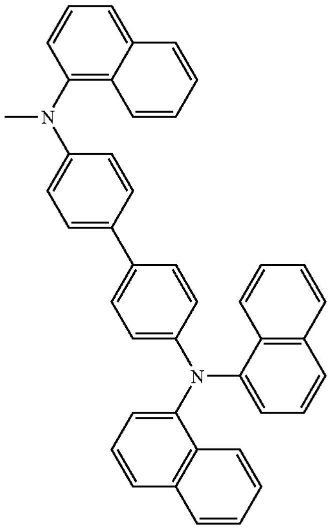
343
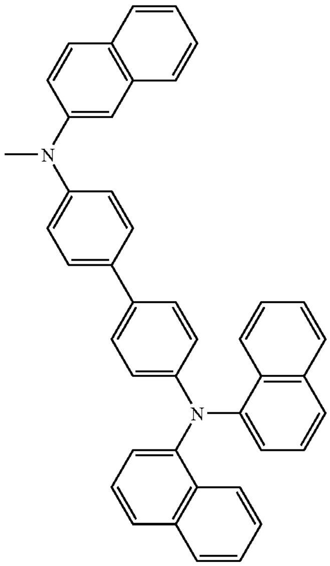

-continued
344
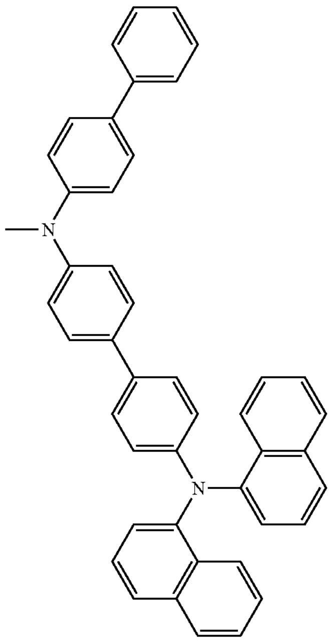
345
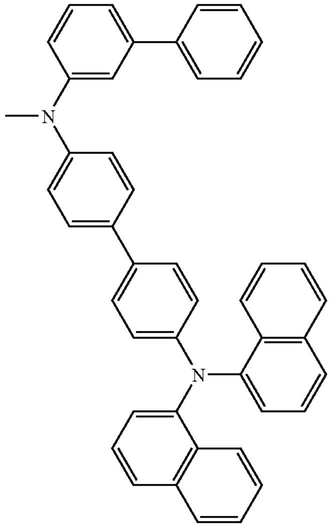
-continued
346
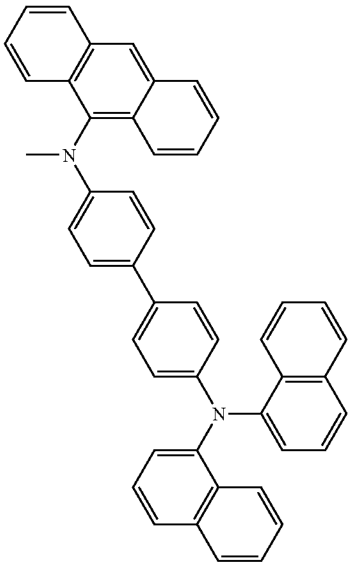
347
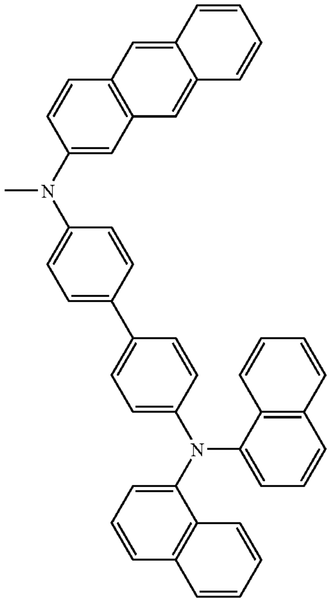

-continued
348
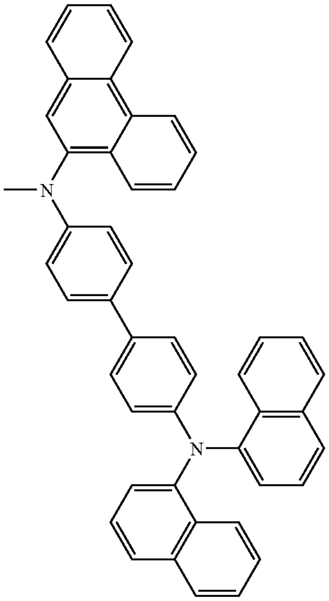
349
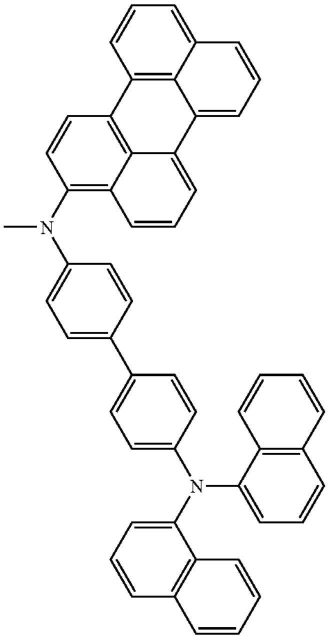
-continued
350
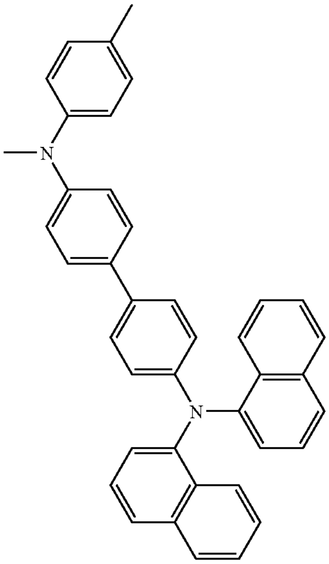
351
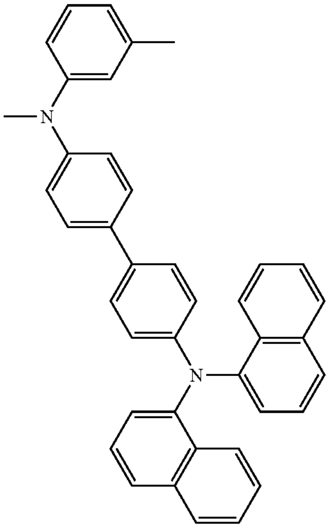

-continued
352
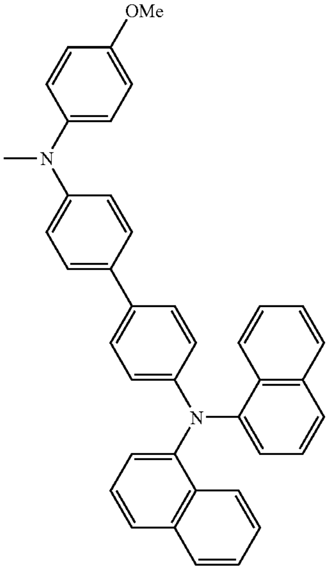
353
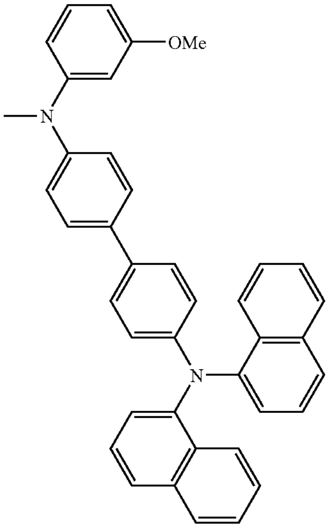
354
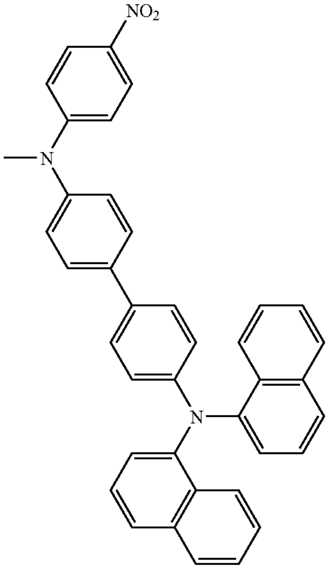
-continued
355
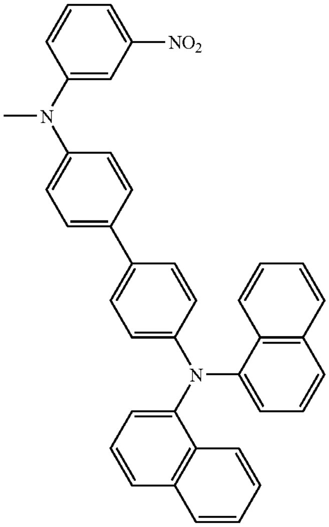
356
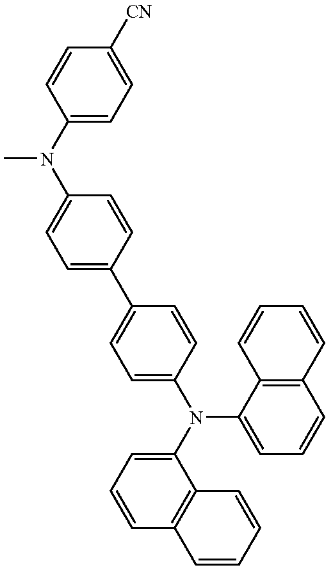
357
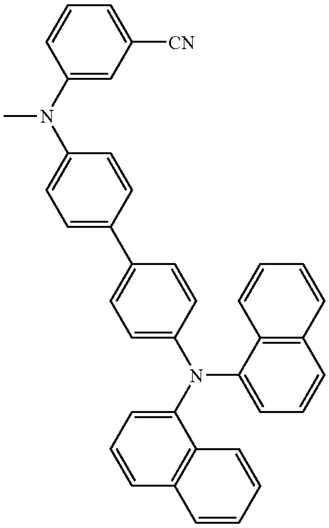

-continued
358
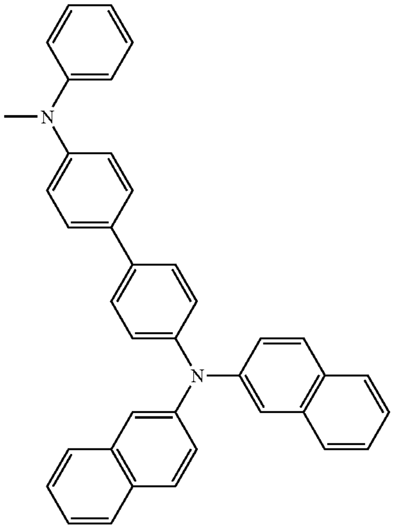
359
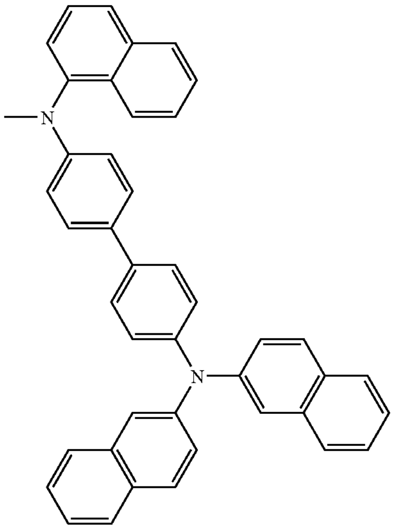
360
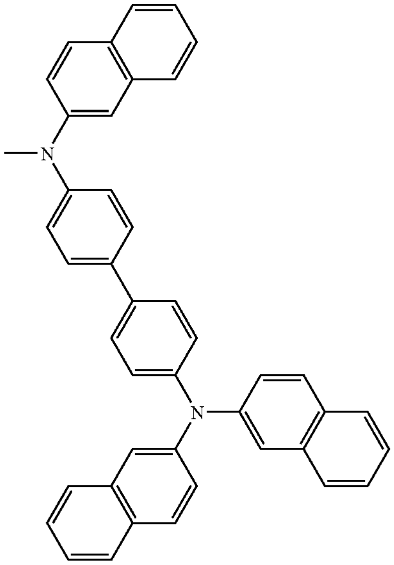
-continued
361
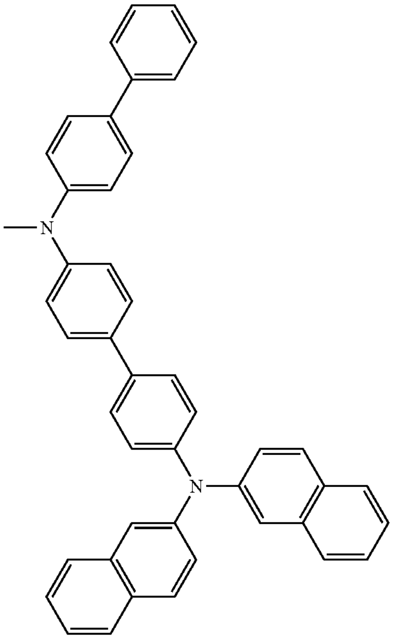
362
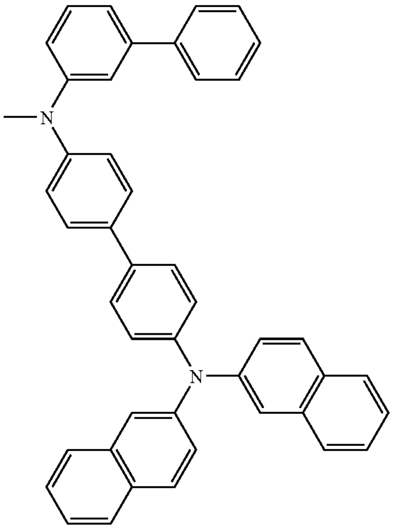

-continued
363
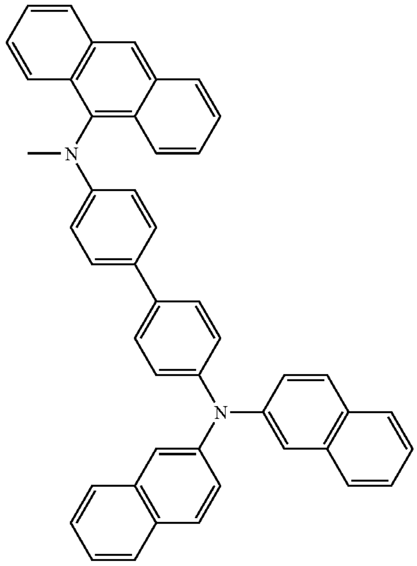
364
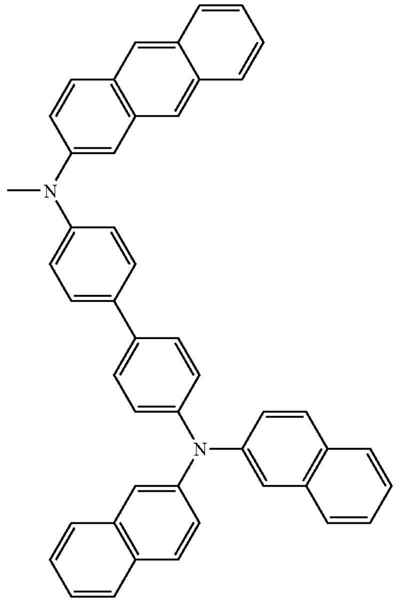
-continued
365
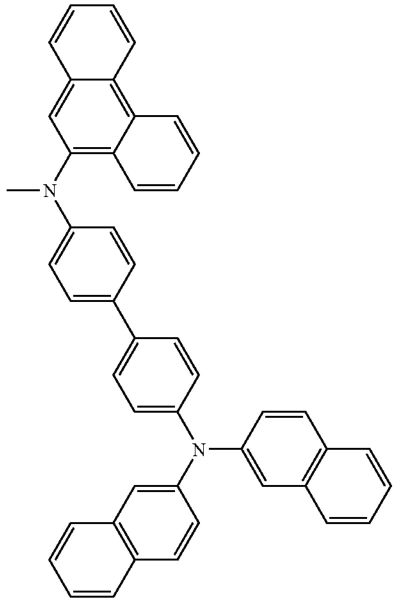
366
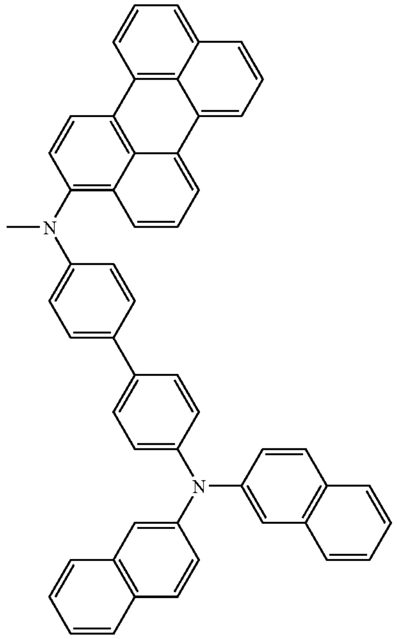

-continued
367
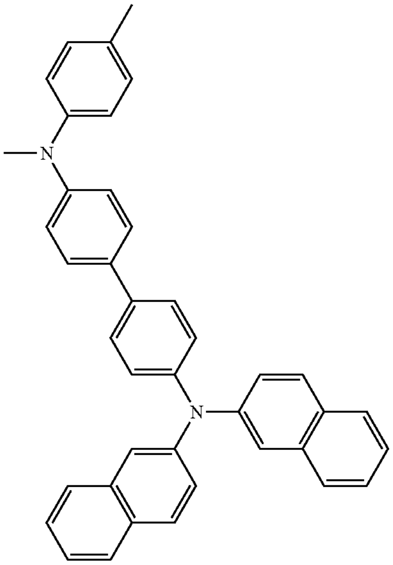
368
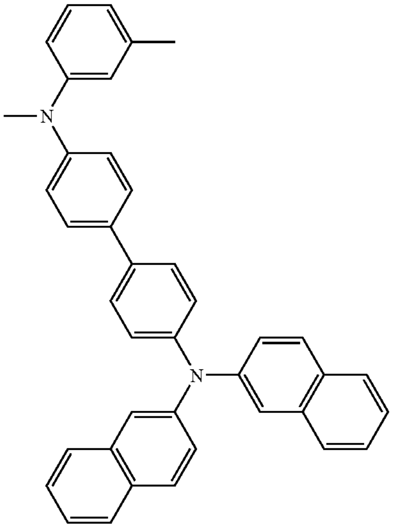
-continued
369
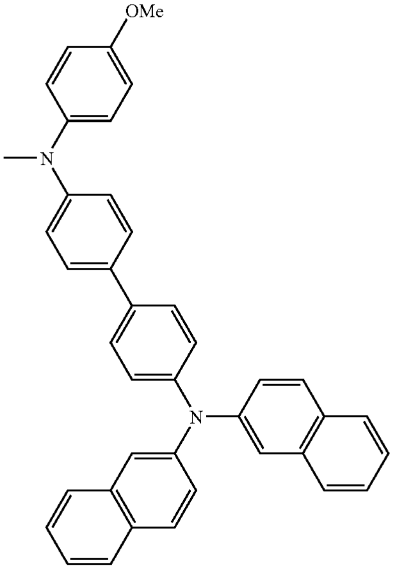
370
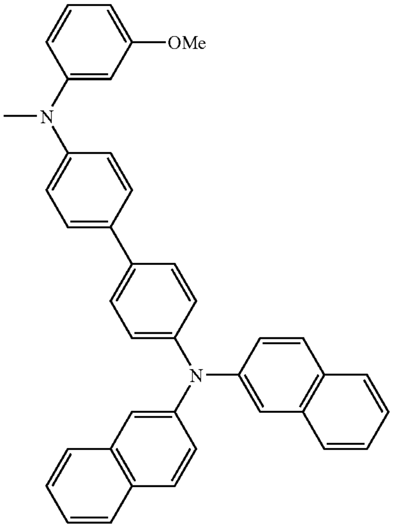
371
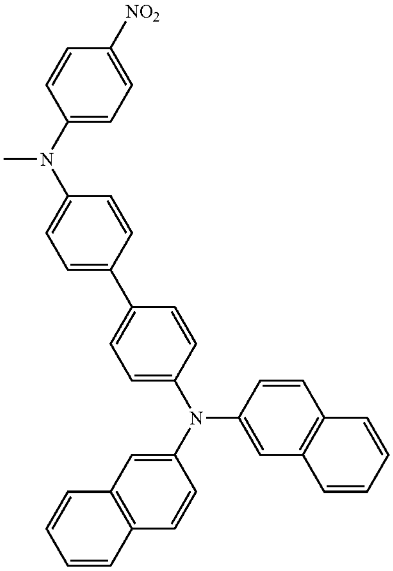

-continued
372
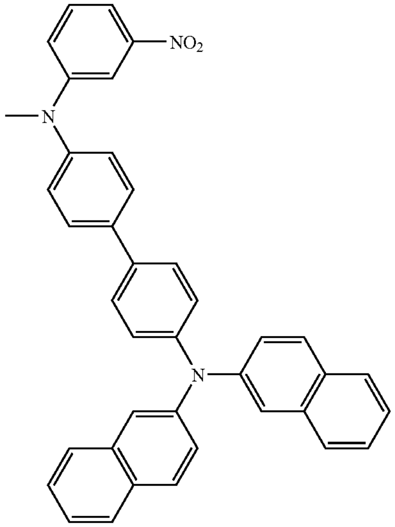
373
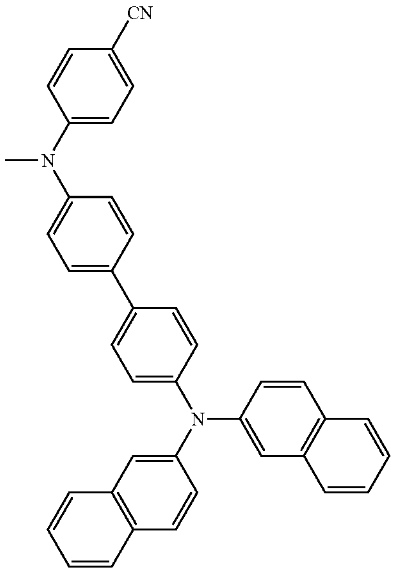
374
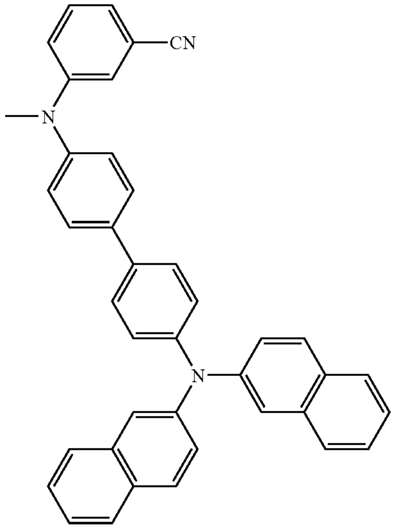
-continued
375
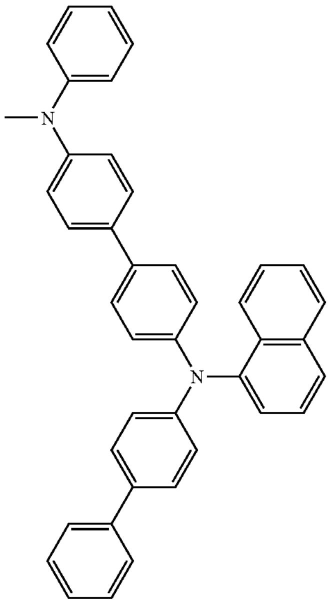
376
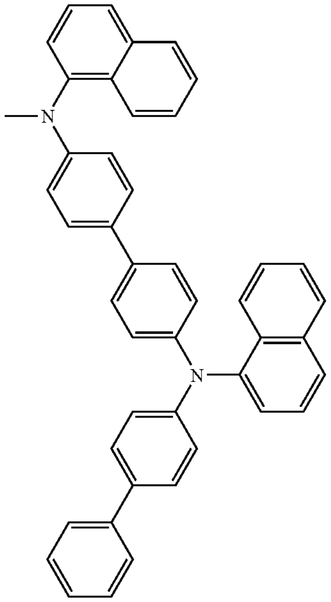

-continued
377
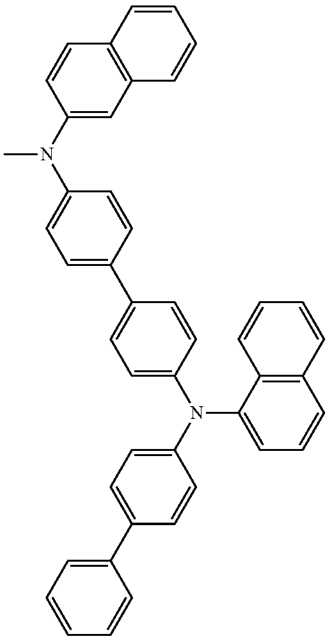
378
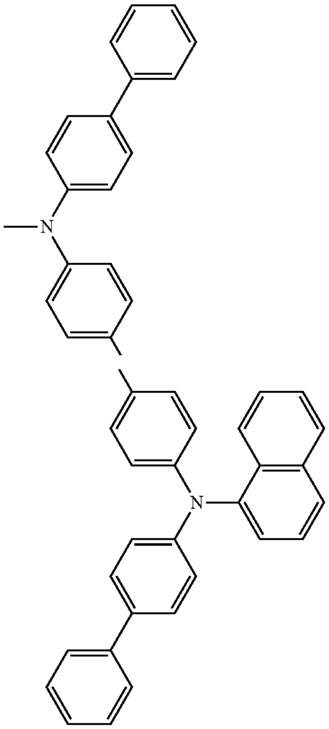
-continued
379
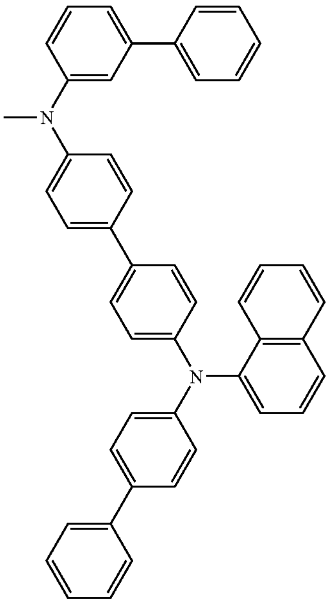
380
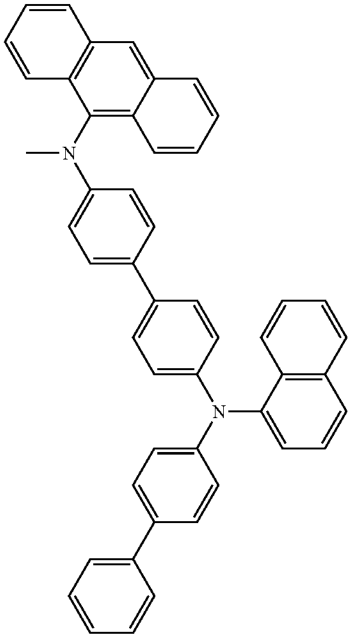
381
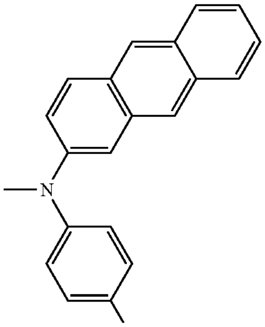

-continued
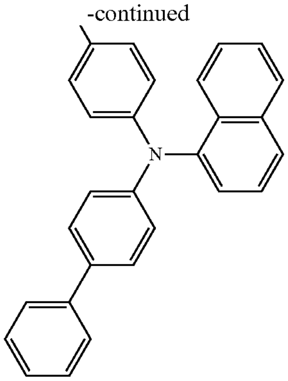
382
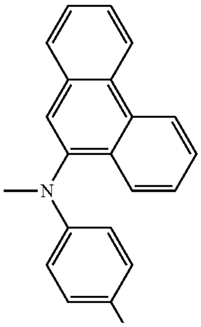
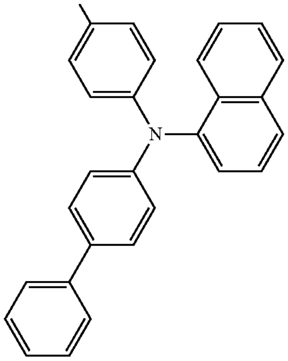
383
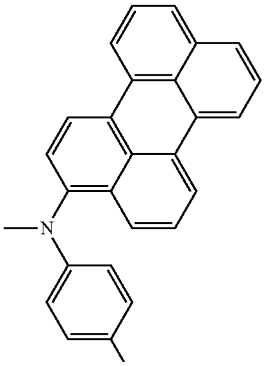
-continued
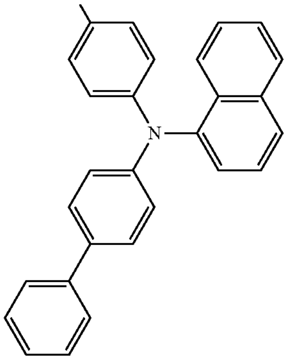
384
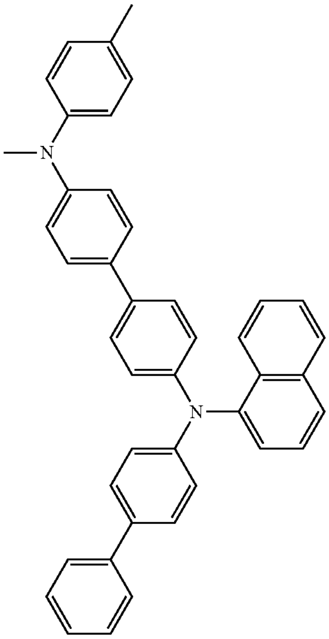
385
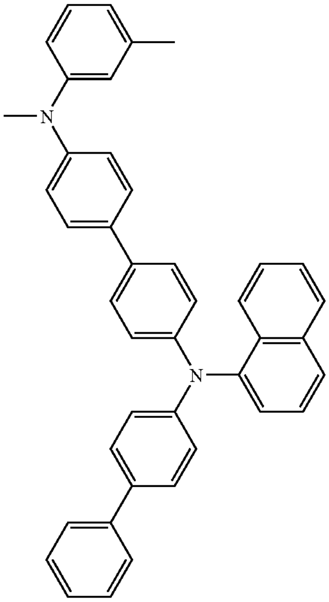

-continued
386
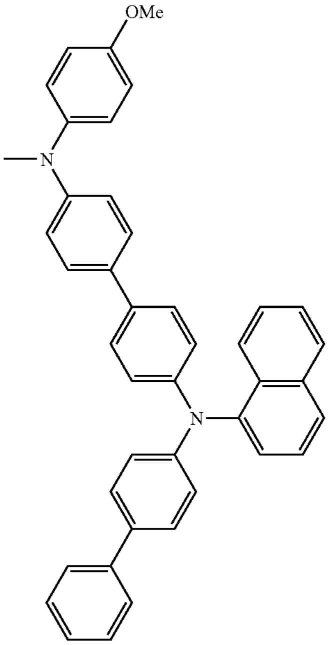
387
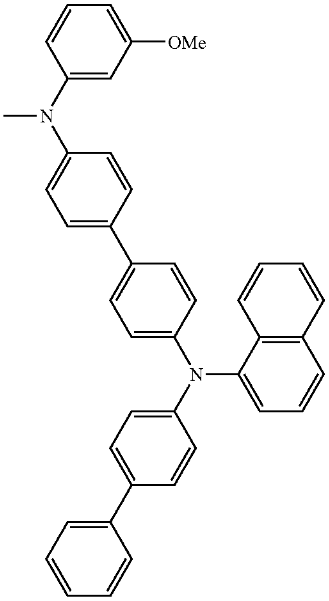
-continued
388
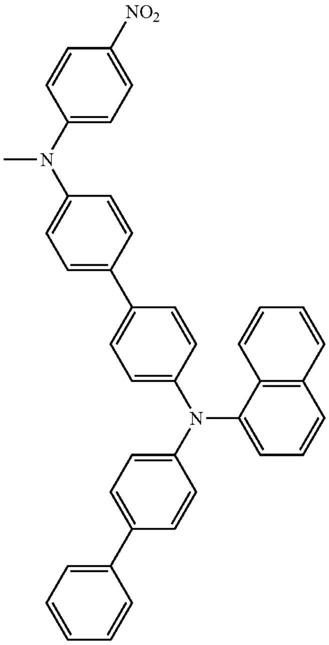
389
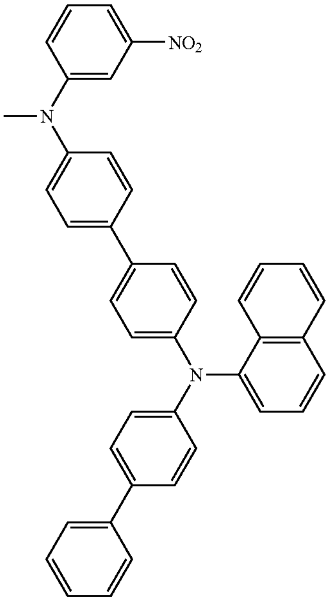

-continued
390
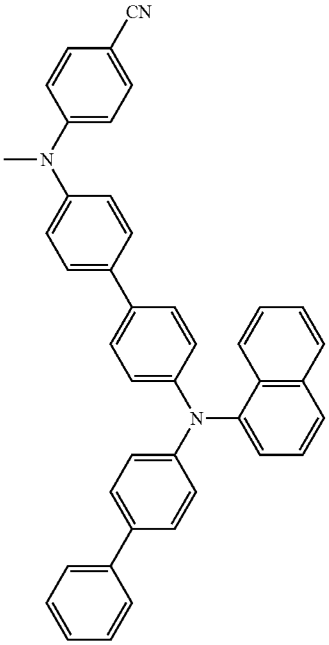
391
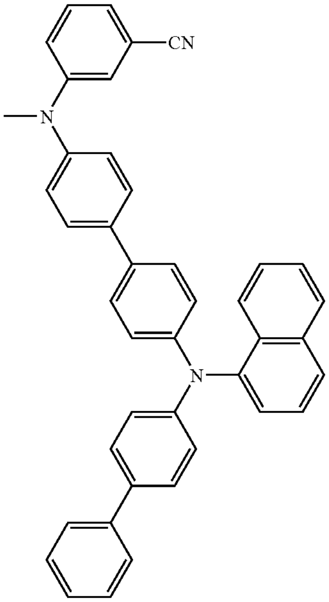
-continued
392
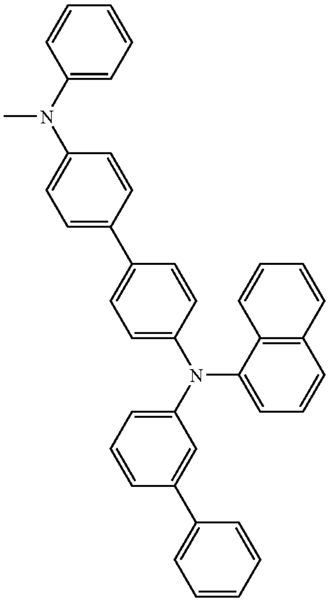
393
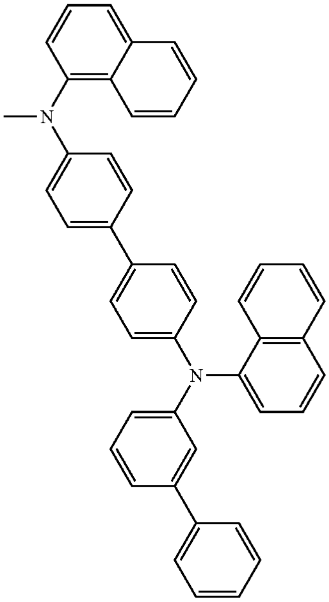

-continued
394
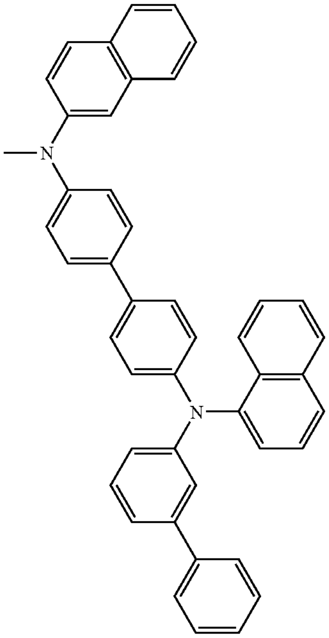
395
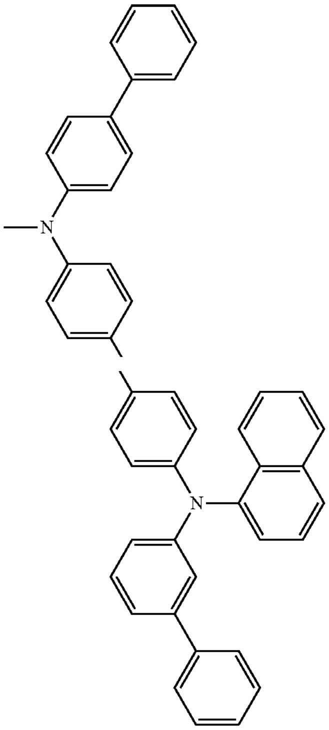
-continued
396
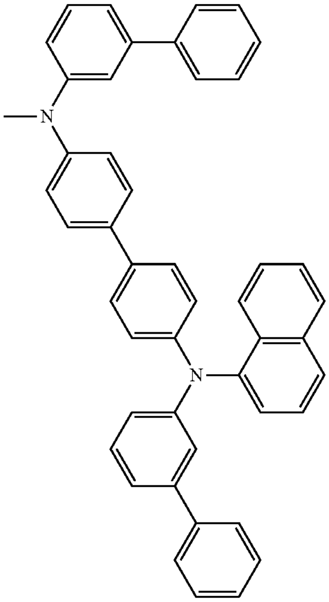
397
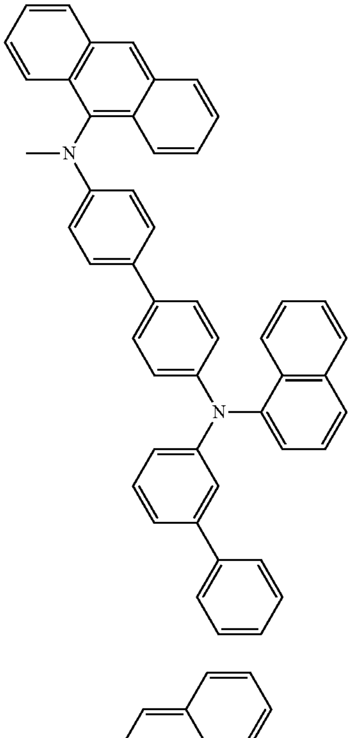
398
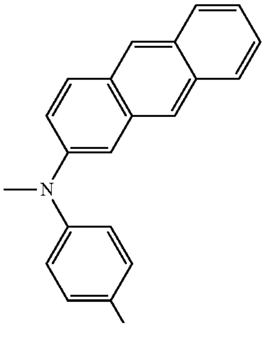

-continued
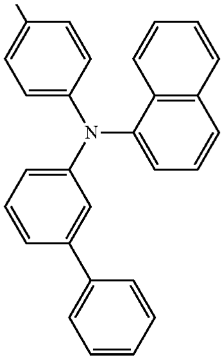
399
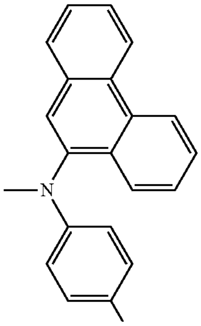
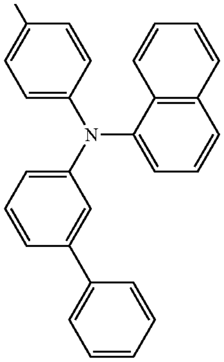
400
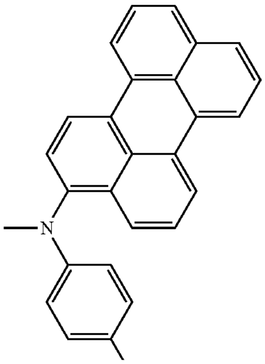
-continued
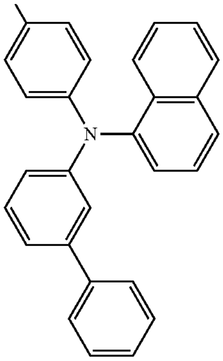
401
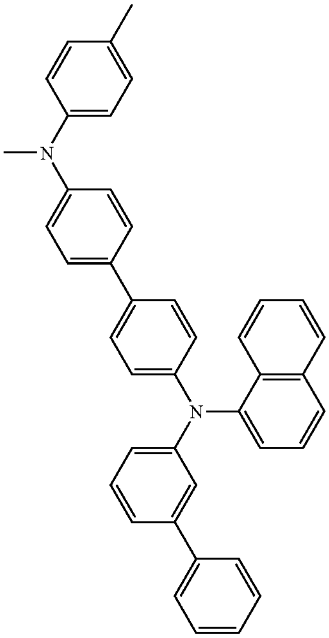
402
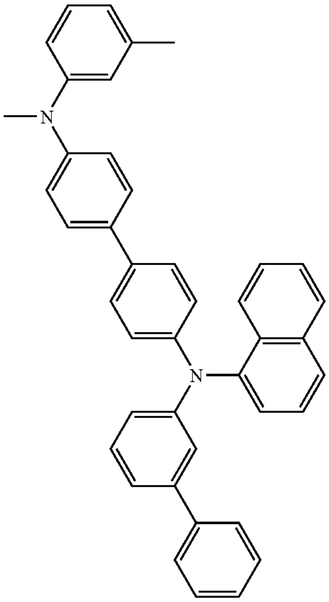

-continued
403
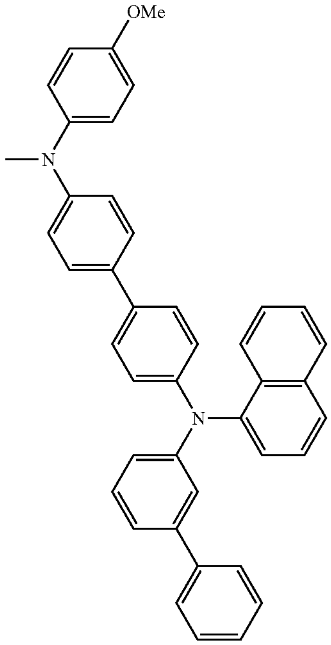
404
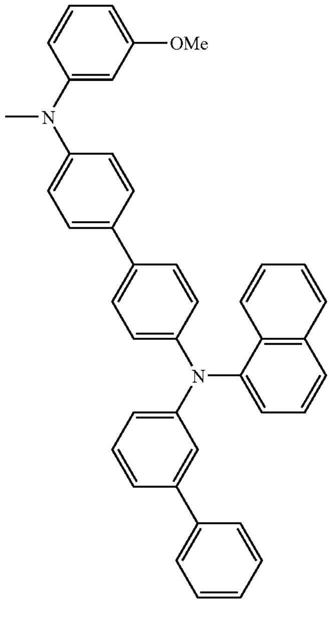
-continued
405
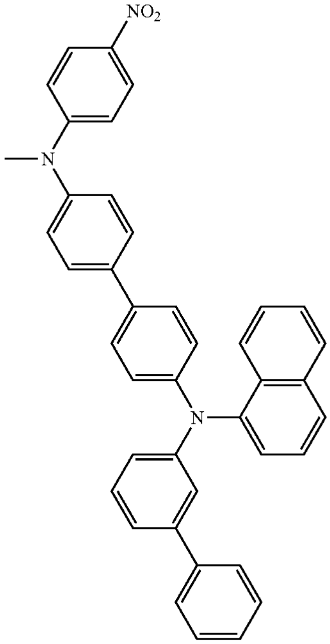
406
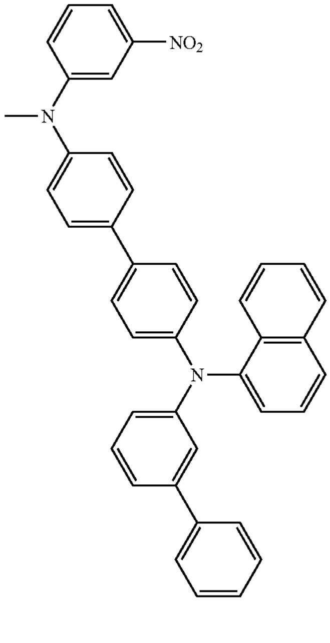

-continued
407
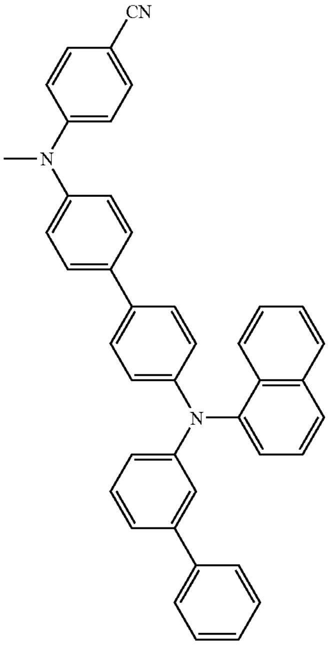
408
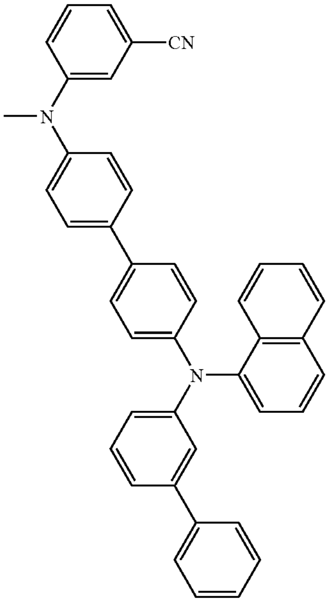
-continued
409
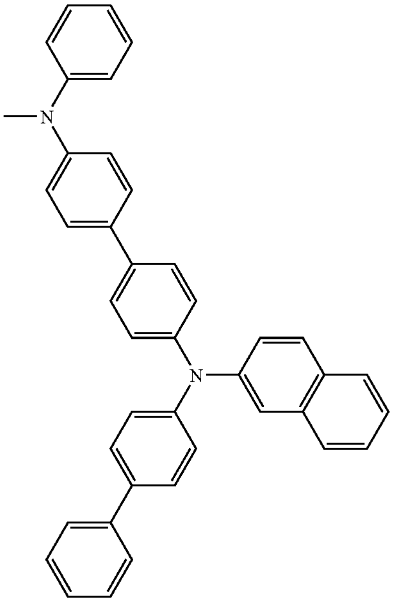
410
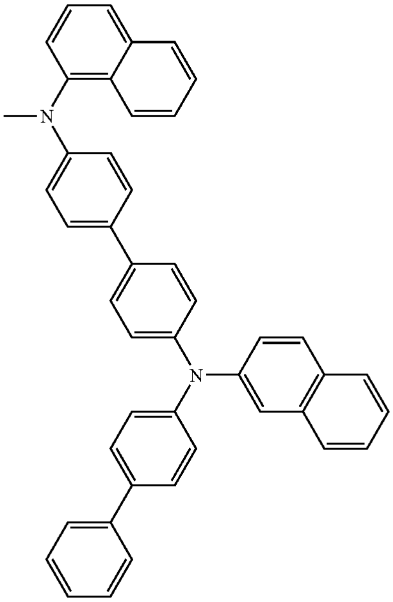

-continued
411
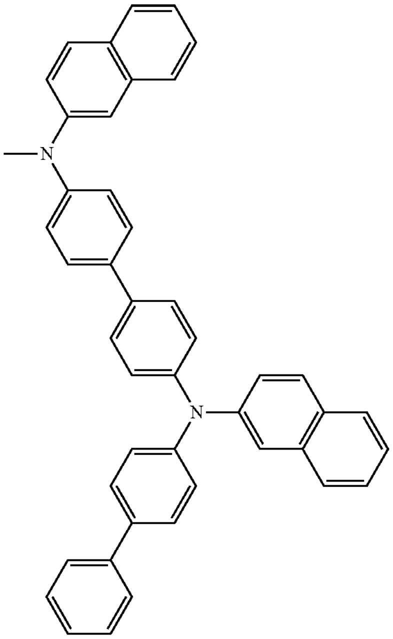
412
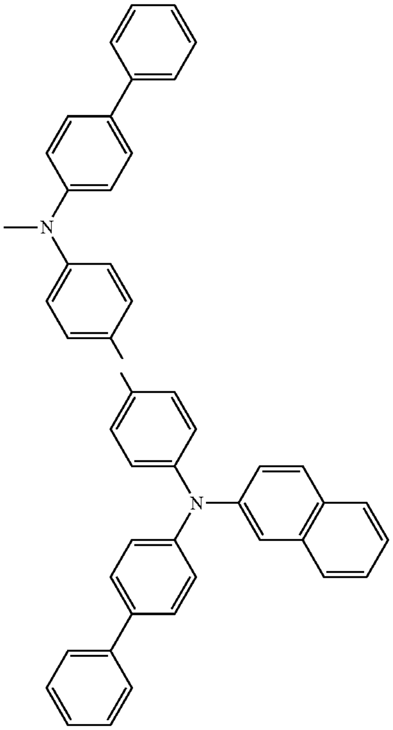
-continued
413
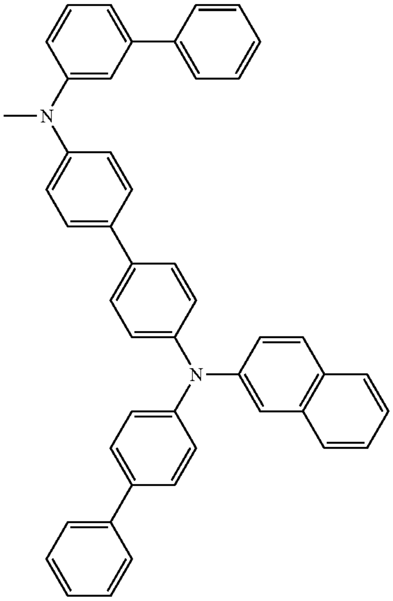
414
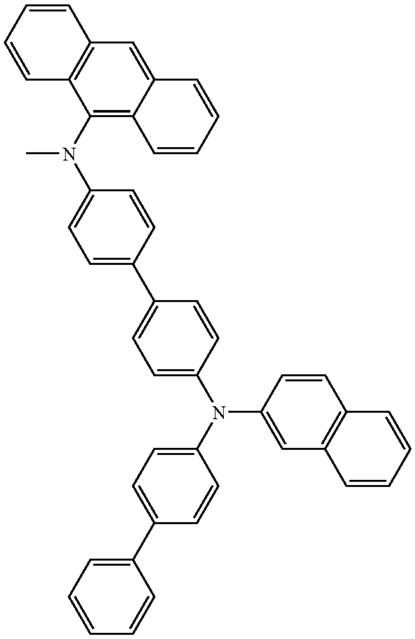
415
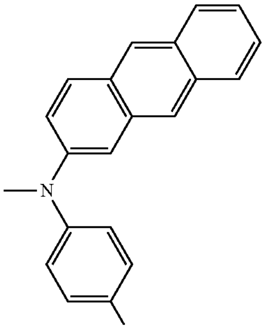

-continued
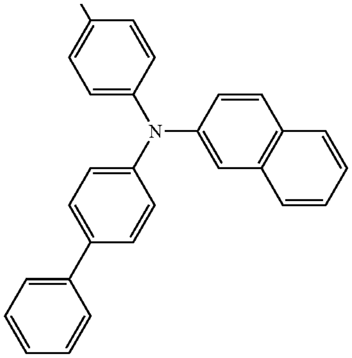
416
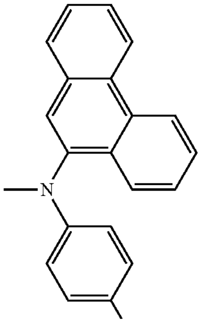
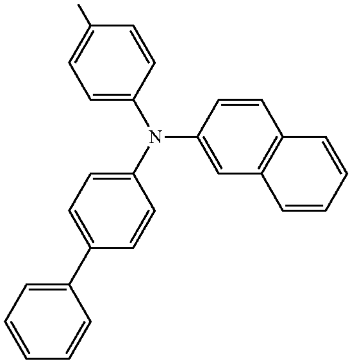
417
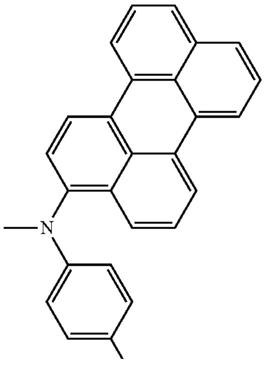
-continued
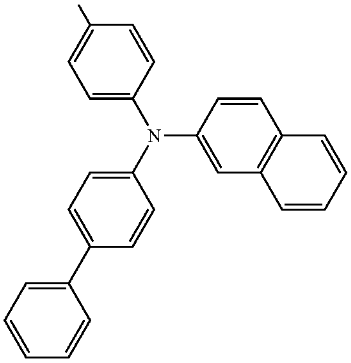
418
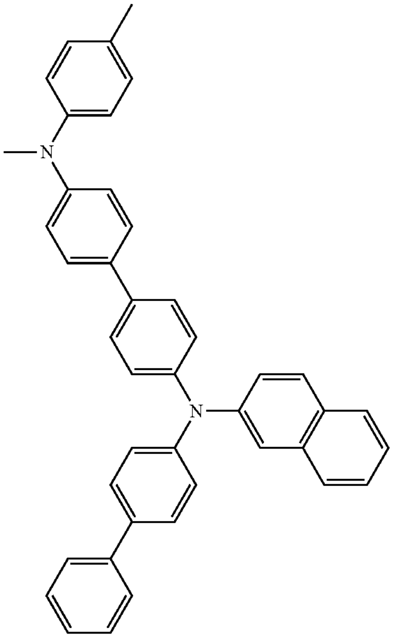
419
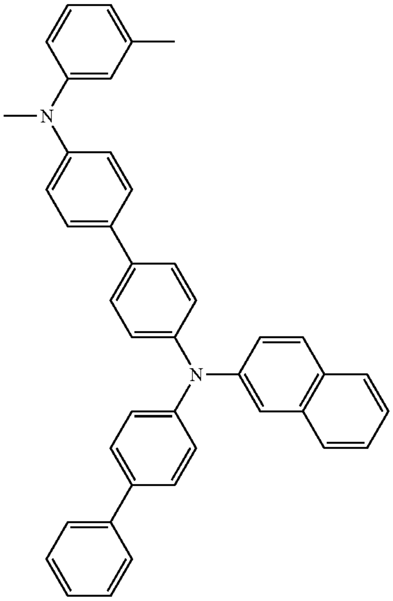

-continued
420
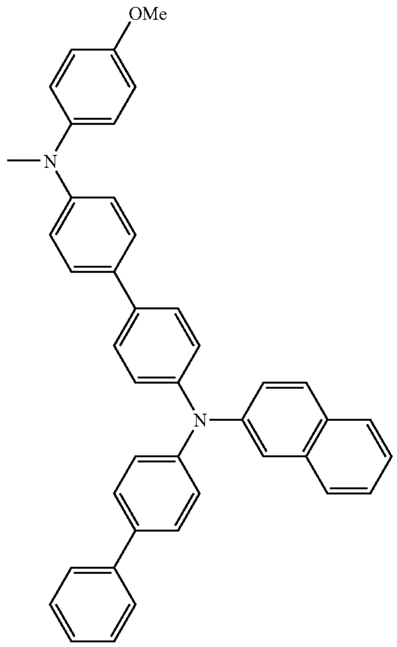
421
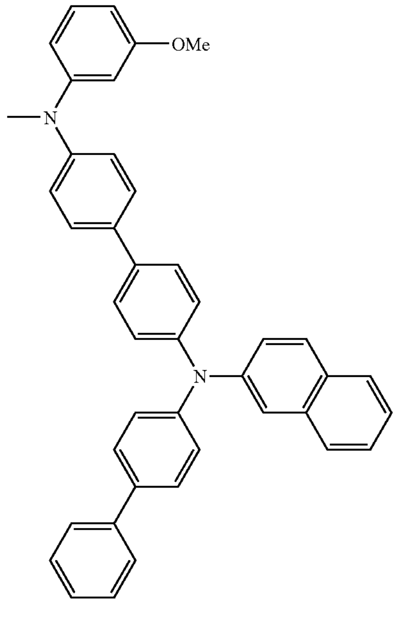
-continued
422
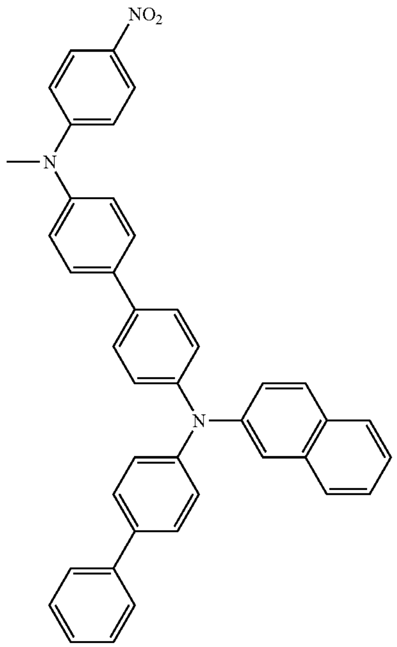
423
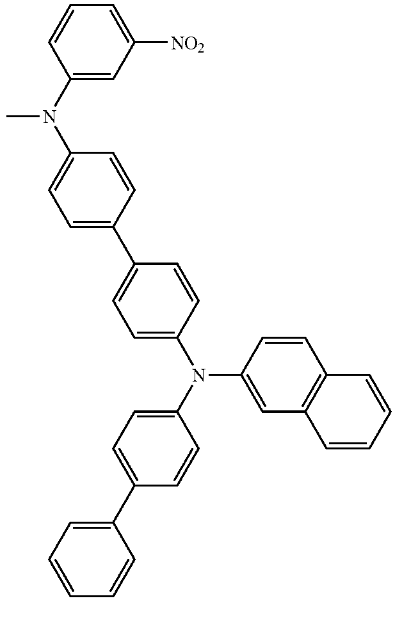

-continued
424
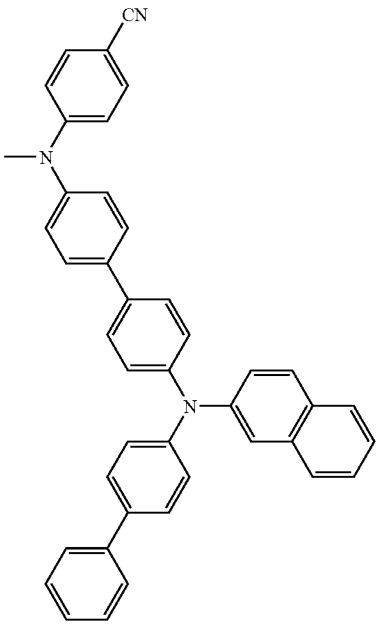
425
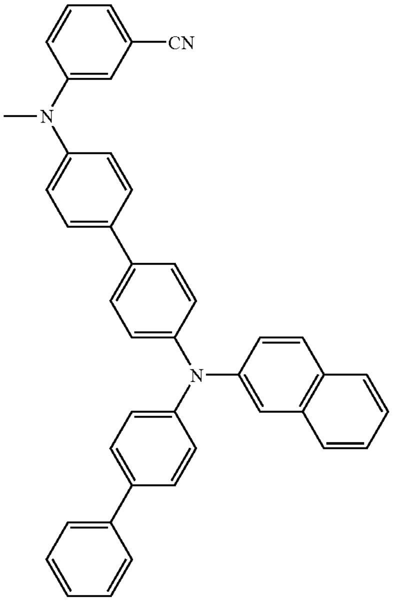
-continued
426
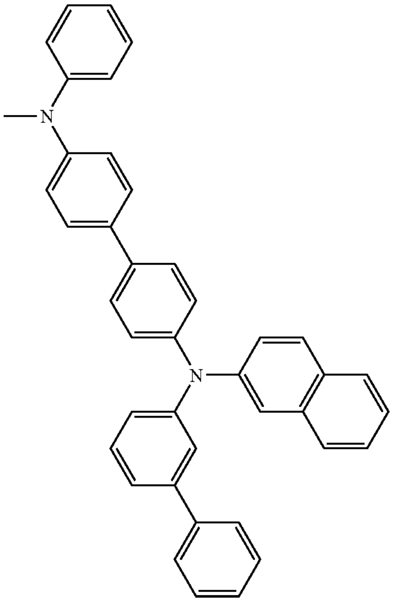
427
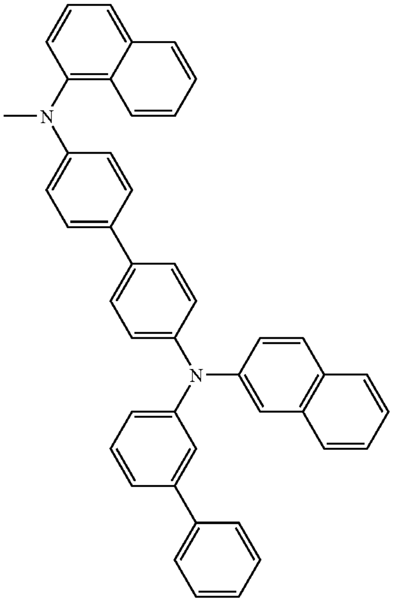

-continued
428
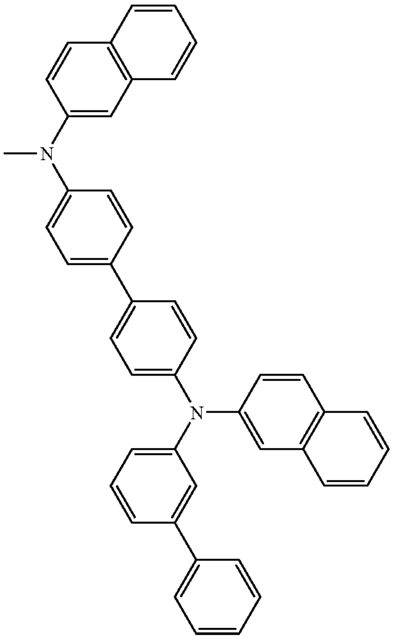
429
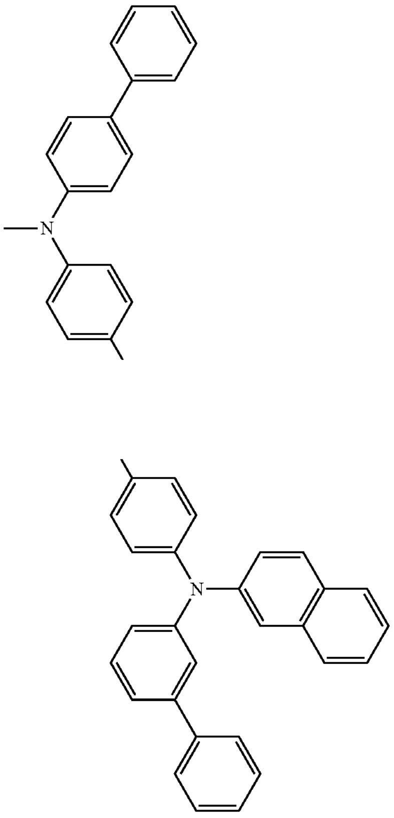
-continued
430
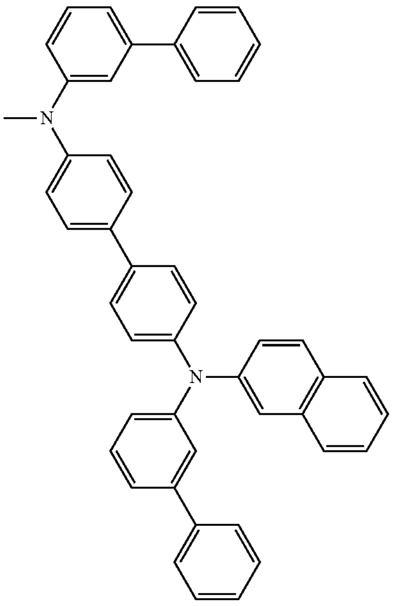
431
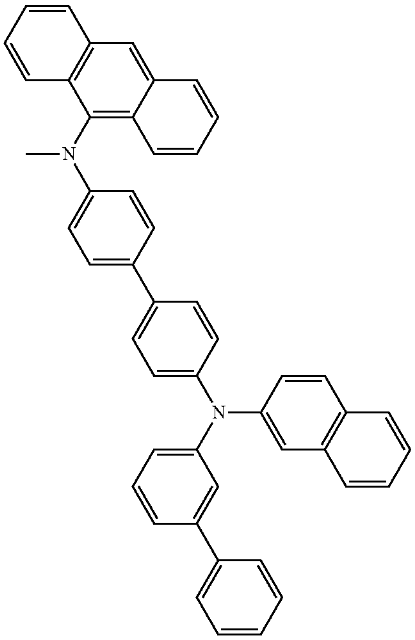
432
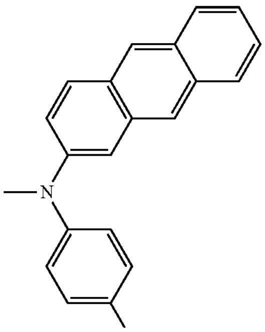

-continued
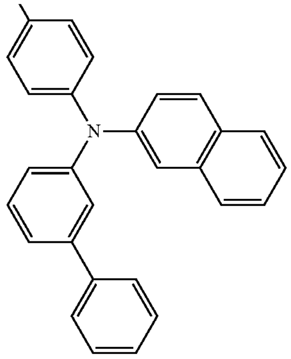
433
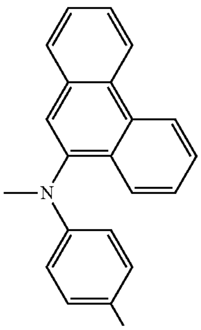
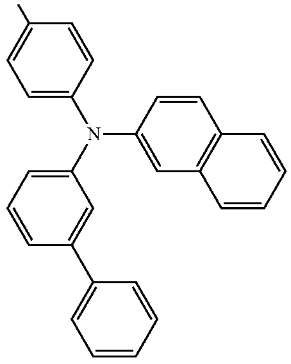
434
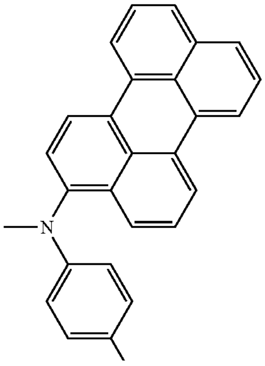
-continued
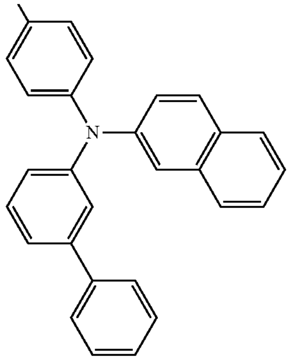
435
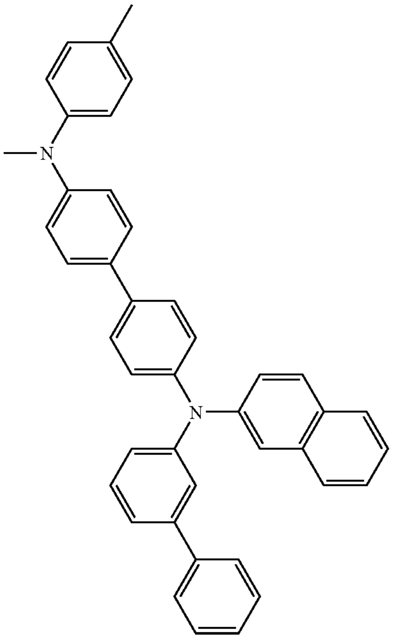
436
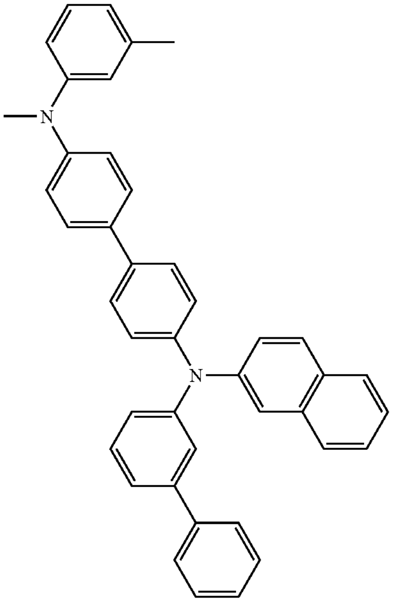

-continued
437
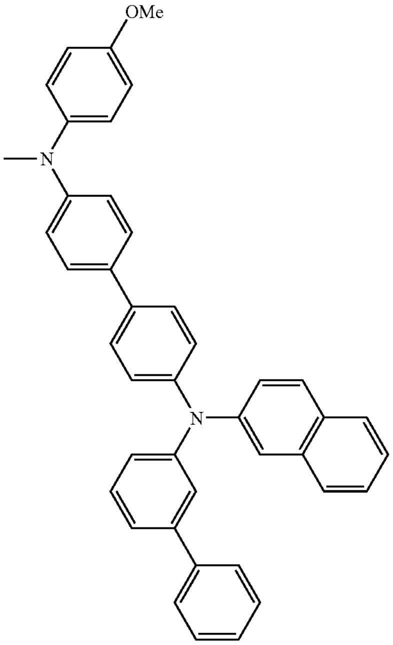
438
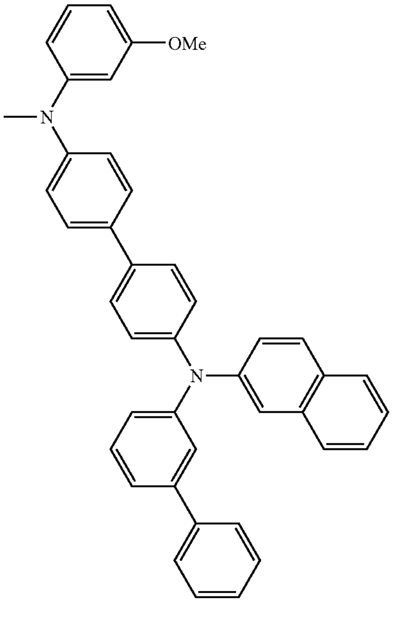
-continued
439
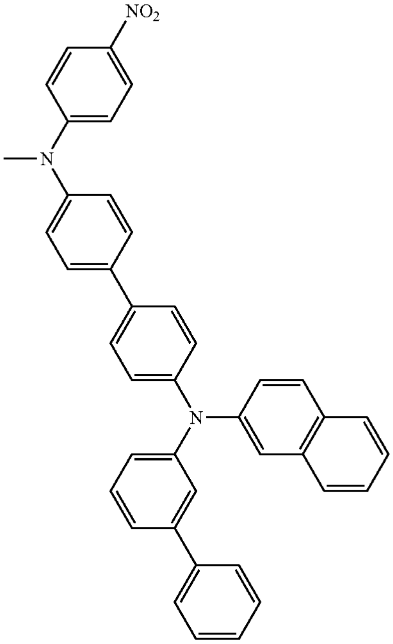
440
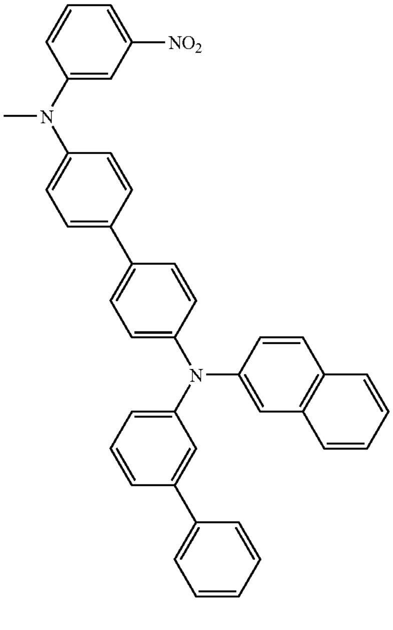

-continued
441
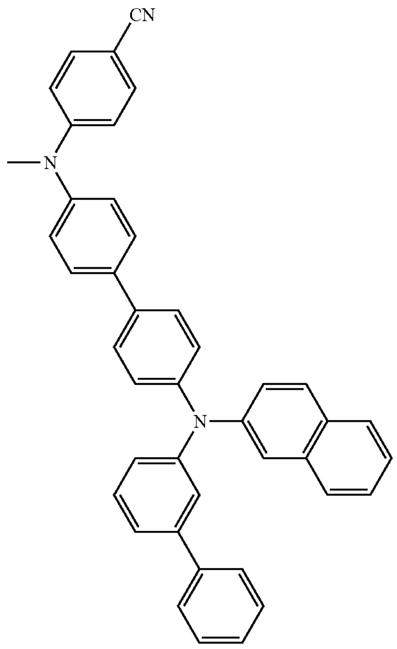
442
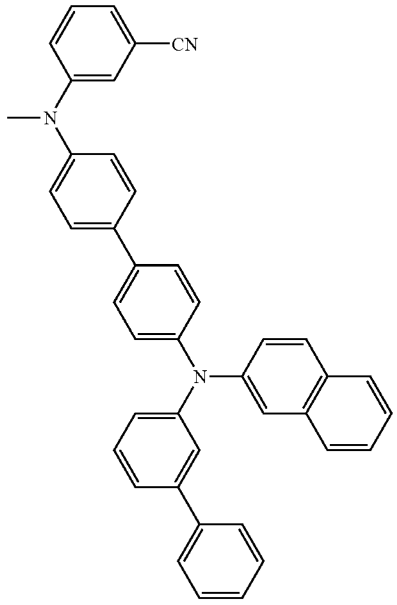
-continued
443
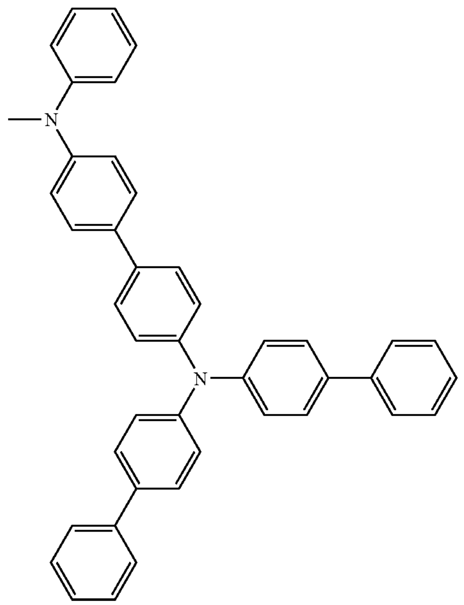
444
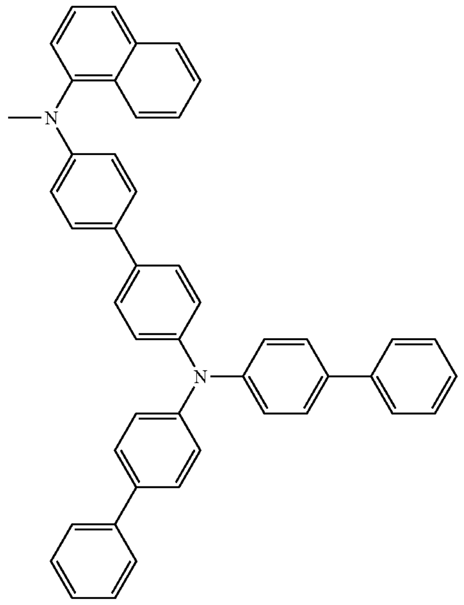

-continued
445
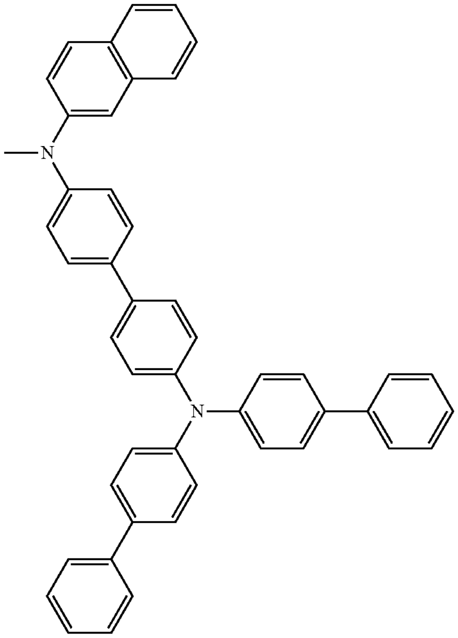
446
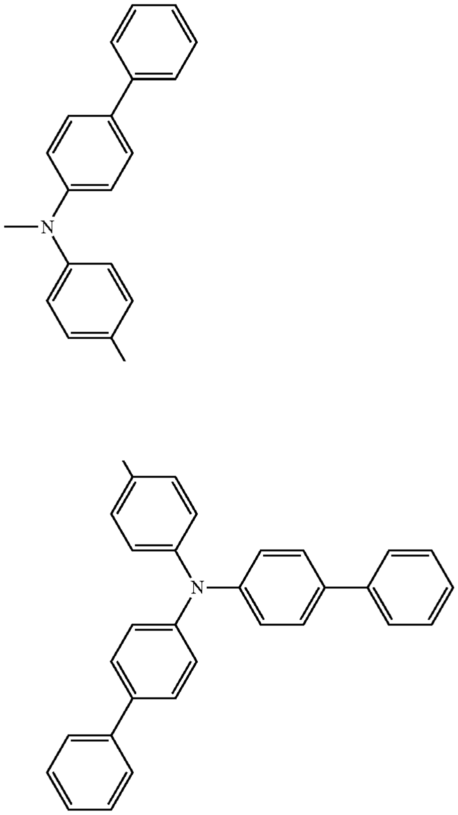
-continued
447
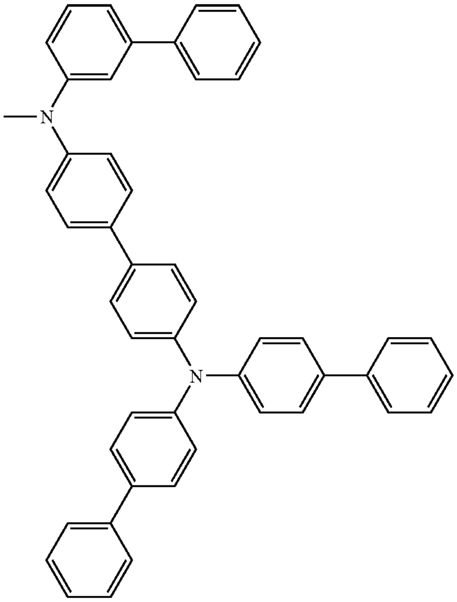
448
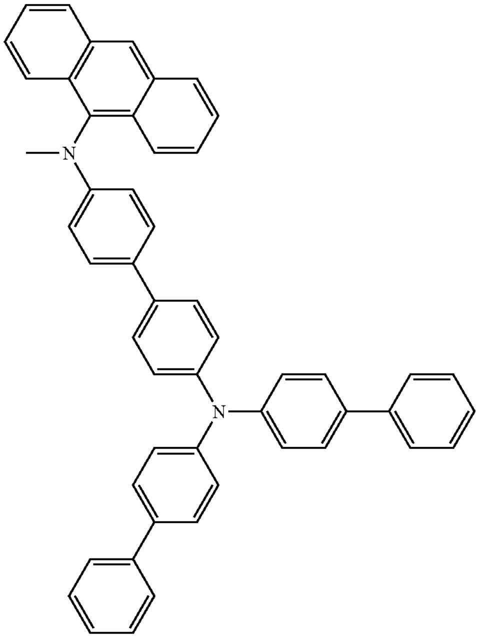
449
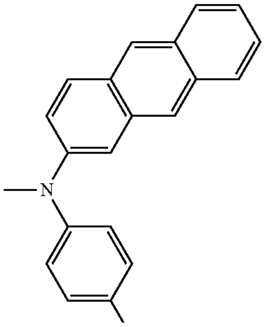

-continued
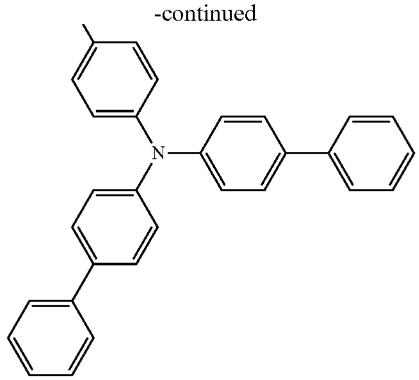
450
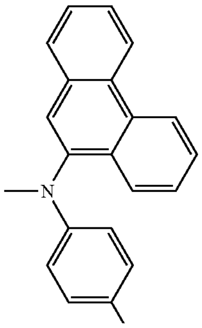
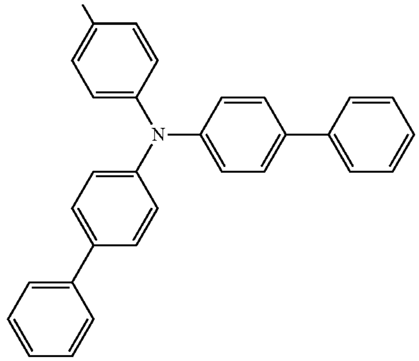
451
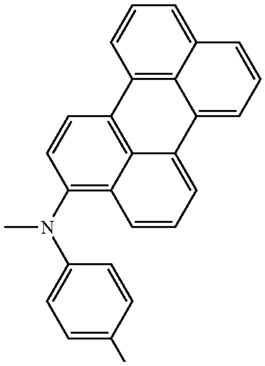
-continued
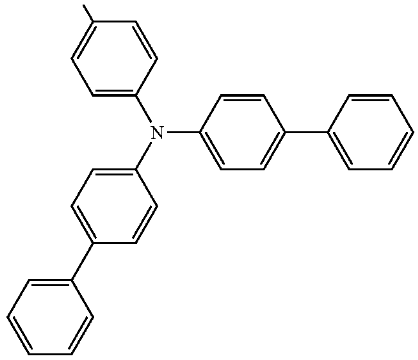
452
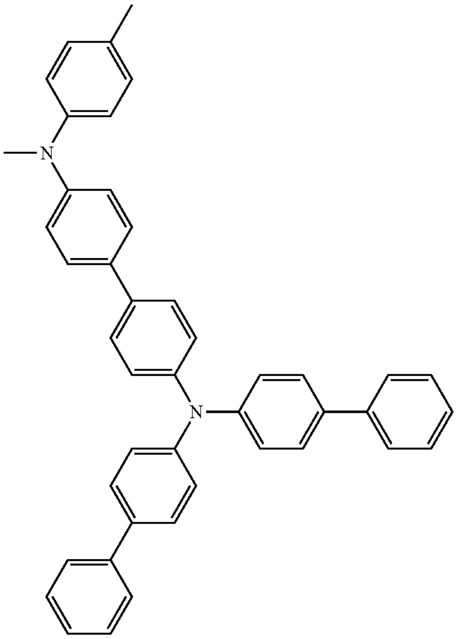
453
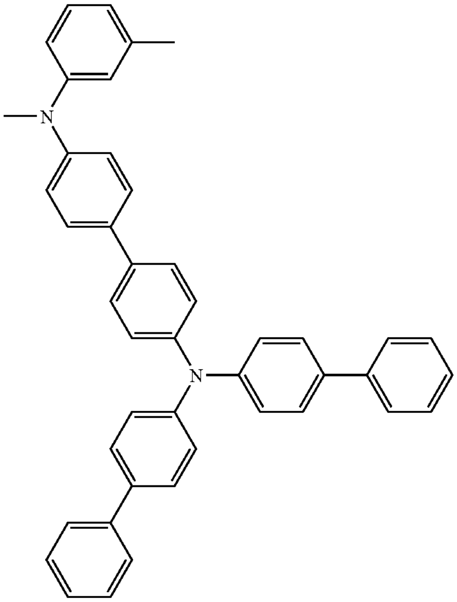

-continued
454
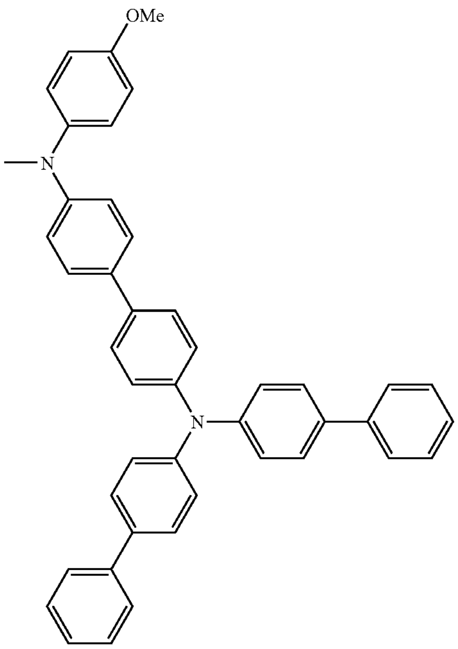
455
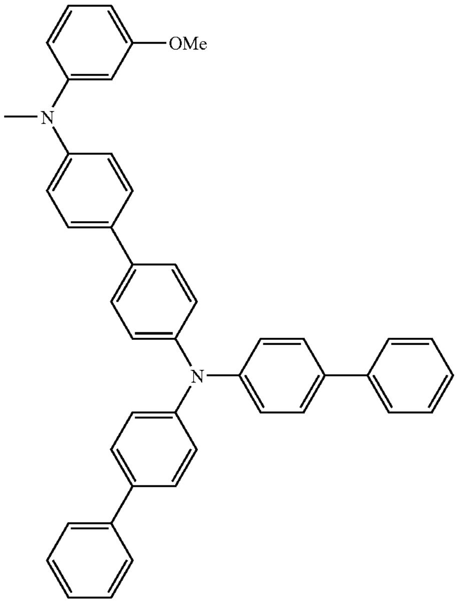
-continued
456
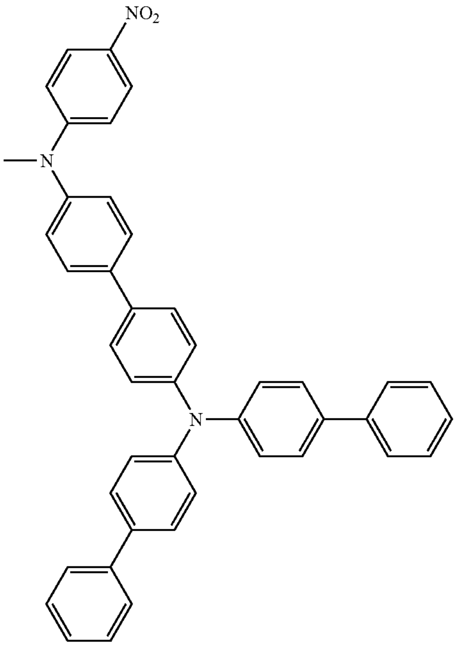
457
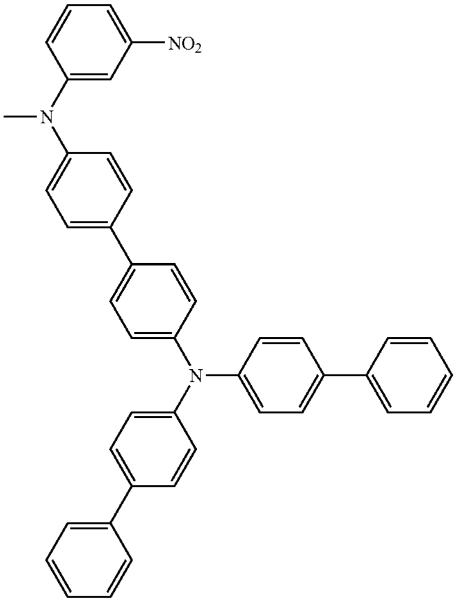

-continued
458
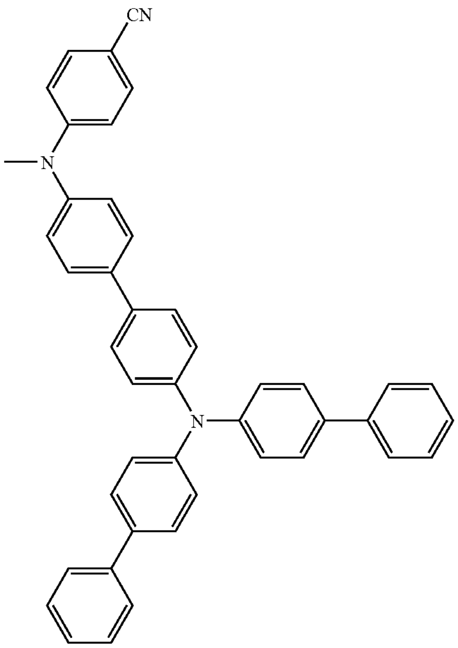
459
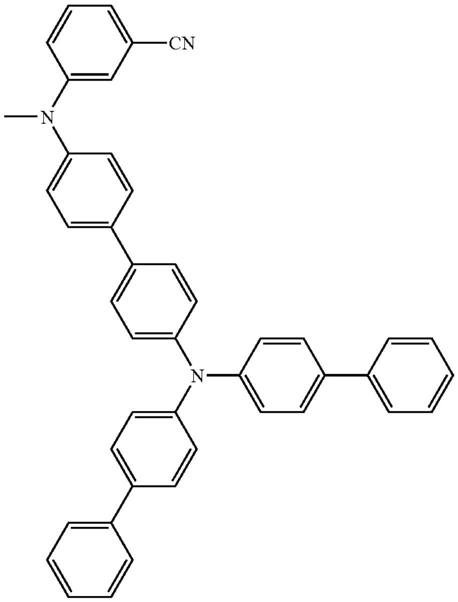
-continued
460
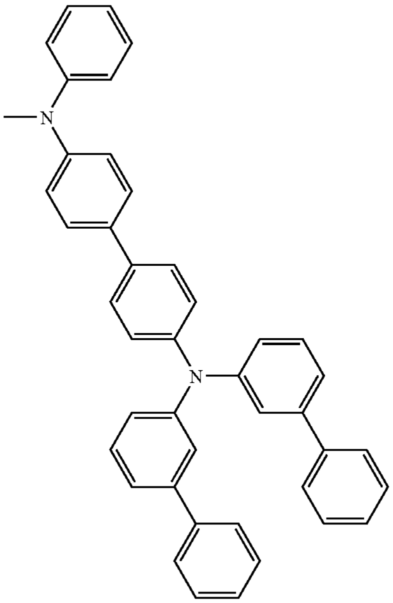
461
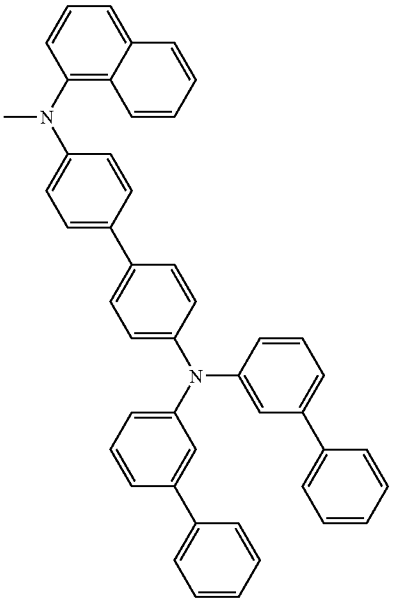

-continued
462
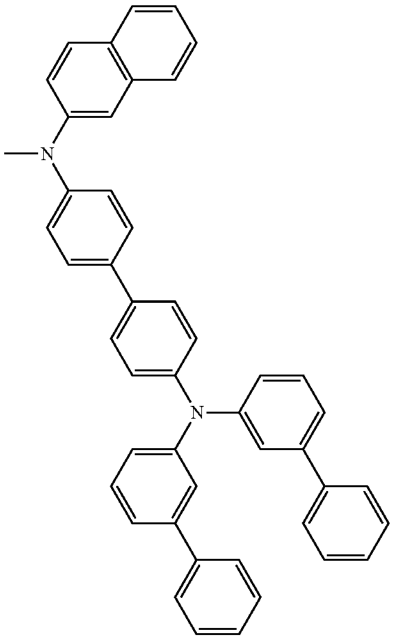
463
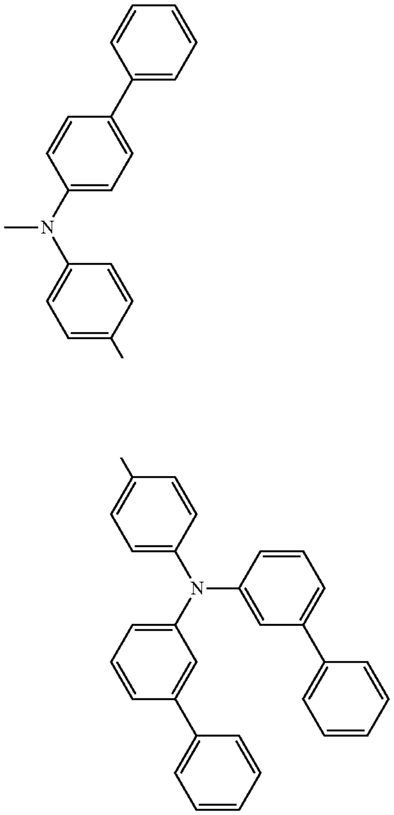
-continued
464
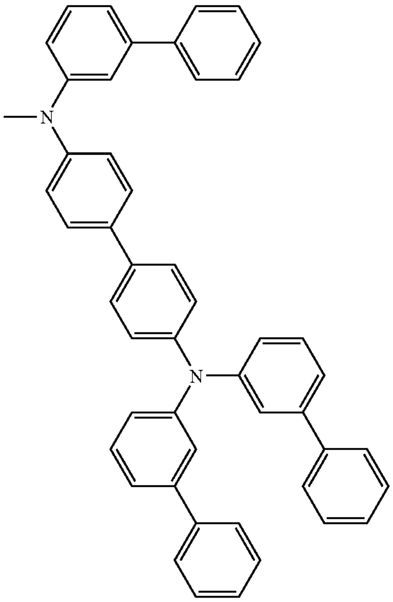
465
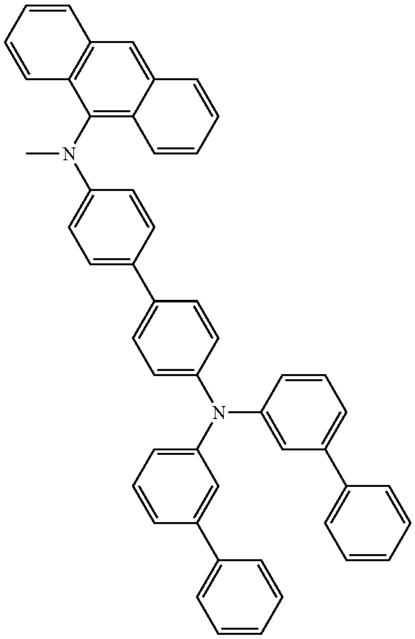
466
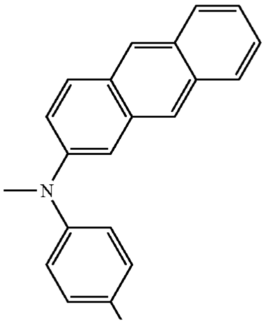

-continued
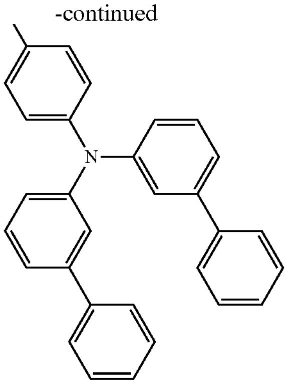
467
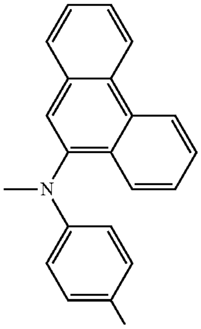
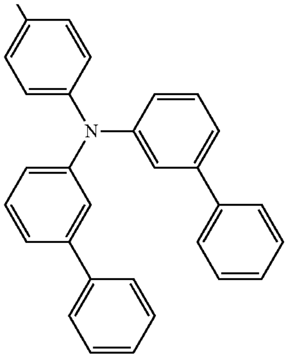
468
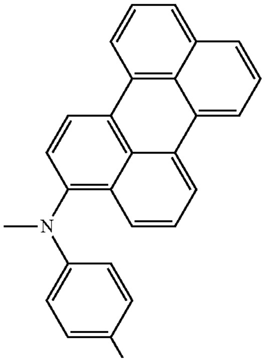
-continued
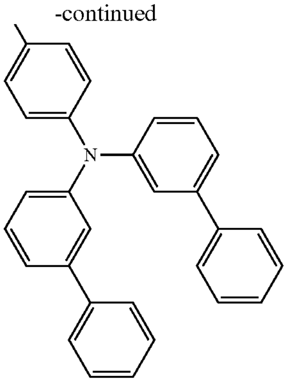
469
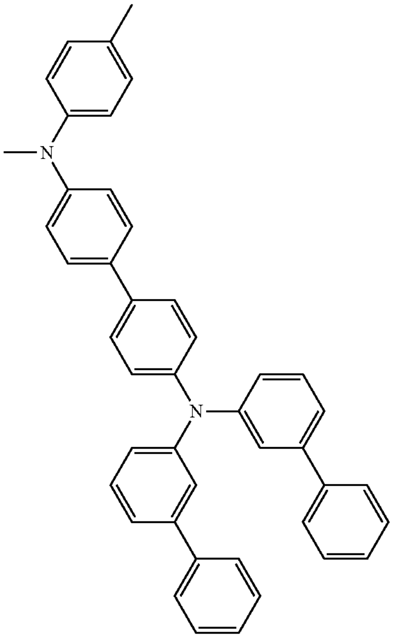
470
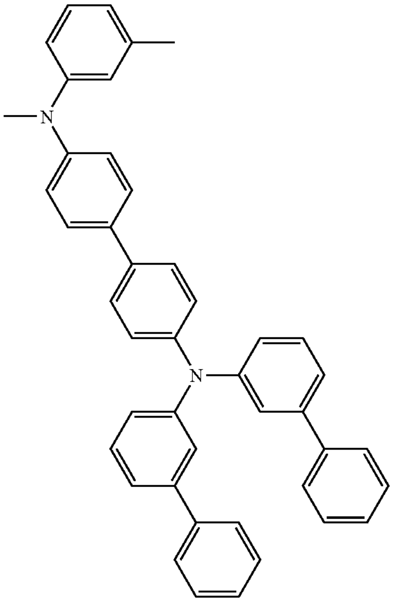

-continued
471
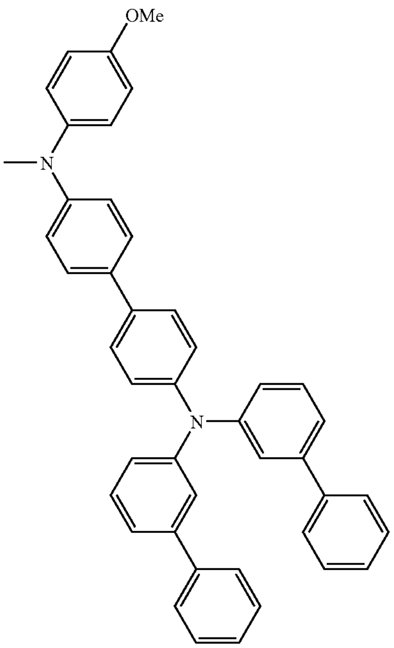
472
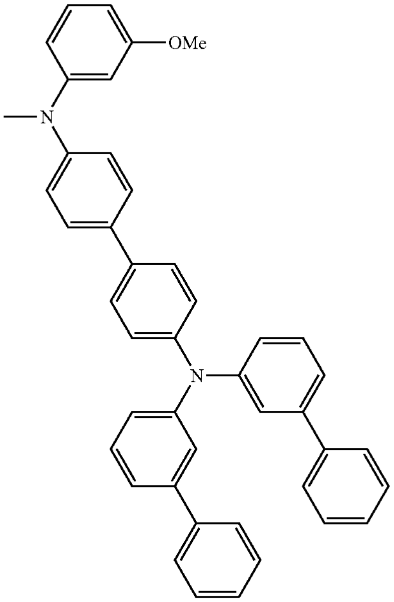
-continued
473
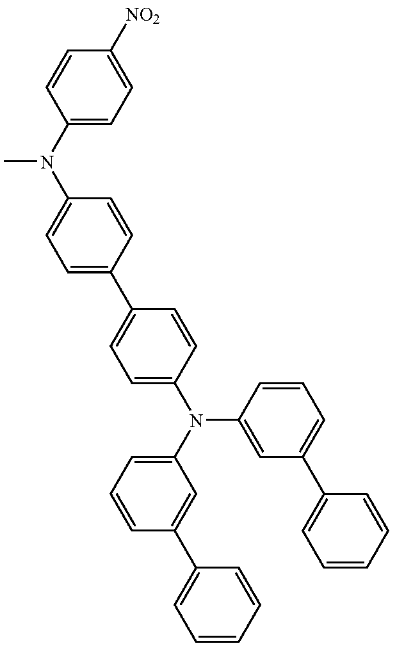
474
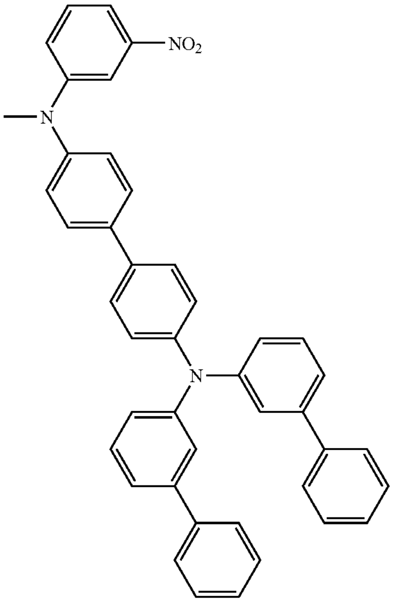

-continued

475

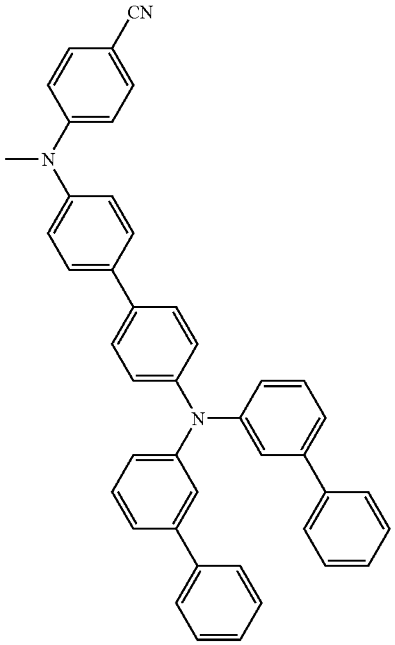

476

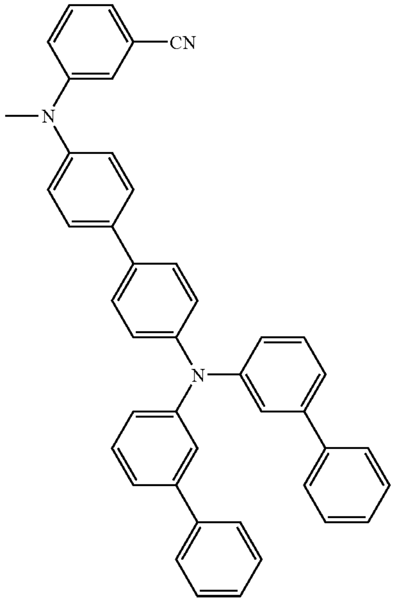

BRIEF DESCRIPTION OF THE DRAWINGS

FIG. 1 illustrates an organic light emitting device comprising a substrate 1, an anode, 2, a light emitting layer 3, and a cathode 4; and FIG. 2 illustrates an organic light emitting device comprising a substrate 1, an anode 2, a hole injection layer 5, a hole transport layer 6, a light emitting layer 7, an electron transport layer 8, and a cathode 4.

BEST MODE FOR CARRYING OUT THE INVENTION

Hereinafter, a detailed description will be given of the present invention.

Various substituent groups are introduced into a core structure shown in Formula 1, in detail, the core structure in which a fluorene group is bonded to a combination of an acridine group and a carbazolyl group to form a spiro structure, thereby the compound of Formula 1 has characteristics suitable for application to an organic material layer used in an organic light emitting device. This will be described in detail, below.

The steric core structure of the compound of Formula 1, for convenience of explanation, can be divided into two portions, A and B, as shown in the following Formula.

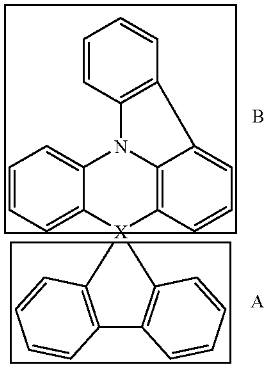

The compound of Formula 1 has the steric core structure in which a plane A meets with a plane B at right angles around X, and conjugation does not occur between the A and B portions around X. Furthermore, since one nitrogen atom is positioned among three aryl groups in the plane B, conjugation is limited in the plane B.

The conjugation length of the compound has a close relationship with an energy band gap. In detail, the energy band gap is reduced as the conjugation length of the compound increases. As described above, since a conjugation structure is limited in the core structure of the compound of Formula 1, the core structure has a large energy band gap.

As described above, in the present invention, various substituent groups are introduced to R1 to R15 positions and Z1 to Z2 positions of the core structure having the large energy band gap so as to produce compounds having various energy band gaps. Generally, it is easy to control the energy band gap by introducing substituent groups into a core structure having a large energy band gap, but it is difficult to significantly control the energy band gap by introducing substituent groups into a core structure having a small energy band gap. Furthermore, in the present invention, it is possible to control HOMO and LUMO energy levels of the compound by introducing various substituent groups into the R1 to R15 positions and the Z1 to Z4 positions of the core structure.

Additionally, by introducing various substituent groups into the core structure, compounds having intrinsic characteristics of the substituent groups can be synthesized. For example, substituent groups, which are frequently applied to hole injection layer materials, hole transport layer materials, light emitting layer materials, and electron transport layer materials which are used during the production of the organic light emitting device, are introduced into the core structure so as to produce substances capable of satisfying requirements of each organic material layer. For example, since the core structure of the compound of Formula 1 includes the arylamine structure, it has an energy level suitable for the hole injection and/or hole transport materials in the organic light emitting device. In the present invention, the compound having the proper energy level is selected depending on the substituent group among the compounds represented by Formula 1 to be used in the organic light emitting device, thereby it is possible to realize a device having a low actuating voltage and a high light efficiency.

Furthermore, various substituent groups are asymmetrically introduced into the core structure (A is located at one side of the core structure) so as to precisely control the energy band gap, improve interfacial characteristics with organic materials, and apply the compound to various fields.

As well, if the number of amine contained in the substituent group A is set to 2 or more (if Z1 and Z2 are hetero aromatic amine compounds, the number of nitrogen contained in them is not counted), it is possible to precisely control the HOMO and LUMO energy levels and the energy band gap, and on the other hand interfacial characteristics with the organic materials is improved and thereby make it possible to apply the compound to various fields.

Additionally, various substituent groups are introduced into the steric structure of the compound of Formula 1 using spiro bonding to control the three-dimensional structure of the organic material so as to minimize π-π interaction in the organic material, thereby formation of excimers is prevented.

With respect to the energy band gap and the energy level, for example, since the compound of Formula 2-2, in which arylamine is introduced into the hole transport material or the hole injection material of the structure of Formula 1, has HOMO of 5.31 eV, it has an energy level suitable for the hole injection layer or the hole transport layer. Meanwhile, the compound of Formula 2-1 has the band gap of 2.99 eV, which is still larger than that of NPB, typically used as the hole transport layer material, thus it has a LUMO value of about 2.32 eV, which is considered to be very high. If a compound having a high LUMO value is used as the hole transport layer, it increases the energy wall of LUMO of the material constituting the light emitting layer to prevent the movement of electrons from the light emitting layer to the hole transport layer. Accordingly, the above-mentioned compound improves the light emission efficiency of the organic light emitting device so that efficiency is higher than that of conventionally used NPB (HOMO 5.4 eV, LUMO 2.3 eV, and energy band gap 3.1 eV). In the present invention, the energy band gap is calculated by a typical method using a UV-VIS spectrum.

As well, the compound of Formula 1 has stable redox characteristics. Redox stability is estimated using a CV (cyclovoltammetry) method. For example, if oxidation voltage is repeatedly applied to the compound of Formula 2-1, oxidation repeatedly occurs at the same voltage and the current amount is the same. This means that the compound has excellent stability to oxidation.

Meanwhile, since the compound of Formula 1 has a high glass transition temperature (Tg), it has excellent thermal stability. For example, the glass transition temperature of the compound of Formula 2-1 is 150° C., which is still higher than that of conventionally used NPB (Tg: 96° C.). Such increase in thermal stability is an important factor providing actuating stability to the device.

Furthermore, the compound of Formula 1 may be used to form the organic material layer using a vacuum deposition process or a solution coating process during the production of the organic light emitting device. In connection with this, illustrative, but non-limiting, examples of the solution coating process include a spin coating process, a dip coating process, an inkjet printing process, a screen printing process, a spray process, and a roll coating process.

Tertiary alcohol, which is produced by a reaction of a lithiated aryl and keto group, is heated in the presence of an acid catalyst to form a hexagonal cyclic structure while water is removed, thereby producing the compound having a spiro structure according to the present invention. The above-mentioned procedure for producing the compound is well known in the art, and those skilled in the art can change the production conditions during the production of the compound of Formula 1. The production will be described in detail in the preparation examples later.

The organic light emitting device of the present invention can be produced using known materials through a known process, modified only in that at least one layer of organic material layer(s) include the compound of the present invention, that is, the compound of Formula 1.

The organic material layer(s) of the organic light emitting device according to the present invention may have a single layer structure, or alternatively, a multilayered structure in which two or more organic material layers are layered. For example, the organic light emitting device of the present invention may comprise a hole injection layer, a hole transport layer, a light emitting layer, an electron transport layer, and an electron injection layer as the organic material layer(s). However, the structure of the organic light emitting device is not limited to this, but may comprise a smaller number of organic material layers.

Furthermore, the organic light emitting device of the present invention may be produced, for example, by sequentially layering a first electrode, organic material layer(s), and a second electrode on a substrate. In connection with this, a physical vapor deposition (PVD) method, such as a sputtering method or an e-beam evaporation method, may be used, but the method is not limited to these.

A method of producing the compound of Formula 1 and the production of the organic light emitting device using the same will be described in detail in the following preparation examples and examples. However, the following preparation examples and examples are set forth to illustrate, but are not to be construed to limit the present invention.

Mode for the Invention

A better understanding of a method of producing an organic compound represented by Formula 1 and the production of an organic light emitting device using the same may be obtained in light of the following preparation examples and examples which are set forth to illustrate, but are not to be construed to limit the present invention.

In order to produce the compound represented by Formula 1, any one of the compounds of the following Formulae, a to c, may be used as a starting material.

[formula a]

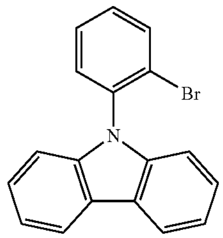

-continued

[formula b]

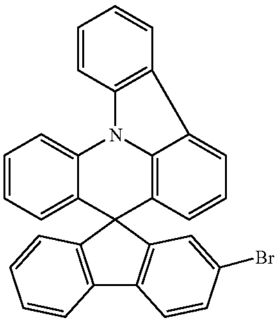

[formula c]

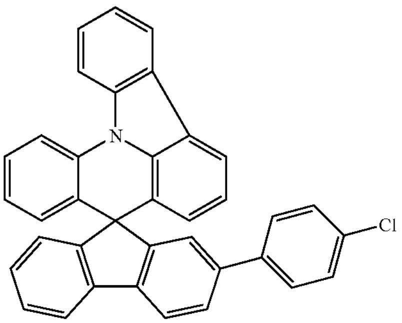

PREPARATION EXAMPLE 1

Preparation of a Starting Material Represented by Formula a

Carbazole (1.672 g, 10 mmol), 1-bromo-2-iodobenzene (1.5 ml, 12 mmol), potassium carbonate ($K_2CO_3$, 2.7646 g, 20 mmol), copper iodide (CuI, 95 mg, 0.5 mmol), and 25 ml of xylene were refluxed in a nitrogen atmosphere. After cooling to normal temperature, a product was extracted with ethyl acetate, water was removed with anhydrous magnesium sulfate ($MgSO_4$), and the solvent was removed at a reduced pressure. The resulting product was passed through a silica gel column using a hexane solvent to produce a compound, the solvent was removed at a reduced pressure, and vacuum drying was conducted to produce the resulting white solid compound (800 mg, 25% yield). MS: $[M+H]^+=323$.

PREPARATION EXAMPLE 2

Preparation of a Starting Material Represented by Formula b 4.19 g of starting material represented by Formula a (13 mmol) were dissolved in 50 ml of purified THF, and 4.8 ml of n-BuLi (2.5 M in hexane, 12 mmol) were slowly dropped thereon at −78° C. Stirring was conducted at the same temperature for 45 min, and 2.59 g of 2-bromo-9-fluorenone (10.0 mmol) were added thereto. After stirring at the same temperature for 1 hour, the temperature was raised to normal temperature, stirring was carried out for an additional 2 hours, and the reaction was completed in a $NH_4Cl$ aqueous solution. An organic material was extracted with ethyl ether, water was removed therefrom, and an organic solvent was removed to produce yellow solid. The produced solid was dispersed in ethanol, stirred, filtered, and vacuum dried to obtain 4.5 g of intermediate material. The intermediate solid was dispersed in 40 ml of acetic acid, 12 drops of concentrated sulfuric acid were added thereto, and reflux was conducted for 3 hours. After cooling to normal temperature, the resulting solid was filtered, washed with ethanol, and vacuum dried to create 3.98 g of product (82.2% yield). MS: $[M+H]^+=484$.

PREPARATION EXAMPLE 3

Preparation of a Starting Material Represented by Formula c

The starting material represented by Formula c (5.0 g, 10.32 mmol) was completely dissolved in 40 ml of THF, 4-chloro-phenylboronic acid (2.42 g, 15.48 mmol), 2M potassium carbonate solution, tetrakis(triphenylphosphine) palladium(0) (0.31 mmol, 0.36 g), and 10 ml of ethanol were added thereto, and reflux was conducted for 24 hours. After the reaction was completed, cooling to normal temperature was conducted, and filtration was conducted. Washing was conducted with water and ethanol, several times. Recrystallization was conducted with ethanol, and vacuum drying was conducted to produce a compound (4.97 g, yield 93%). MS: $[M+H]^+=515$.

Example 1

Preparation of the Compound Represented by Formula 2-2

1) Synthesis of arylamine (4-(N-phenyl-N-phenylamino) phenyl-1-naphthylamine) to produce the compound represented by Formula 2-2: 15.0 g of 4-bromophenyl-N-phenyl-N-phenylamine (46.3 mmol) and 7.29 g of 1-naphthylamine (50.9 mmol) were dissolved in 200 ml of toluene, 13.34 g of sodium-tert-butoxide (138.8 mmol), 0.53 g of bis(dibenzylidene acetone)palladium(0) (0.93 mmol), and 0.56 ml of 50 wt % tri-tert-butylphosphine toluene solution (1.39 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (13 g, yield 73%). MS: $[M+H]^+=386$.

2) 5.00 g of compound of Formula b (10.3 mmol) and 4.78 g of 4-(N-phenyl-N-phenylamino)phenyl-1-naphthylamine (12.4 mmol) were dissolved in 50 ml of toluene, 5.89 g of sodium-tert-butoxide (61.3 mmol), 0.12 g of bis(dibenzylidene acetone)dipalladium(0) (0.21 mmol), and 0.15 ml of 50 wt % tri-tert-butylphosphine toluene solution (0.31 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 4:1, stirring was conducted using petroleum ether, and vacuum drying was conducted to produce the compound of Formula 2-2 (4.3 g, yield 53%). MS: $[M+H]^+=789$.

Example 2

Preparation of the Compound Represented by Formula 2-256

1) Synthesis of arylamine (4-(N,N-diphenylamino)-biphenyl-N-phenylamine) to produce the compound represented by Formula 2-256: 4.00 g of 4-chlorobiphenyl-N,N-diphenylamine (11.2 mmol) and 1.13 ml of aniline (12.4 mmol) were dissolved in 100 ml of toluene, 2.70 g of sodium-tert-butoxide (28.1 mmol), 0.13 g of bis(dibenzylidene acetone)palladium (0) (0.23 mmol), and 0.17 ml of 50 wt % tri-tert-butylphosphine toluene solution (0.34 mmol) were added thereto, and reflux was conducted in a nitrogen atmosphere for 5 hours. Distilled water was added to the reaction solution to complete the reaction, and the organic layer was extracted. After a column separation process was conducted using a solvent of n-hexane and tetrahydrofuran at a ratio of 10:1, stirring was conducted using petroleum ether, and vacuum drying was conducted to produce an arylamine connection group (3.8 g, yield 81%). MS: $[M+H]^+$=413.

2) 3.62 g of compound of Formula b (7.47 mmol) and 3.4 g of 4-(N,N-diphenylamino)-biphenyl-N-phenylamine (8.2 mmol) were dissolved in 40 ml of toluene, 1.94 g of sodium-tert-butoxide (22.4 mmol), 0.09 g of bis(dibenzylidene acetone)palladium(0) (0.16 mmol), and 0.11 ml of 50 wt % tri-tert-butylphosphine toluene solution (0.22 mmol) were added thereto, and reflux was conducted in a nitrogen atmosphere for 2 hours. Distilled water was added to the reaction solution to complete the reaction, and the organic layer was extracted. After a column separation process was conducted using a solvent of n-hexane and tetrahydrofuran at a ratio of 8:1, stirring was conducted using petroleum ether, and vacuum drying was conducted to produce the compound of Formula 2-256 (3.5 g, yield 53%). MS: $[M+H]^+$=817.

Example 3

Preparation of the Compound Represented by Formula 2-257

1) Synthesis of arylamine (4-(N,N-diphenylamino)-biphenyl-N-naphthylamine) to produce the compound represented by Formula 2-257: 8.80 g of 4-chlorobiphenyl-N,N-diphenylamine (24.7 mmol) and 5.31 g of 1-naphthylamine (37.1 mmol) were dissolved in 200 ml of toluene, 5.94 g of sodium-tert-butoxide (61.8 mmol), 0.43 g of bis(dibenzylidene acetone)palladium(0) (0.74 mmol), and 0.61 ml of 50 wt % tri-tert-butylphosphine toluene solution (1.24 mmol) were added thereto, and reflux was conducted in a nitrogen atmosphere for 5 hours. Distilled water was added to the reaction solution to complete the reaction, and the organic layer was extracted. After a column separation process was conducted using a solvent of n-hexane and tetrahydrofuran at a ratio of 10:1, stirring was conducted using petroleum ether, and vacuum drying was conducted to produce an arylamine connection group (7.0 g, yield 61%). MS: $[M+H]^+$=413.

2) 3.62 g of compound of Formula b (7.47 mmol) and 3.8 g of 4-(N,N-diphenylamino)-biphenyl-N-naphthylamine (8.2 mmol) were dissolved in 40 ml of toluene, 1.94 g of sodium-tert-butoxide (22.4 mmol), 0.09 g of bis(dibenzylidene acetone)palladium(0) (0.16 mmol), and 0.11 ml of 50 wt % tri-tert-butylphosphine toluene solution (0.22 mmol) were added thereto, and reflux was conducted in a nitrogen atmosphere for 2 hours. Distilled water was added to the reaction solution to complete the reaction, and the organic layer was extracted. After a column separation process was conducted using a solvent of n-hexane and tetrahydrofuran at a ratio of 8:1, stirring was conducted using petroleum ether, and vacuum drying was conducted to produce the compound of Formula 2-257 (3.5 g, yield 54%). MS: $[M+H]^+$=867.

Example 4

Preparation of the Compound Represented by Formula 2-259

1) Synthesis of arylamine (4-(N,N-diphenylamino)-biphenyl-N-biphenylamine) to produce the compound represented by Formula 2-259: 8.80 g of 4-chlorobiphenyl-N,N-diphenylamine (24.7 mmol) and 6.28 g of 4-aminobiphenyl (37.1 mmol) were dissolved in 200 ml of toluene, 5.94 g of sodium-tert-butoxide (61.8 mmol), 0.43 g of bis(dibenzylidene acetone)palladium(0) (0.74 mmol), and 0.61 ml of 50 wt % tri-tert-butylphosphine toluene solution (1.24 mmol) were added thereto, and reflux was conducted in a nitrogen atmosphere for 5 hours. Distilled water was added to the reaction solution to complete the reaction, and the organic layer was extracted. After a column separation process was conducted using a solvent of n-hexane and tetrahydrofuran at a ratio of 10:1, stirring was conducted using petroleum ether, and vacuum drying was conducted to produce an arylamine connection group (7.0 g, yield 58%). MS: $[M+H]^+$=489.

2) 3.62 g of compound of Formula b (7.47 mmol) and 4.0 g of 4-(N,N-diphenylamino)-biphenyl-N-biphenylamine (8.2 mmol) were dissolved in 40 ml of toluene, 1.94 g of sodium-tert-butoxide (22.4 mmol), 0.09 g of bis(dibenzylidene acetone)palladium(0) (0.16 mmol), and 0.11 ml of 50 wt % tri-tert-butylphosphine toluene solution (0.22 mmol) were added thereto, and reflux was conducted in a nitrogen atmosphere for 2 hours. Distilled water was added to the reaction solution to complete the reaction, and the organic layer was extracted. After a column separation process was conducted using a solvent of n-hexane and tetrahydrofuran at a ratio of 8:1, stirring was conducted using petroleum ether, and vacuum drying was conducted to produce the compound of Formula 2-259 (3.5 g, yield 53%). MS: $[M+H]^+$=893.

Example 5

Preparation of the Compound Represented by Formula 2-273

1) Synthesis of arylamine (4-(N-phenyl-N-naphthylamino)-biphenyl-N-phenylamine) to produce the compound represented by Formula 2-273: 4.08 g of 4-chlorobiphenyl-N-phenyl-N-naphthylamine (10.1 mmol) and 1.38 ml of aniline (15.1 mmol) were dissolved in 100 ml of toluene, 2.90 g of sodium-tert-butoxide (30.2 mmol), 0.17 g of bis(dibenzylidene acetone)palladium(0) (0.30 mmol), and 0.26 ml of 50 wt % tri-tert-butylphosphine toluene solution (0.53 mmol) were added thereto, and reflux was conducted in a nitrogen atmosphere for 7 hours. Distilled water was added to the reaction solution to complete the reaction, and the organic layer was extracted. After a column separation process was conducted using a solvent of n-hexane and tetrahydrofuran at a ratio of 10:1, stirring was conducted using petroleum ether, and vacuum drying was conducted to produce an arylamine connection group (3.8 g, yield 82%). MS: $[M+H]^+$=463.

2) 3.13 g of compound of Formula b (6.47 mmol) and 3.3 g of 4-(N-phenyl-N-naphthylamino)-biphenyl-N-phenylamine (7.1 mmol) were dissolved in 40 ml of toluene, 1.94 g of sodium-tert-butoxide (22.4 mmol), 0.08 g of bis(dibenzylidene acetone)palladium(0) (0.14 mmol), and 0.11 ml of 50 wt % tri-tert-butylphosphine toluene solution (0.22 mmol) were added thereto, and reflux was conducted in a nitrogen atmosphere for 2 hours. Distilled water was added to the reaction solution to complete the reaction, and the organic layer was extracted. After a column separation process was conducted using a solvent of n-hexane and tetrahydrofuran at a ratio of 8:1, stirring was conducted using petroleum ether, and vacuum drying was conducted to produce the compound of Formula 2-273 (2.5 g, yield 45%). MS: $[M+H]^+$=867.

Example 6

Preparation of the Compound Represented by Formula 2-274

1) Synthesis of arylamine (4-(N-phenyl-N-naphthylamino)-biphenyl-N-naphthylamine) to produce the compound represented by Formula 274: 4.08 g of 4-chlorobiphenyl-N-phenyl-N-naphthylamine (10.1 mmol) and 2.16 g of 1-naphthylamine (15.1 mmol) were dissolved in 100 ml of toluene, 2.90 g of sodium-tert-butoxide (30.2 mmol), 0.17 g of bis(dibenzylidene acetone)palladium(0) (0.30 mmol), and 0.26 ml of 50 wt % tri-tert-butylphosphine toluene solution (0.53 mmol) were added thereto, and reflux was conducted in a nitrogen atmosphere for 7 hours. Distilled water was added to the reaction solution to complete the reaction, and the organic layer was extracted. After a column separation process was conducted using a solvent of n-hexane and tetrahydrofuran at a ratio of 10:1, stirring was conducted using petroleum ether, and vacuum drying was conducted to produce an arylamine connection group (3.8 g, yield 74%). MS: $[M+H]^+$=513.

2) 3.62 g of compound of Formula b (7.47 mmol) and 3.8 g of 4-(N-phenyl-N-naphthylamino)-biphenyl-N-naphthylamine (7.4 mmol) were dissolved in 40 ml of toluene, 1.94 g of sodium-tert-butoxide (22.4 mmol), 0.089 g of bis(dibenzylidene acetone)palladium(0) (0.16 mmol), and 0.11 ml of 50 wt % tri-tert-butylphosphine toluene solution (0.22 mmol) were added thereto, and reflux was conducted in a nitrogen atmosphere for 2 hours. Distilled water was added to the reaction solution to complete the reaction, and the organic layer was extracted. After a column separation process was conducted using a solvent of n-hexane and tetrahydrofuran at a ratio of 8:1, stirring was conducted using petroleum ether, and vacuum dying was conducted to produce the compound of Formula 2-274 (3.0 g, yield 44%). MS: $[M+H]^+$=917.

Example 7

Preparation of the Compound Represented by Formula 2-276

1) Synthesis of arylamine (4-(N-phenyl-N-naphthylamino)-biphenyl-N'-biphenylamine) to produce the compound represented by Formula 276: 4.08 g of 4-chlorobiphenyl-N-phenyl-N-naphthylamine (10.1 mmol) and 2.55 g of 4-aminobiphenyl (15.1 mmol) were dissolved in 100 ml of toluene, 2.90 g of sodium-tert-butoxide (30.2 mmol), 0.17 g of bis(dibenzylidene acetone)palladium(0) (0.30 mmol), and 0.26 ml of 50 wt % tri-tert-butylphosphine toluene solution (0.53 mmol) were added thereto, and reflux was conducted in a nitrogen atmosphere for 7 hours. Distilled water was added to the reaction solution to complete the reaction, and the organic layer was extracted. After a column separation process was conducted using a solvent of n-hexane and tetrahydrofuran at a ratio of 10:1, stirring was conducted using petroleum ether, and vacuum drying was conducted to produce an arylamine connection group (3.8 g, yield 70%). MS: $[M+H]^+$=539.

2) 3.13 g of compound of Formula b (6.47 mmol) and 3.8 g of 4-(N-phenyl-N-naphthylamino)-biphenyl-N'-biphenylamine (7.1 mmol) were dissolved in 40 ml of toluene, 1.94 g of sodium-tert-butoxide (22.4 mmol), 0.081 g of bis(dibenzylidene acetone)palladium(0) (0.14 mmol), and 0.11 ml of 50 wt % tri-tert-butylphosphine toluene solution (0.22 mmol) were added thereto, and reflux was conducted in a nitrogen atmosphere for 2 hours. Distilled water was added to the reaction solution to complete the reaction, and the organic layer was extracted. After a column separation process was conducted using a solvent of n-hexane and tetrahydrofuran at a ratio of 8:1, stirring was conducted using petroleum ether, and vacuum drying was conducted to produce the compound of Formula 2-276 (2.5 g, yield 41%). MS: $[M+H]^+$=943.

Example 8

Preparation of the Compound Represented by Formula 2-307

1) Synthesis of arylamine (4-(N-phenyl-N-biphenylamino)-biphenyl-N'-phenylamine) to produce the compound represented by Formula 307: 4.86 g of 4-chlorobiphenyl-N-phenyl-N-biphenylamine (11.2 mmol) and 1.13 ml of aniline (12.4 mmol) were dissolved in 100 ml of toluene, 2.70 g of sodium-tert-butoxide (28.1 mmol), 0.13 g of bis(dibenzylidene acetone)palladium(0) (0.23 mmol), and 0.17 ml of 50 wt % tri-tert-butylphosphine toluene solution (0.34 mmol) were added thereto, and reflux was conducted in a nitrogen atmosphere for 7 hours. Distilled water was added to the reaction solution to complete the reaction, and the organic layer was extracted. After a column separation process was conducted using a solvent of n-hexane and tetrahydrofuran at a ratio of 10:1, stirring was conducted using petroleum ether, and vacuum drying was conducted to produce an arylamine connection group (3.8 g, yield 69%). MS: $[M+H]^+$=489.

2) 3.13 g of compound of Formula b (6.47 mmol) and 3.5 g of 4-(N-phenyl-N-biphenylamino)-biphenyl-N'-phenylamine (7.1 mmol) were dissolved in 40 ml of toluene, 1.94 g of sodium-tert-butoxide (22.4 mmol), 0.081 g of bis(dibenzylidene acetone)palladium(0) (0.14 mmol), and 0.11 ml of 50 wt % tri-tert-butylphosphine toluene solution (0.22 mmol) were added thereto, and reflux was conducted in a nitrogen atmosphere for 2 hours. Distilled water was added to the reaction solution to complete the reaction, and the organic layer was extracted. After a column separation process was conducted using a solvent of n-hexane and tetrahydrofuran at a ratio of 8:1, stirring was conducted using petroleum ether, and vacuum drying was conducted to produce the compound of Formula 2-307 (2.6 g, yield 45%). MS: $[M+H]^+$=893.

Example 9

Preparation of the Compound Represented by Formula 2-308

1) Synthesis of arylamine (4-(N-phenyl-N-biphenylamino)-biphenyl-N'-naphthylamine) to produce the compound represented by Formula 308: 4.86 g of 4-chlorobiphenyl-N-phenyl-N-biphenylamine (11.2 mmol) and 1.78 ml of 1-naphthylamine (12.4 mmol) were dissolved in 100 ml of toluene, 2.70 g of sodium-tert-butoxide (28.1 mmol), 0.13 g of bis(dibenzylidene acetone)palladium(0) (0.23 mmol), and 0.17 ml of 50 wt % tri-tert-butylphosphine toluene solution (0.34 mmol) were added thereto, and reflux was conducted in a nitrogen atmosphere for 7 hours. Distilled water was added to the reaction solution to complete the reaction, and the organic layer was extracted. After a column separation process was conducted using a solvent of n-hexane and tetrahydrofuran at a ratio of 10:1, stirring was conducted using petroleum ether, and vacuum drying was conducted to produce an arylamine connection group (4.0 g, yield 69%). MS: $[M+H]^+$=539.

2) 3.13 g of compound of Formula b (6.47 mmol) and 3.8 g of 4-(N-phenyl-N-biphenylamino)-biphenyl-N'-naphthylamine (7.1 mmol) were dissolved in 40 ml of toluene, 1.94 g of sodium-tert-butoxide (22.4 mmol), 0.081 g of bis(dibenzylidene acetone)palladium(0) (0.14 mmol), and 0.11 ml of 50 wt % tri-tert-butylphosphine toluene solution (0.22 mmol) were added thereto, and reflux was conducted in a nitrogen atmosphere for 2 hours. Distilled water was added to the reaction solution to complete the reaction, and the organic layer was extracted. After a column separation process was conducted using a solvent of n-hexane and tetrahydrofuran at a ratio of 8:1, stirring was conducted using petroleum ether, and vacuum drying was conducted to produce the compound of Formula 2-308 (3.1 g, yield 51%). MS: $[M+H]^+=943$.

Example 10

Preparation of the Compound Represented by Formula 2-310

1) Synthesis of arylamine (4-(N-phenyl-N-biphenylamino)-biphenyl-N'-biphenylamine) to produce the compound represented by Formula 310: 4.86 g of 4-chlorobiphenyl-N-phenyl-N-biphenylamine (11.2 mmol) and 2.09 ml of 4-aminobiphenyl (12.4 mmol) were dissolved in 100 ml of toluene, 2.70 g of sodium-tert-butoxide (28.1 mmol), 0.13 g of bis(dibenzylidene acetone)palladium(0) (0.23 mmol), and 0.17 ml of 50 wt % tri-tert-butylphosphine toluene solution (0.34 mmol) were added thereto, and reflux was conducted in a nitrogen atmosphere for 5 hours. Distilled water was added to the reaction solution to complete the reaction, and the organic layer was extracted. After a column separation process was conducted using a solvent of n-hexane and tetrahydrofuran at a ratio of 10:1, stirring was conducted using petroleum ether, and vacuum drying was conducted to produce an arylamine connection group (3.6 g, yield 56%). MS: $[M+H]^+=565$.

2) 2.92 g of compound of Formula b (6.02 mmol) and 3.57 g of 4-(N-phenyl-N-biphenylamino)-biphenyl-N'-biphenylamine (6.32 mmol) were dissolved in 40 ml of toluene, 1.94 g of sodium-tert-butoxide (22.4 mmol), 0.073 g of bis(dibenzylidene acetone)palladium(0) (0.13 mmol), and 0.10 ml of 50 wt % tri-tert-butylphosphine toluene solution (0.19 mmol) were added thereto, and reflux was conducted in a nitrogen atmosphere for 2 hours. Distilled water was added to the reaction solution to complete the reaction, and the organic layer was extracted. After a column separation process was conducted using a solvent of n-hexane and tetrahydrofuran at a ratio of 8:1, stirring was conducted using petroleum ether, and vacuum drying was conducted to produce the compound of Formula 2-310 (2.5 g, yield 43%). MS: $[M+H]^+=969$.

Example 11

Preparation of the Compound Represented by Formula 3-2

1) Synthesis of arylamine (4-(N-phenyl-N-phenylamino) phenyl-1-naphthylamine) to produce the compound represented by Formula 3-2: Synthesis was conducted through the same procedure as in synthesis of the arylamine connection group of Formula 2-2.

2) 4.97 g of compound of Formula c (9.63 mmol) and 5.58 g of 4-(N-phenyl-N-phenylamino)phenyl-1-naphthylamine (12.4 mmol) were dissolved in 50 ml of toluene, 1.85 g of sodium-tert-butoxide (19.3 mmol), 0.11 g of bis(dibenzylidene acetone)palladium(0) (0.19 mmol), and 0.14 ml of 50 wt % tri-tert-butylphosphine toluene solution (0.29 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 4:1, stirring was conducted using petroleum ether, and vacuum drying was conducted to produce the compound of Formula 3-2 (4.5 g, yield 54%). MS: $[M+H]^+=865$.

Example 12

Production of an Organic Light Emitting Device

Hexanitrile hexaazatriphenylene (hereinafter, referred to as "HAT") of the following Formula was vacuum deposited to a thickness of 500 Å by heating on a transparent ITO electrode, which was prepared through the above procedure, so as to form an anode including an ITO conductive layer and an N-type organic material.

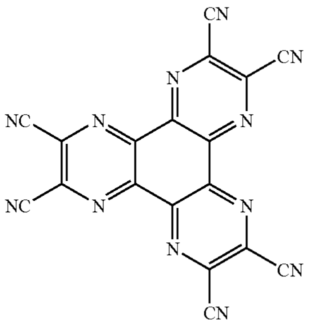

[HAT]

The compound of Formula 2-2 (400 Å) was vacuum deposited thereon to form a hole transport layer. Alq3 was vacuum deposited to a thickness of 300 Å on the hole transport layer to form a light emitting layer. An electron transport layer material of the following Formula was deposited to a thickness of 200 Å on the light emitting layer to form an electron transport layer.

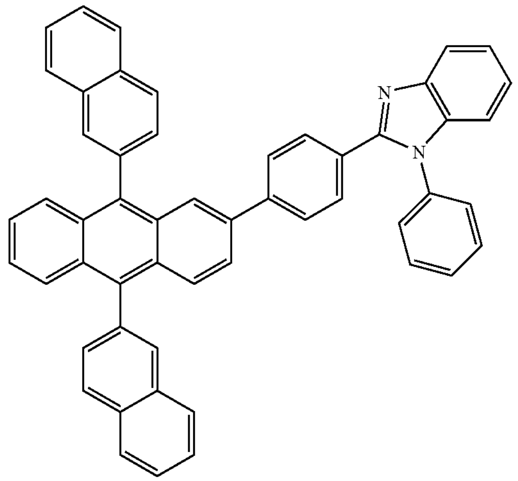

Electron transport layer material

Lithium fluoride (LiF) having a thickness of 12 Å and aluminum having a thickness of 2000 Å were sequentially deposited on the electron transport layer to form a cathode.

In the above procedure, the deposition speed of an organic material was maintained at 0.3-0.8 Å/sec. Furthermore, lithium fluoride and aluminum were deposited at speeds of 0.3 Å/sec and 1.5-2.5 Å/sec, respectively, on the cathode. During the deposition, a vacuum was maintained at $1\text{-}3\times10^{-7}$.

The resulting device had an electric field of 7.44 V at a forward current density of 100 $mA/cm^2$, and a spectrum having a light efficiency of 1.69 lm/W. The operation and light emission of the device at the above-mentioned actuating voltage mean that the compound of Formula 2-2, which formed the layer between the hole injection layer and the light emitting layer, functions to transport holes.

Example 13

Production of an Organic Light Emitting Device

HAT was deposited on an ITO substrate, which was prepared through the procedure of example 12, to a thickness of 80 Å to form a thin film. The thin film can improve the characteristics of an interface of the substrate and a hole injection layer. Subsequently, the compound of Formula 2-2 was deposited on the thin film to a thickness of 800 Å to form the hole injection layer.

NPB was deposited on the hole injection layer to a thickness of 300 Å so as to form a hole transport layer, and Alq3 was then deposited thereon to a thickness of 300 Å to form a light emitting layer. An electron transport layer and a cathode were formed on the light emitting layer through the same procedure as example 14.

In the present example, deposition speeds of an organic material and the cathode were the same as those of example 12.

The resulting device had an electric field of 9.36 V at a forward current density of 100 $mA/cm^2$, and a spectrum having a light efficiency of 2.38 lm/W. The operation and light emission of the device at the above-mentioned actuating voltage mean that the compound of Formula 2-2, which formed the layer between the thin film on the substrate and the hole transport layer, functions to inject holes.

Example 14

Production of an Organic Light Emitting Device

The procedure of example 12 was repeated to produce a device except that the compound of Formula 2-256 was used as the hole transport layer instead of the compound of Formula 2-2.

The resulting device had an electric field of 8.05 V at a forward current density of 100 $mA/cm^2$, and a spectrum having a light efficiency of 2.01 lm/W.

Example 15

Production of an Organic Light Emitting Device

The procedure of example 12 was repeated to produce a device except that the compound of Formula 2-257 was used as the hole transport layer instead of the compound of Formula 2-2.

The resulting device had an electric field of 8.08 V at a forward current density of 100 $mA/cm^2$, and a spectrum having a light efficiency of 2.37 ml/W.

Example 16

Production of an Organic Light Emitting Device

The procedure of example 12 was repeated to produce a device except that the compound of Formula 2-259 was used as the hole transport layer instead of the compound of Formula 2-2.

The resulting device had an electric field of 8.00 V at a forward current density of 100 $mA/cm^2$, and a spectrum having a light efficiency of 2.23 lm/W.

Example 17

Production of an Organic Light Emitting Device

The procedure of example 12 was repeated to produce a device except that the compound of Formula 2-273 was used as the hole transport layer instead of the compound of Formula 2-2.

The resulting device had an electric field of 8.02 V at a forward current density of 100 $mA/cm^2$, and a spectrum having a light efficiency of 2.16 lm/W.

Example 18

Production of an Organic Light Emitting Device

The procedure of example 12 was repeated to produce a device except that the compound of Formula 2-274 was used as the hole transport layer instead of the compound of Formula 2-2.

The resulting device had an electric field of 4.43 V at a forward current density of 100 $mA/cm^2$, and a spectrum having a light efficiency of 2.24 lm/W.

Example 19

Production of an Organic Light Emitting Device

The procedure of example 12 was repeated to produce a device except that the compound of Formula 2-276 was used as the hole transport layer instead of the compound of Formula 2-2.

The resulting device had an electric field of 8.13 V at a forward current density of 100 $mA/cm^2$, and a spectrum having a light efficiency of 2.32 lm/W.

Example 20

Production of an Organic Light Emitting Device

The procedure of example 12 was repeated to produce a device except that the compound of Formula 2-307 was used as the hole transport layer instead of the compound of Formula 2-2.

The resulting device had an electric field of 8.05 V at a forward current density of 100 $mA/cm^2$, and a spectrum having a light efficiency of 2.03 lm/W.

Example 21

Production of an Organic Light Emitting Device

The procedure of example 12 was repeated to produce a device except that the compound of Formula 2-308 was used as the hole transport layer instead of the compound of Formula 2-2.

The resulting device had an electric field of 8.07 V at a forward current density of 100 $mA/cm^2$, and a spectrum having a light efficiency of 2.23 lm/W.

Example 22

Production of an Organic Light Emitting Device

The procedure of example 12 was repeated to produce a device except that the compound of Formula 2-310 was used as the hole transport layer instead of the compound of Formula 2-2.

The resulting device had an electric field of 8.01 V at a forward current density of 100 $mA/cm^2$, and a spectrum having a light efficiency of 2.19 lm/W.

Example 23

Production of an Organic Light Emitting Device

The procedure of example 12 was repeated to produce a device except that the compound of Formula 3-2 was used as the hole transport layer instead of the compound of Formula 2-2.

The resulting device had an electric field of 7.34 V at a forward current density of 100 $mA/cm^2$, and a spectrum having a light efficiency of 1.73 lm/W.

INDUSTRIAL APPLICABILITY

The compound of the present invention can be used as an organic material layer material, particularly, hole injection and/or transport materials in an organic light emitting device, and when applied to an organic light emitting device it is possible to reduce the actuating voltage of the device, to improve the light efficiency thereof, and to improve the lifespan of the device through the thermal stability of the compound.

The invention claimed is:

1. An organic light emitting device, comprising:

a first electrode;

organic material layer(s) comprising a light emitting layer, wherein at least one layer of the organic material layer(s) includes the compound of Formula 1; and a second electrode;

wherein the first electrode, the organic material layer(s), and the second electrode form layered structure,

[Formula 1]

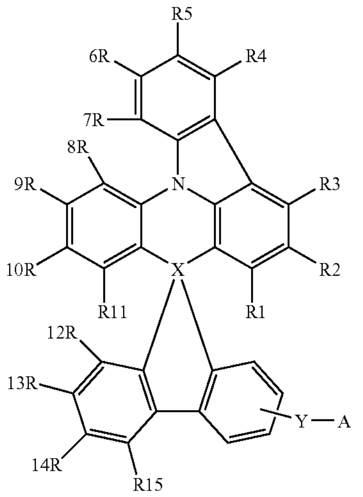

wherein X is C or Si;

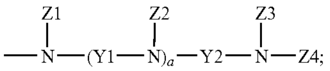

A is a is zero or positive integer;

Y is a bond; bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups;

Y1 and Y2 are each bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups;

Z1 to Z4 are each independently hydrogen; aliphatic hydrocarbons having a carbon number of 1-20; aromatic hydrocarbons; aromatic hydrocarbons which are substituted with at least one substituent group selected from the group consisting of the nitro, nitrile, halogen, alkyl, alkoxy, amino, aromatic hydrocarbon, and heterocyclic groups; a silicon group substituted with aromatic hydrocarbons; a heterocyclic group; a heterocyclic group which is substituted with at least one substituent group selected from the group consisting of the nitro, nitrile, halogen, alkyl, alkoxy, amino, aromatic hydrocarbon, and heterocyclic groups; a thiophenyl group which is substituted with hydrocarbons having a carbon number of 1-20 or aromatic hydrocarbons having a carbon number of 6-20; or a boron group which is substituted with aromatic hydrocarbons;

R1 to R11 are each independently hydrogen, a substituted or unsubstituted alkyl group, a substituted or unsubstituted alkoxy group, a substituted or unsubstituted alkenyl group, a substituted or unsubstituted aryl group, a substituted or un-substituted arylamine group, a substituted or unsubstituted heterocyclic group, an amino group, a nitrile group, a nitro group, a halogen group, an amide group, or an ester group, R1 to R11 may form aliphatic or hetero condensation rings along with adjacent groups;

R12 to R15 are each independently hydrogen, a substituted or unsubstituted alkyl group, a substituted or unsubstituted alkoxy group, a substituted or unsubstituted alkenyl group, a substituted or unsubstituted aryl group, a substituted or un-substituted heterocyclic group, an amino group, a nitrile group, a nitro group, a halogen group, an amide group, or an ester group, R12 to R15 may form aliphatic or hetero condensation rings along with adjacent groups; and R7 and R8 may be directly connected to each other, or may form a condensation ring along with a group selected from the group consisting of O, S, NR, PR, C.dbd.O, CRR', and SiRR', wherein R and R' each independently or collectively are hydrogen, a substituted or unsubstituted alkyl group, a substituted or un-substituted alkoxy group, a substituted or unsubstituted alkenyl group, a substituted or unsubstituted aryl group, a substituted or unsubstituted arylamine group, a substituted or unsubstituted heterocyclic group, a nitrile group, an amide group, or an ester group, and may form a condensation ring to form a spiro compound.

2. The organic light emitting device as set forth in claim 1, wherein R7 and R8 of Formula 1 form a condensation ring along with a group selected from the group consisting of O, S, NR, PR, C.dbd.O, CRR', and SiRR'.

3. The organic light emitting device as set forth in claim 1, wherein the compound of Formula 1 is any one of compounds of Formulae 2 to 5:

[Formula 2]

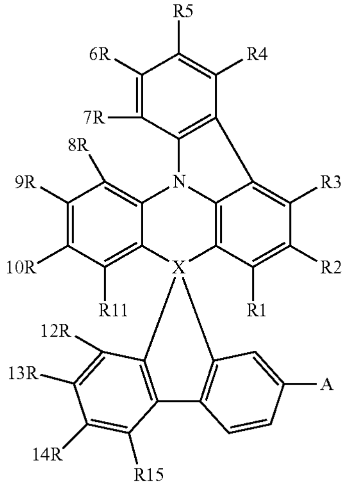

-continued

[Formula 3]

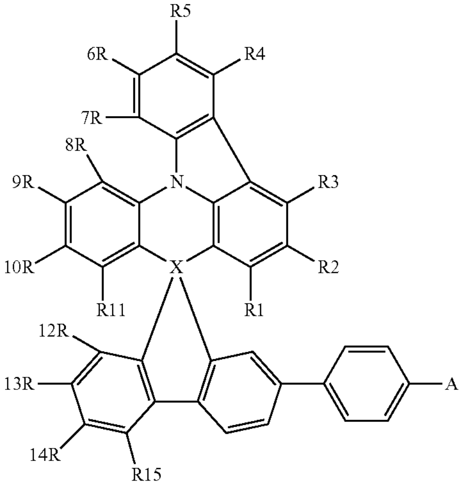

[Formula 4]

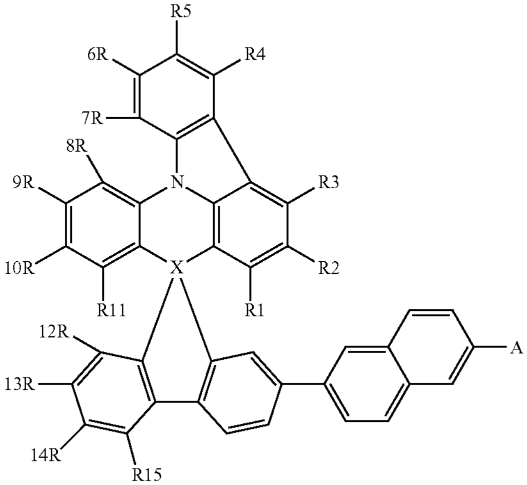

and

[Formula 5]

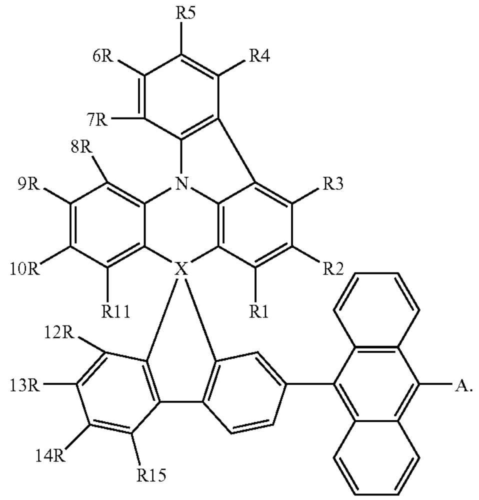

4. The organic light emitting device as set forth in claim 1, wherein A of Formula 1 is any one of following groups:

1
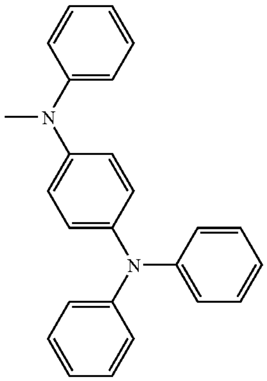
2
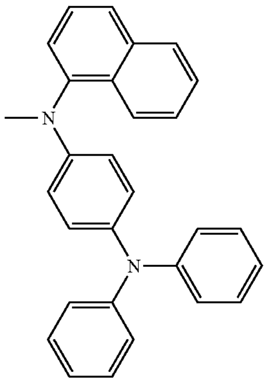
3
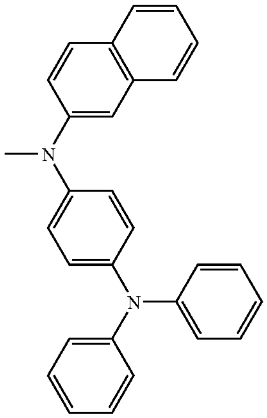
-continued
4
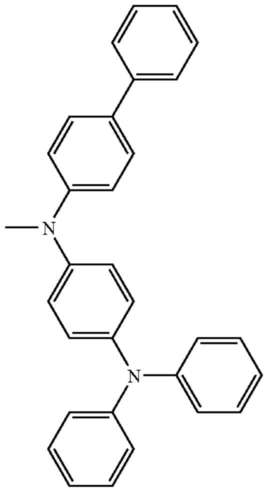
5
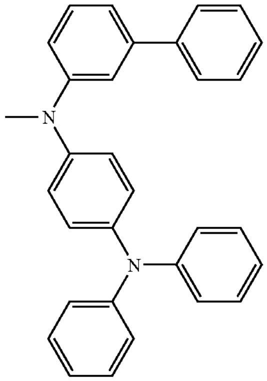
6
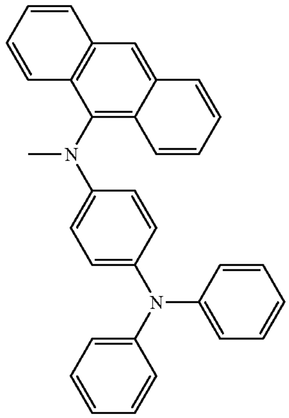

-continued
7
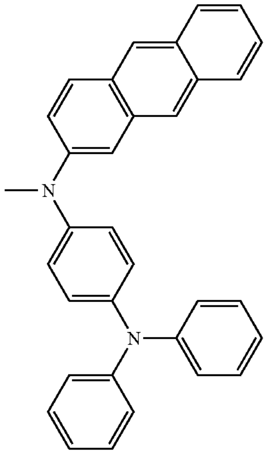
8
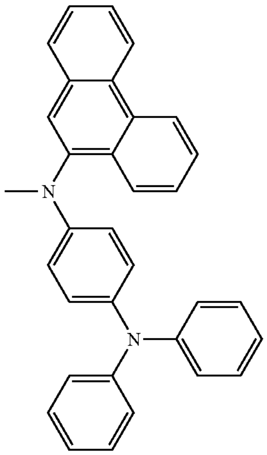
9
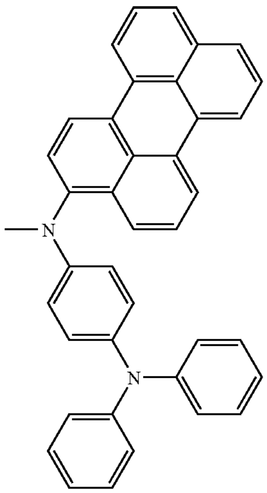
-continued
10
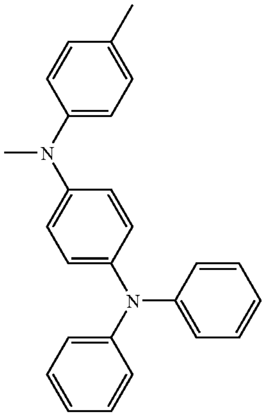
11
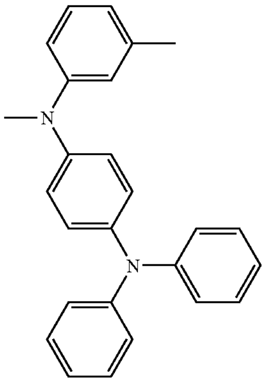
12
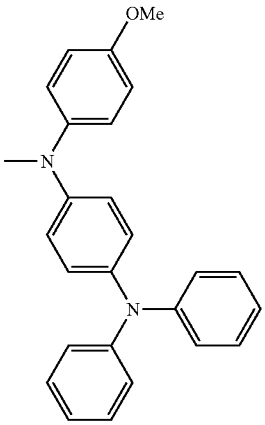
13
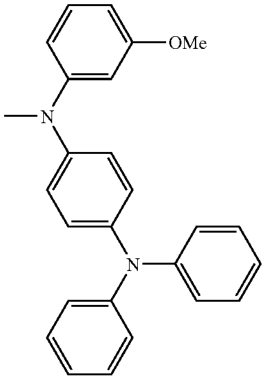

-continued
14
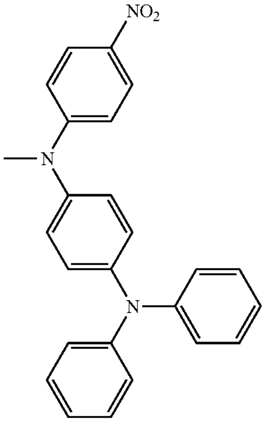
15
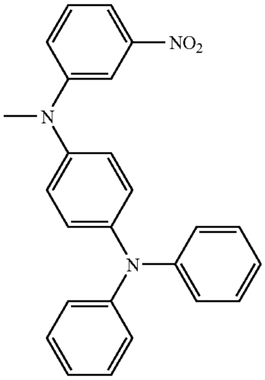
16
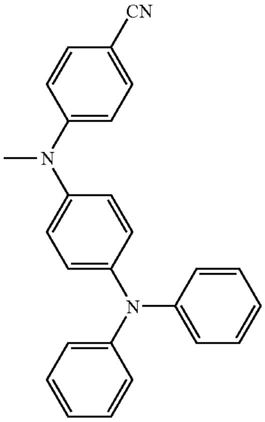
17
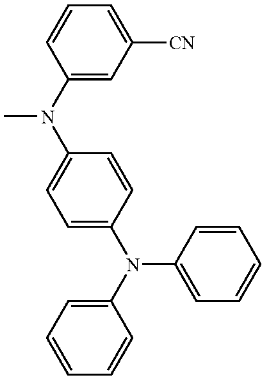
-continued
18
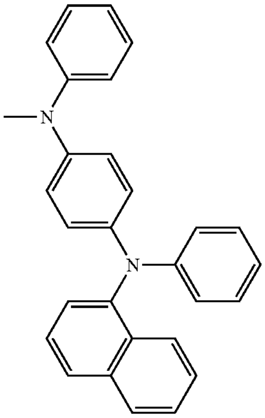
19
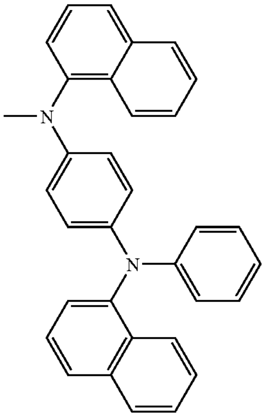
20
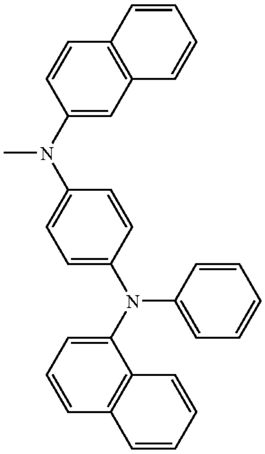

-continued
21
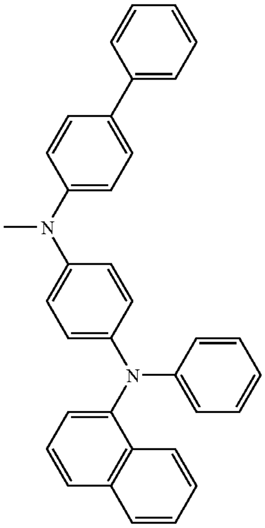
22
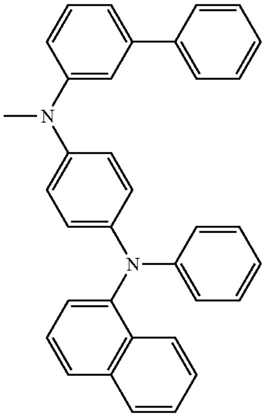
23
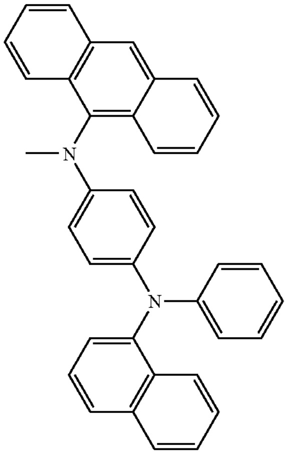
-continued
24
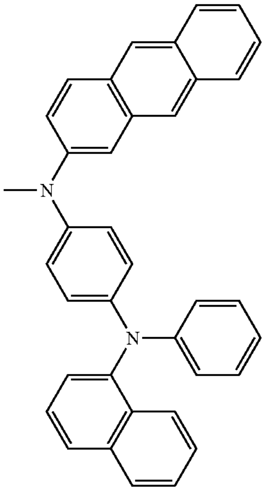
25
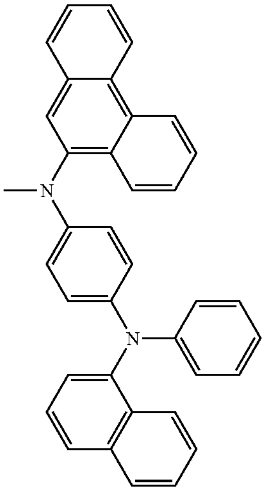
26
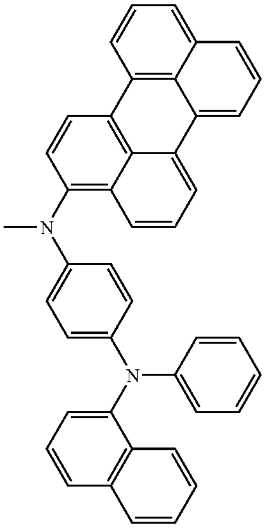

-continued
27
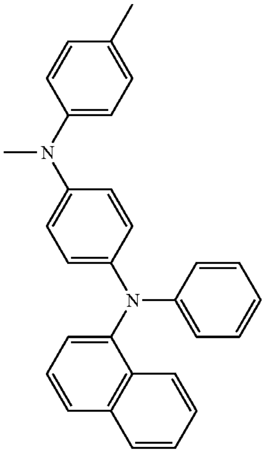
28
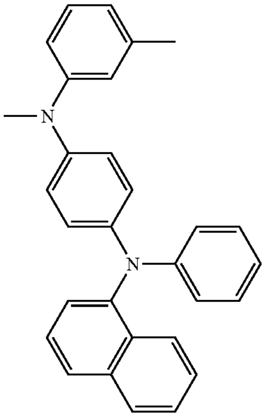
29
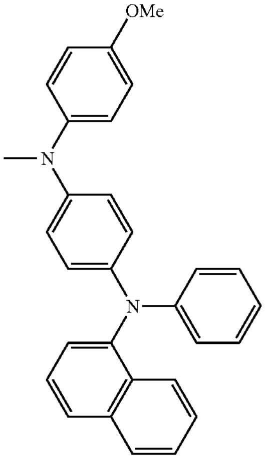
-continued
30
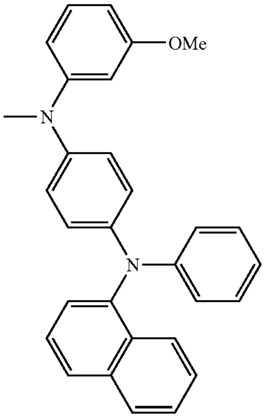
31
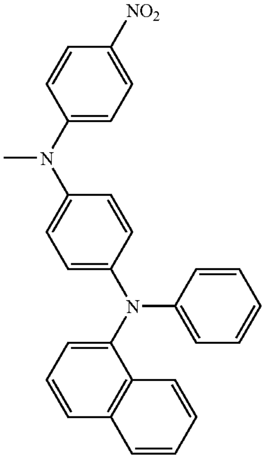
32
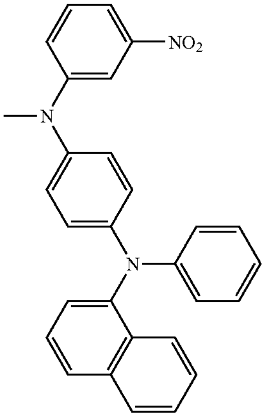

-continued
33
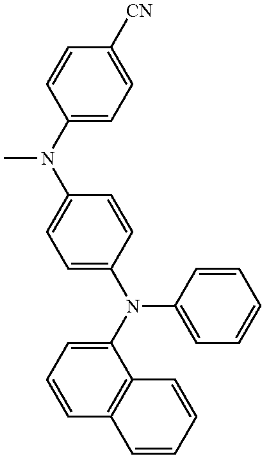
34
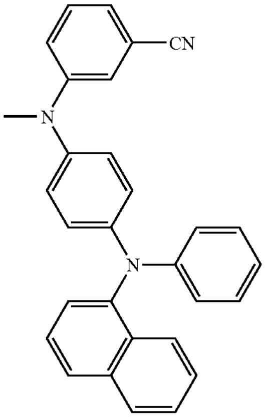
35
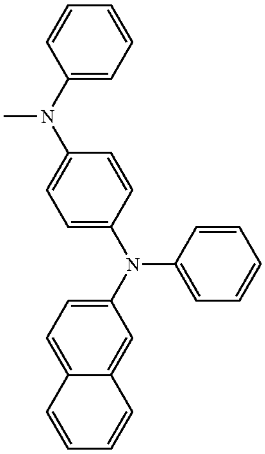
-continued
36
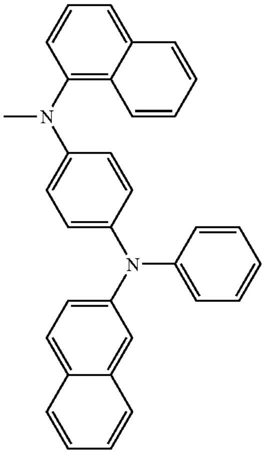
37
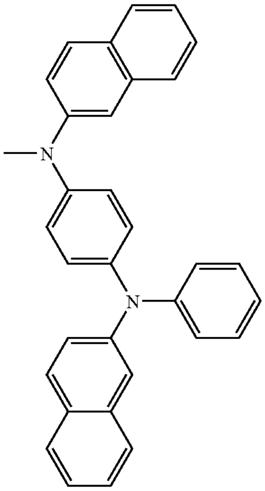
38
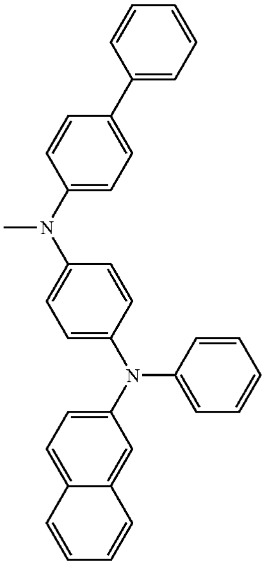

-continued
39
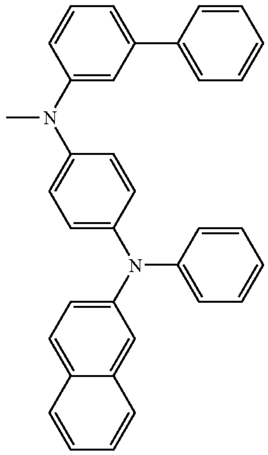
40
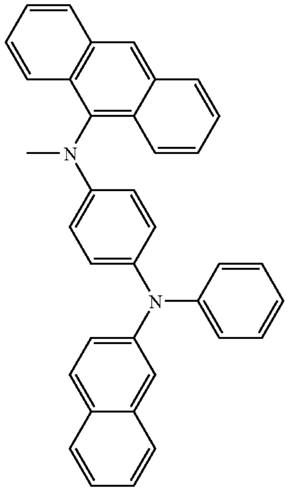
41
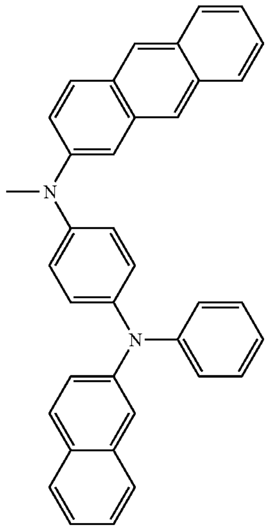
-continued
42
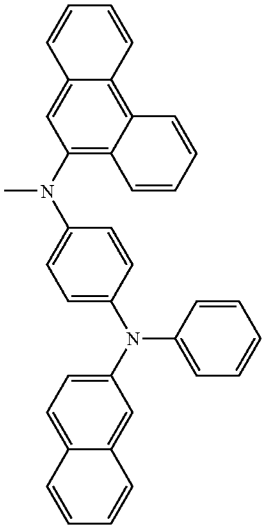
43
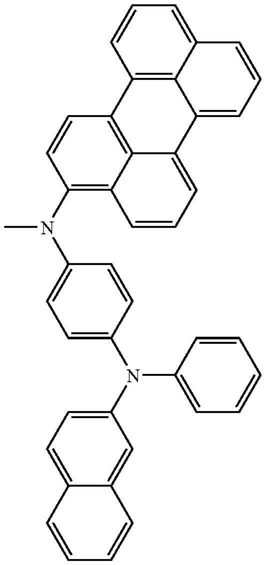
44
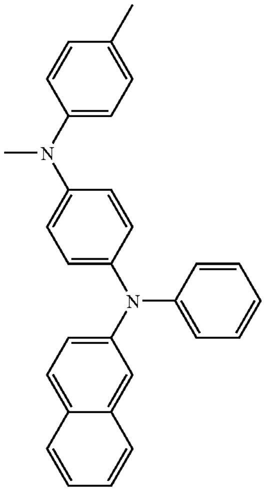

-continued
45
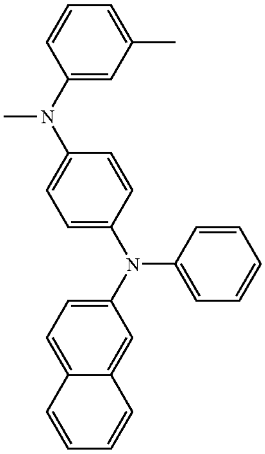
46
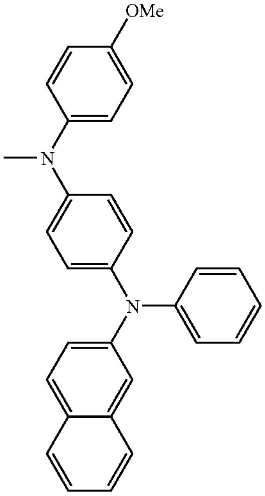
47
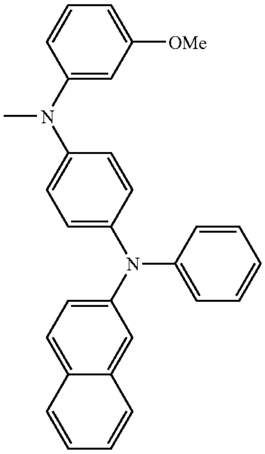
-continued
48
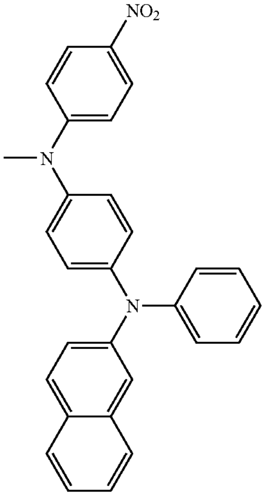
49
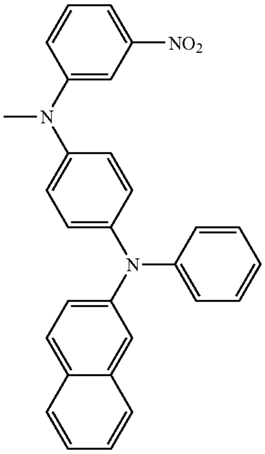
50
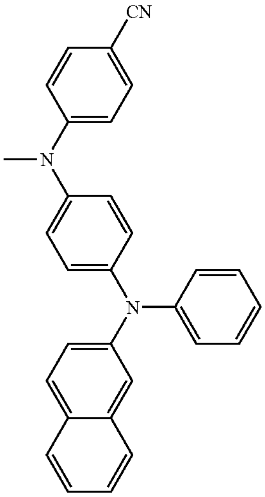

-continued
51
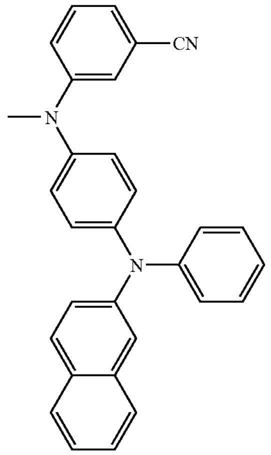
52
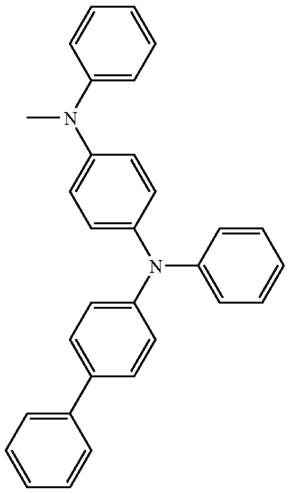
53
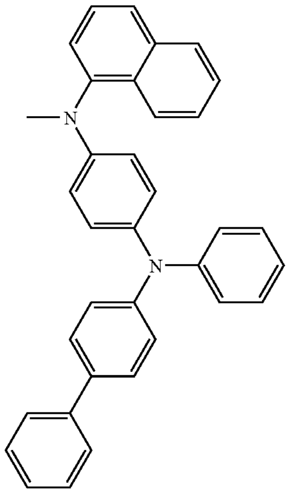
-continued
54
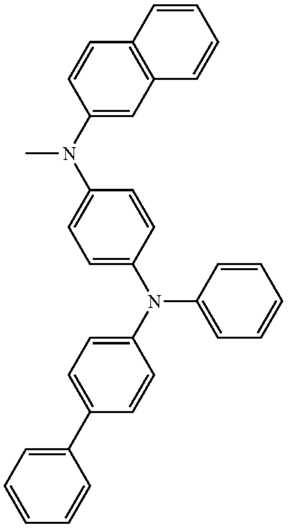
55
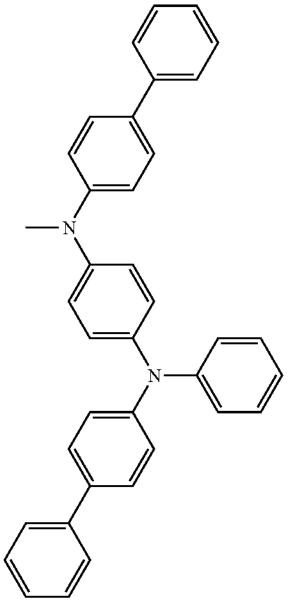
56
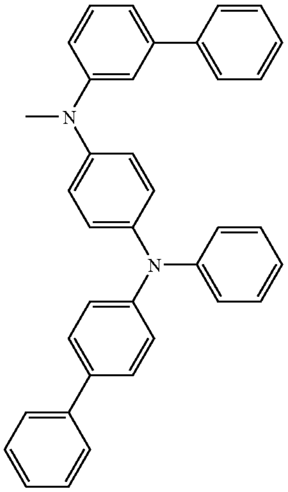

-continued
57
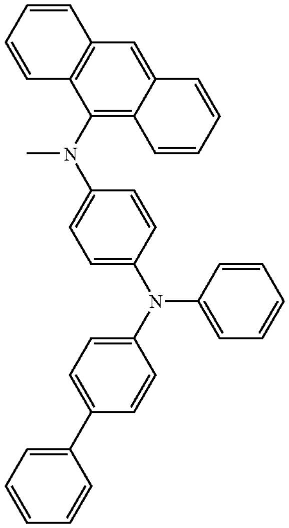
58
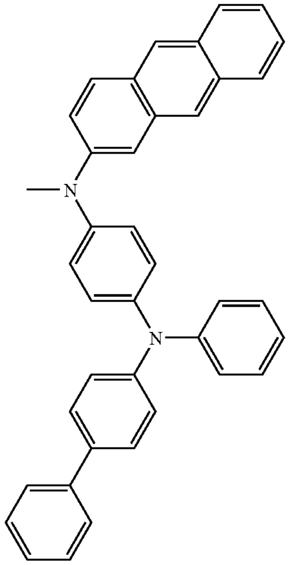
59
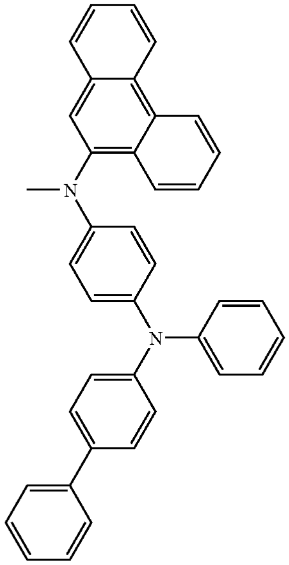
-continued
60
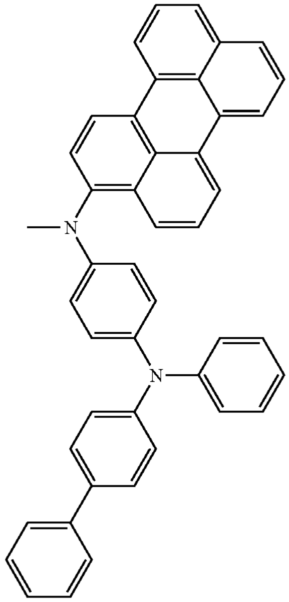
61
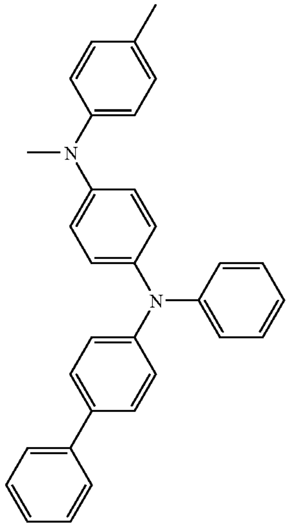
62
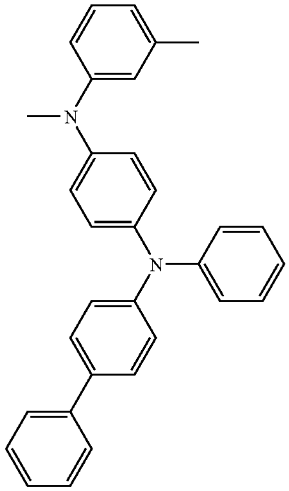

-continued
63
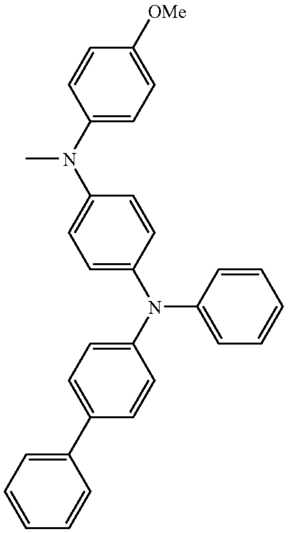
64
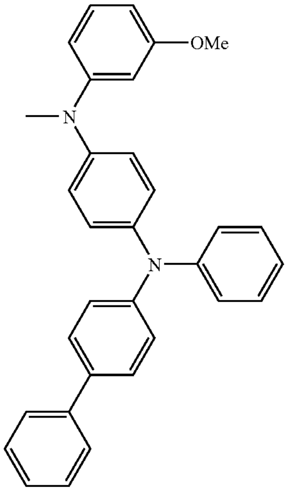
65
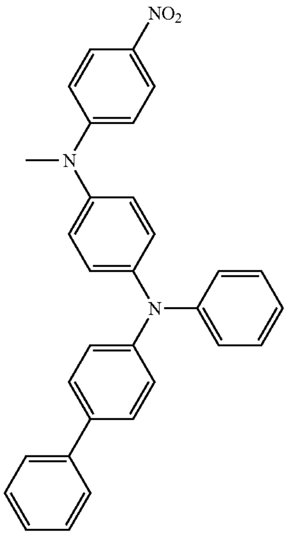
-continued
66
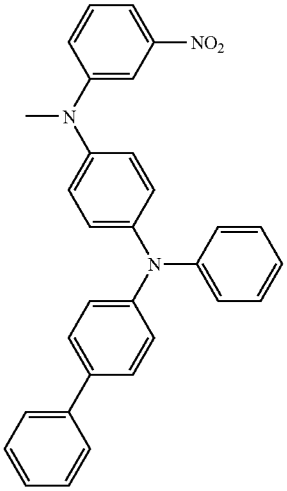
67
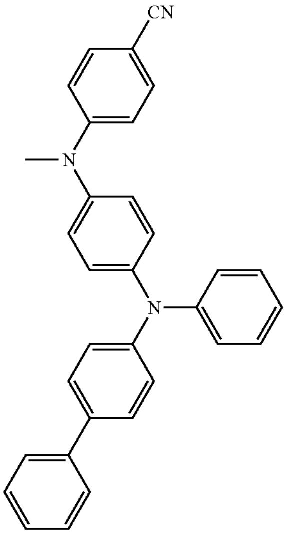
68
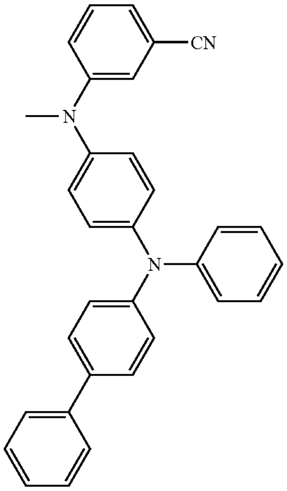

-continued
69
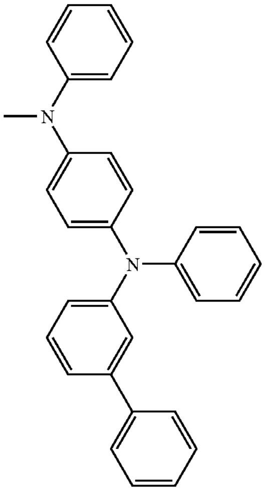
70
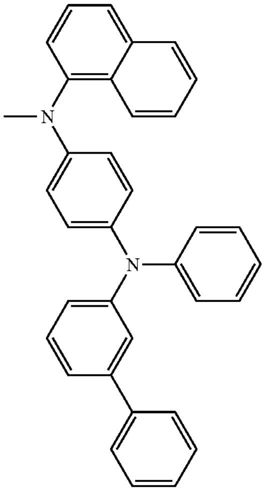
71
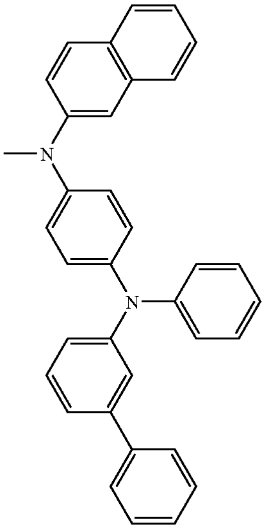
-continued
72
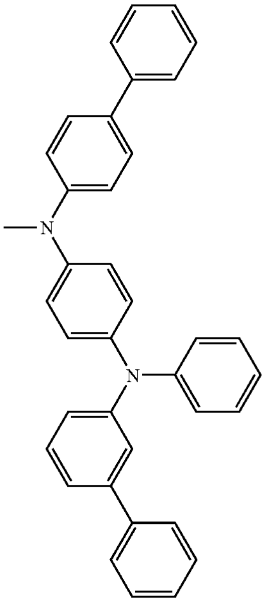
73
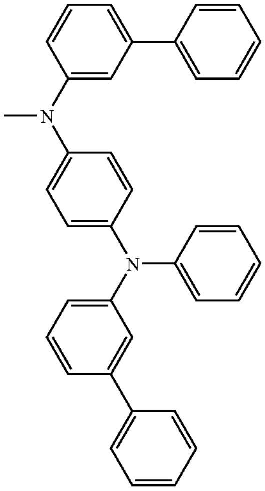
74
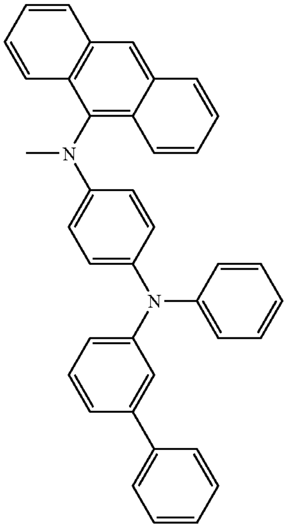

-continued
75
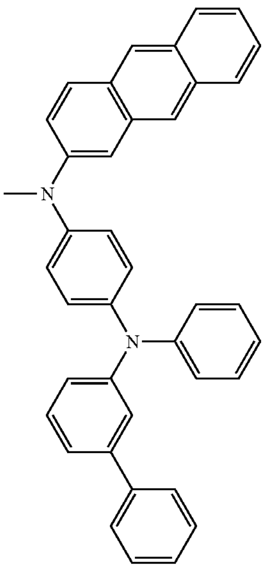
76
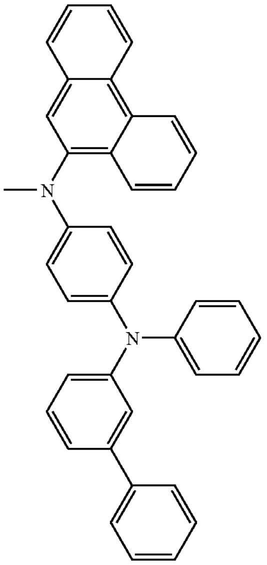
-continued
77
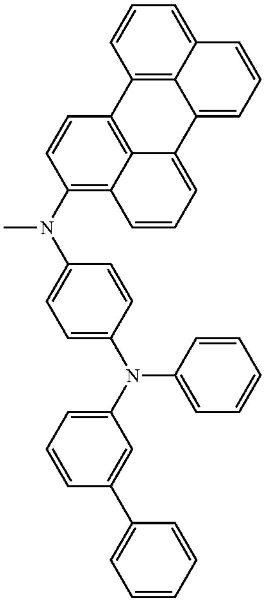
78
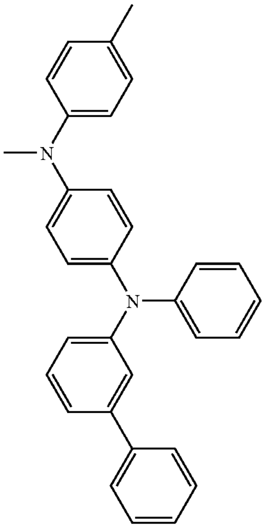
79
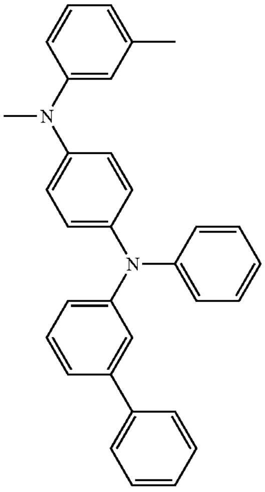

-continued
80
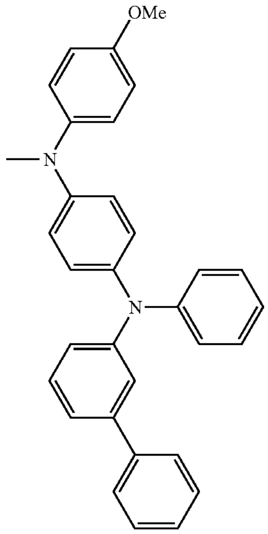
81
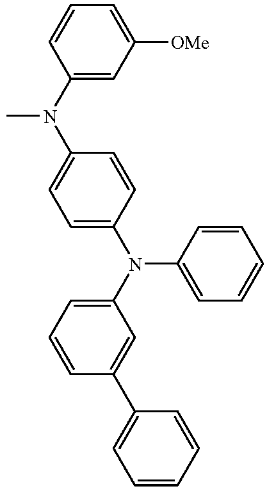
82
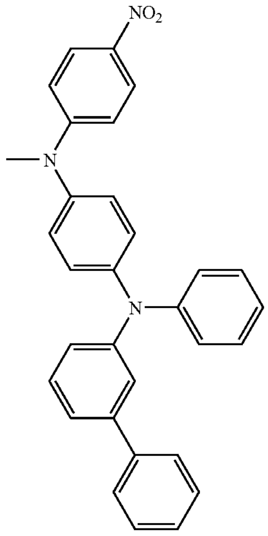
-continued
83
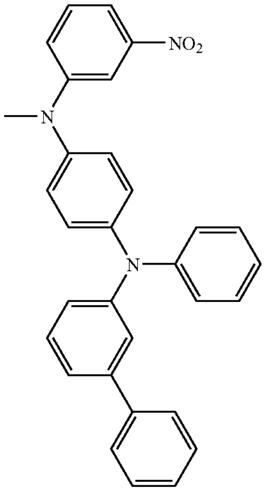
84
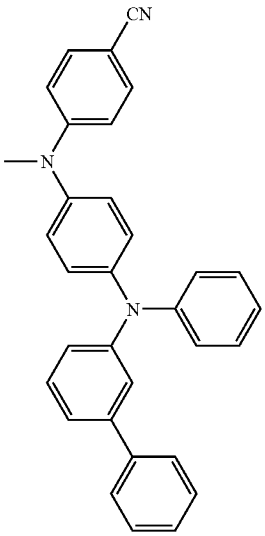
85
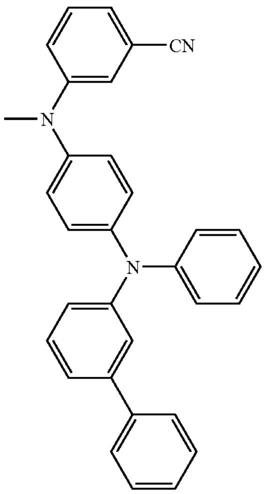

-continued
86
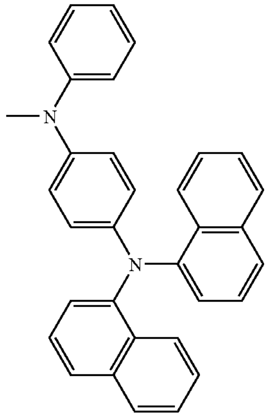
87
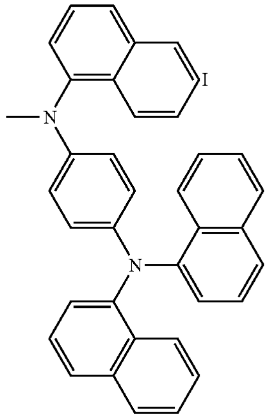
88
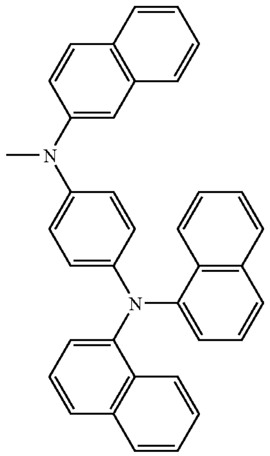
-continued
89
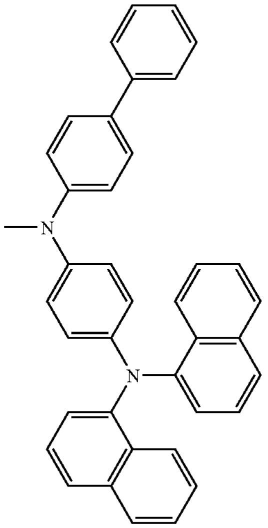
90
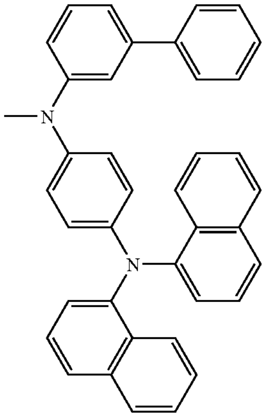
91
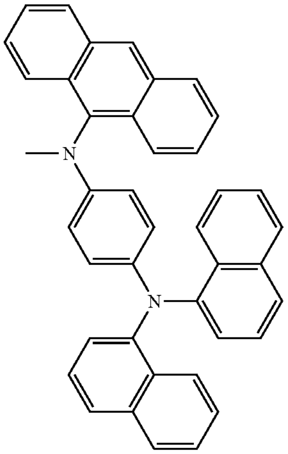

-continued
92
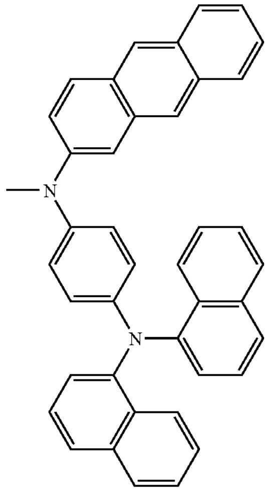
93
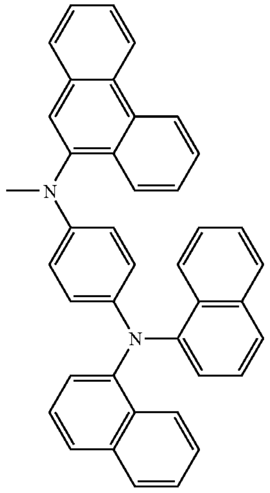
94
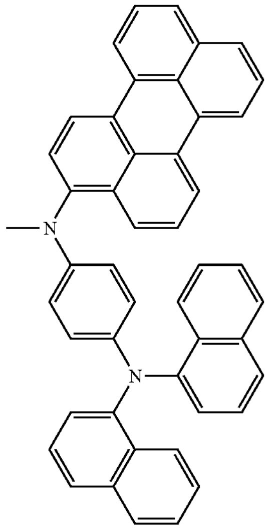
-continued
95
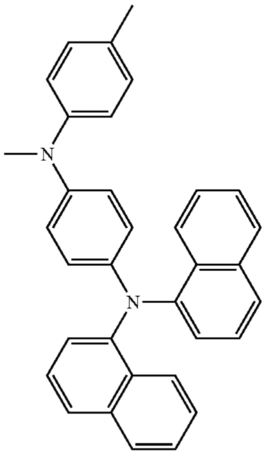
96
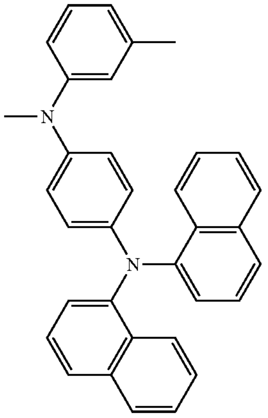
97
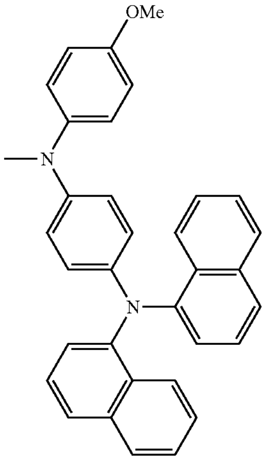

-continued
98
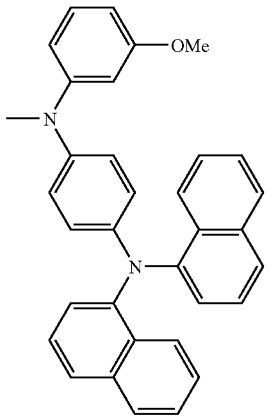
99
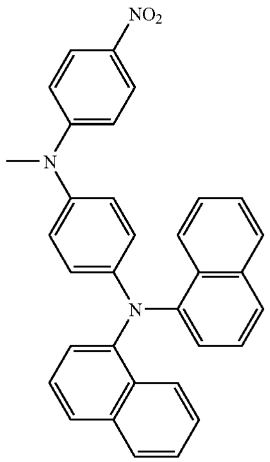
100
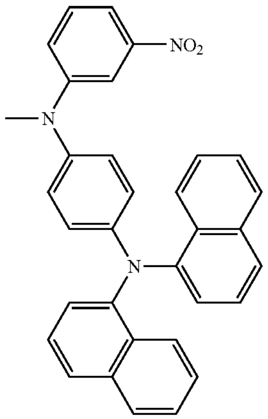
-continued
101
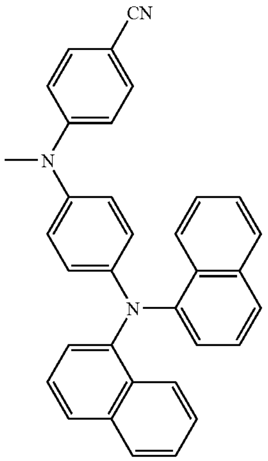
102
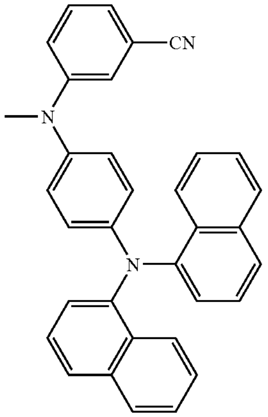
103
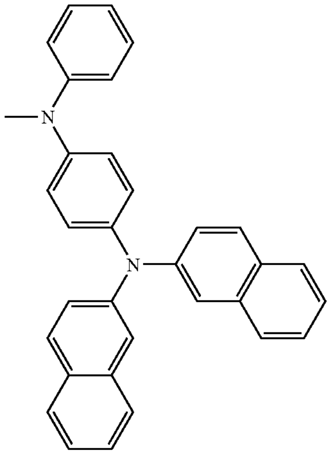

-continued
104
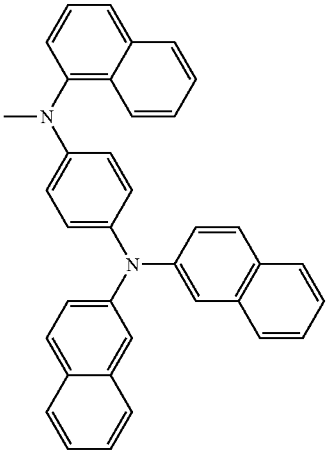
105
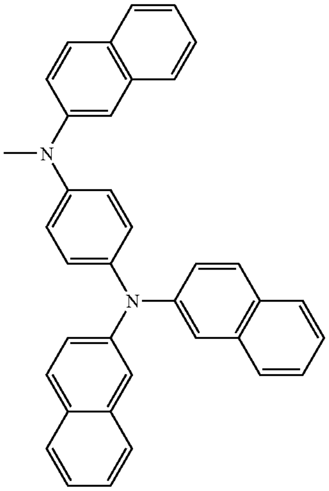
106
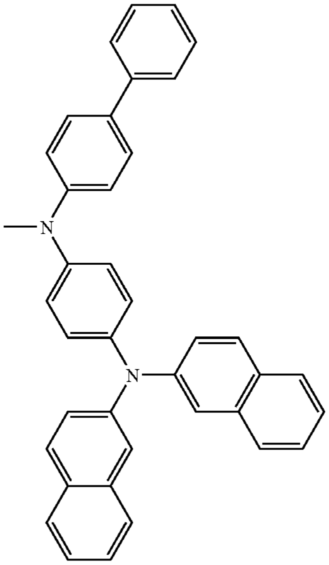
-continued
107
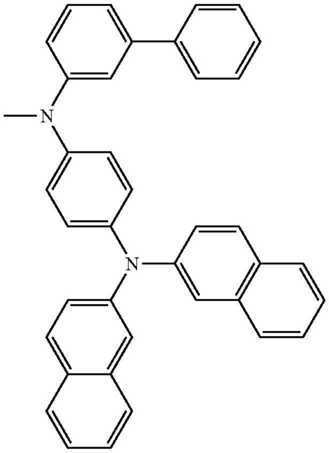
108
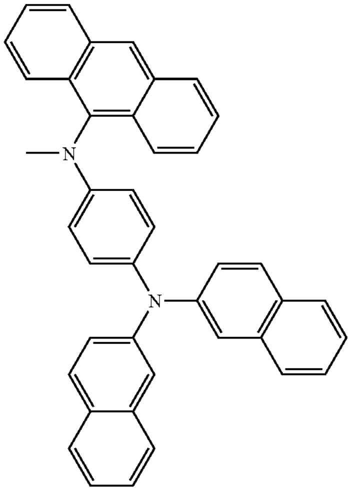
109
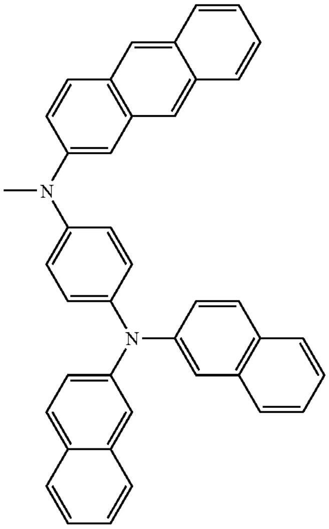

-continued
110
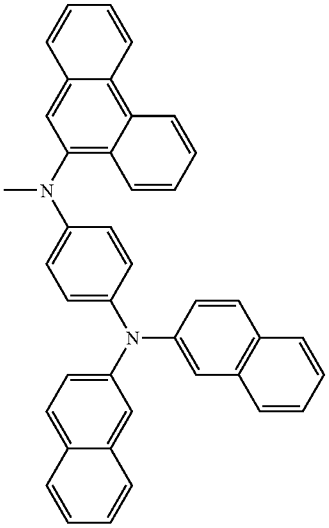
111
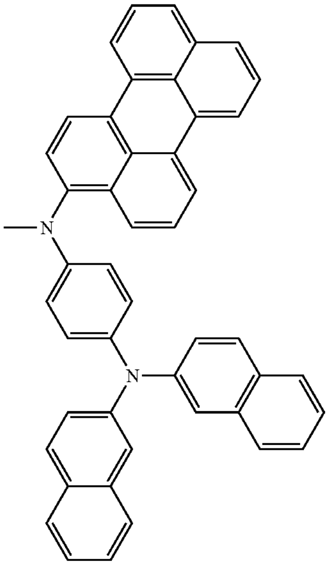
112
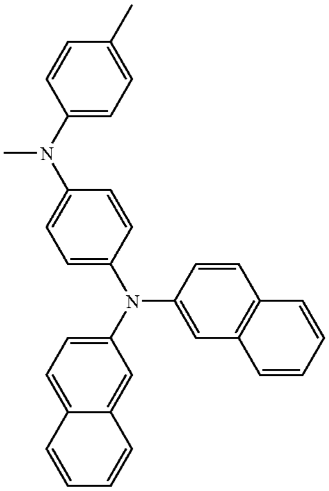
-continued
113
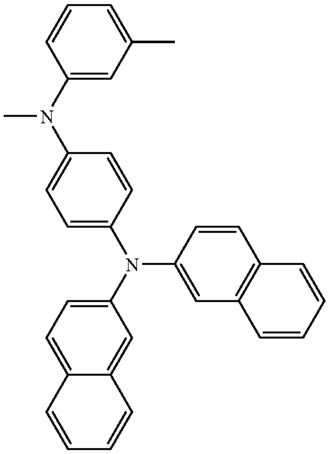
114
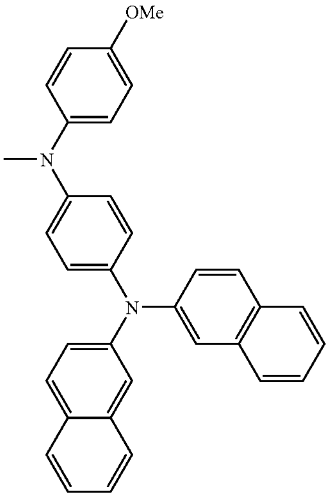
115
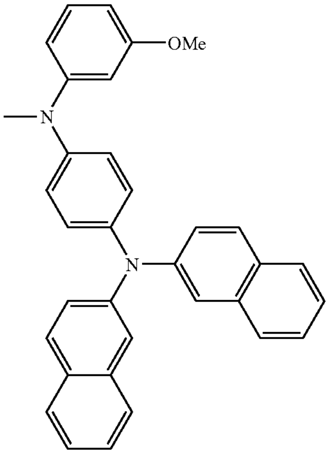

-continued
116
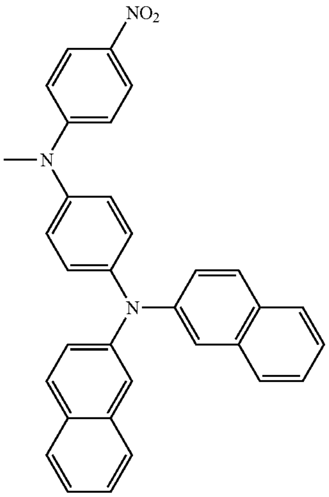
117
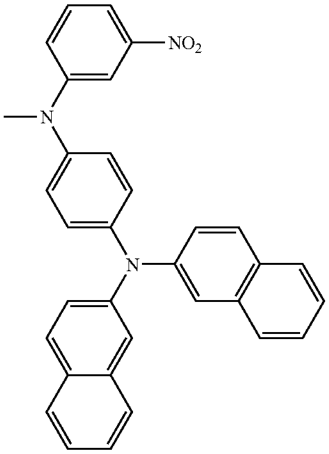
118
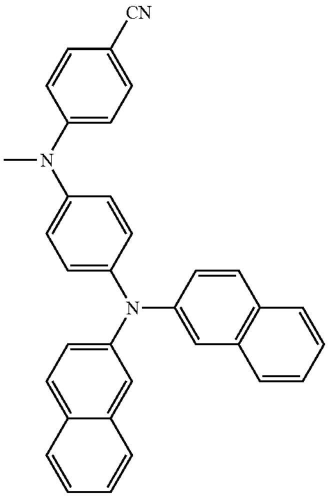
-continued
119
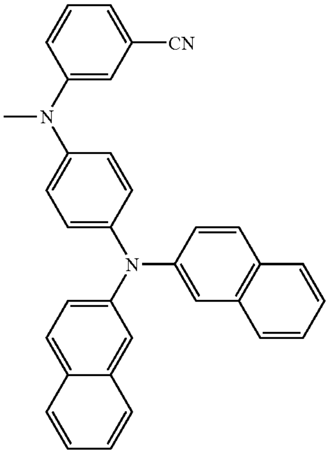
120
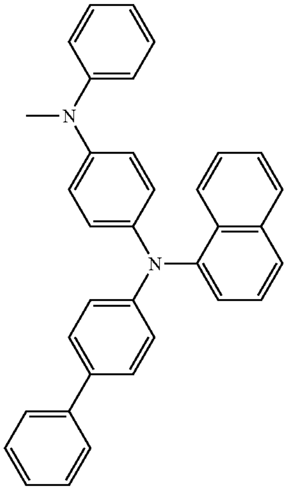
121
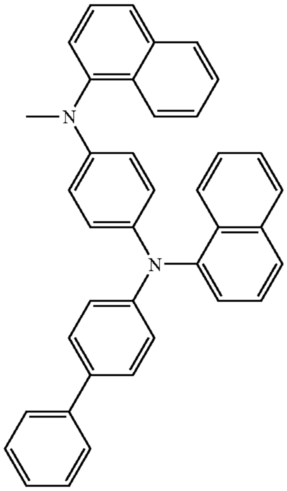

-continued
122
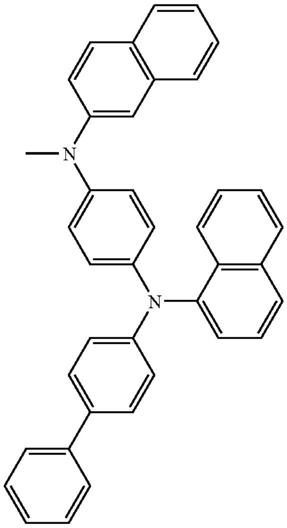
123
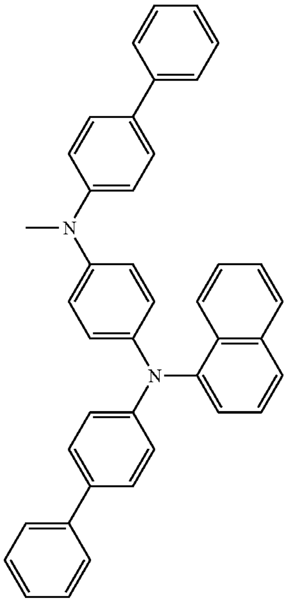
124
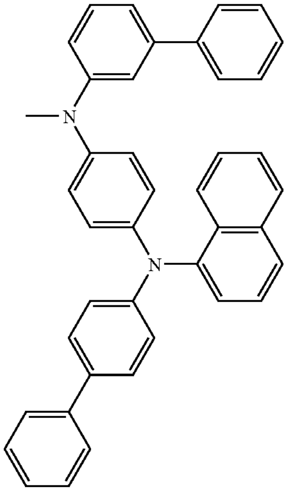
-continued
125
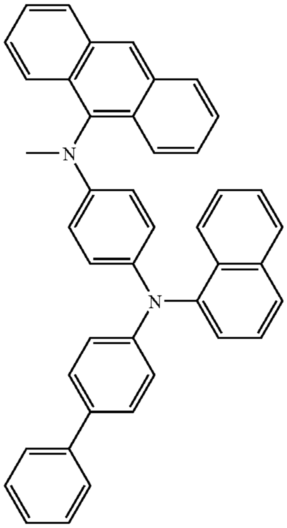
126
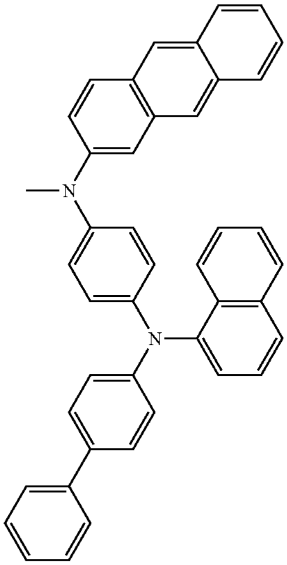
127
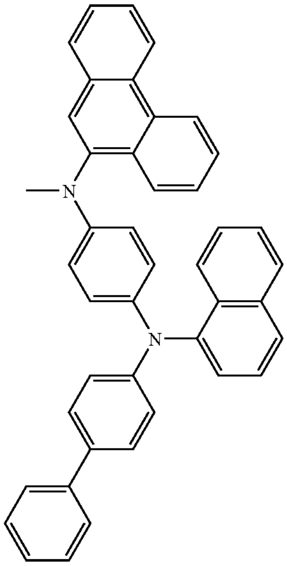

-continued
128
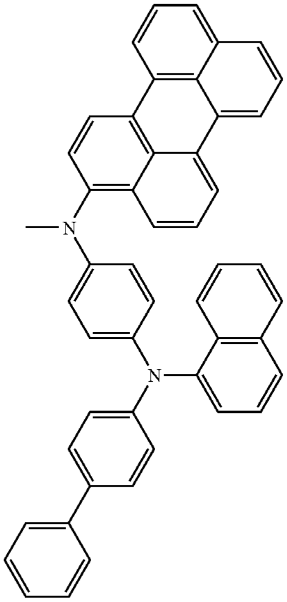
129
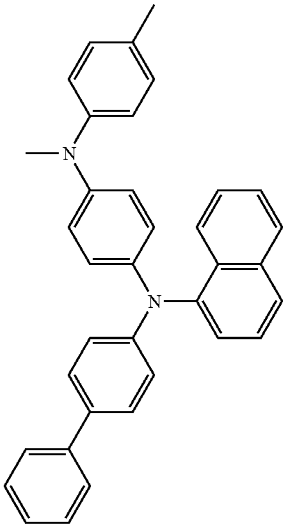
130
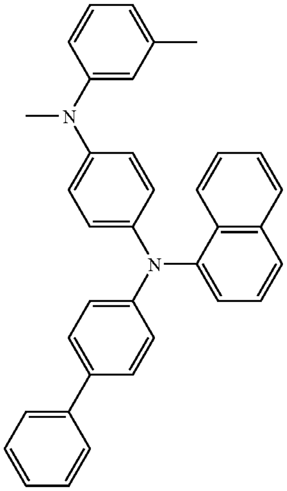
-continued
131
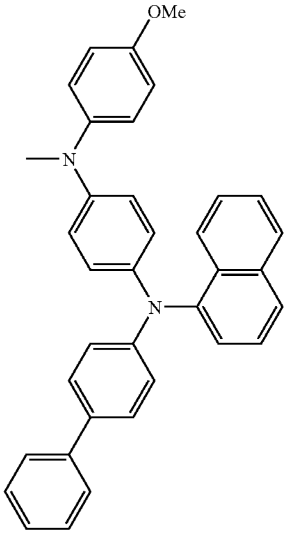
132
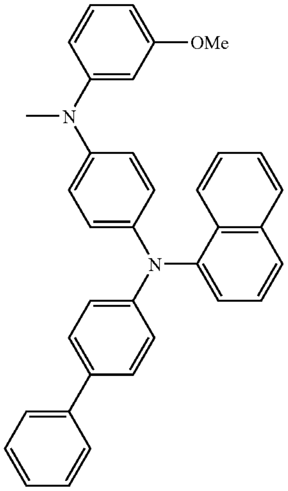
133
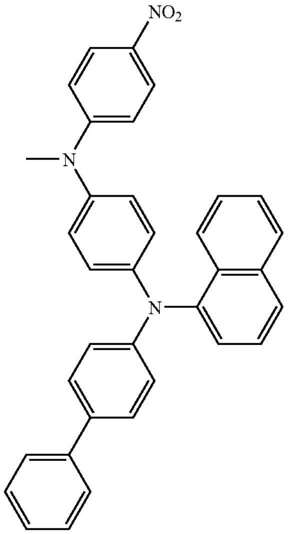

-continued
134
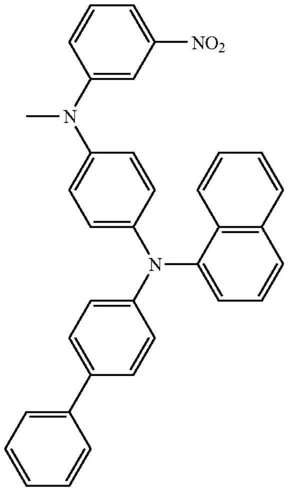
135
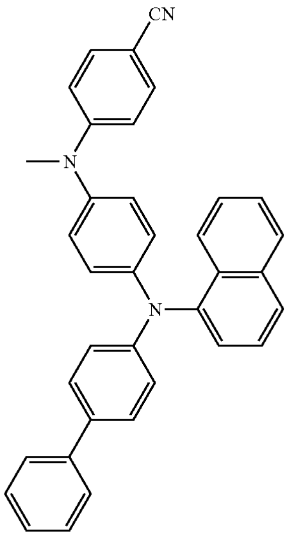
136
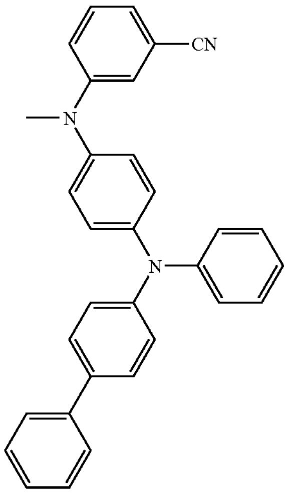
-continued
137
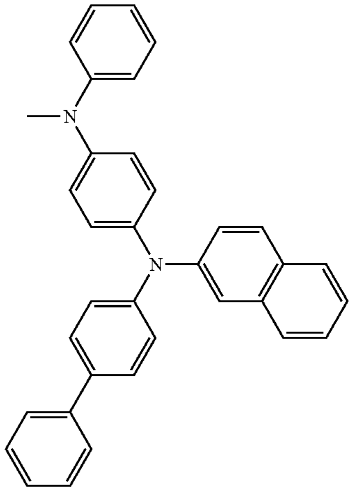
138
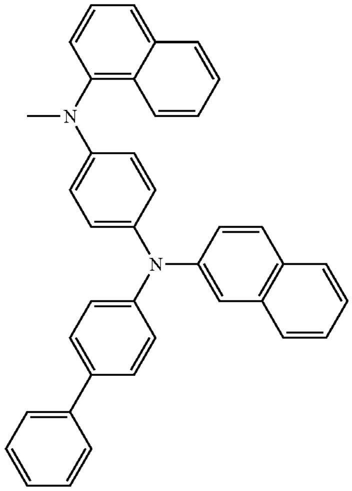
139
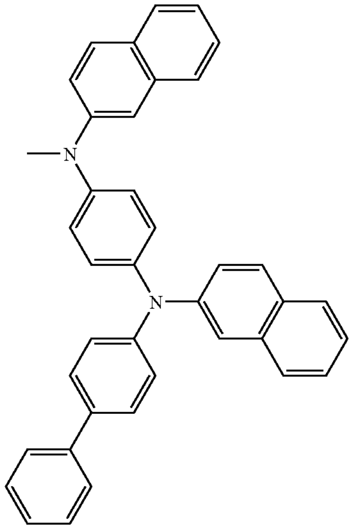

-continued
140
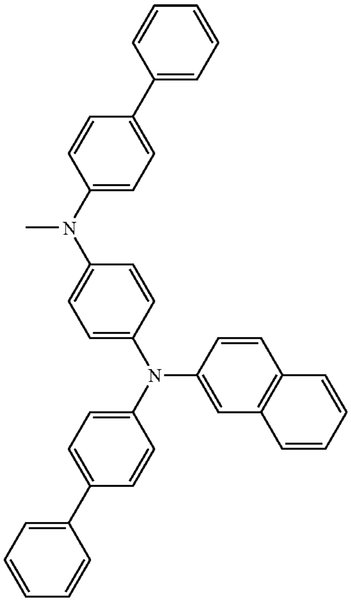
141
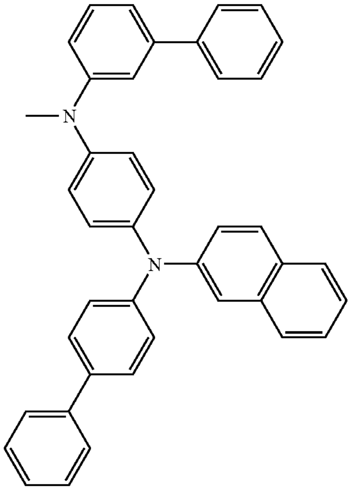
142
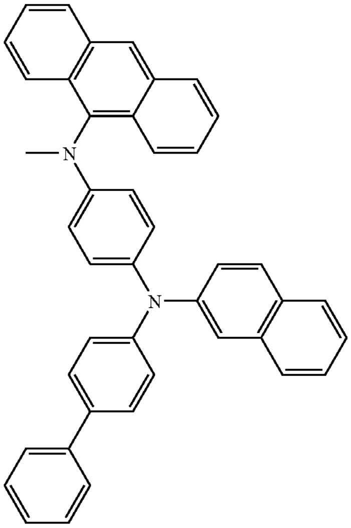
-continued
143
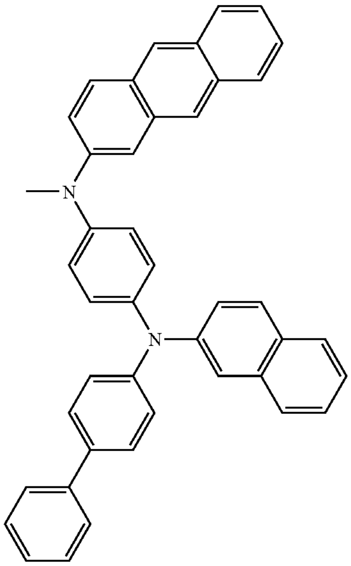
144
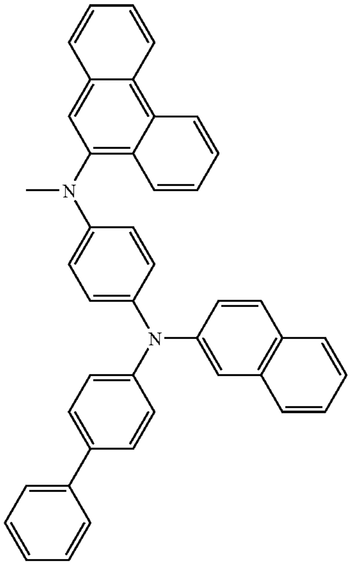

-continued
145
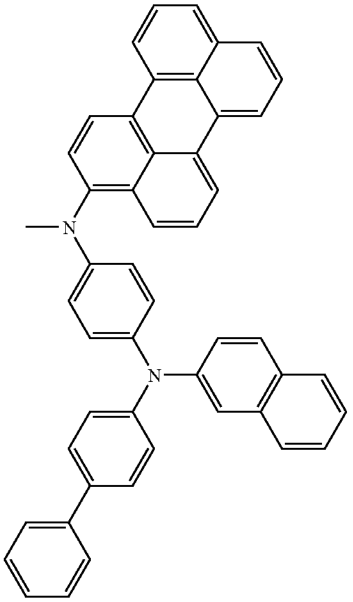
146
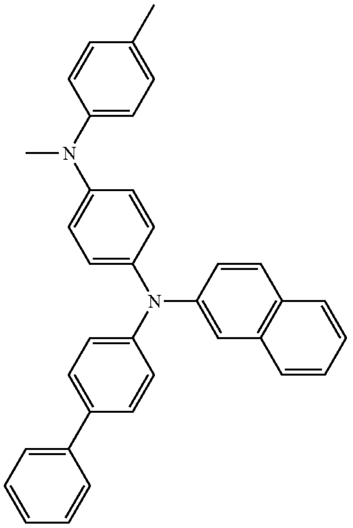
147
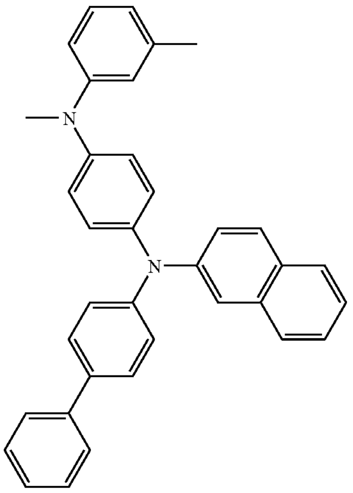
-continued
148
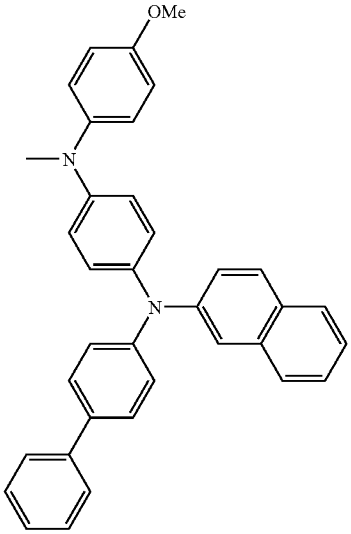
149
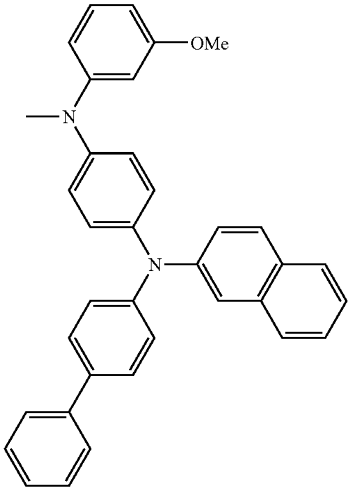
150
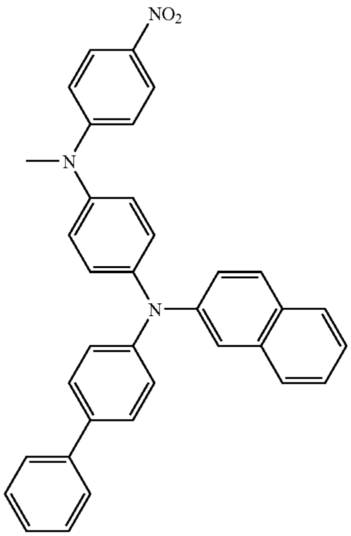

-continued
151
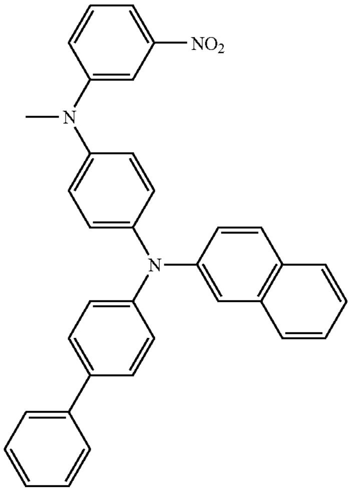
152
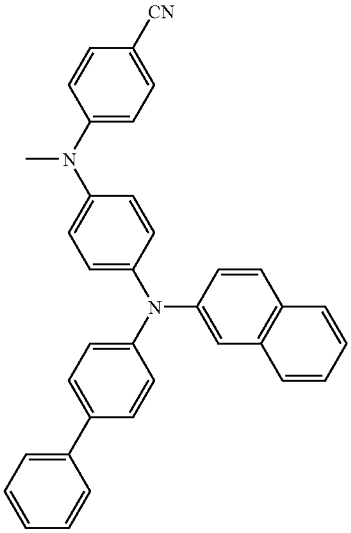
153
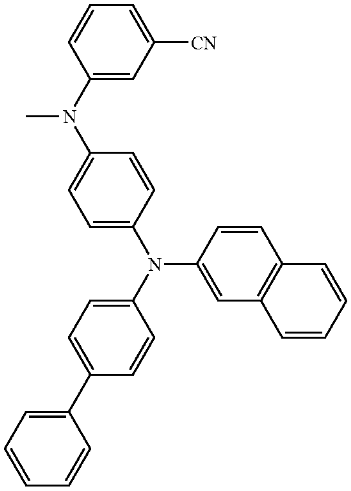
-continued
154
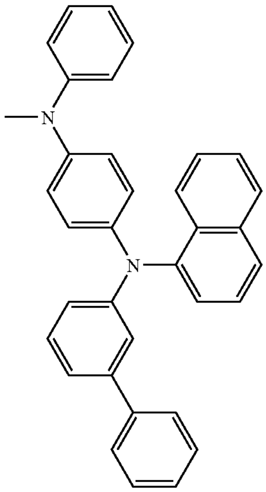
155
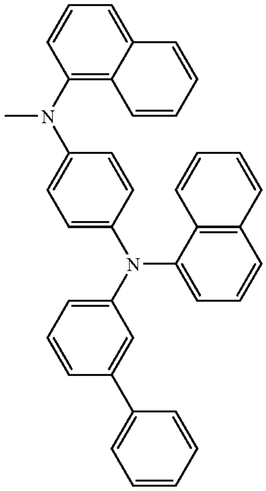
156
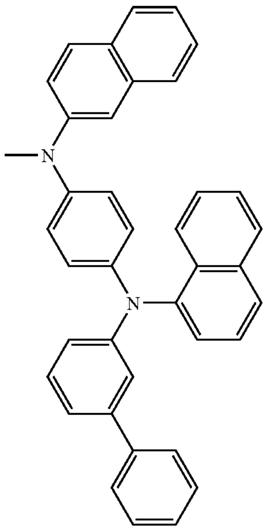

-continued
157
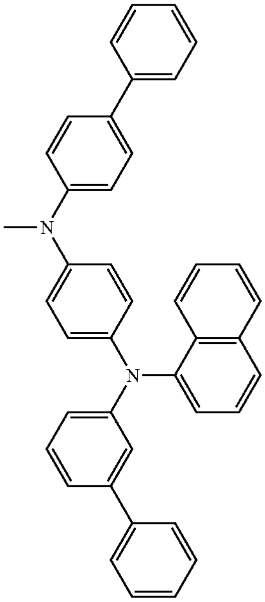
158
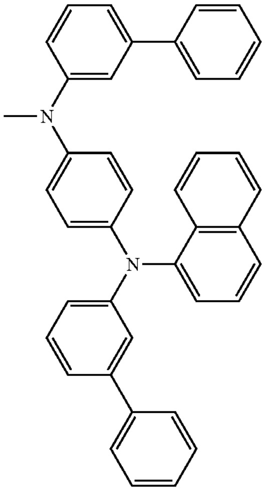
159
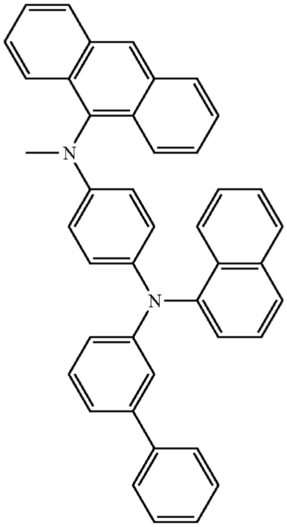
-continued
160
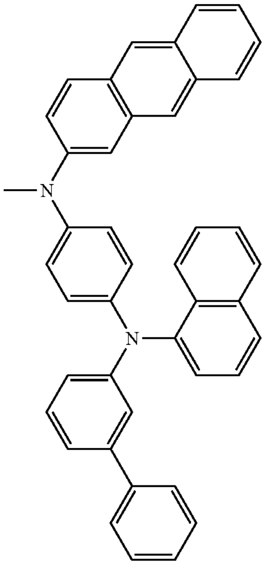
161
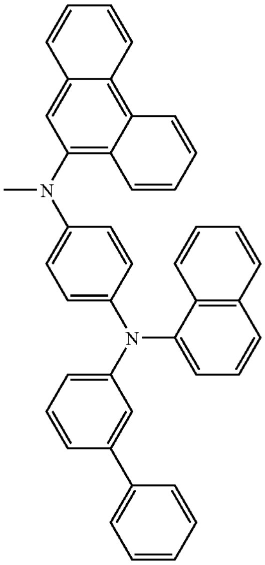

-continued
162
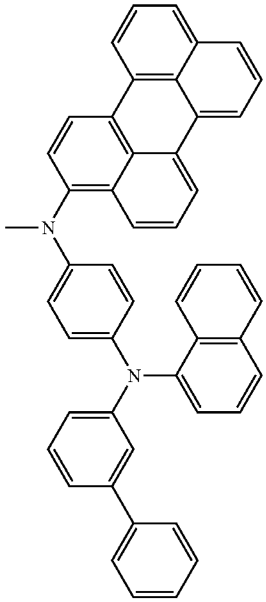
163
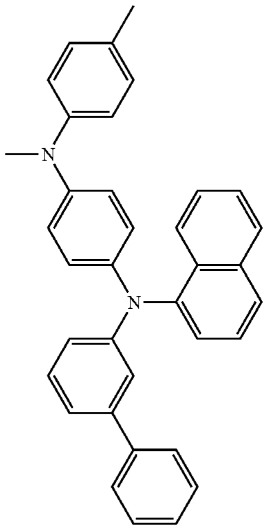
164
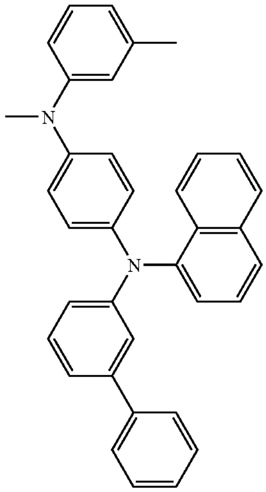
-continued
165
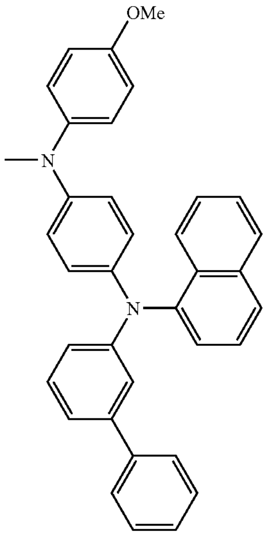
166
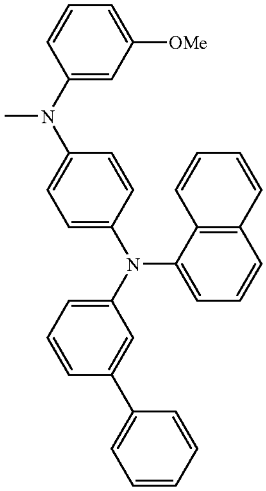
167
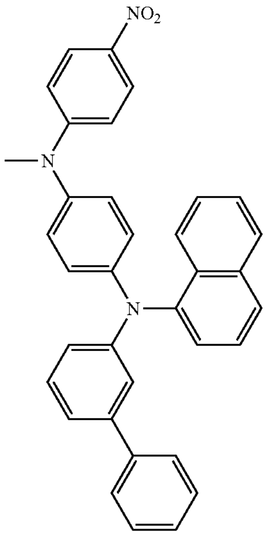

-continued
168
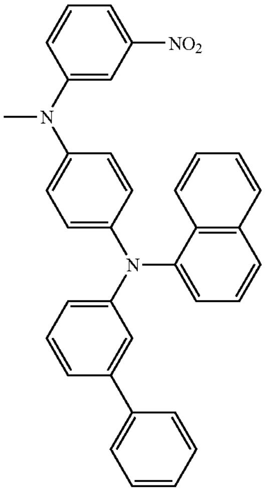
169
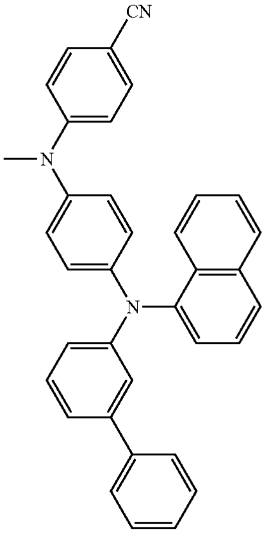
170
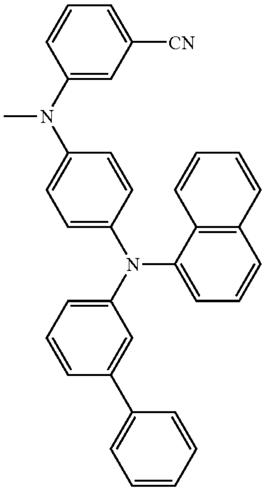
-continued
171
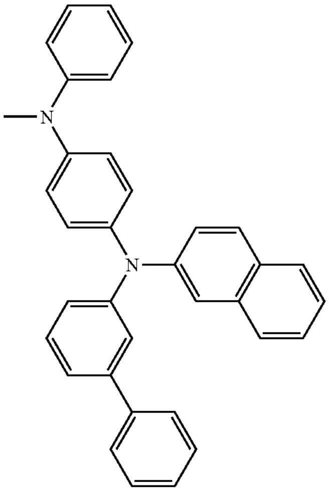
172
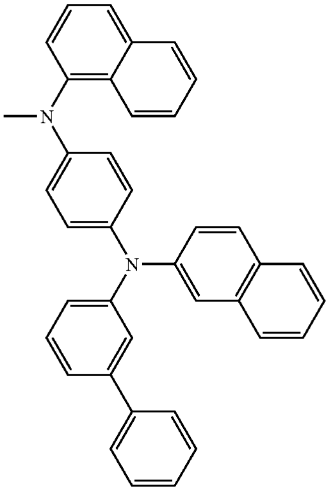
173
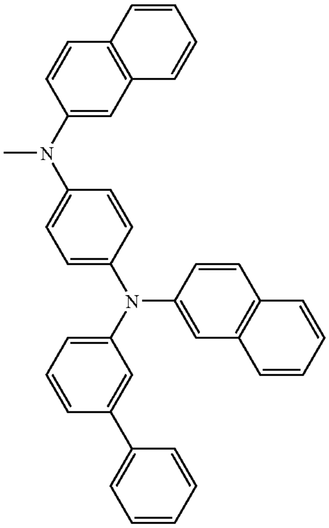

-continued
174
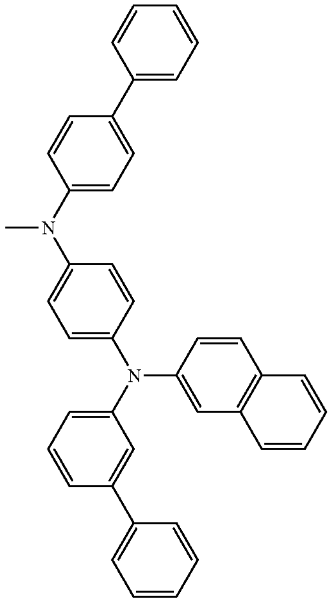
175
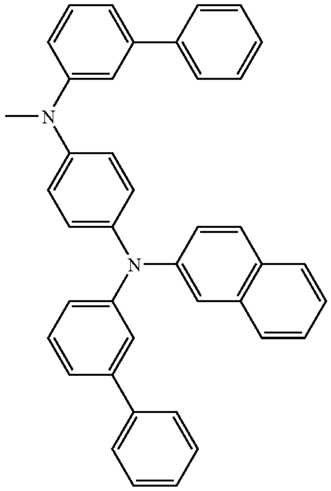
176
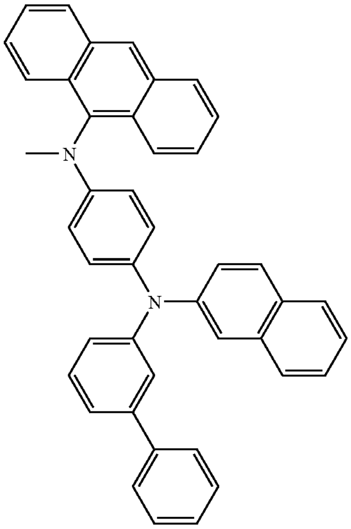
-continued
177
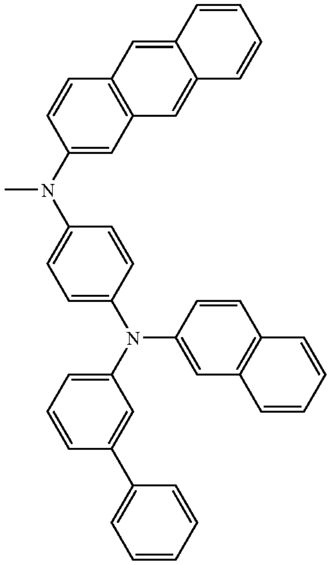
178
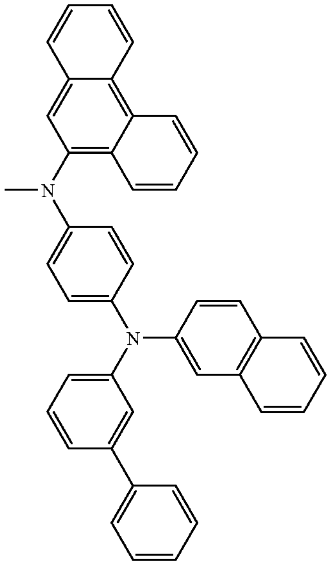

-continued
179
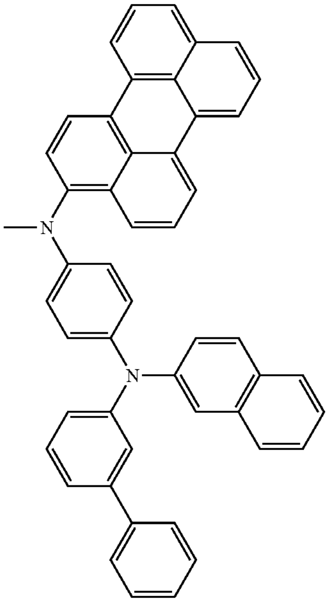
180
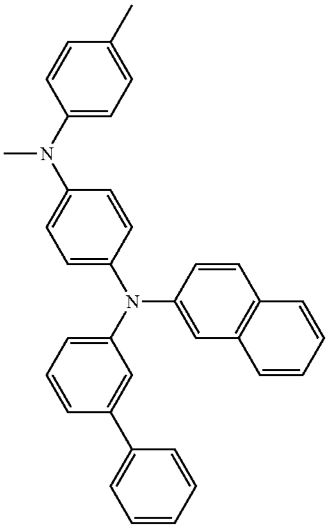
181
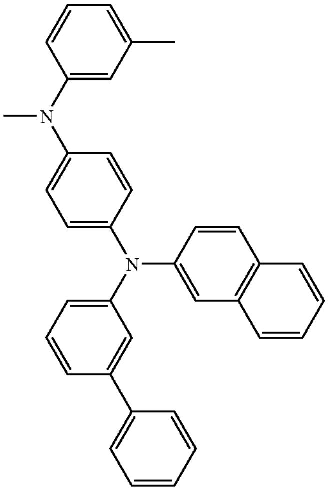
-continued
182
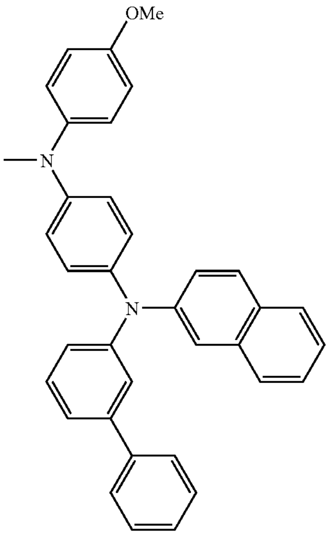
183
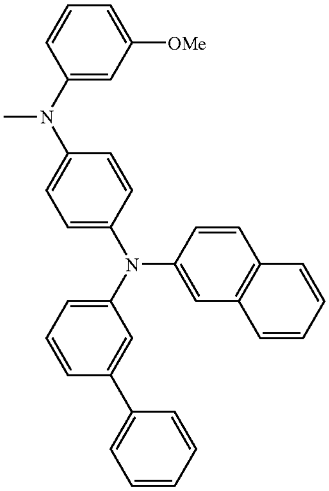
184
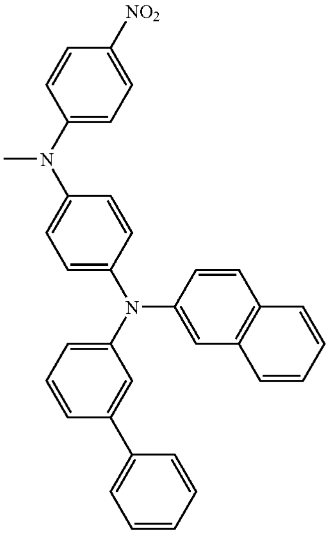

-continued
185
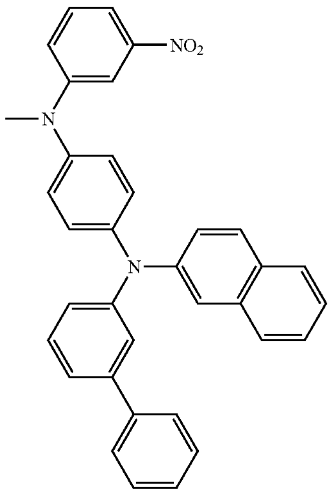
186
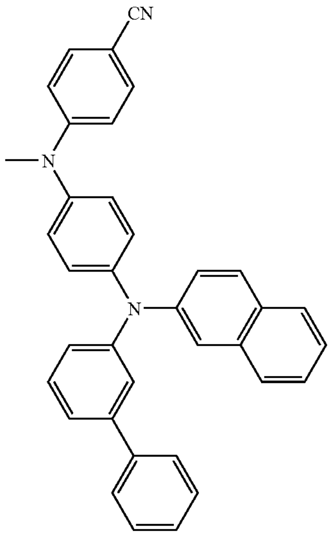
187
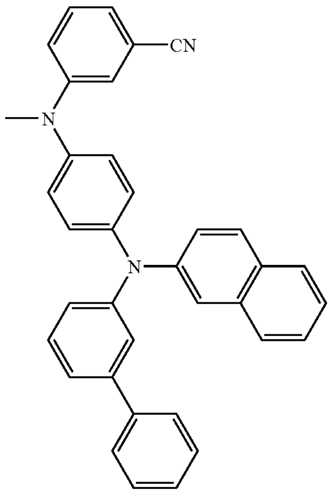
-continued
188
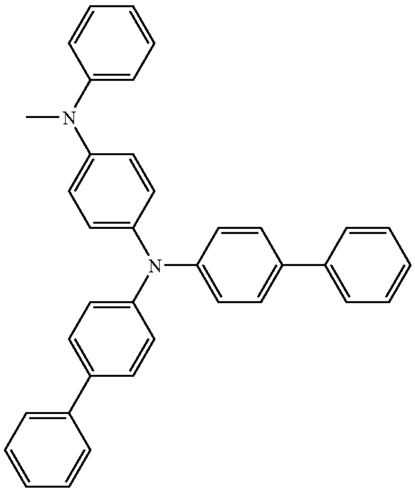
189
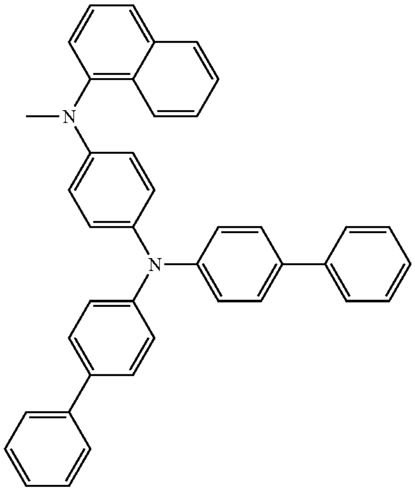
190
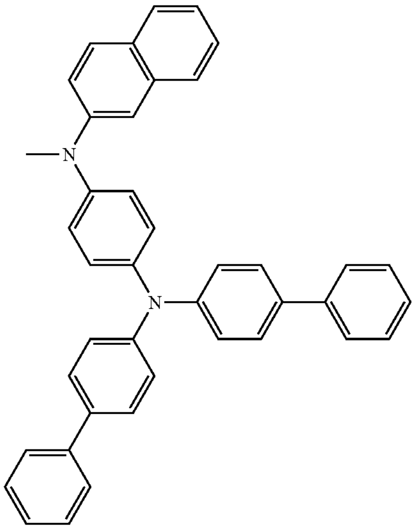

-continued
191
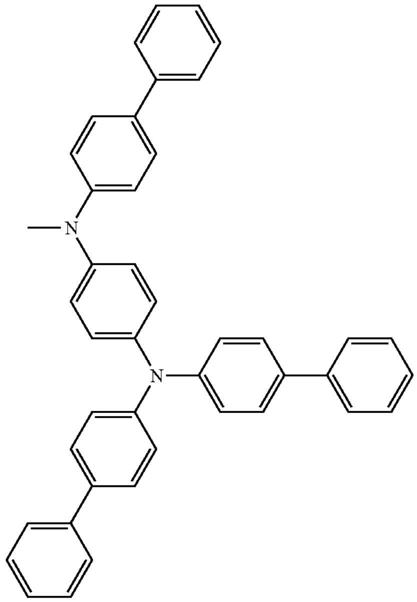
192
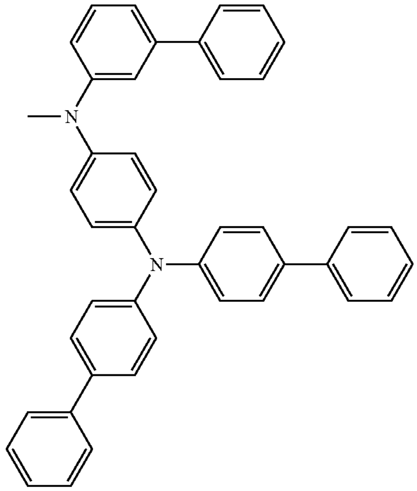
193
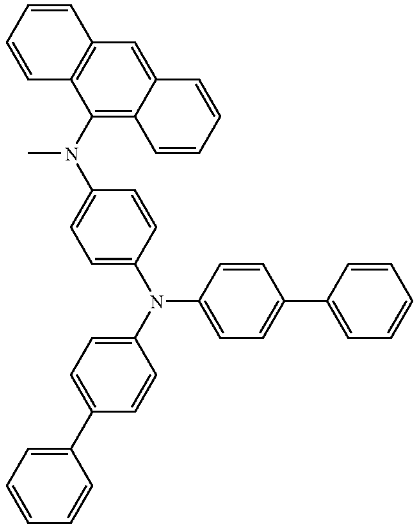
-continued
194
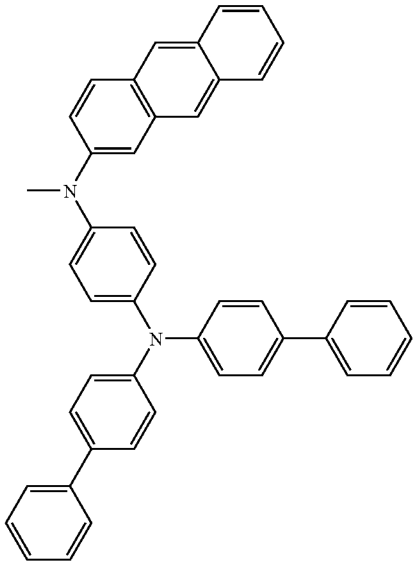
195
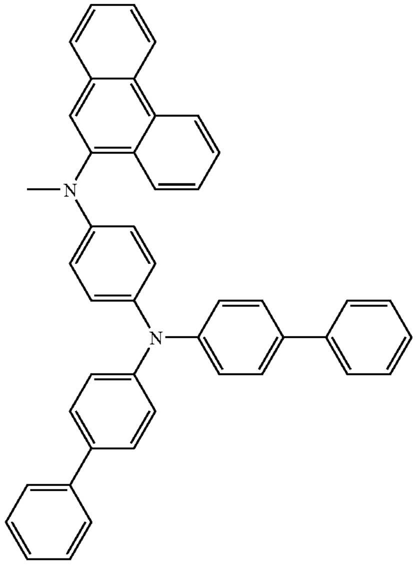

-continued
196
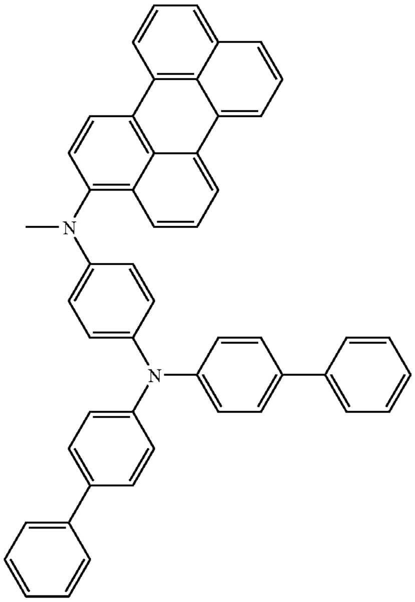
197
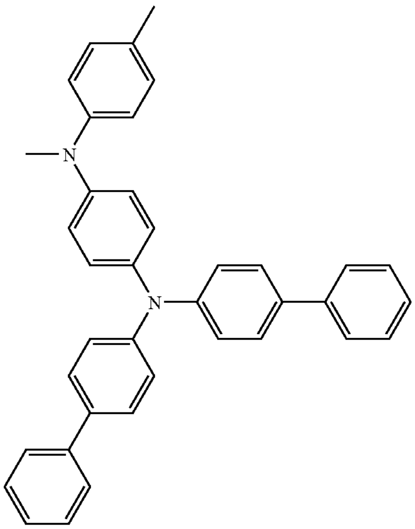
198
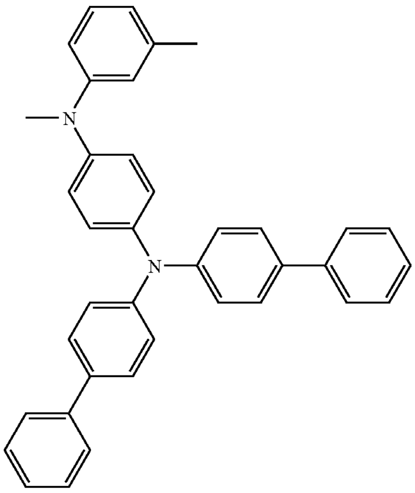
-continued
199
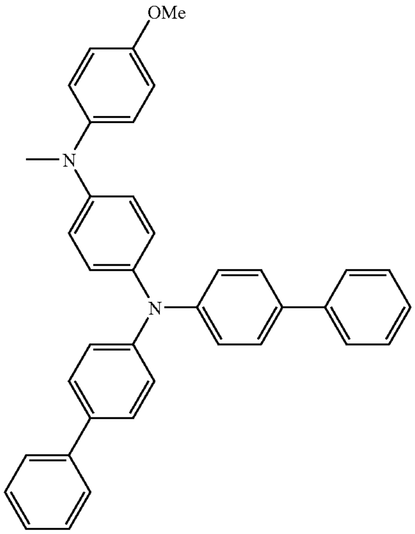
200
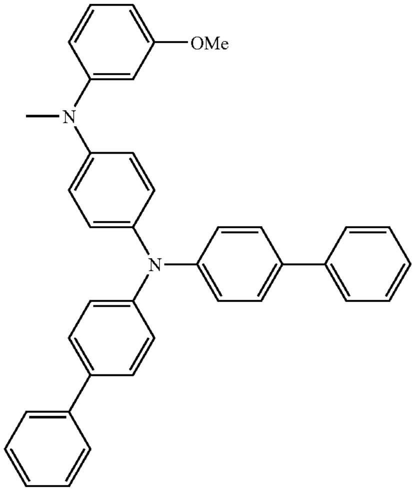
201
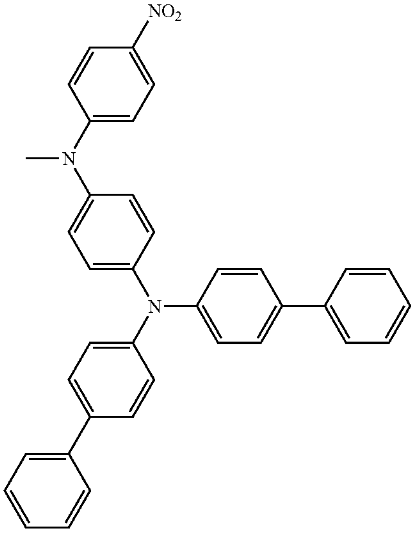

-continued
202
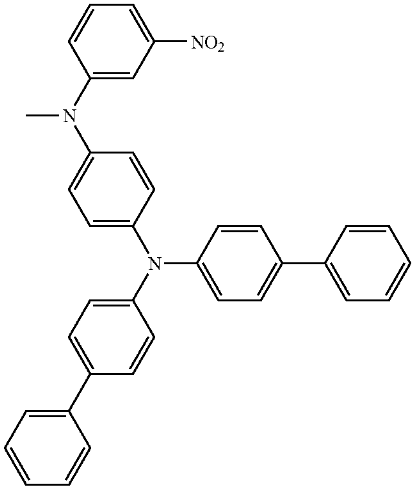
203
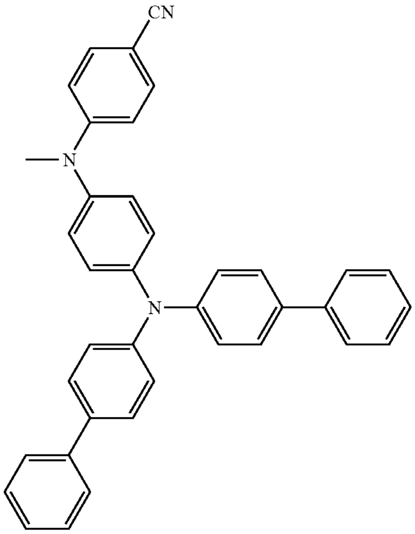
204
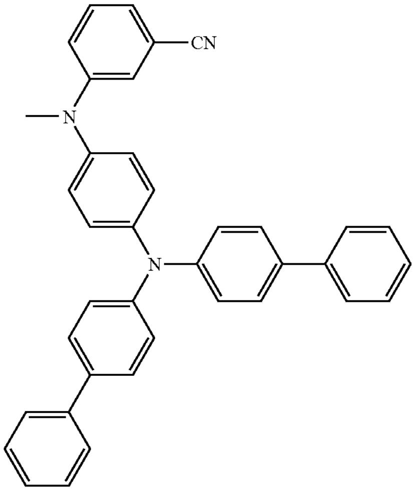
-continued
205
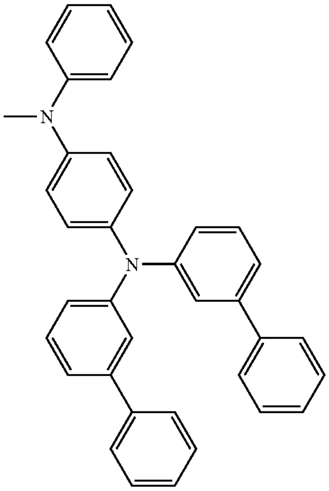
206
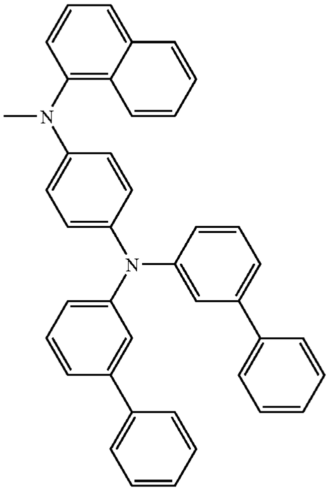
207
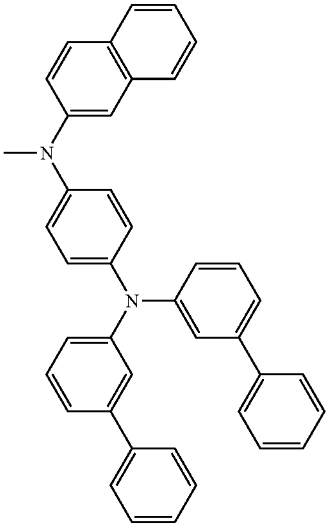

-continued
208
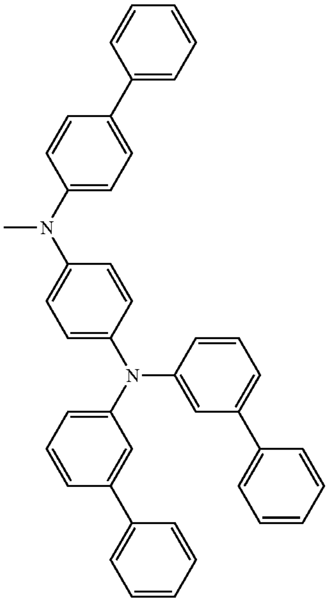
209
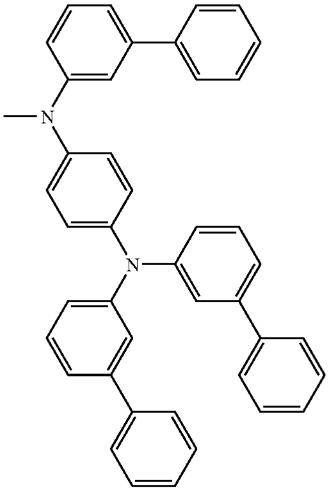
210
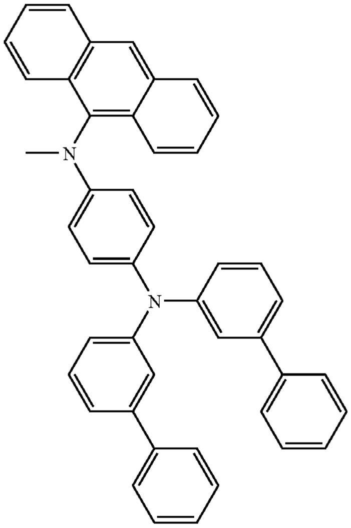
-continued
211
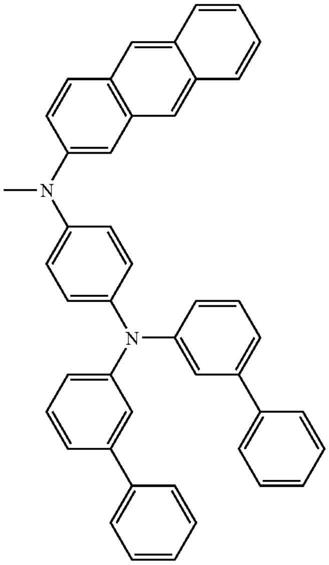
212
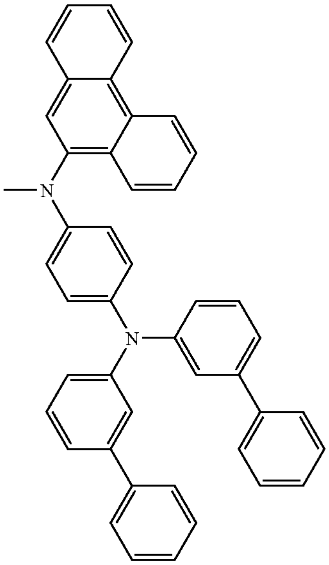

-continued
213
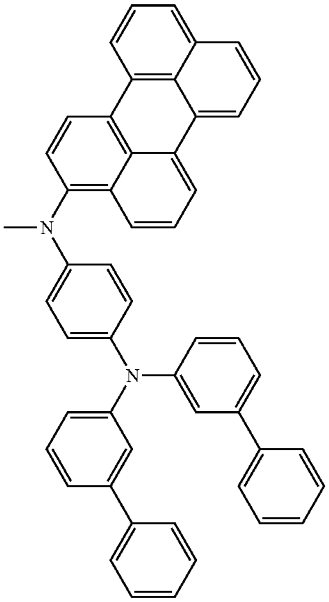
214
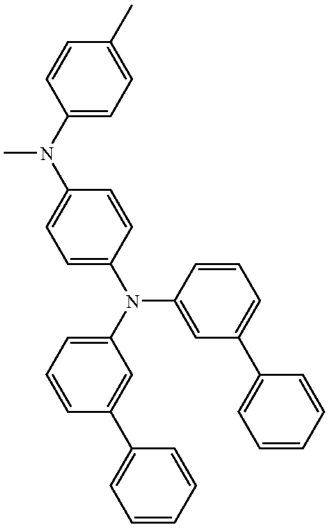
215
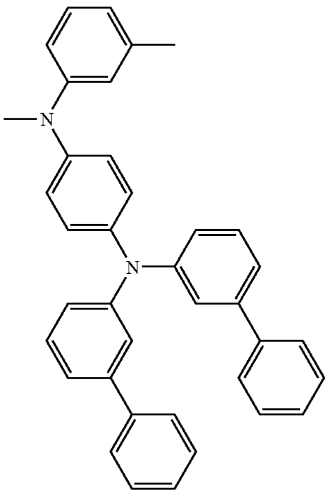
-continued
216
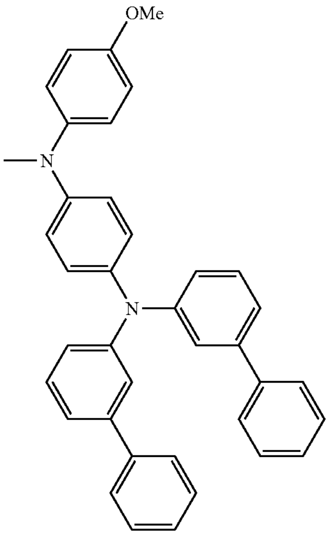
217
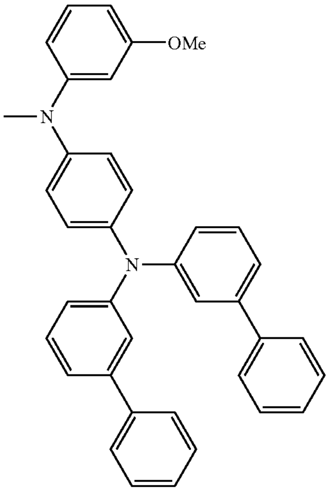
218
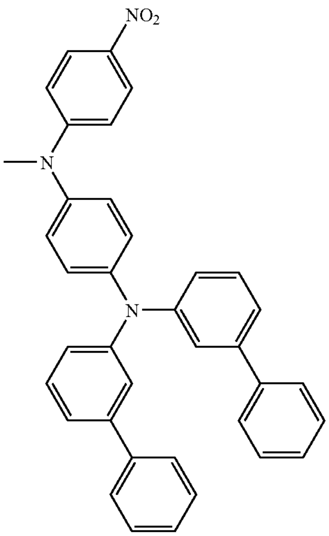

-continued
219
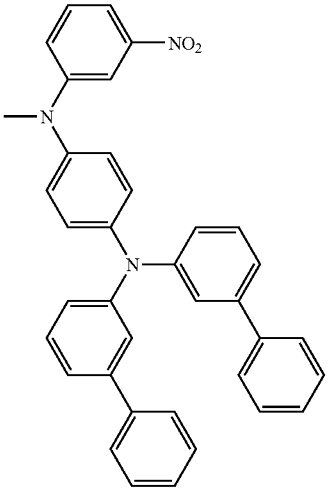
220
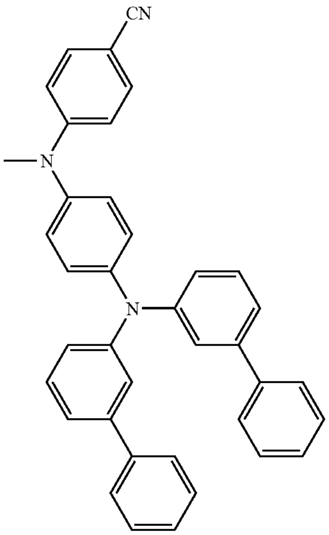
221
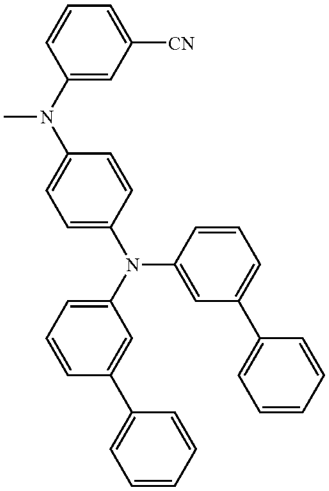
-continued
222
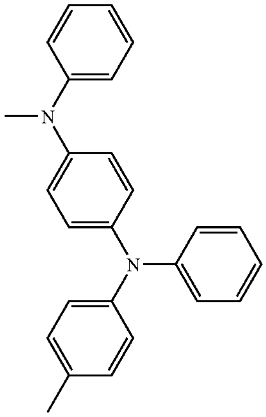
223
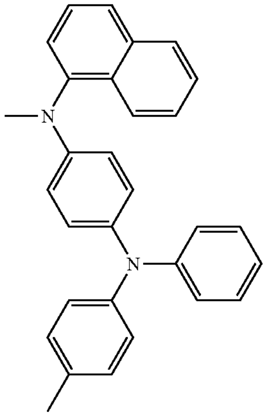
224
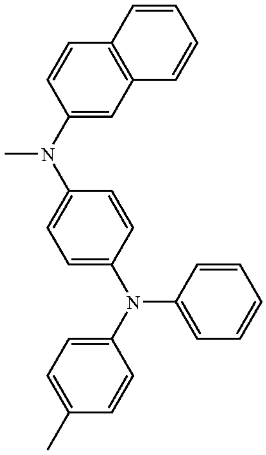

-continued
225
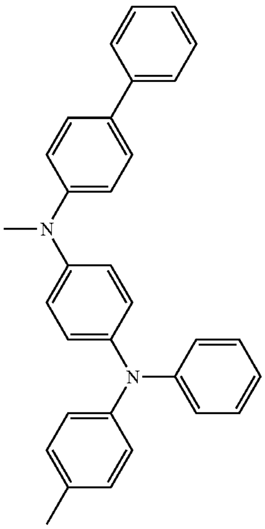
226
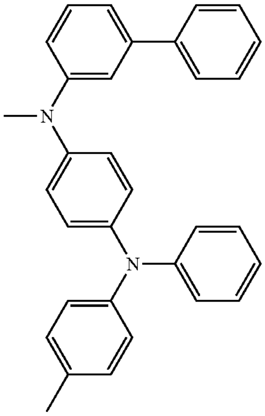
227
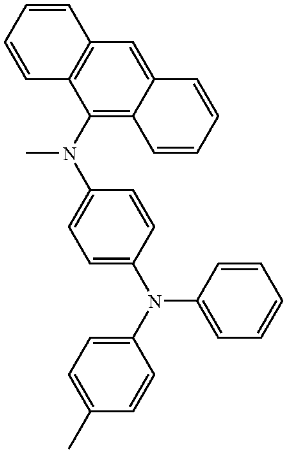
-continued
228
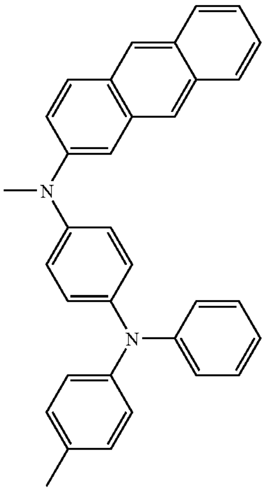
229
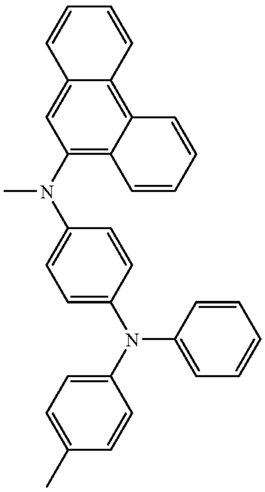
230
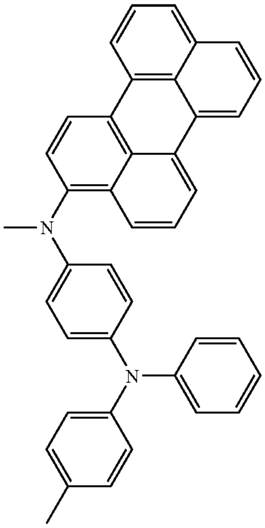

-continued
231
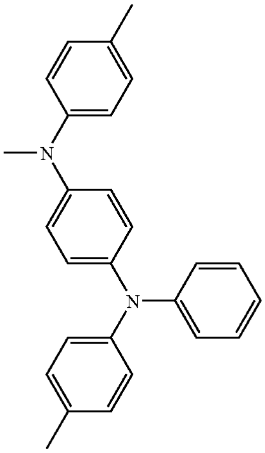
232
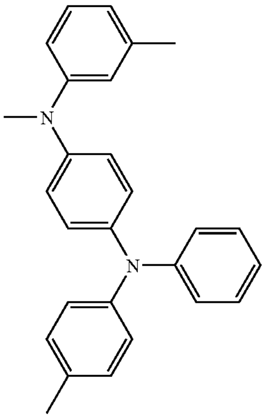
233
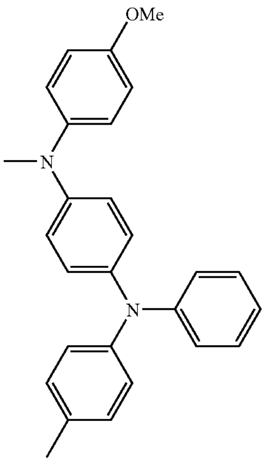
-continued
234
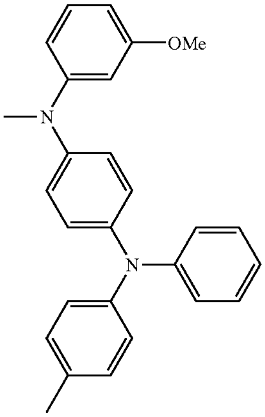
235
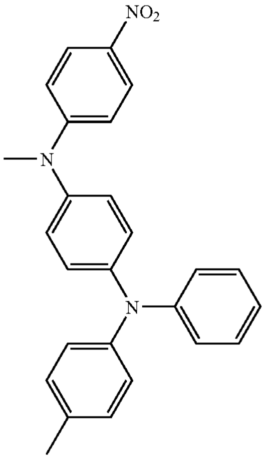
236
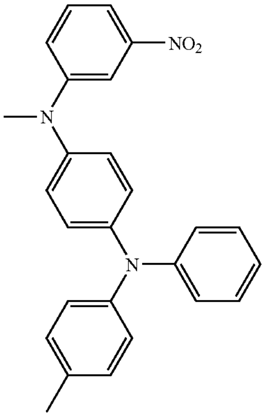

-continued
237
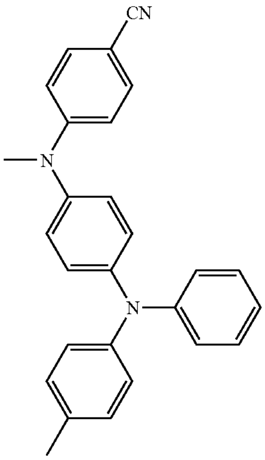
238
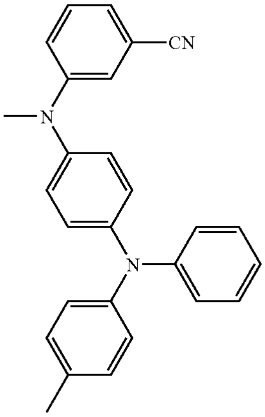
239
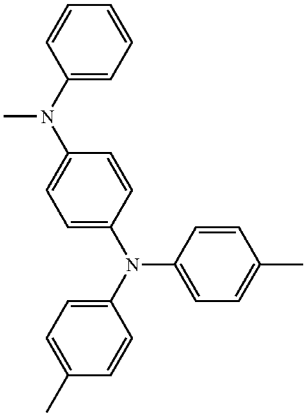
-continued
240
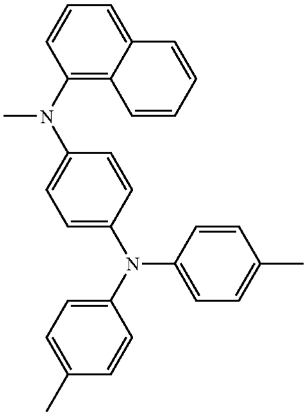
241
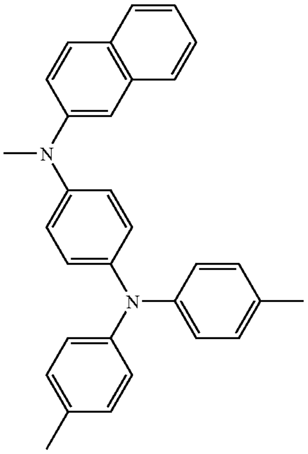
242
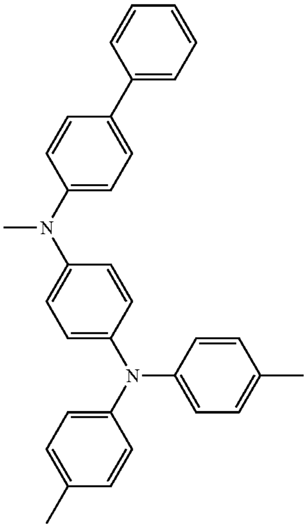

-continued
243
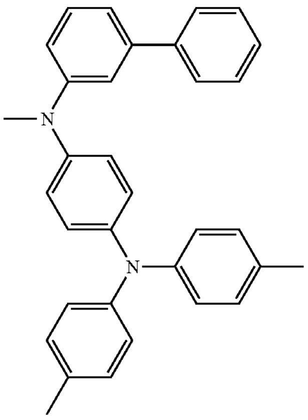
244
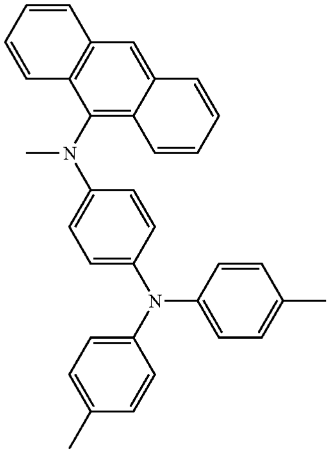
245
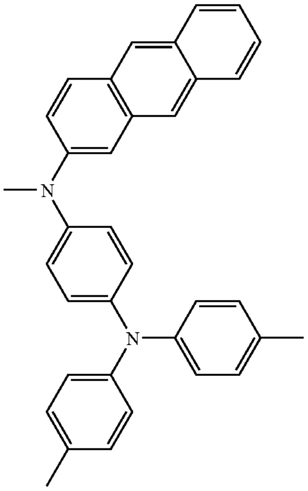
-continued
246
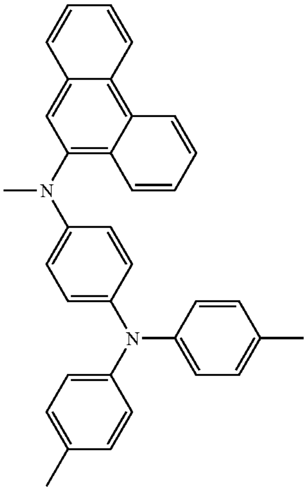
247
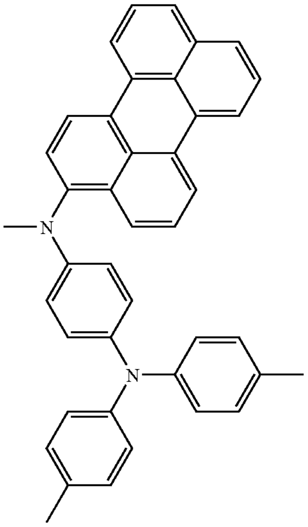
248
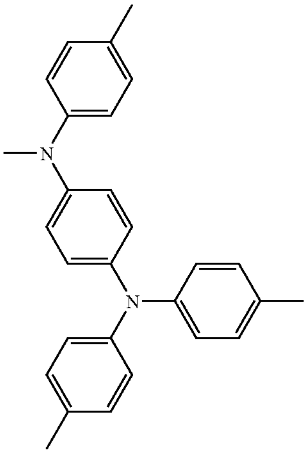

-continued
249
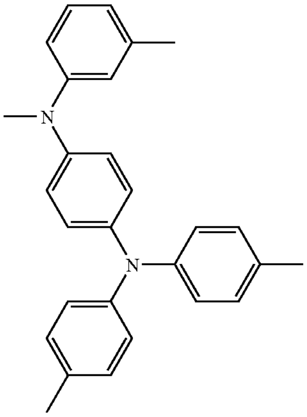
250
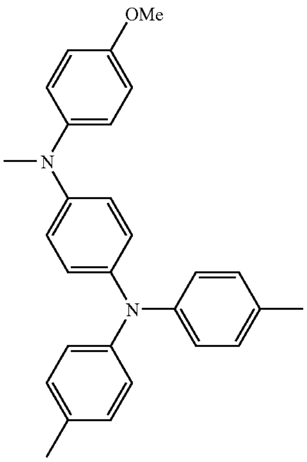
251
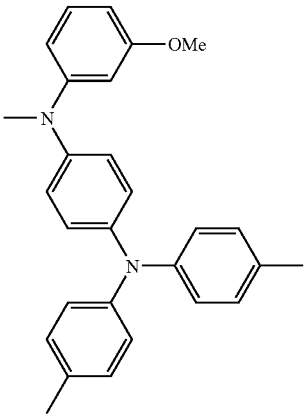
-continued
252
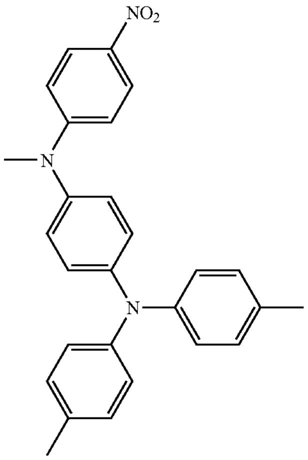
253
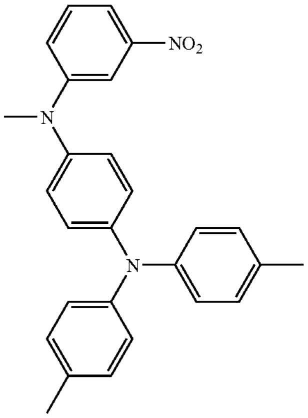
254
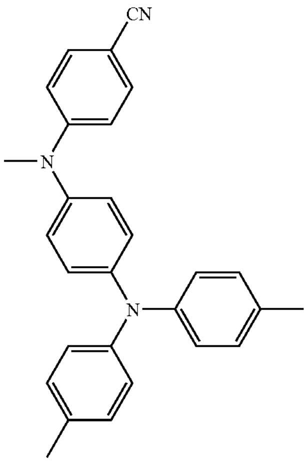

-continued
255
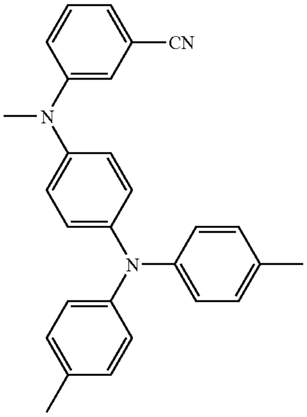
256
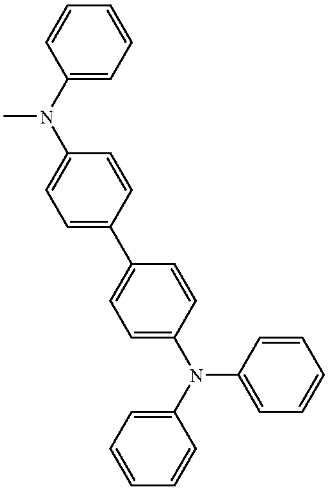
257
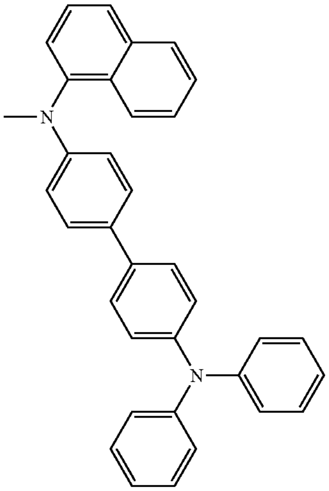
-continued
258
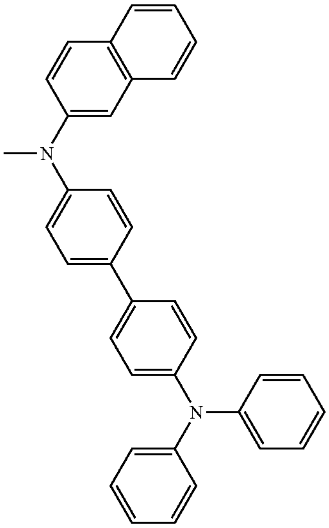
259
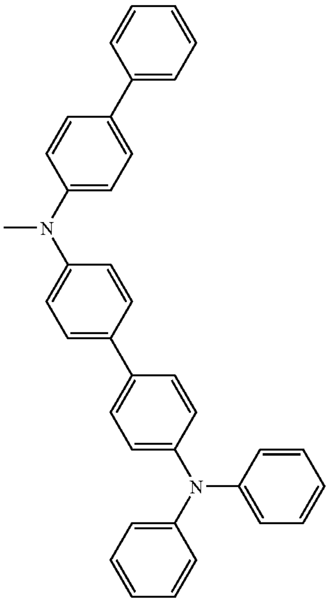
260
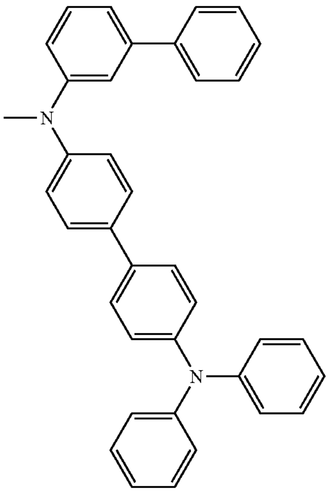

-continued
261
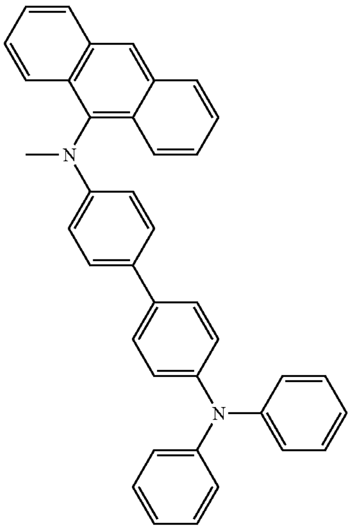
262
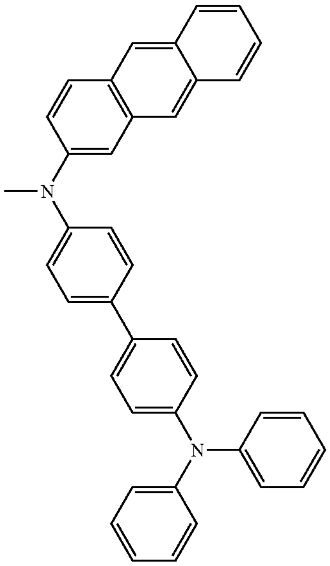
263
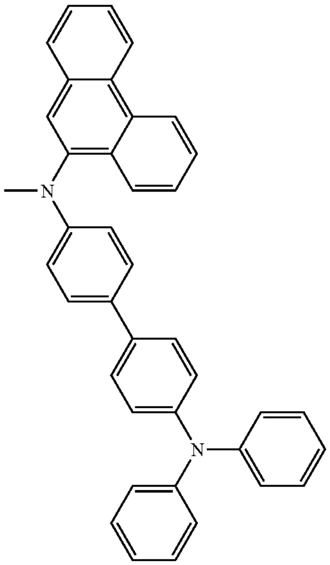
-continued
264
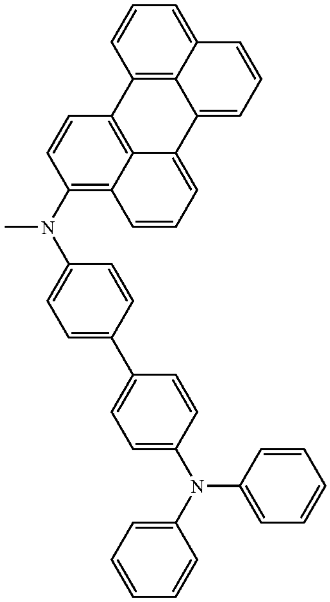
265
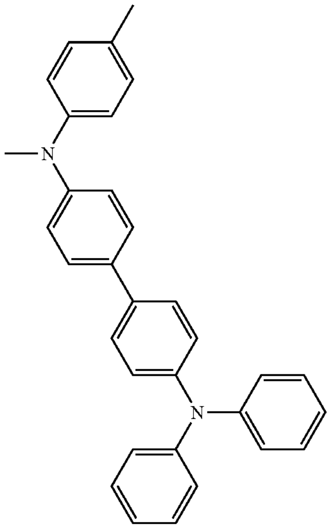
266
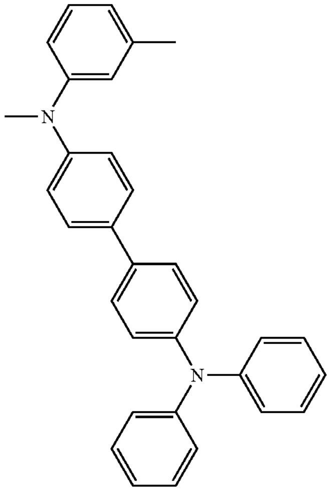

-continued
267
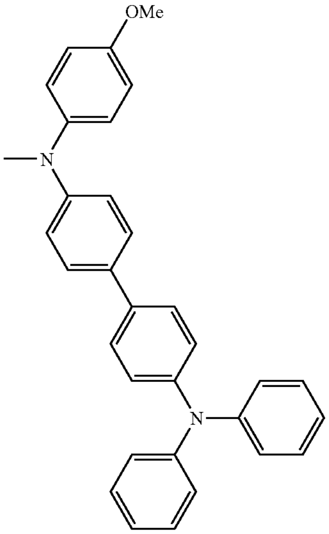
268
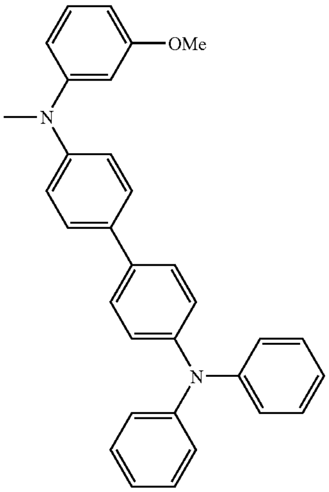
269
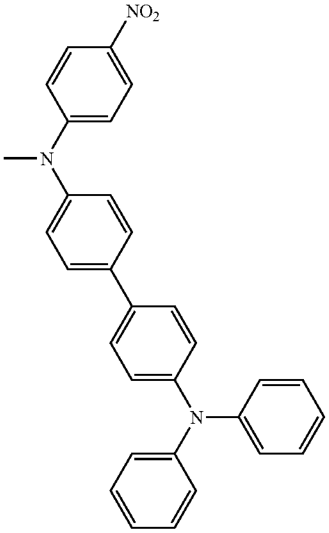
-continued
270
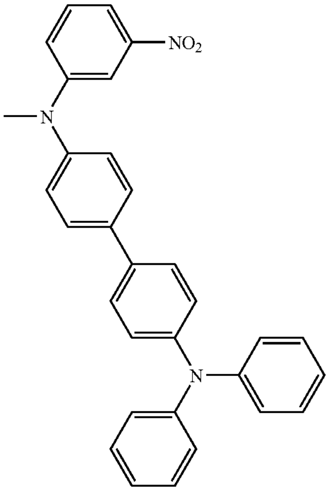
271
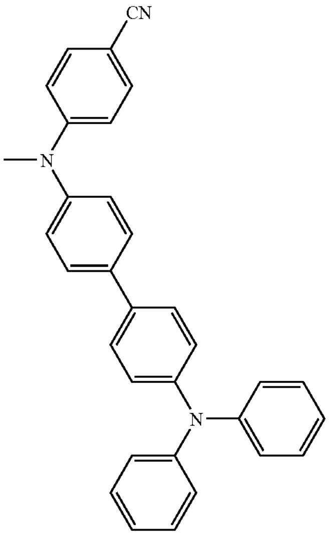
272
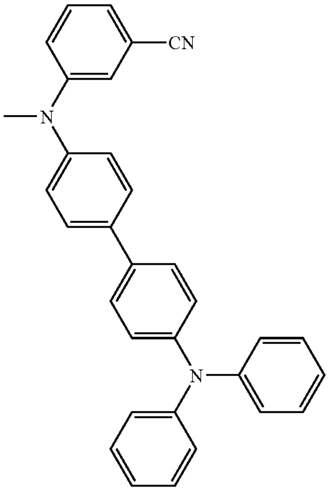

-continued
273
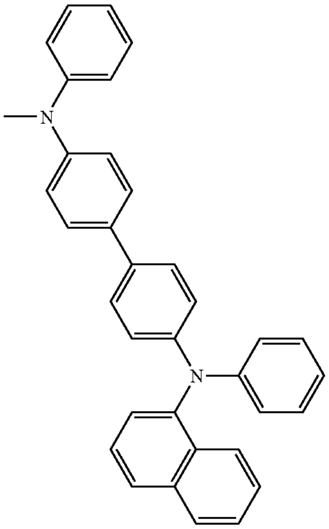
274
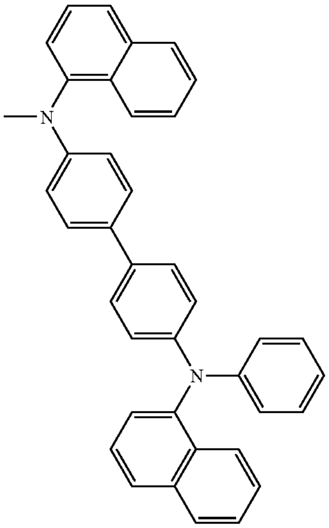
275
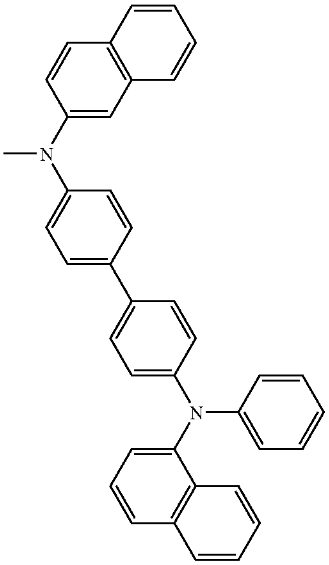
-continued
276
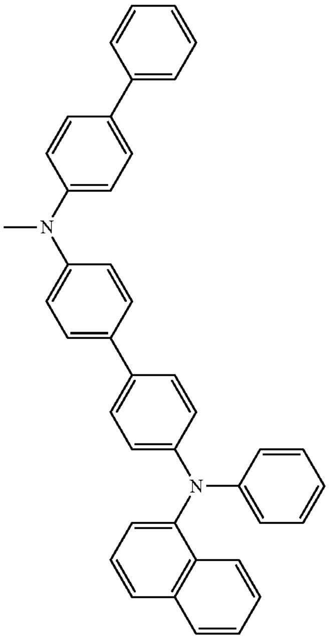
277
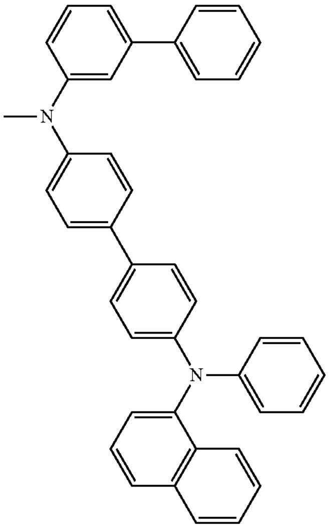

-continued
278
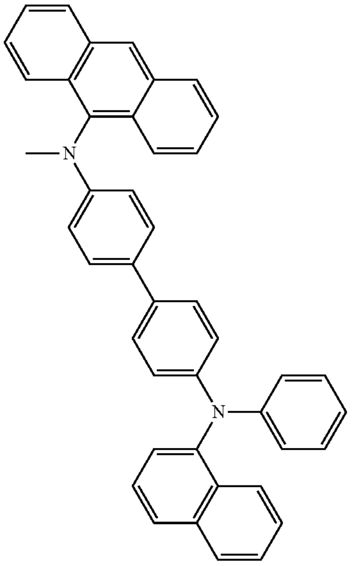
279
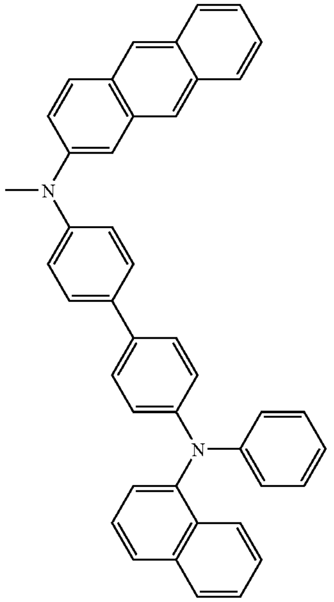
-continued
280
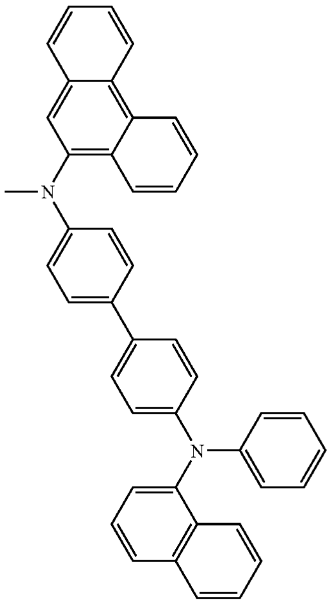
281
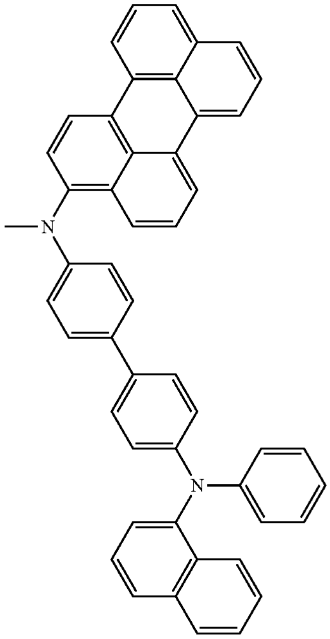

-continued
282
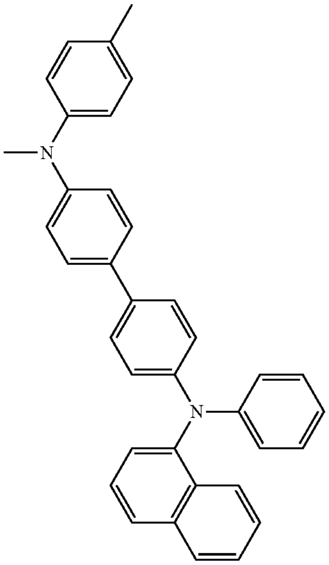
284
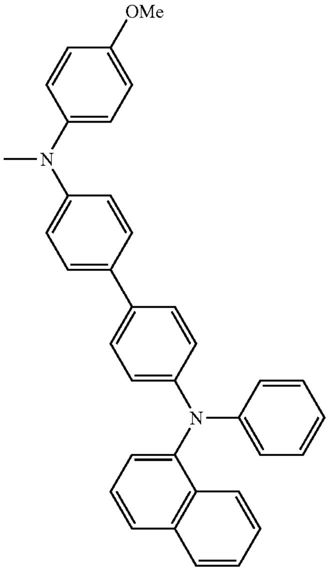
283
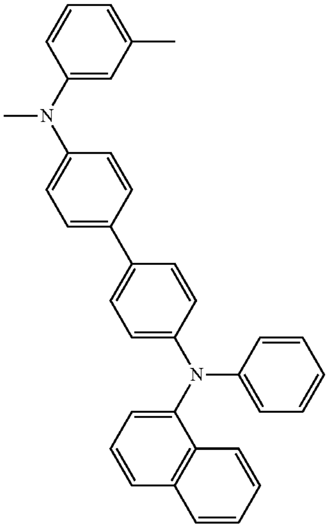
285
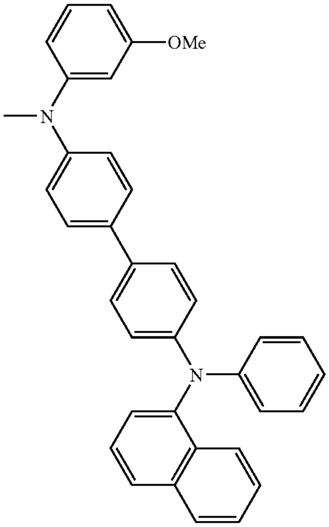

-continued
286
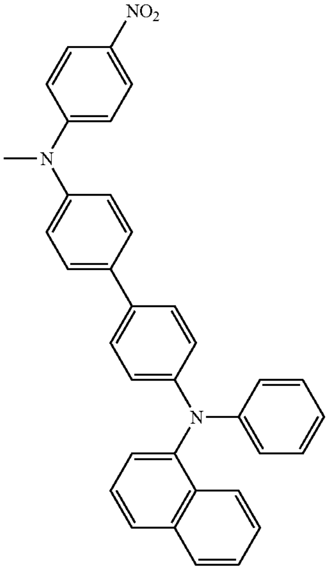
287
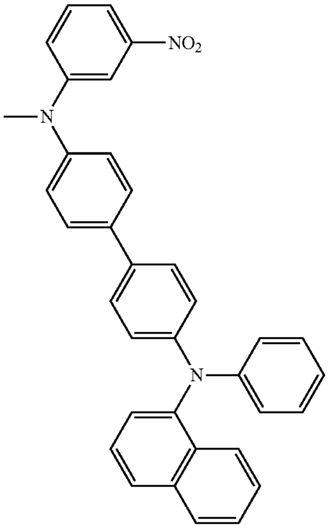
288
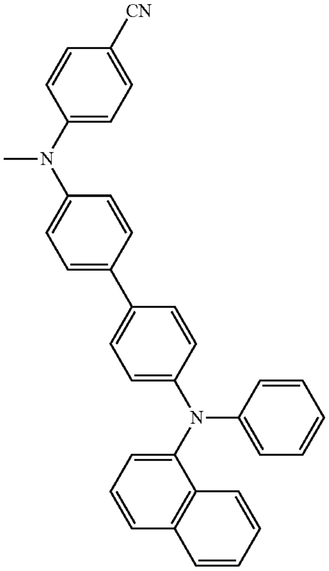
-continued
289
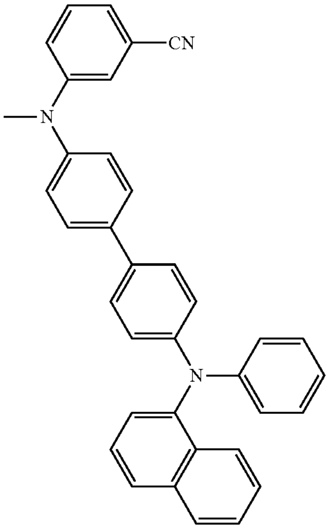
290
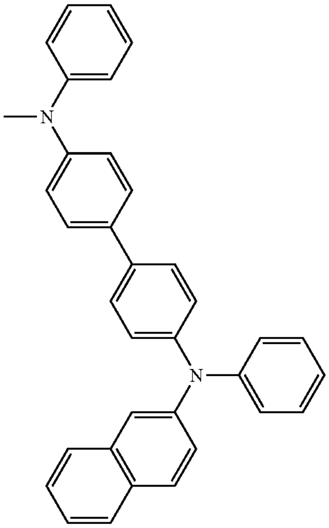
291
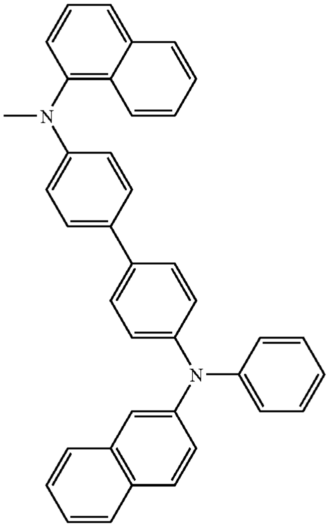

-continued
292
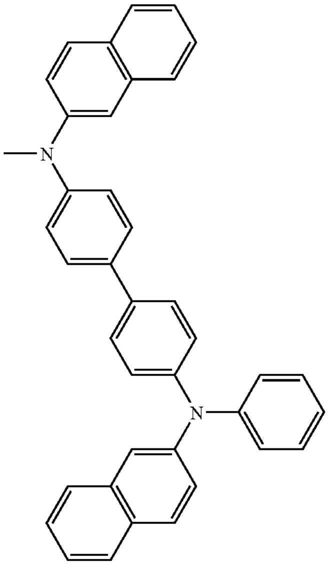
293
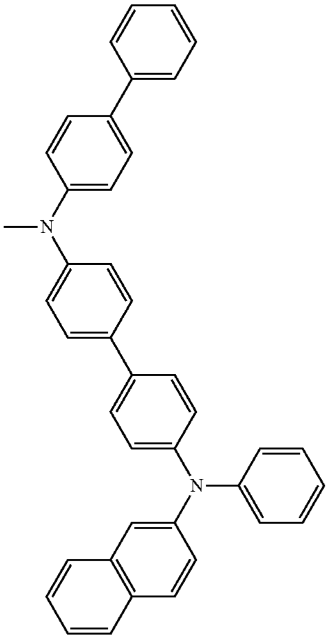
-continued
294
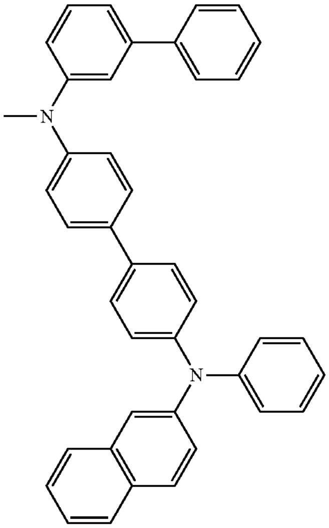
295
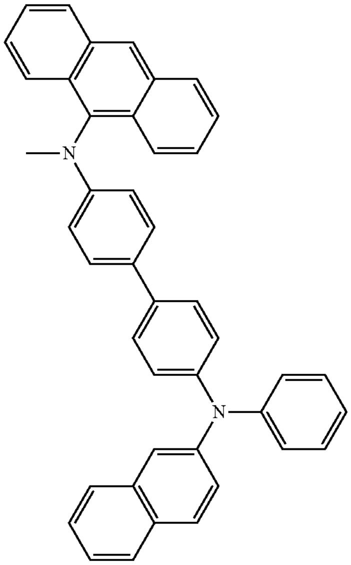

-continued
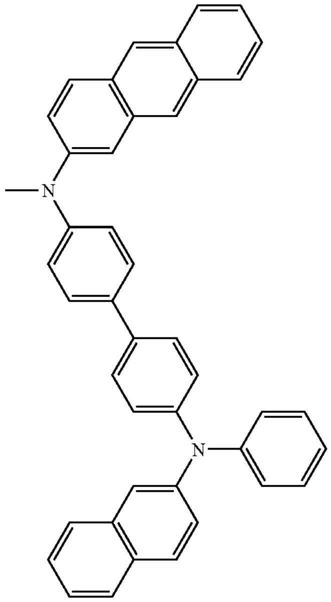
296
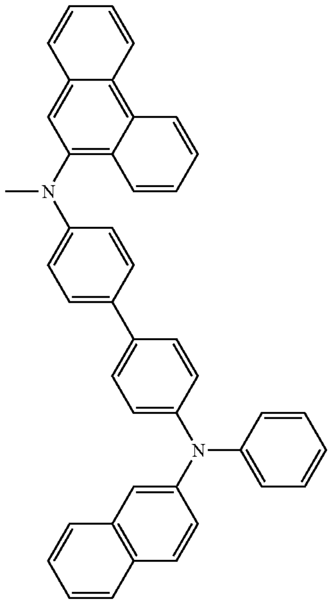
297
-continued
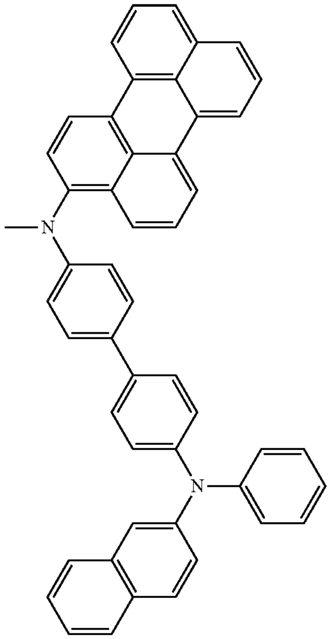
298
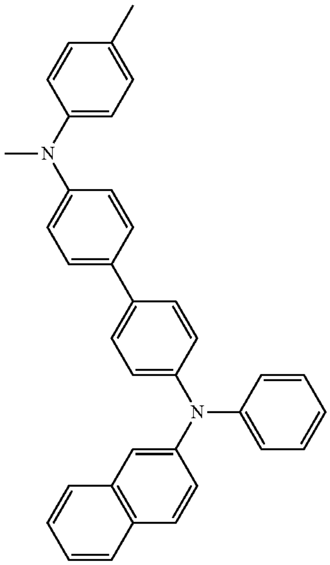
299

-continued
300
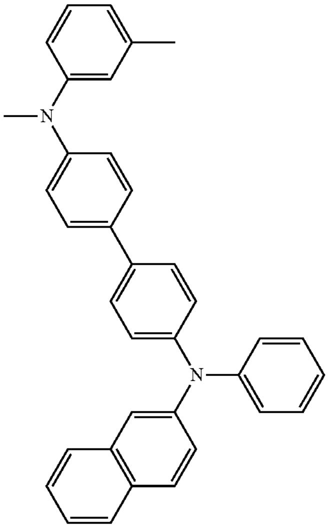
301
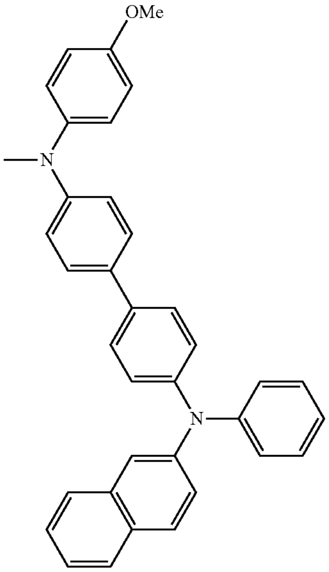
302
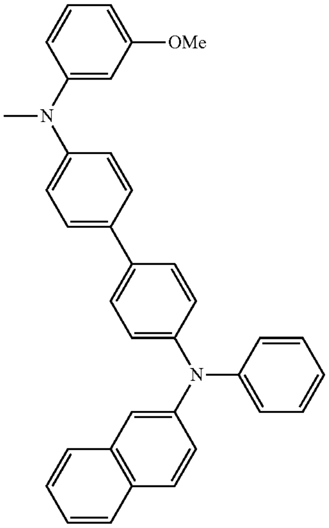
-continued
303
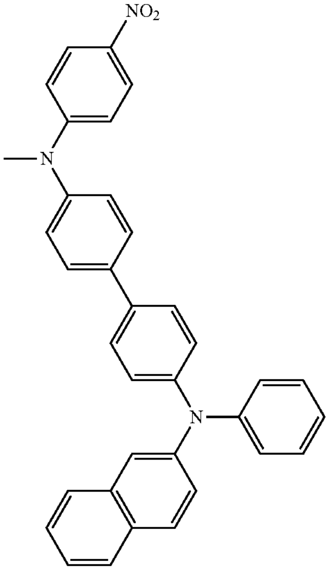
304
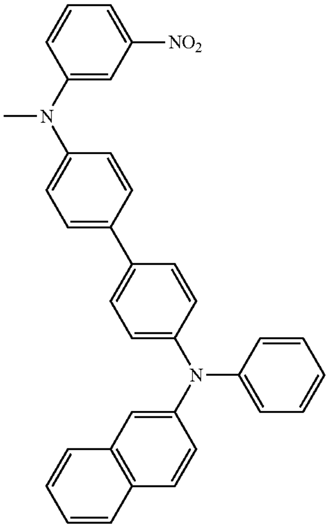
305
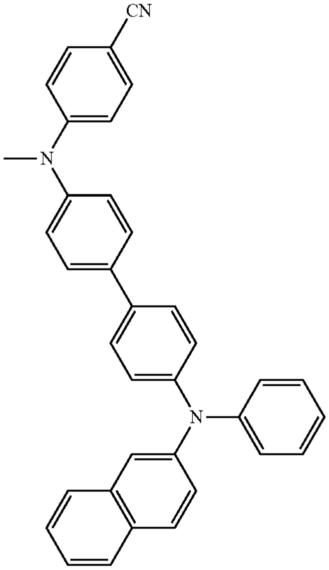

-continued
306
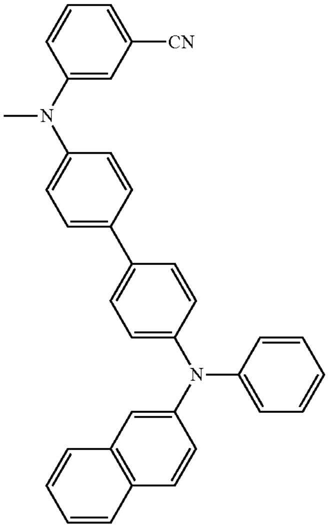
307
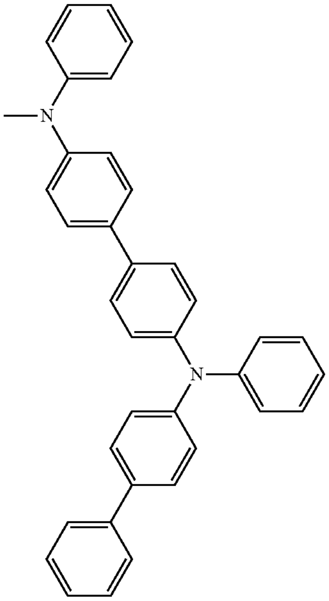
-continued
308
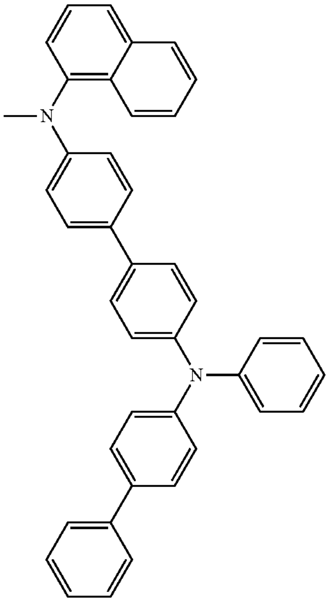
309
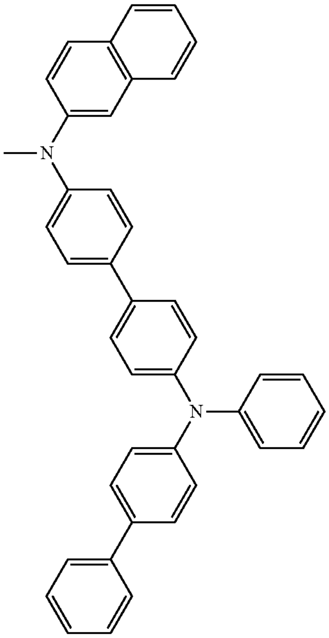
310
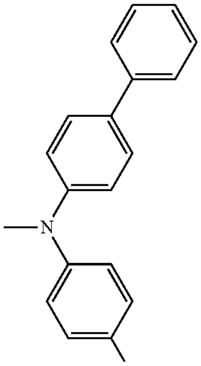

-continued
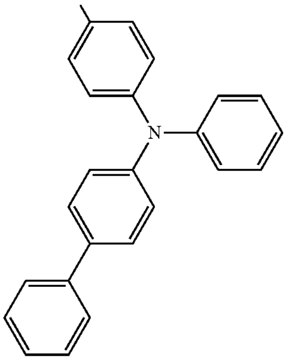
311
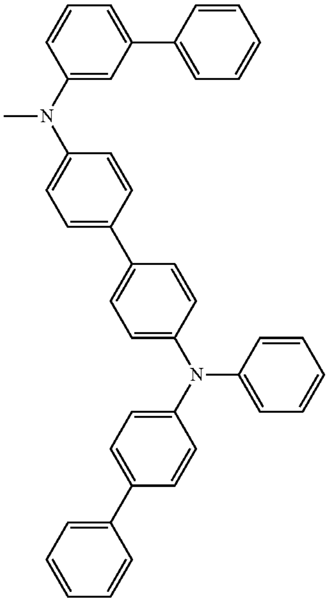
312
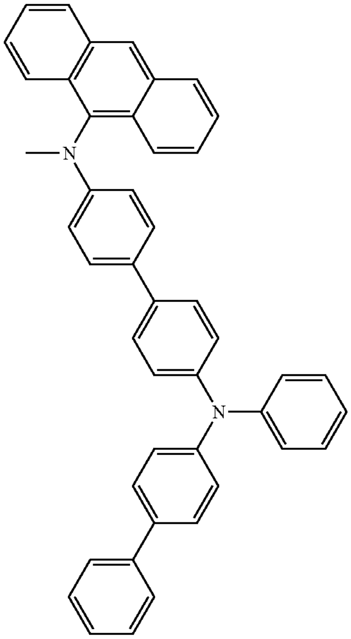
-continued
313
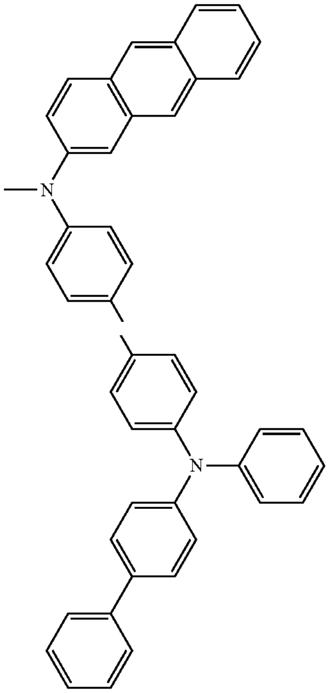
314
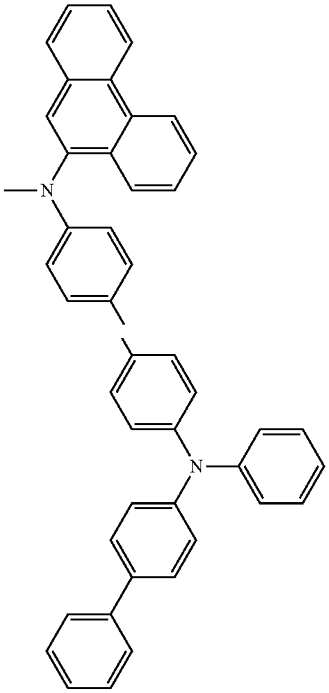

-continued
315
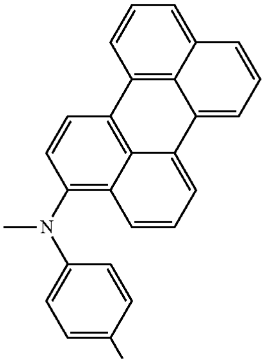
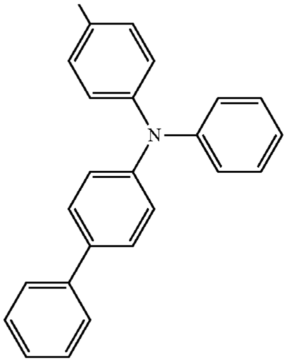
316
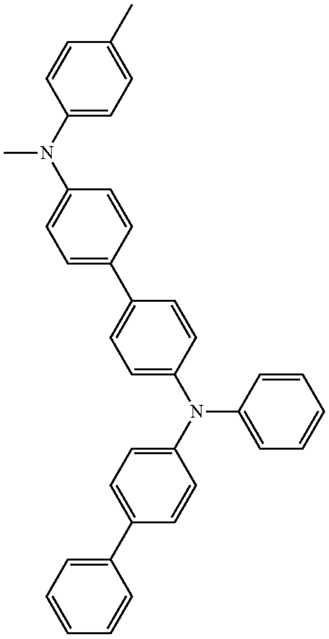
-continued
317
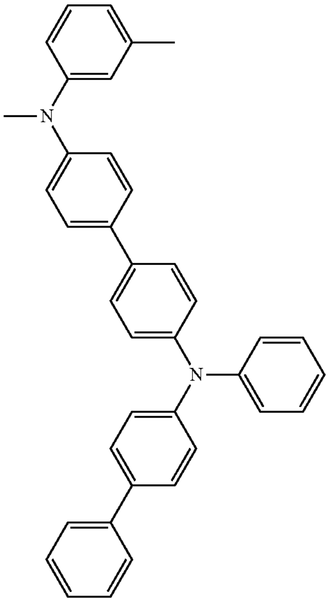
318
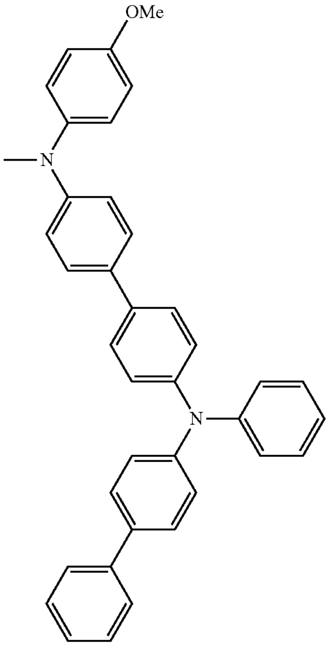

-continued
319
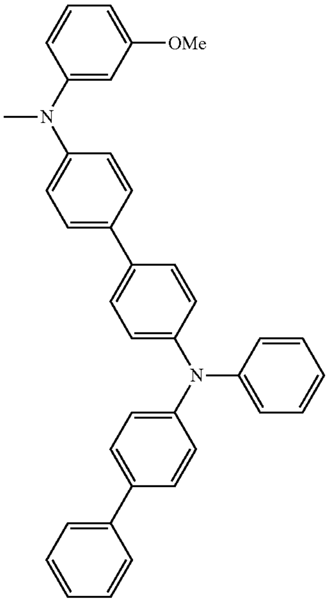
320
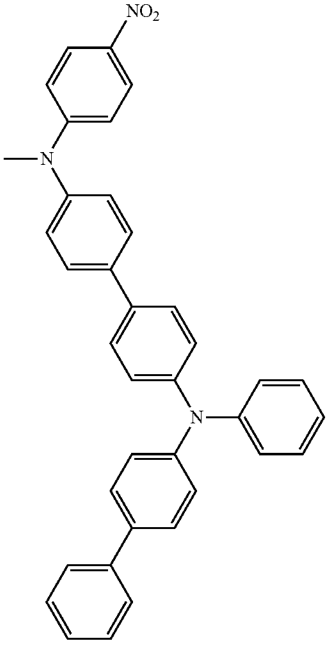
-continued
321
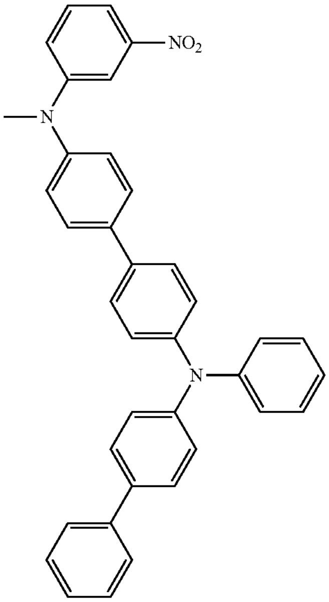
322
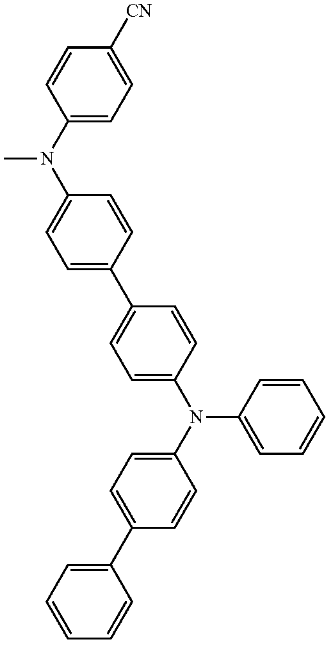

-continued
323
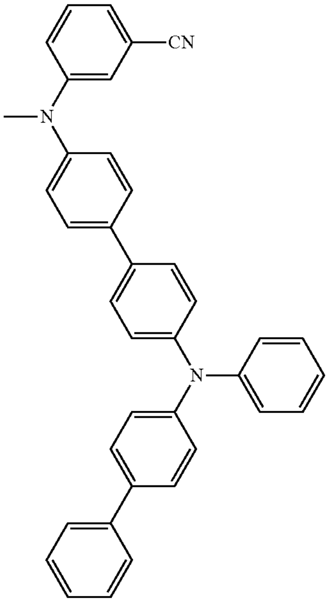
324
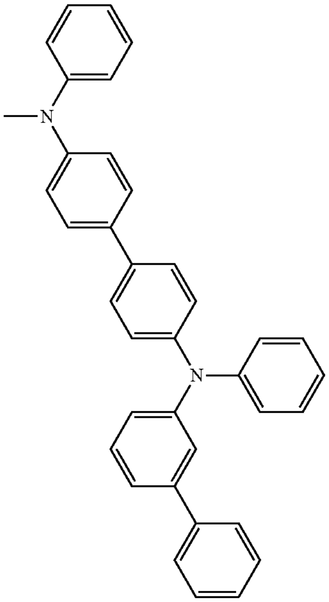
-continued
325
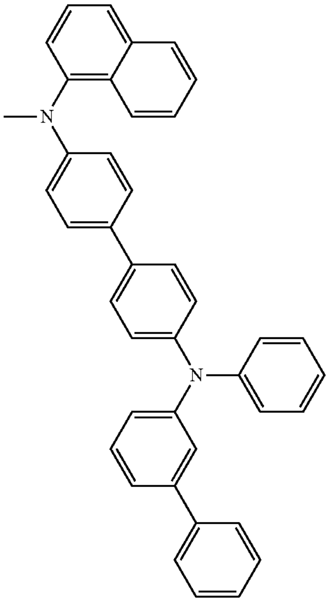
326
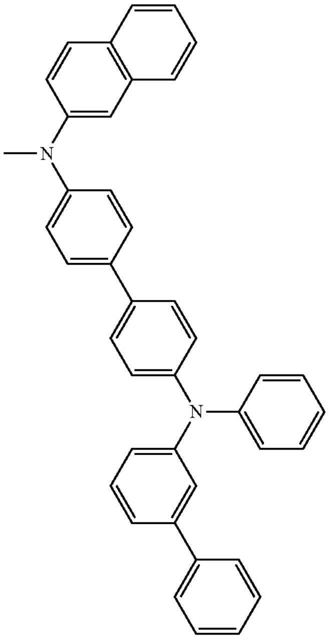
327
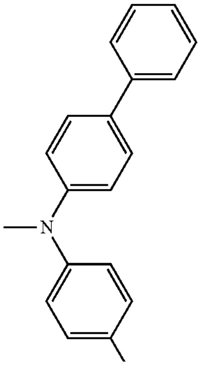

-continued
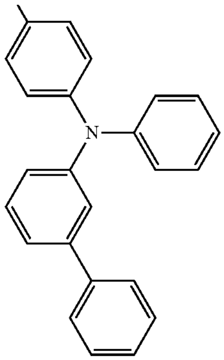
328
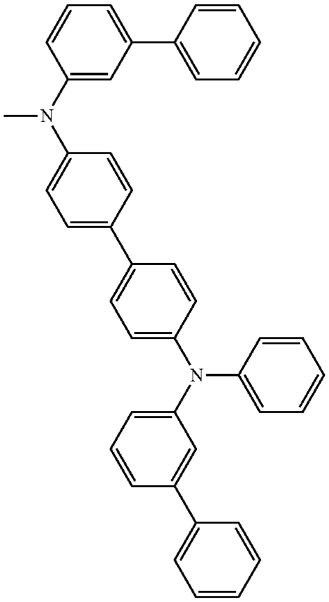
329
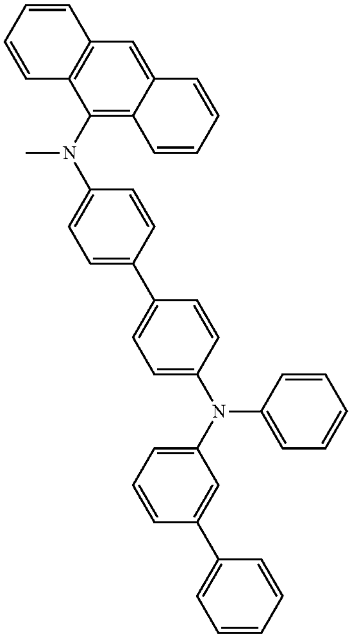
-continued
330
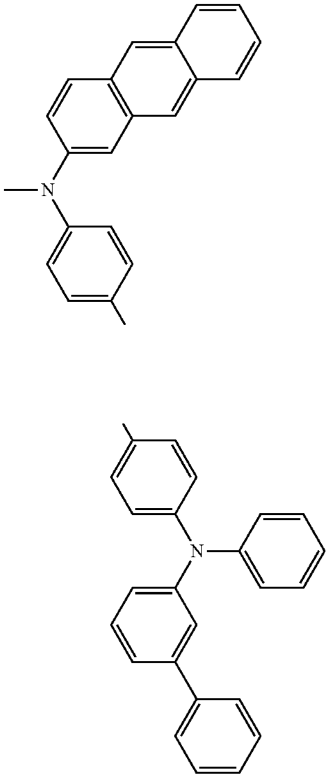
331
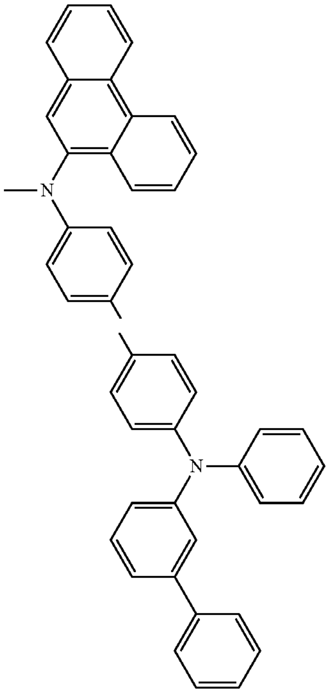

-continued
332
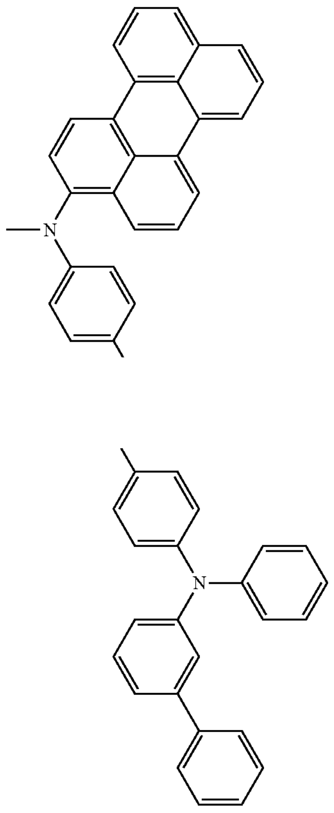
333
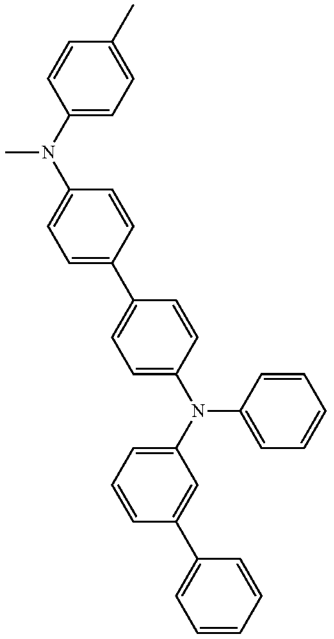
-continued
334
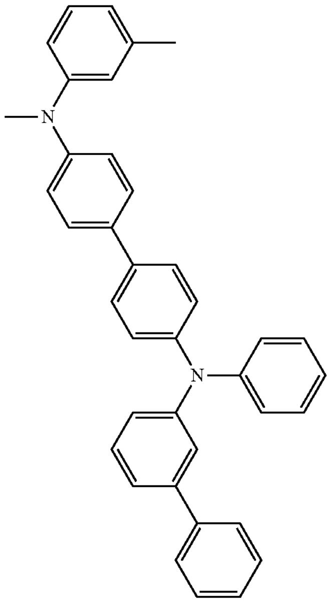
335
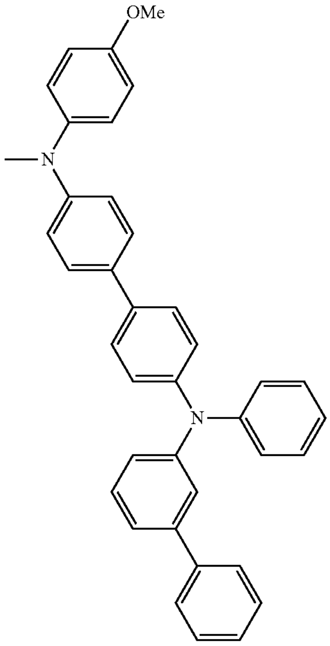

-continued
336
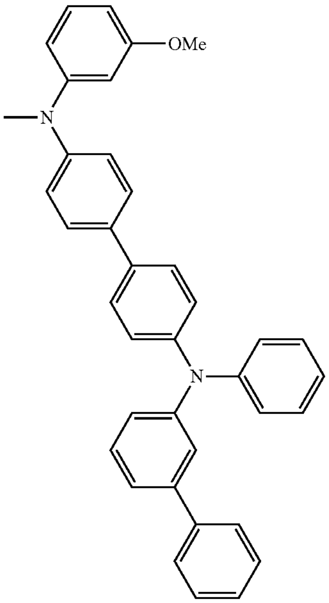
337
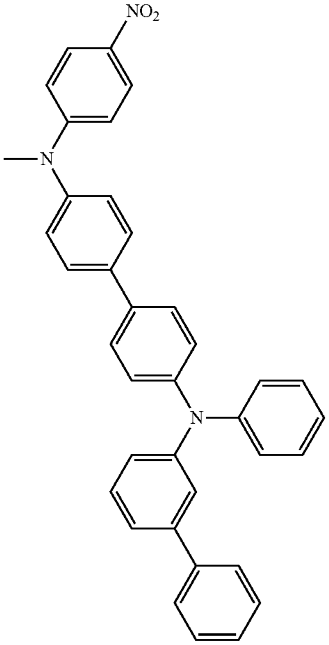
-continued
338
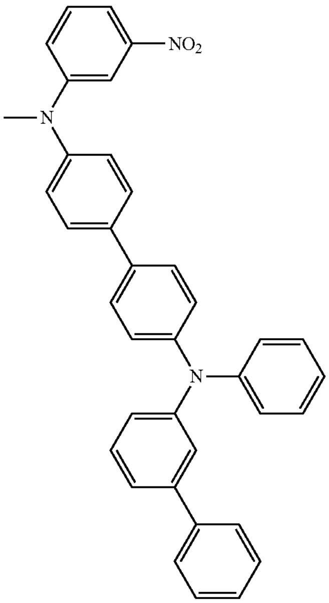
339
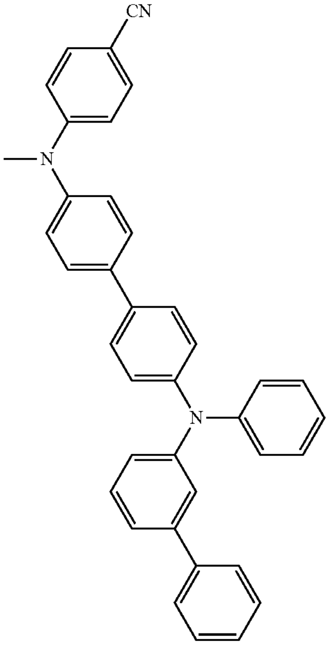

-continued
340
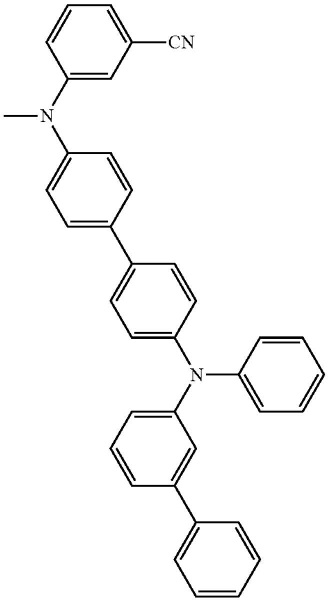
341
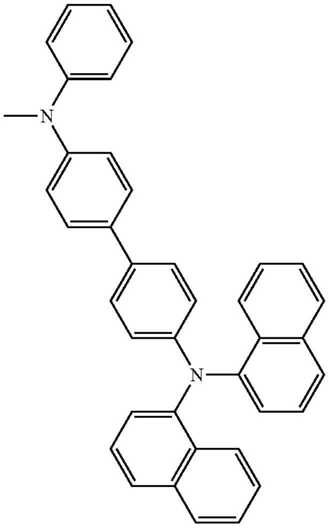
342
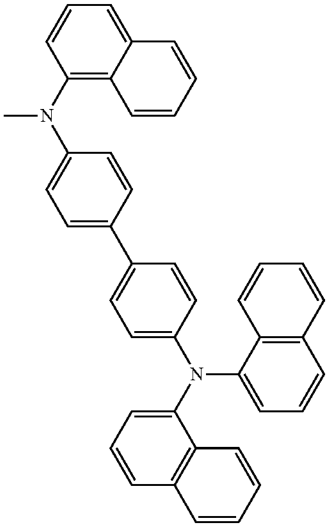
-continued
343
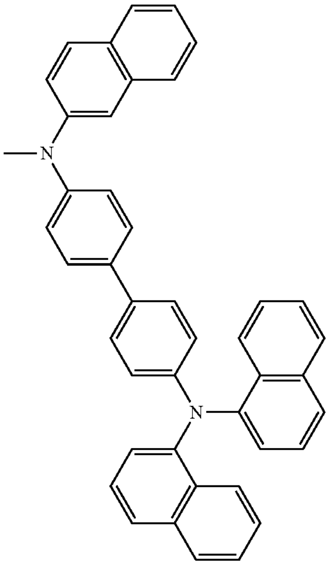
344
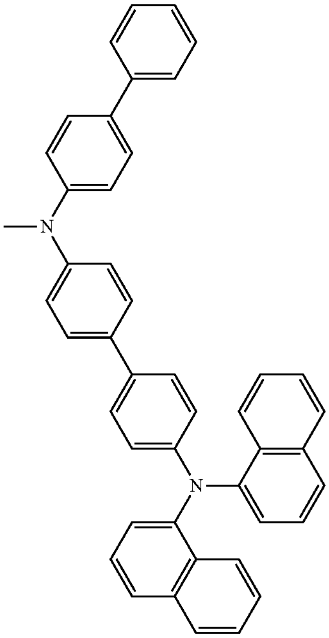

-continued
345
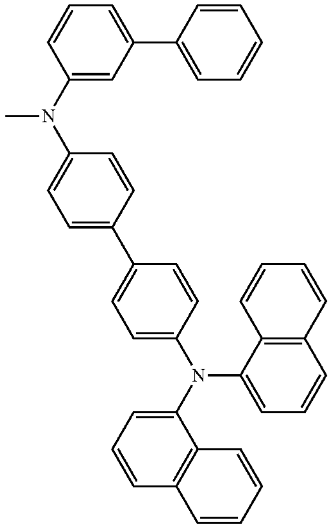
346
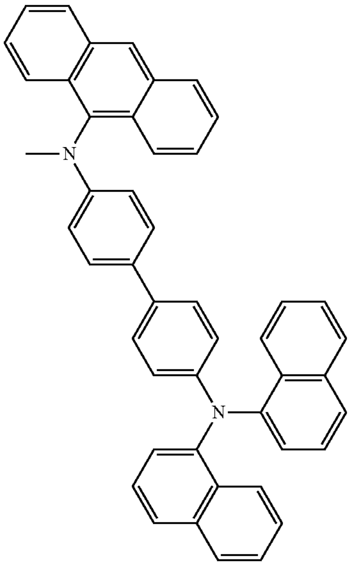
-continued
347
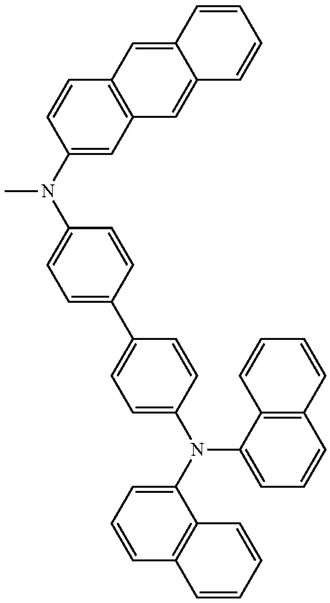
348
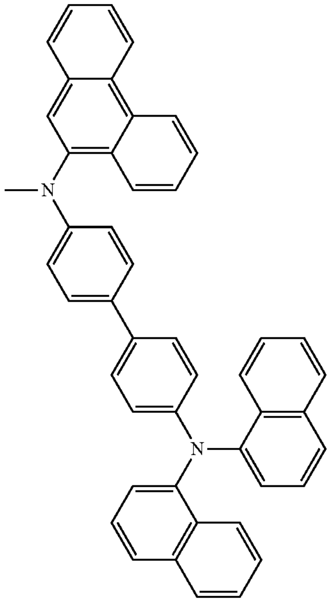

-continued
349
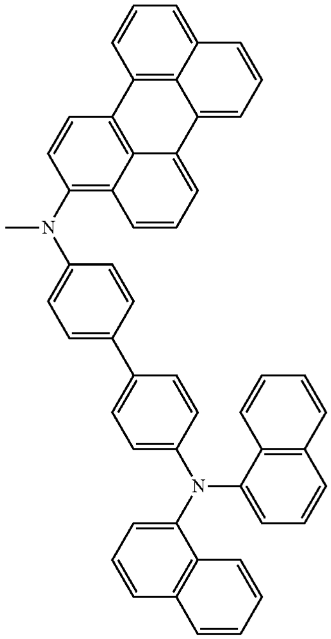
350
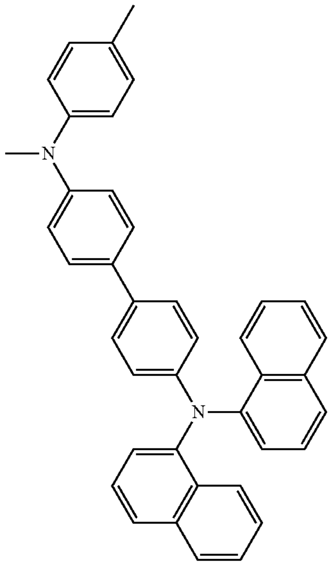
-continued
351
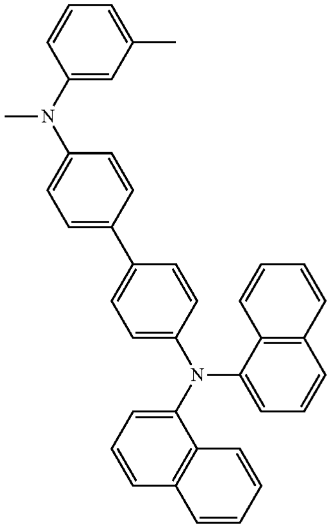
352
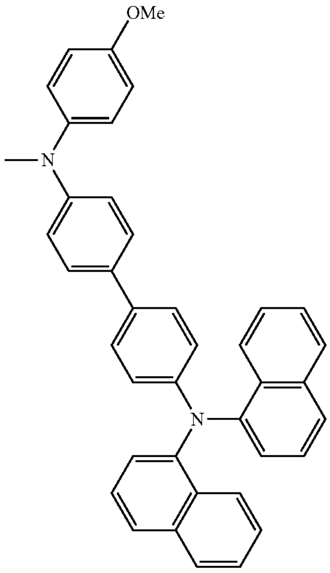
353
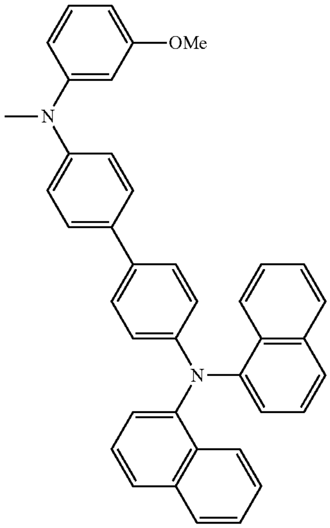

-continued
354
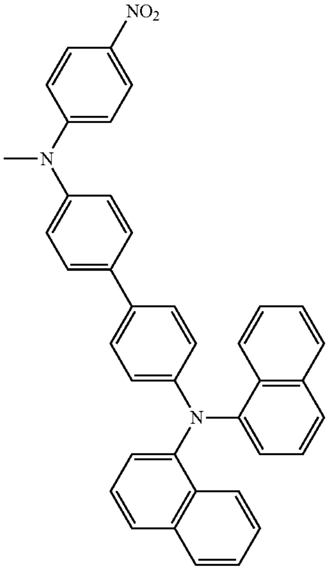
355
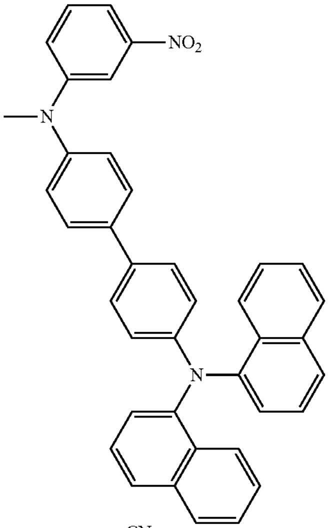
356
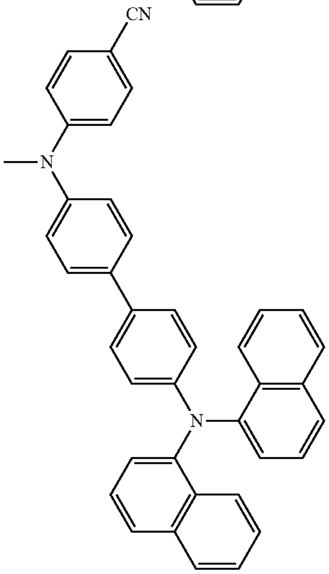
-continued
357
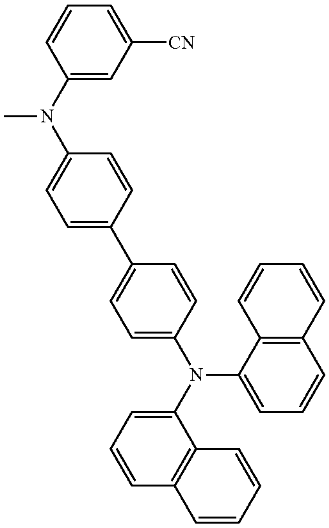
358
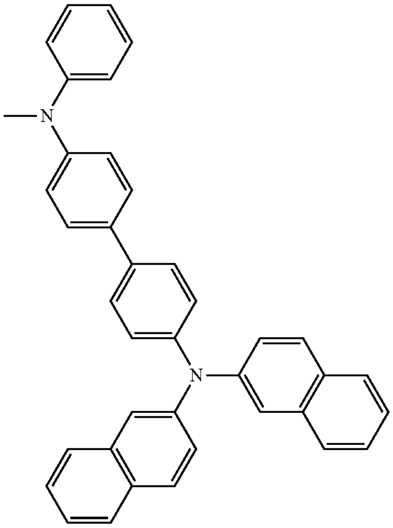
359
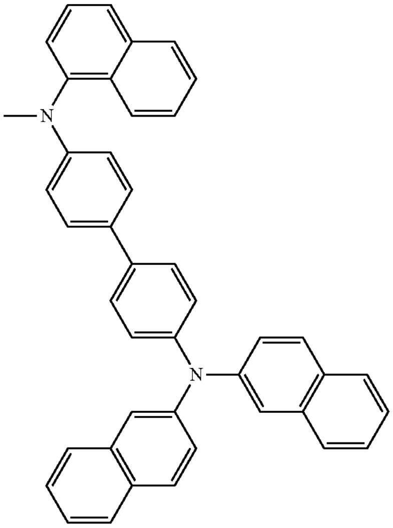

-continued
360
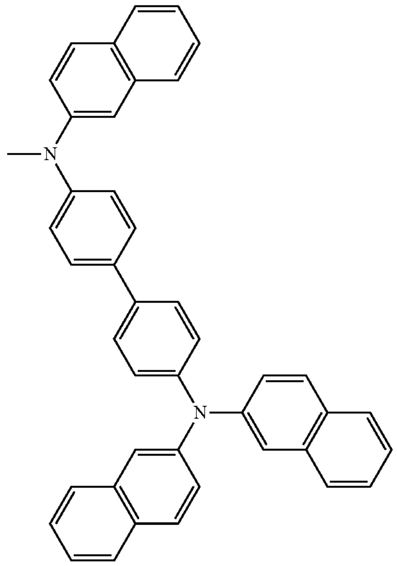
361
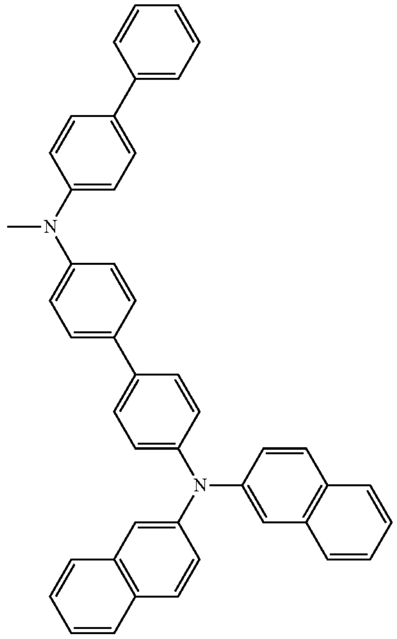
-continued
362
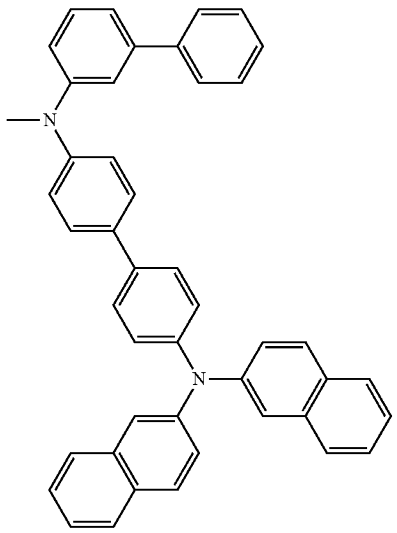
363
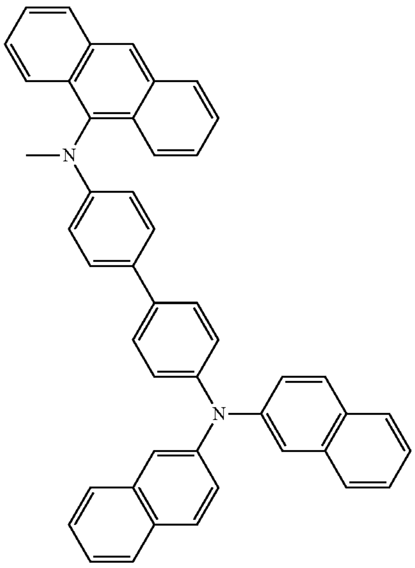

-continued
364
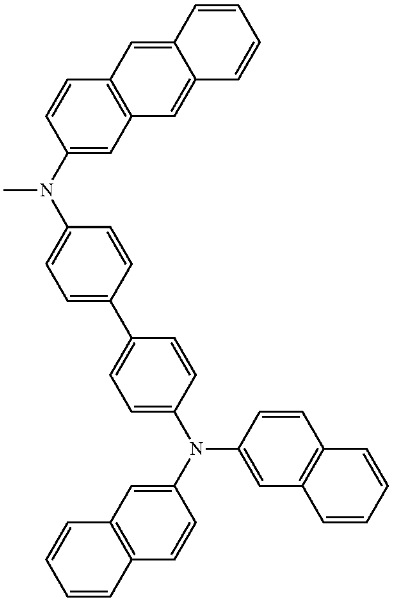
365
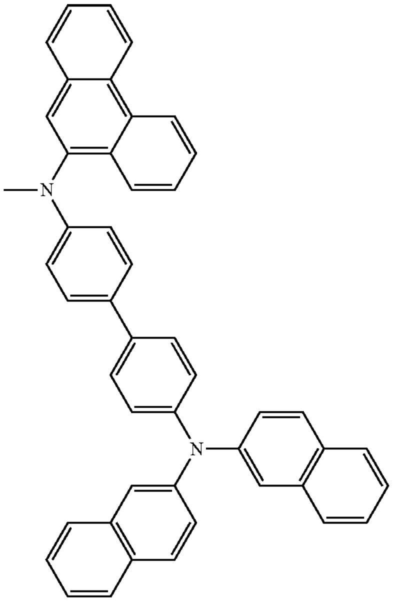
-continued
366
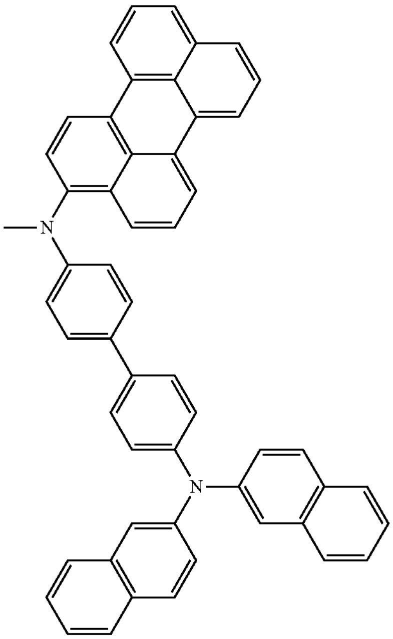
367
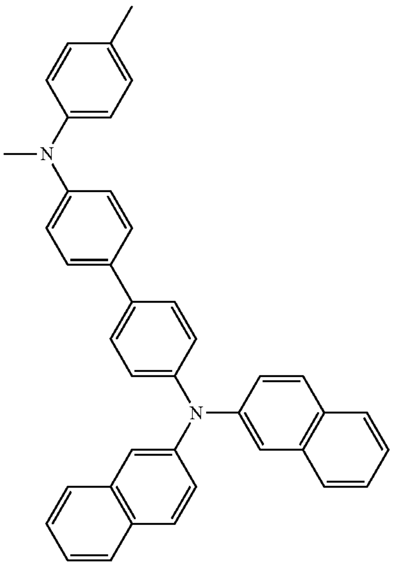

-continued
368
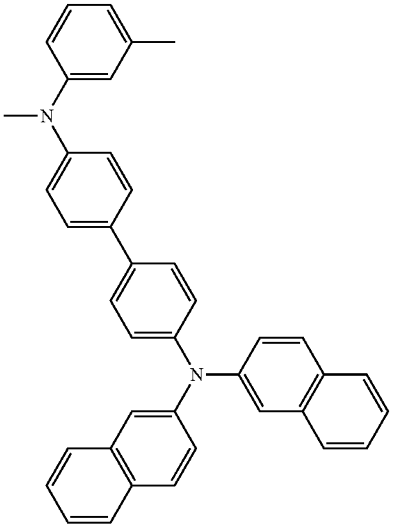
369
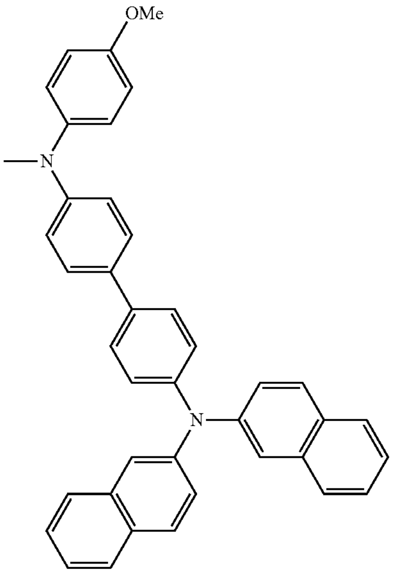
370
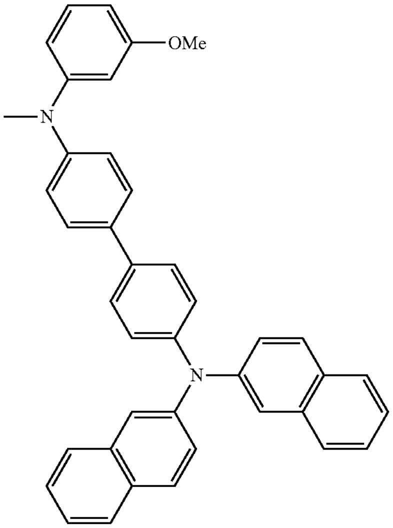
-continued
371
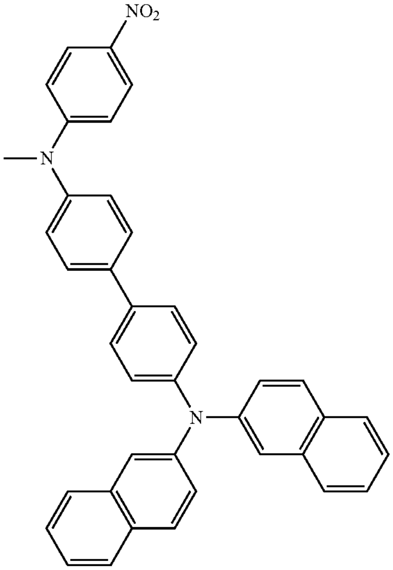
372
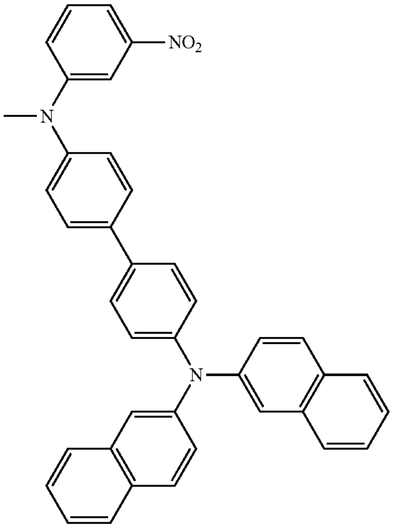

-continued
373
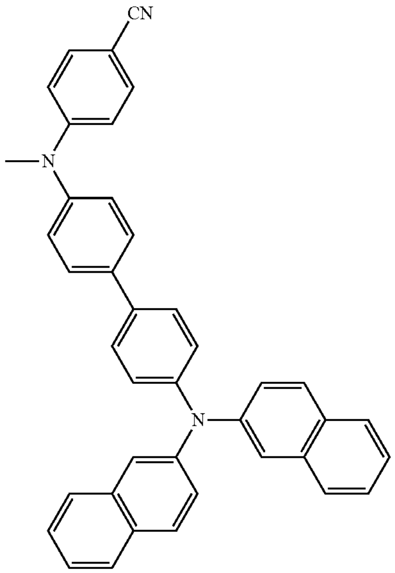
374
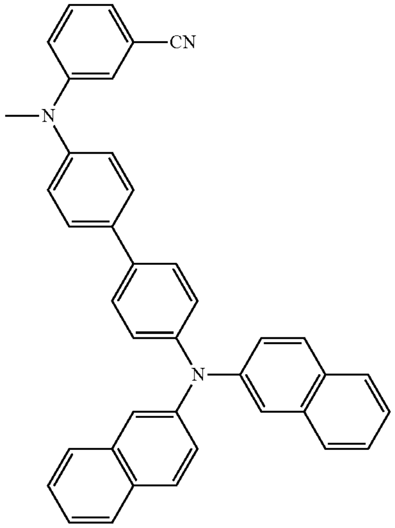
-continued
375
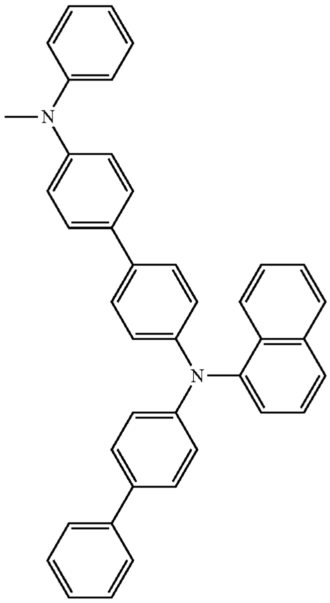
376
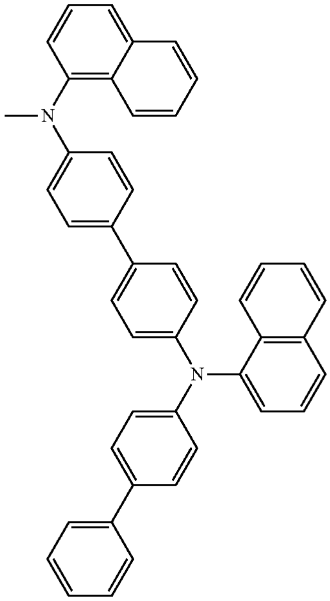

-continued
377
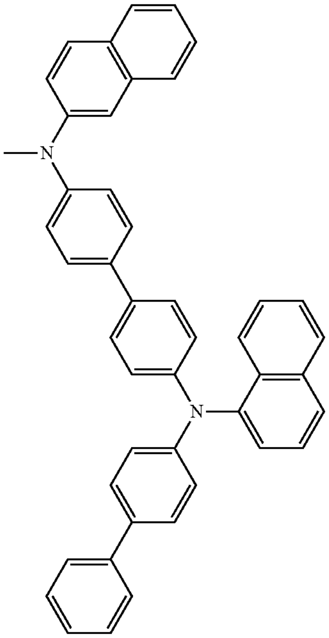
378
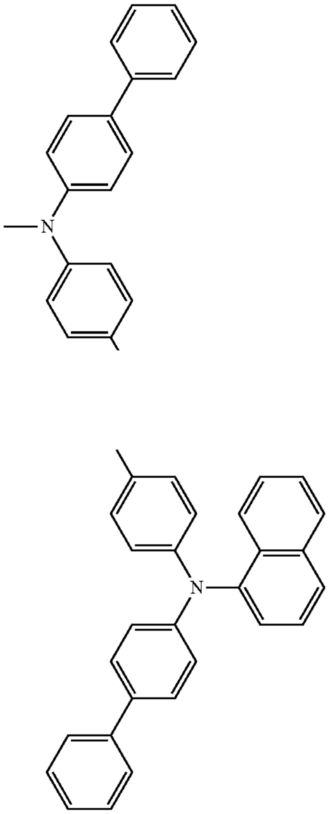
-continued
379
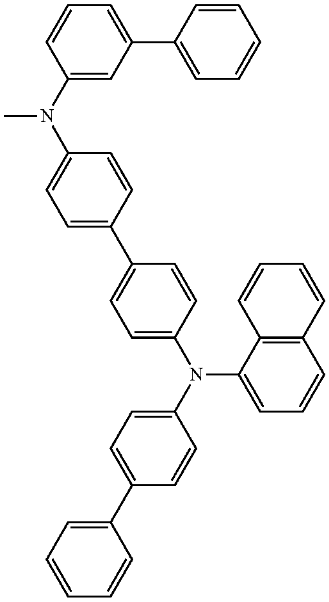
380
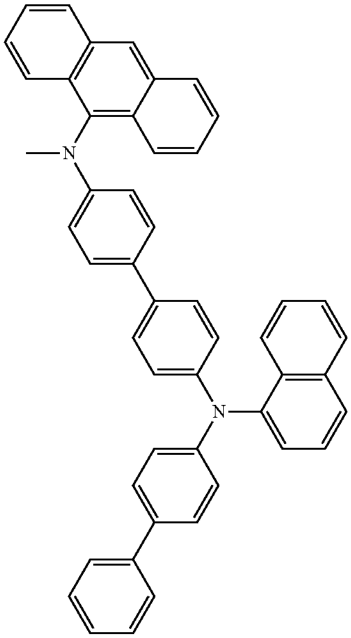
381
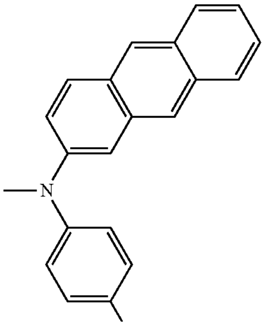

-continued
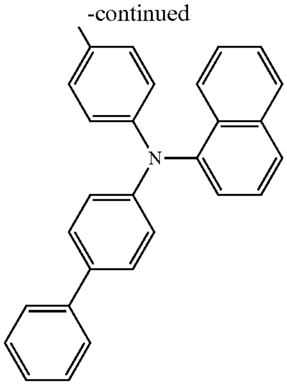
382
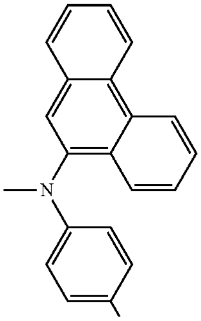
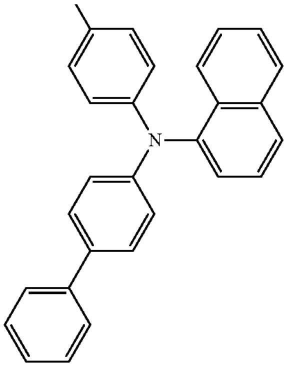
383
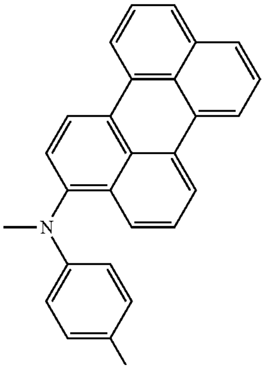
-continued
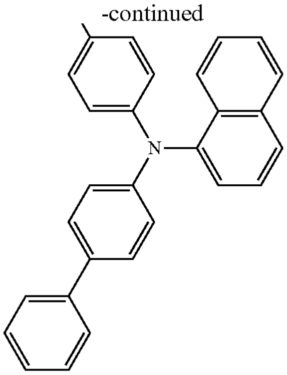
384
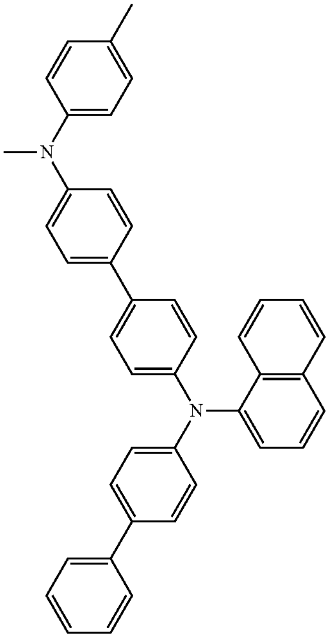
385
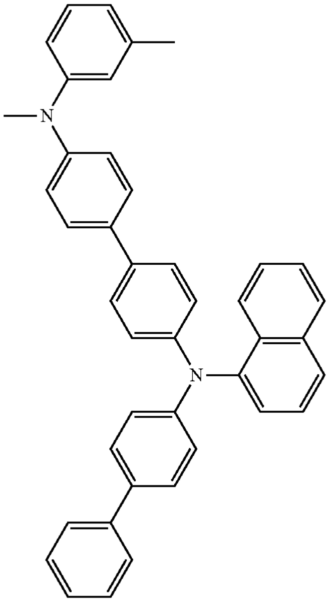

-continued
386
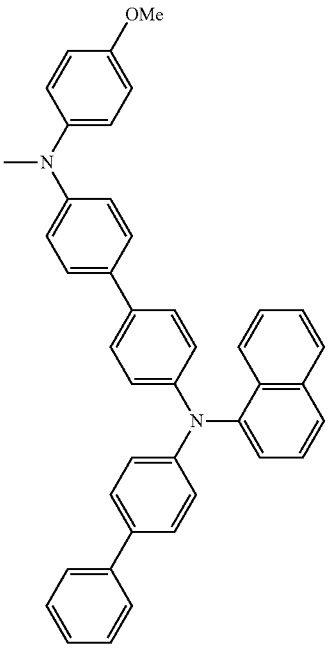
388
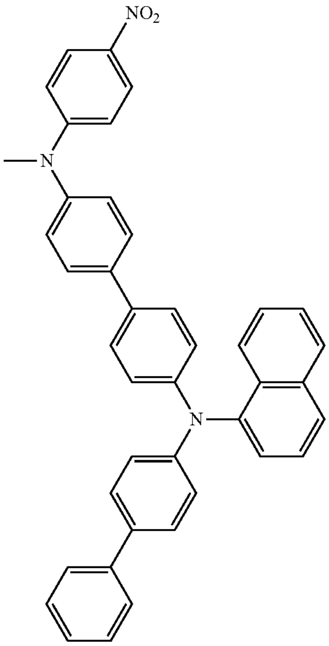
387
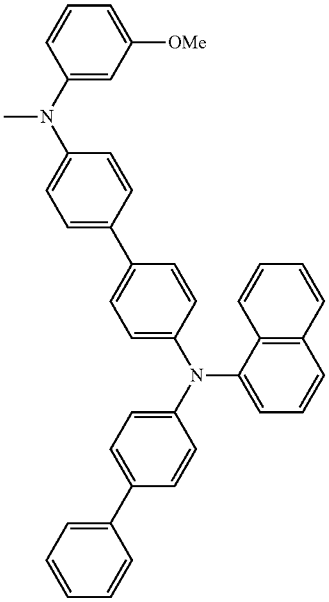
389
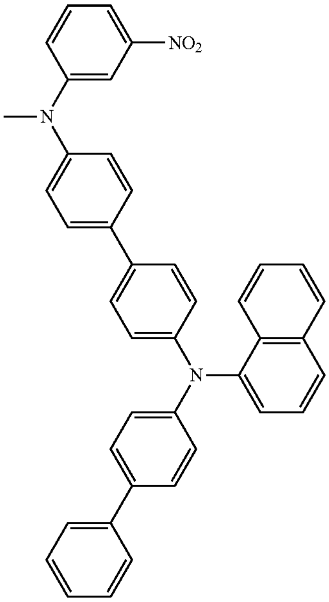
-continued -continued
390
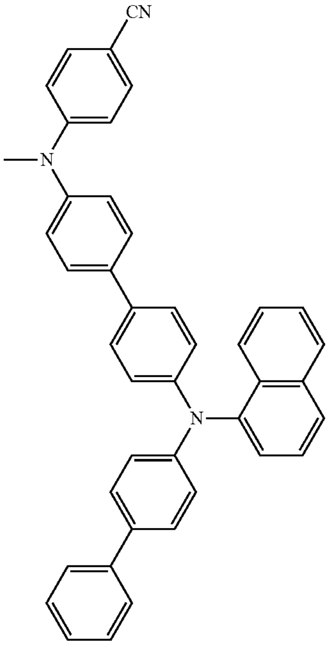
391
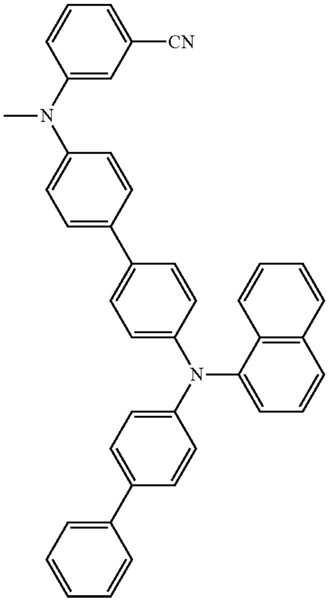
-continued
392
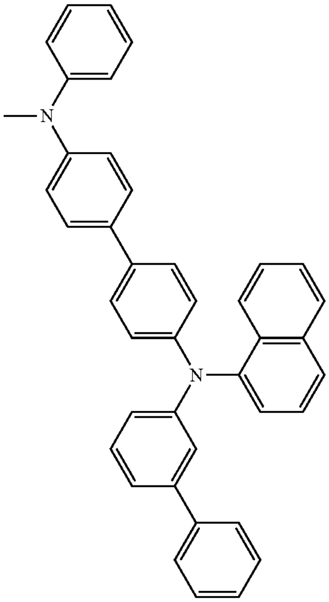
393
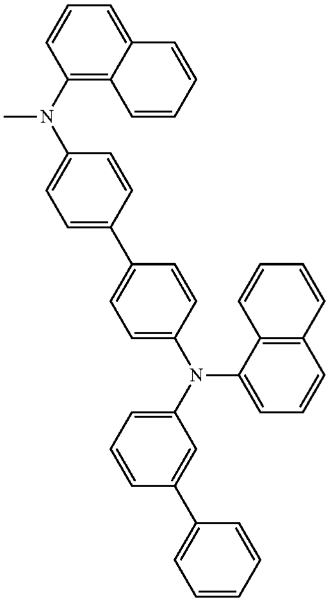

-continued
394
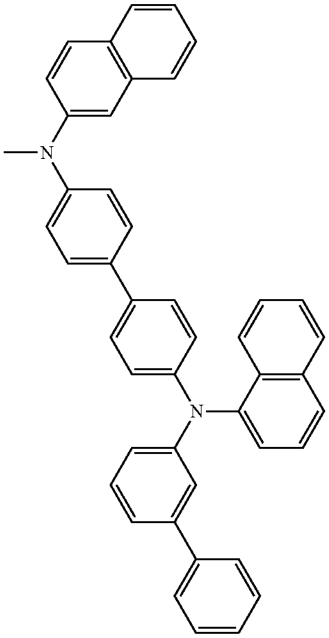
395
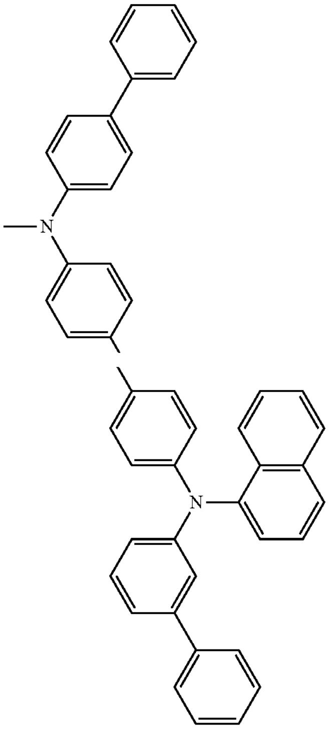
-continued
396
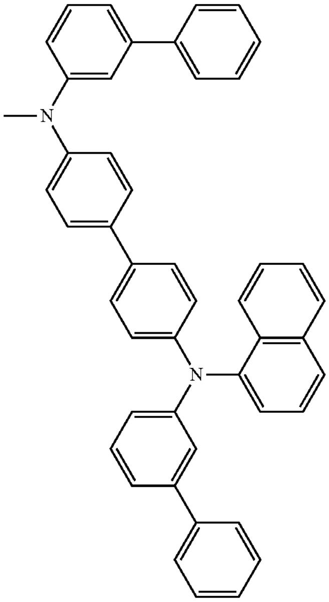
397
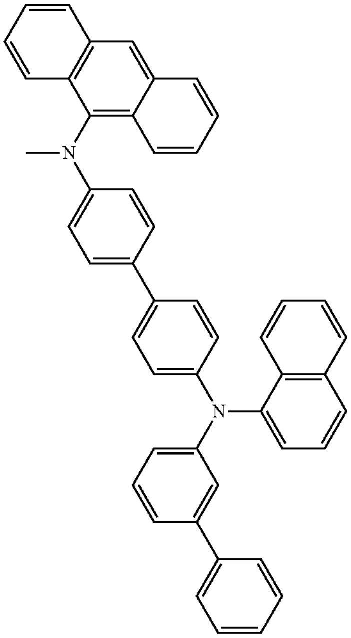
398
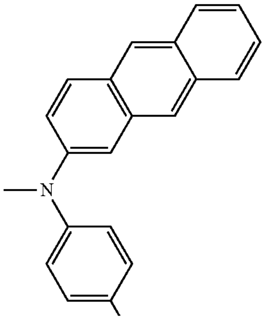

-continued
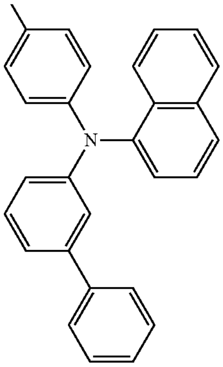
399
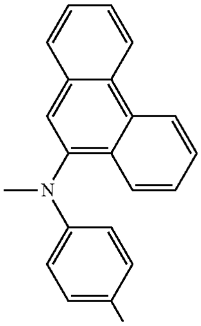
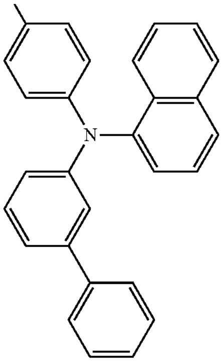
400
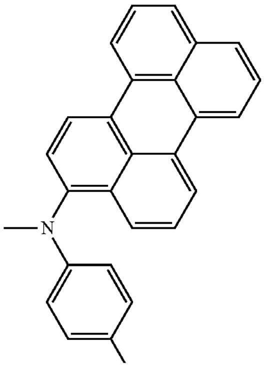
-continued
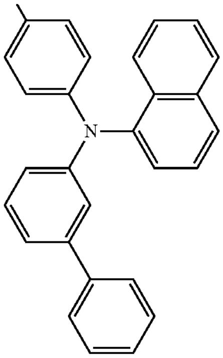
401
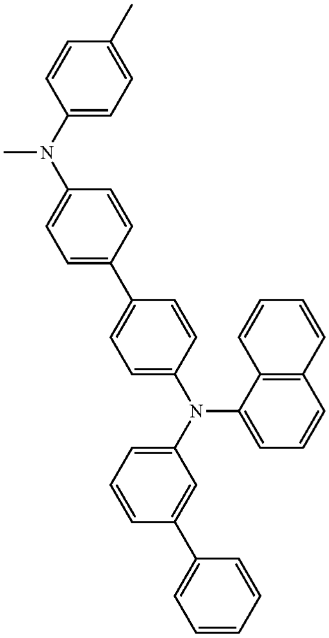
402
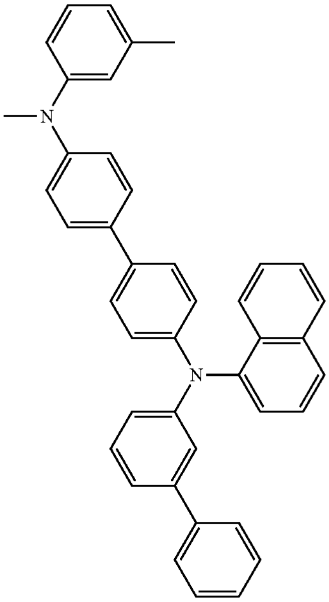

-continued
403
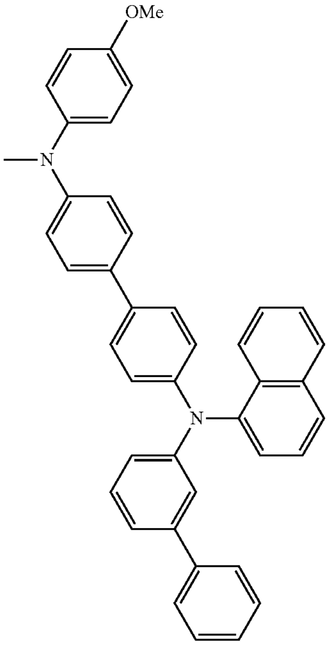
404
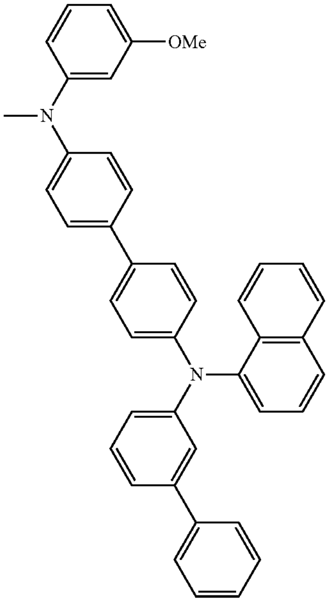
-continued
405
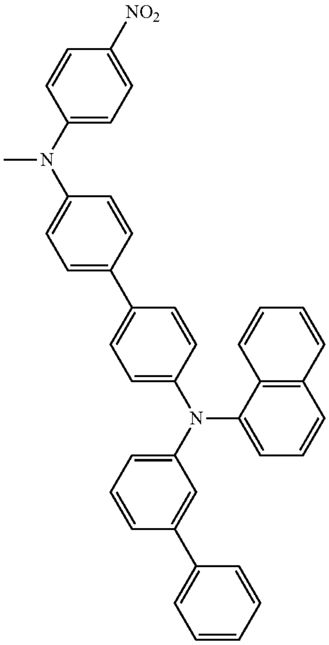
406
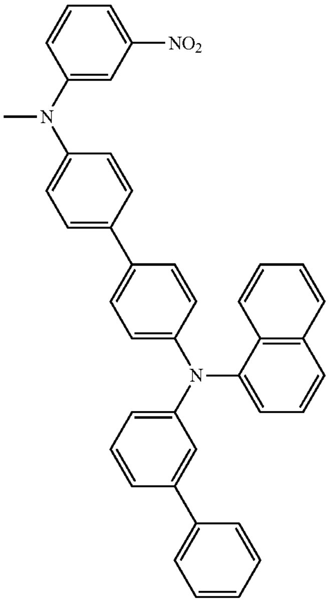

-continued
407
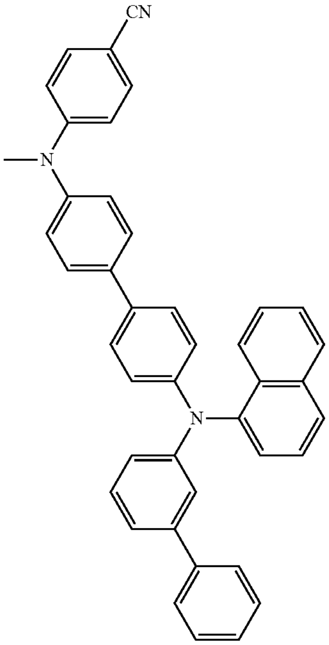
408
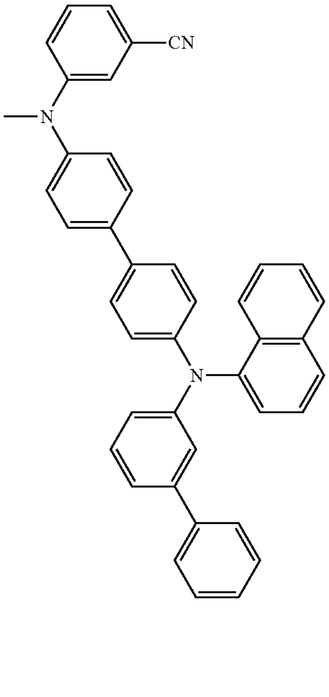
-continued
409
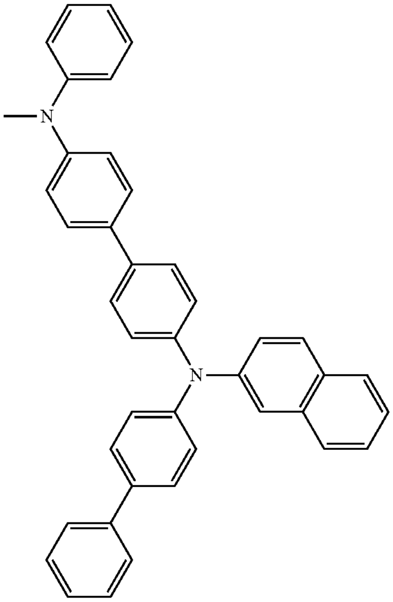
410
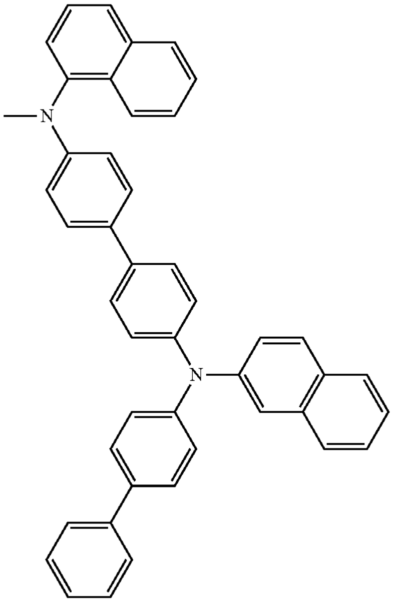

-continued
411
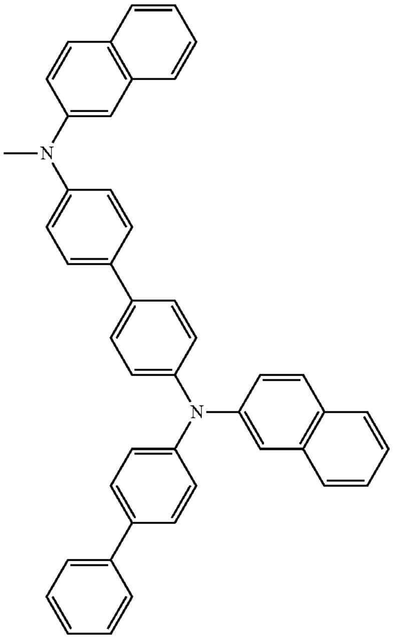
412
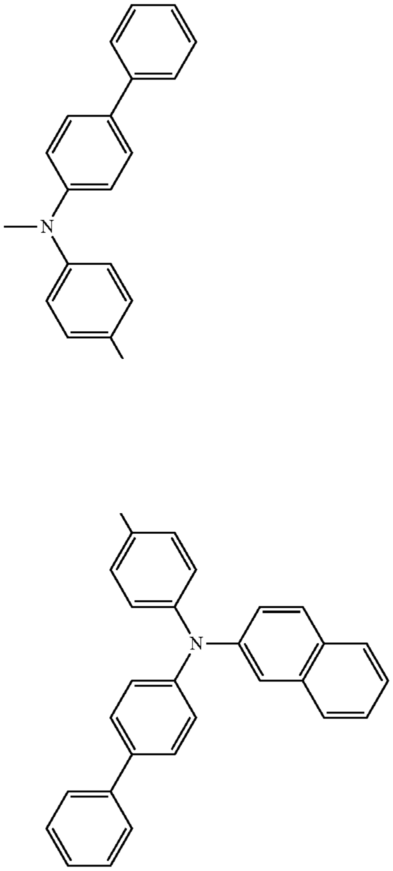
-continued
413
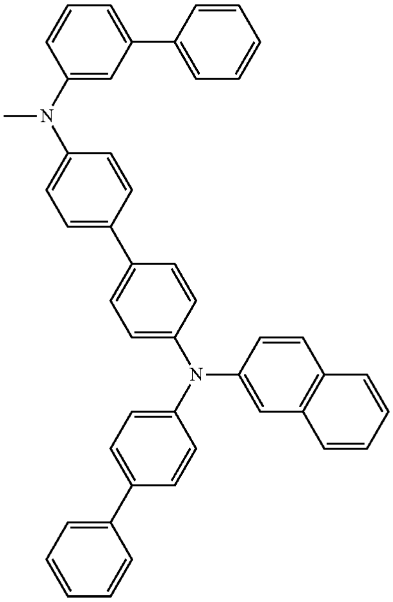
414
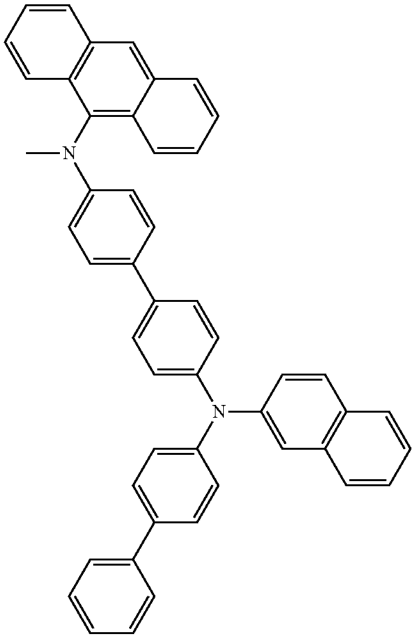
415
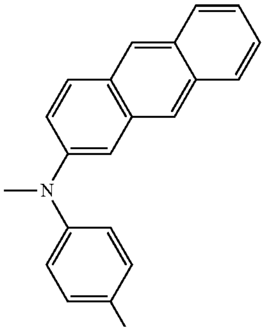

-continued
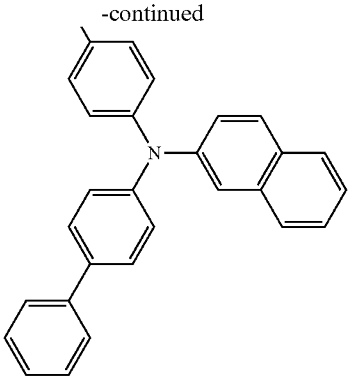
416
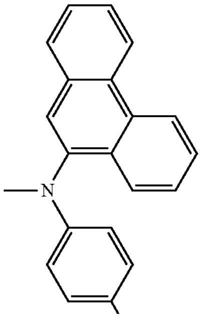
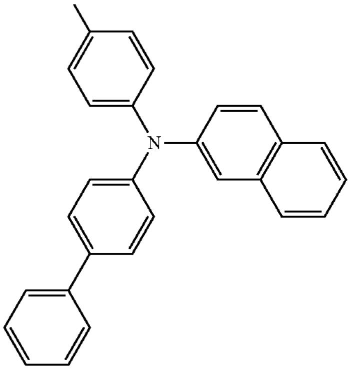
417
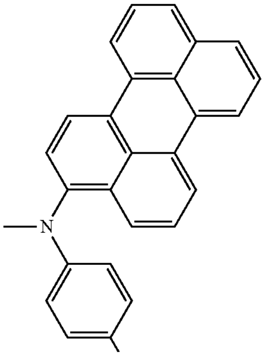
-continued
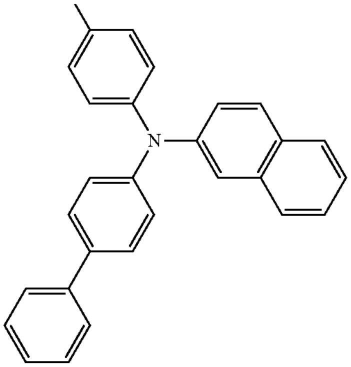
418
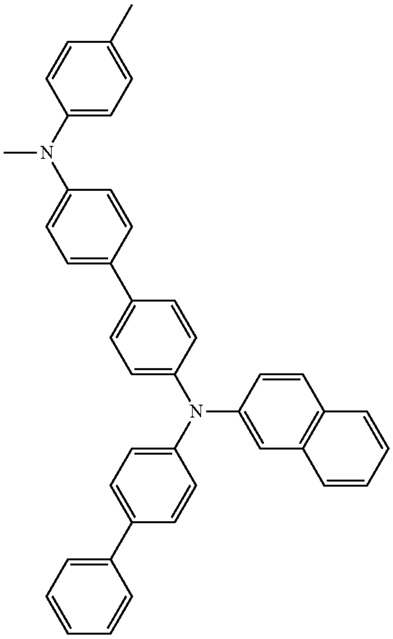
419
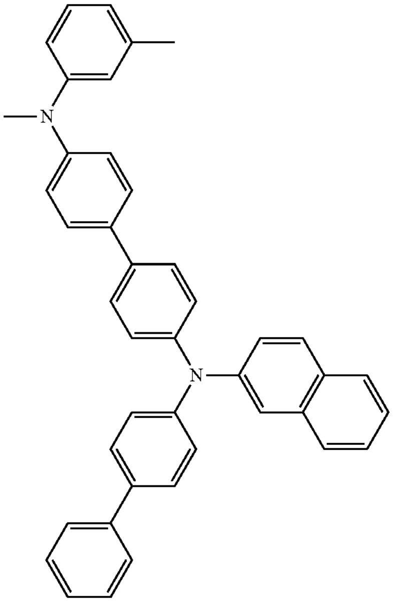

-continued
420
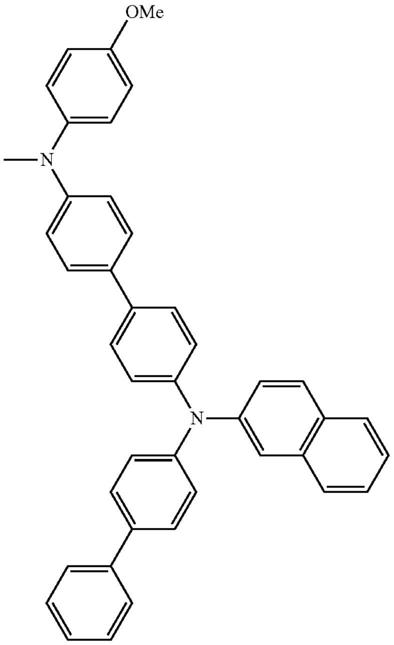
421
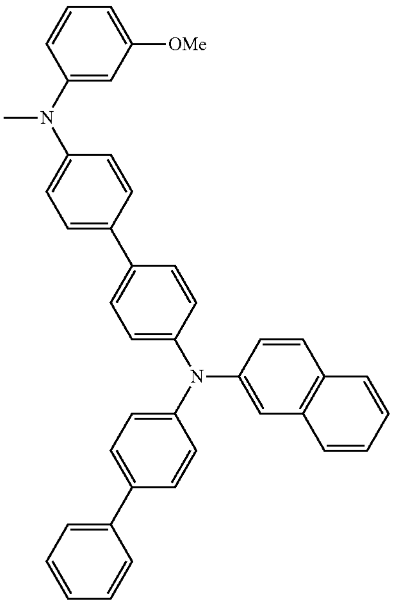
-continued
422
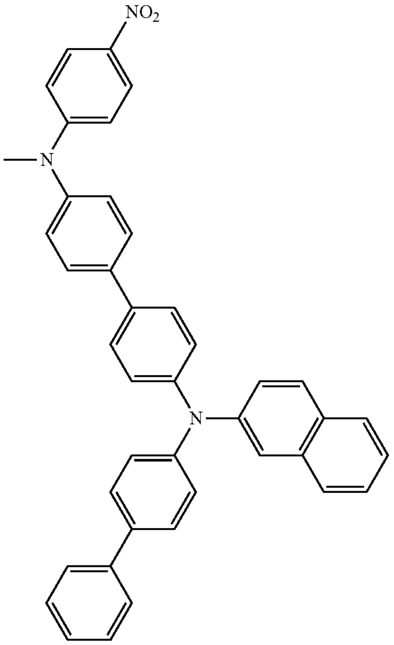
423
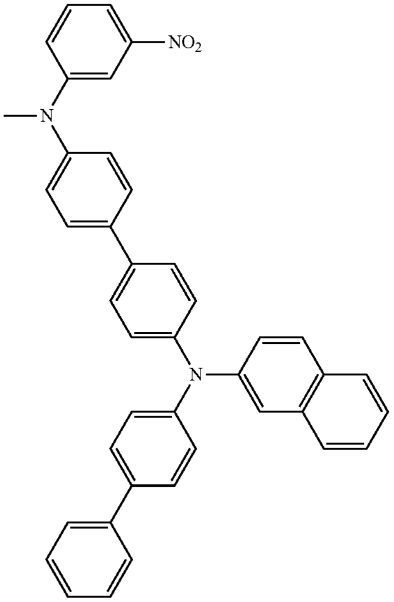

-continued
424
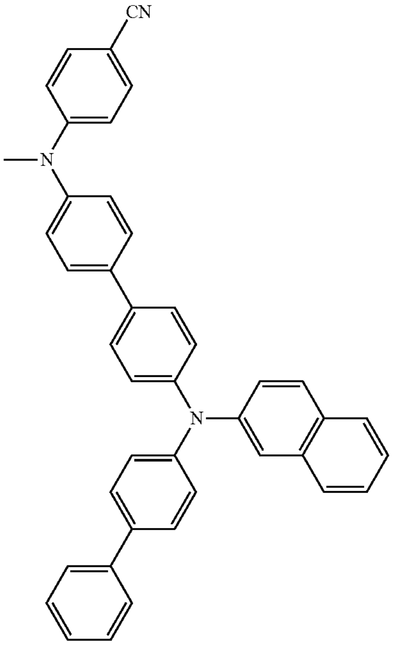
425
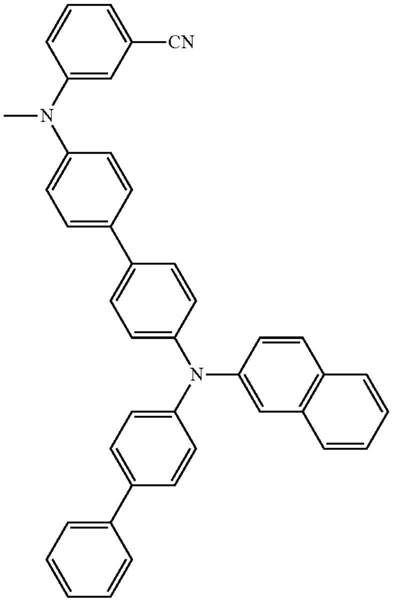
-continued
426
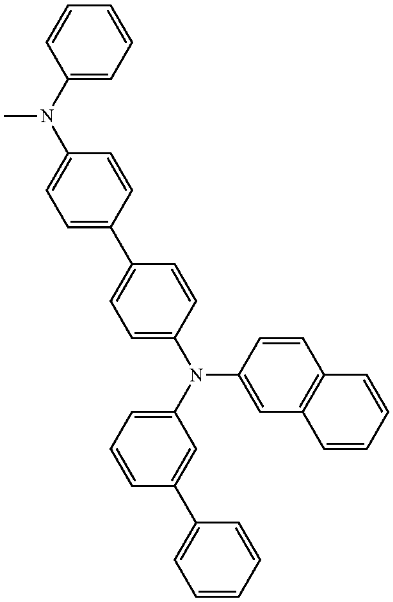
427
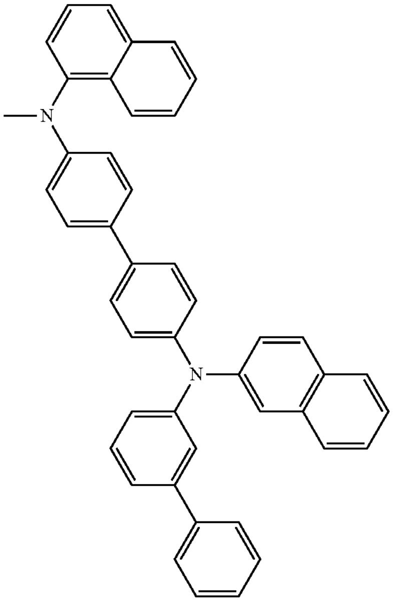

-continued
428
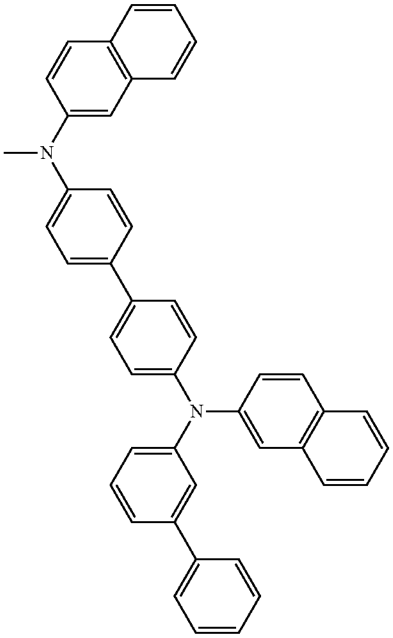
429
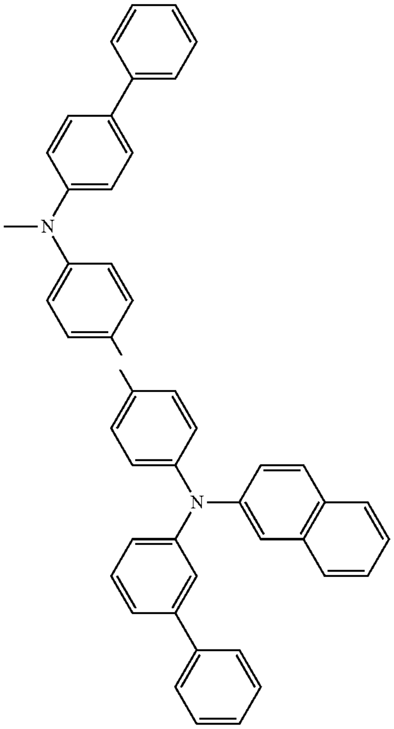
-continued
430
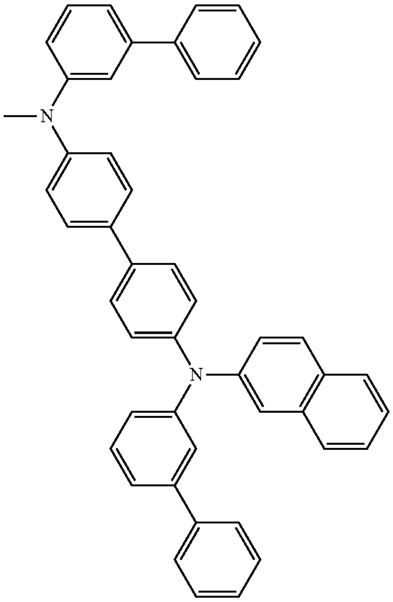
431
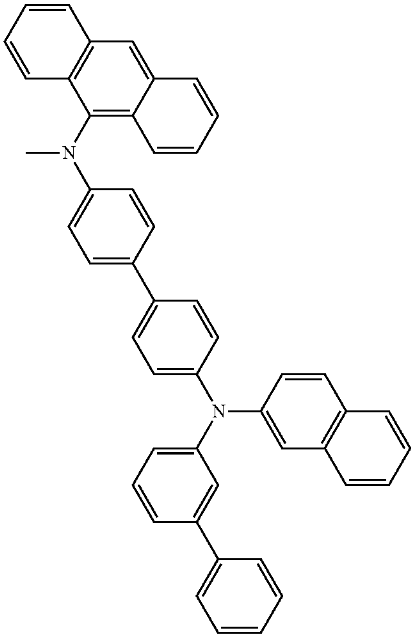
432
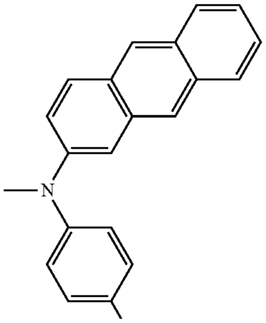

-continued
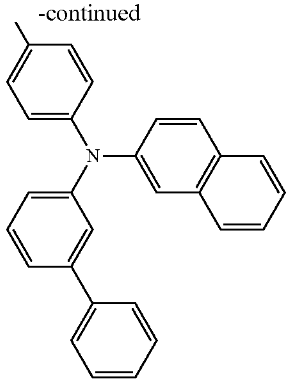
433
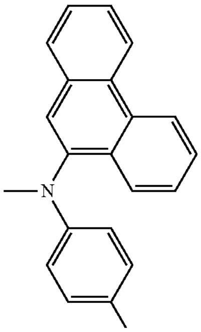
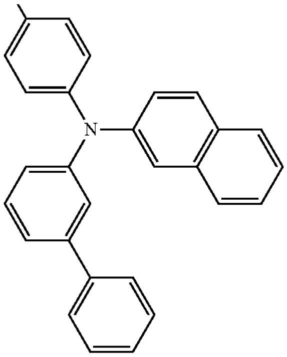
434
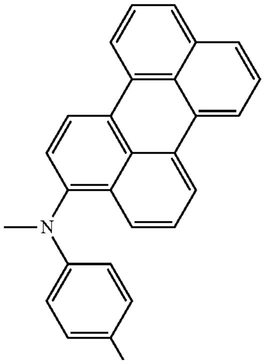
-continued
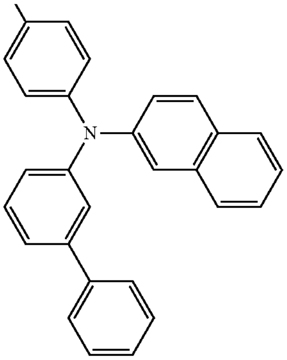
435
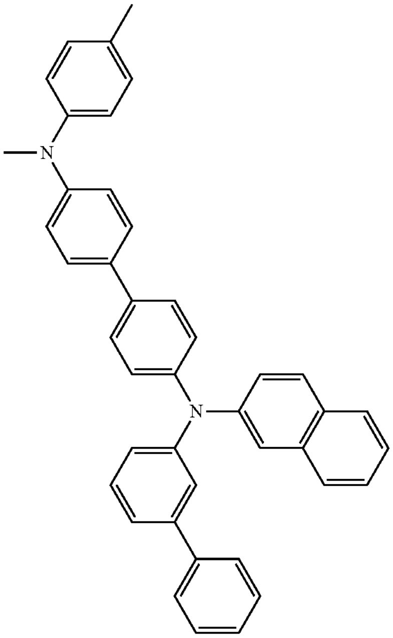
436
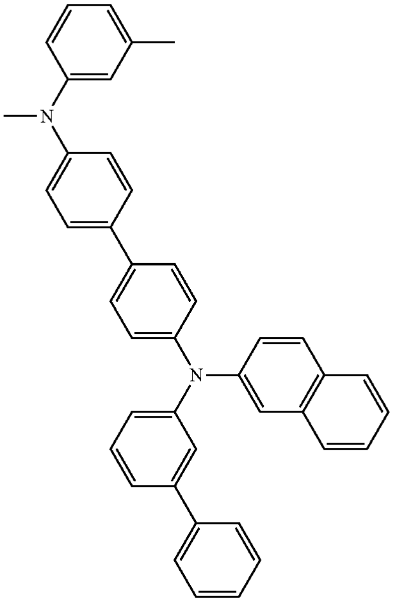

-continued
437
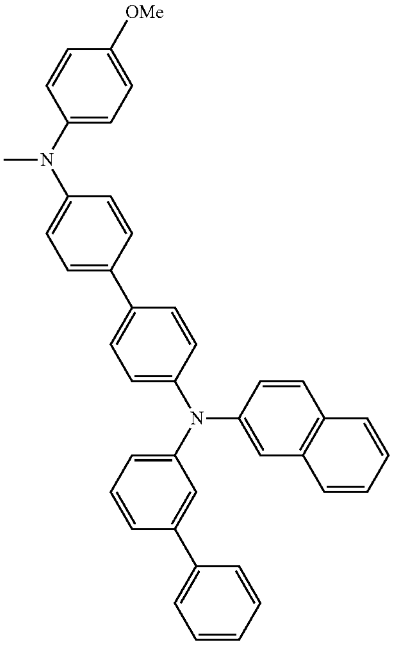
438
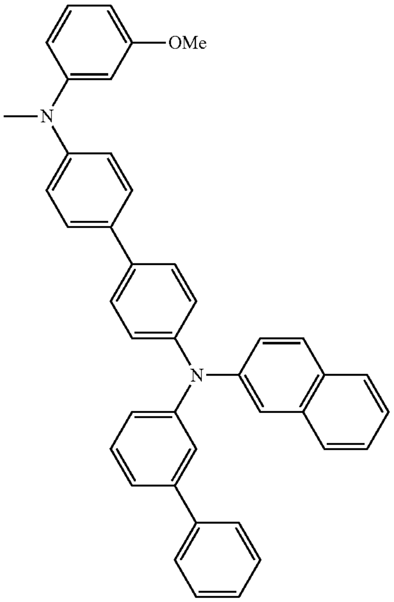
-continued
439
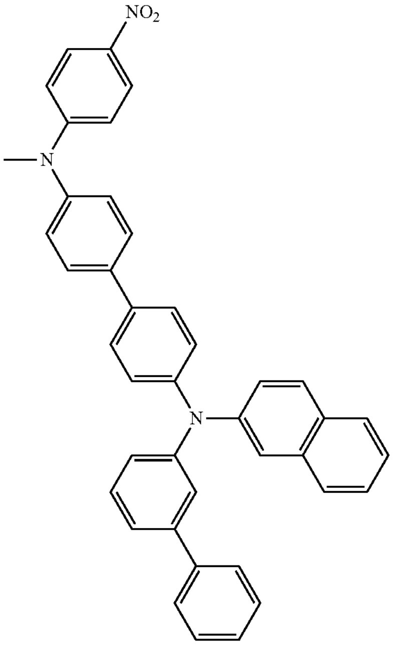
440
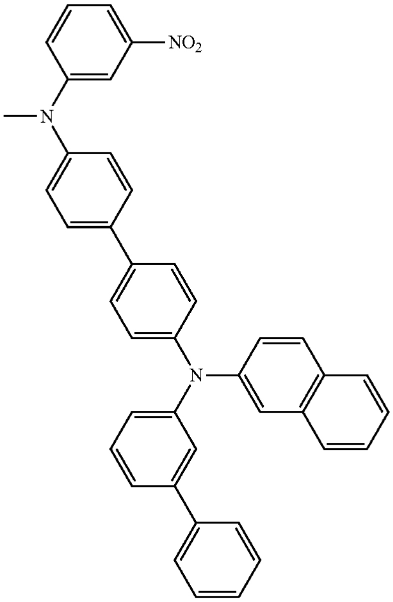

-continued
441
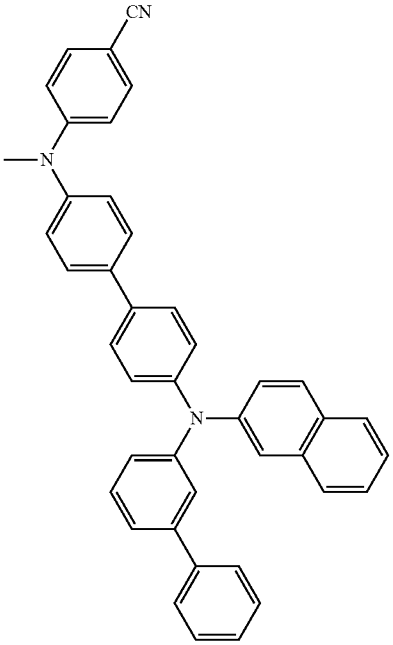
442
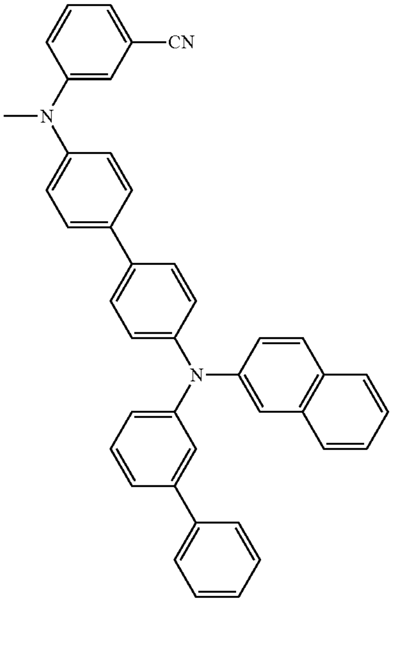
-continued
443
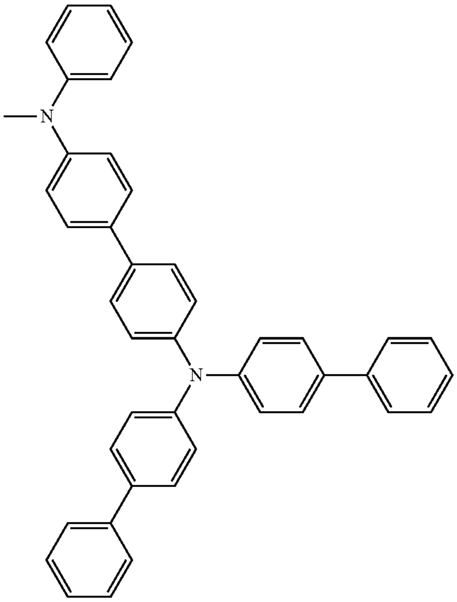
444
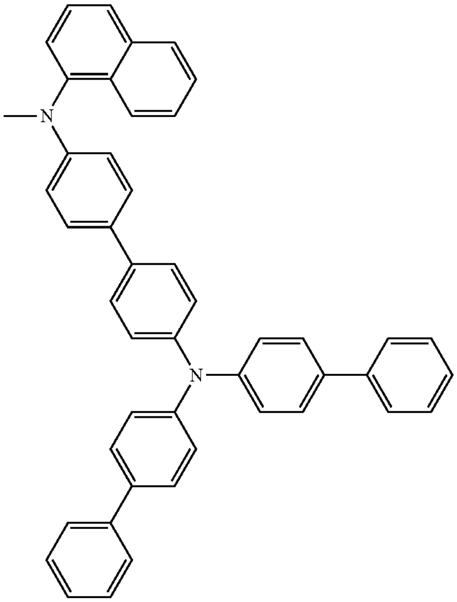

-continued
445
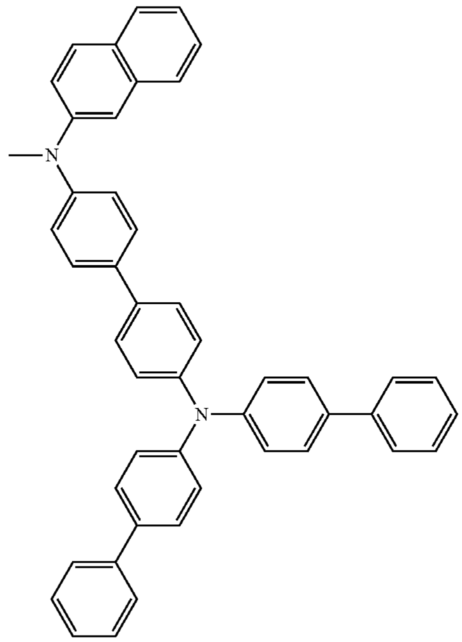
446
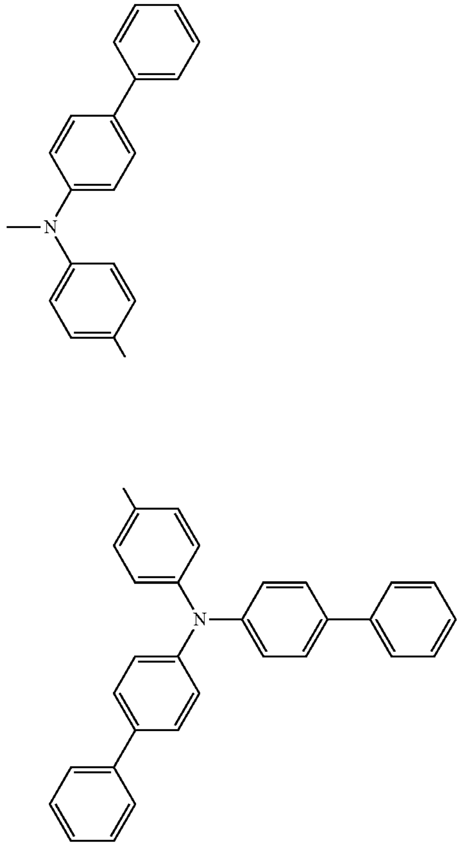
-continued
447
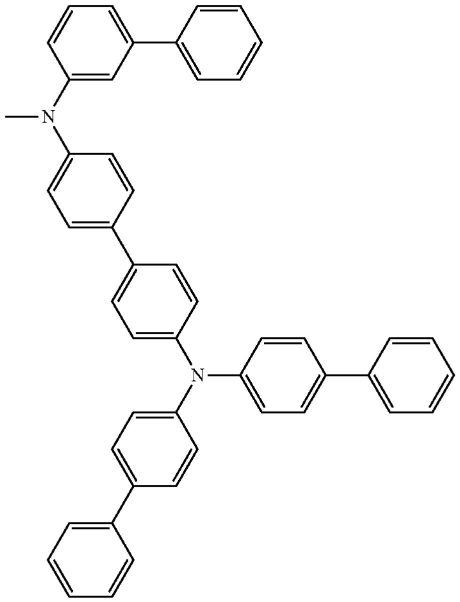
448
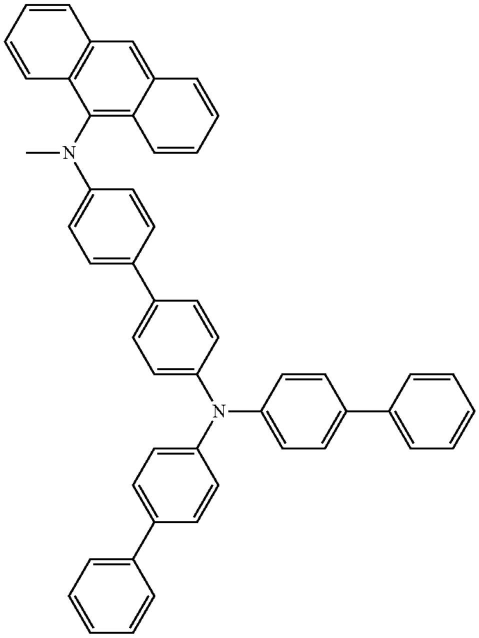
449
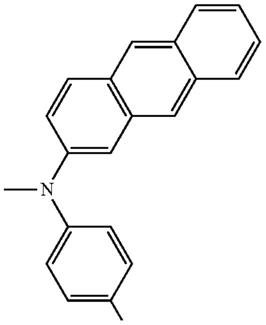

-continued
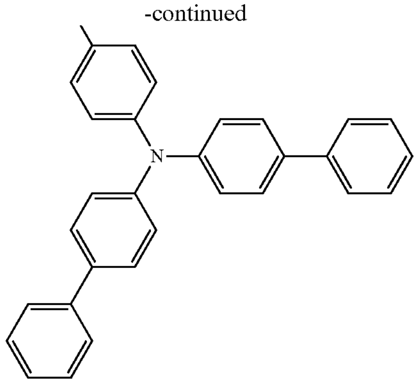
450
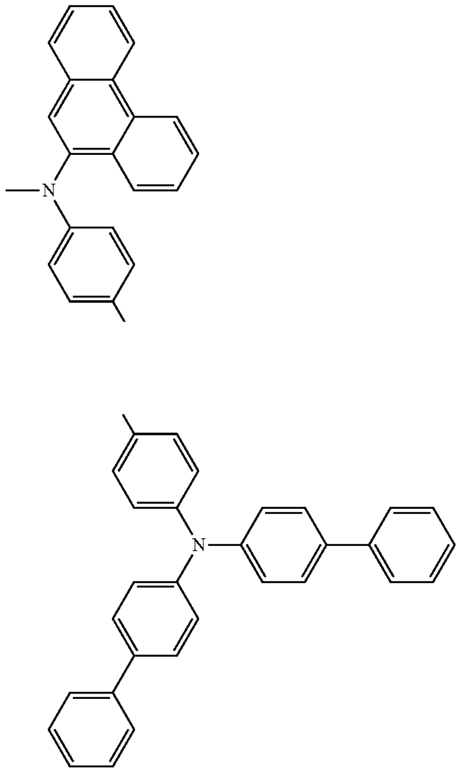
451
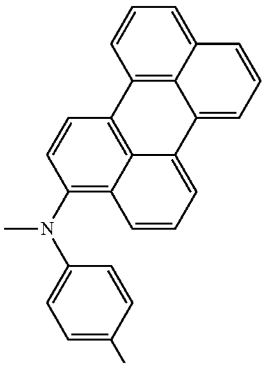
-continued
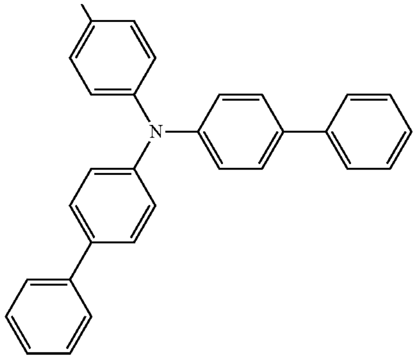
452
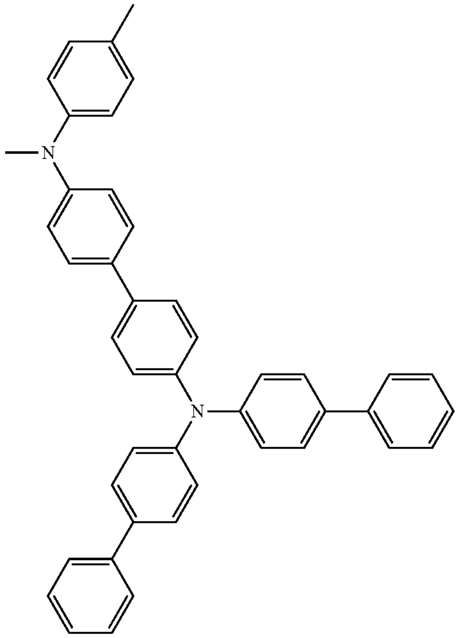
453
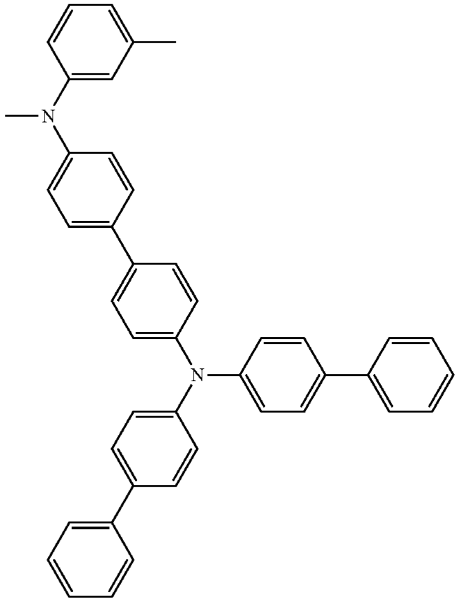

-continued
454
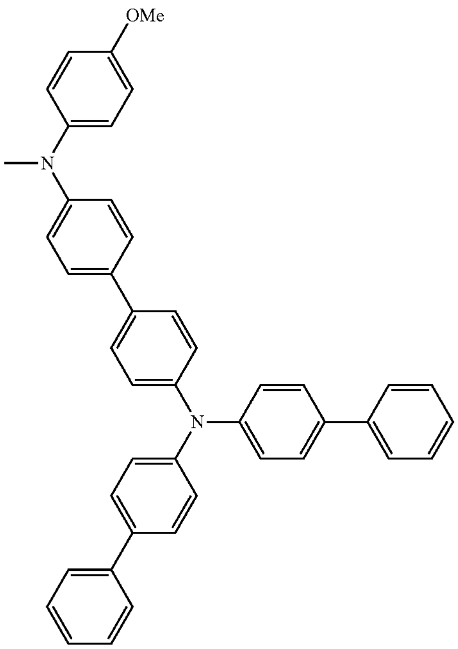
456
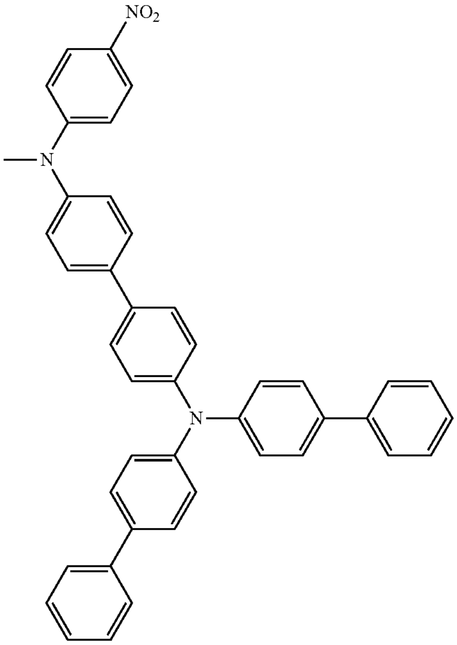
455
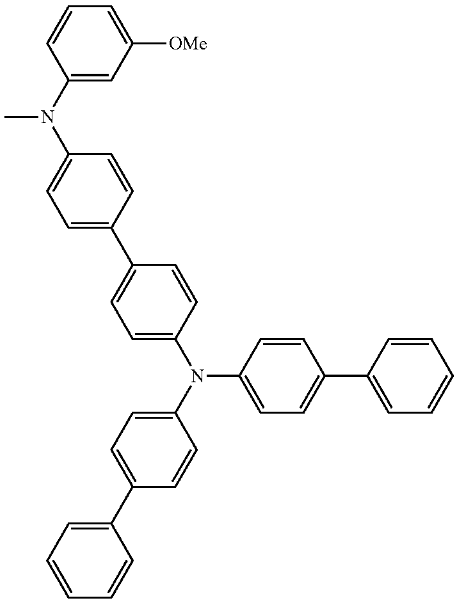
457
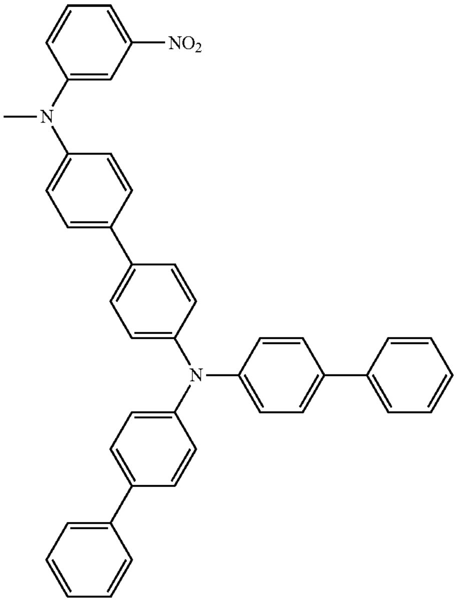

-continued
458
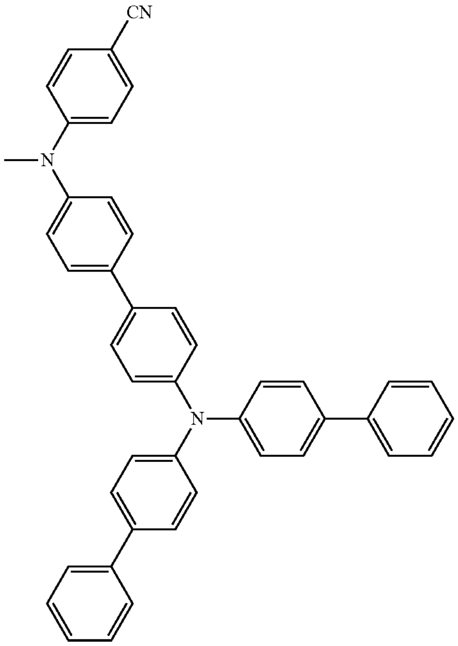
459
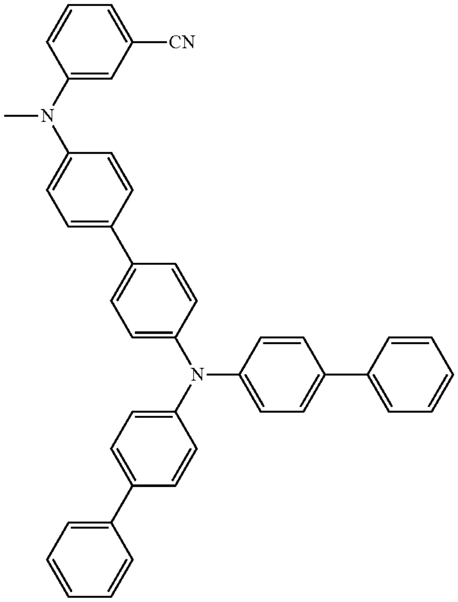
-continued
460
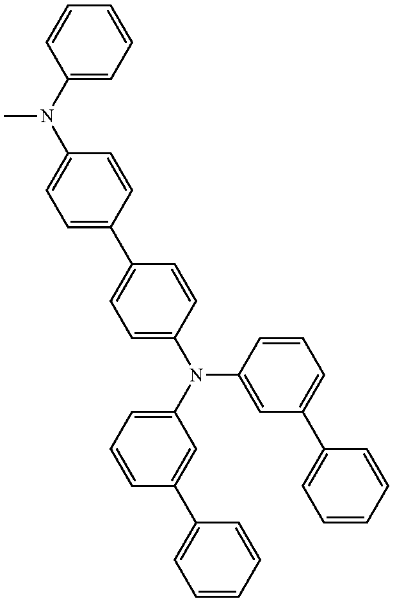
461
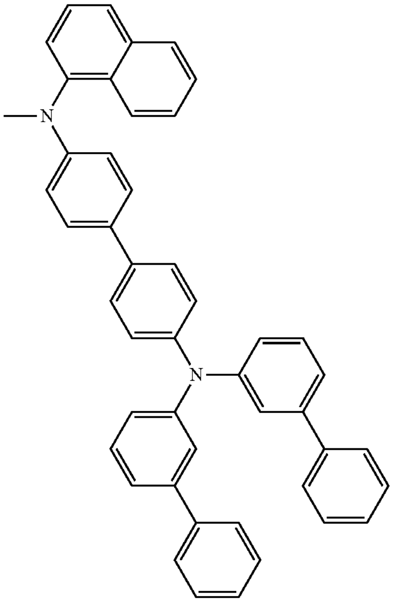

-continued
462
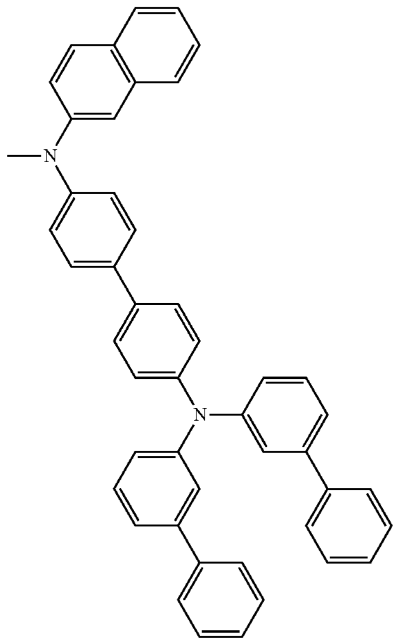
463
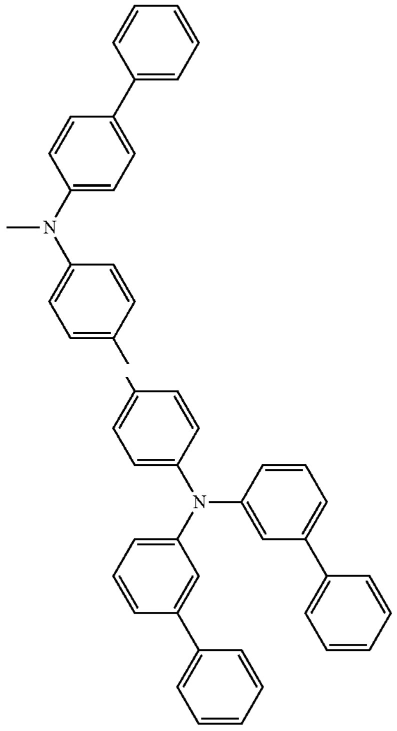
-continued
464
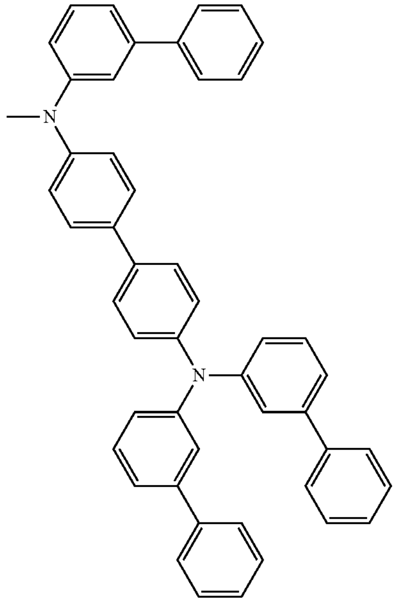
465
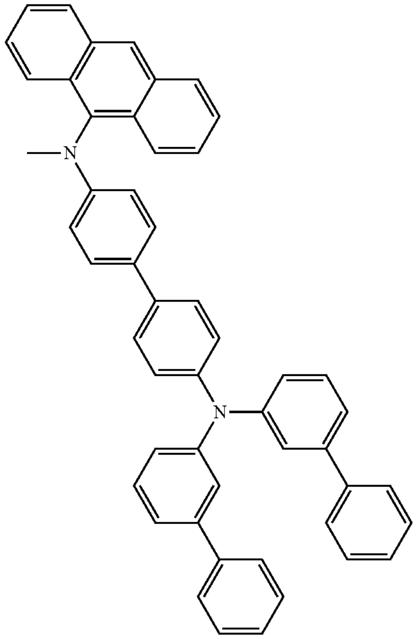

-continued
466
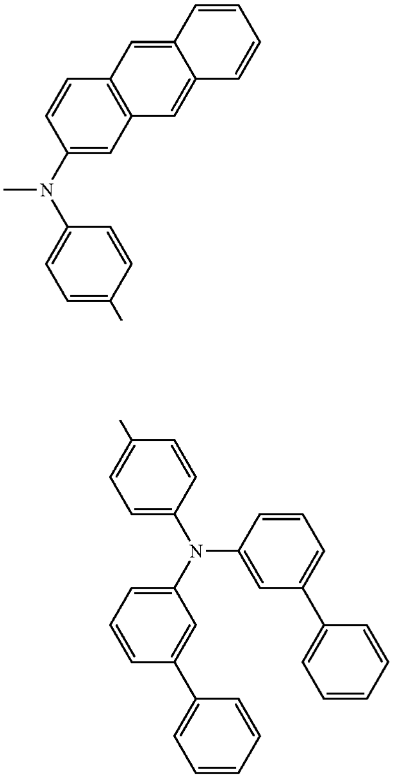
467
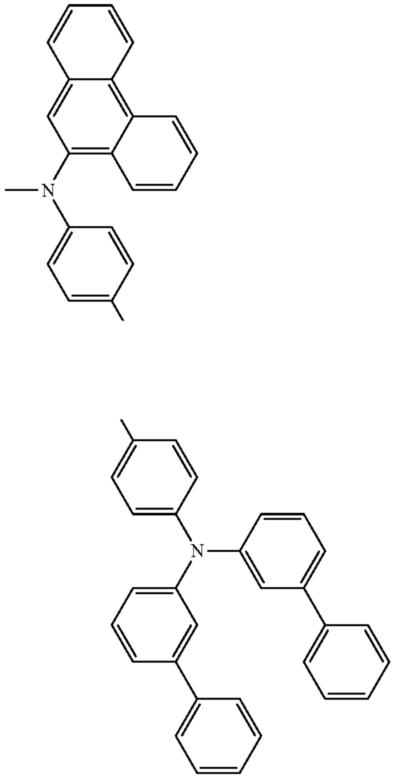
-continued
468
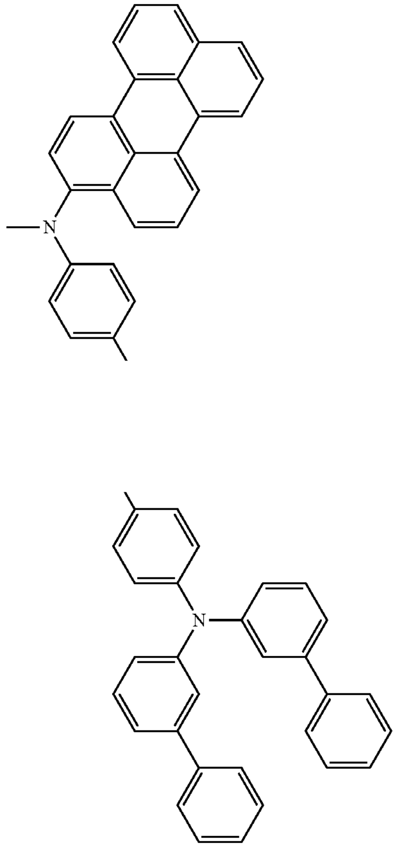
469
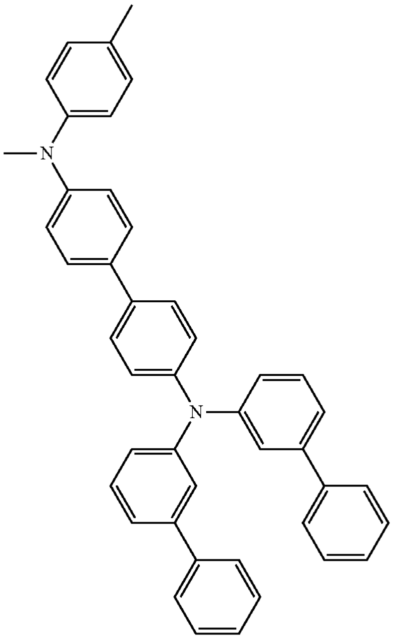

-continued
470
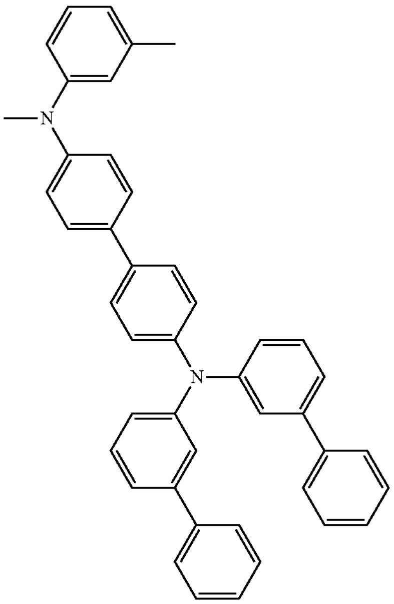
471
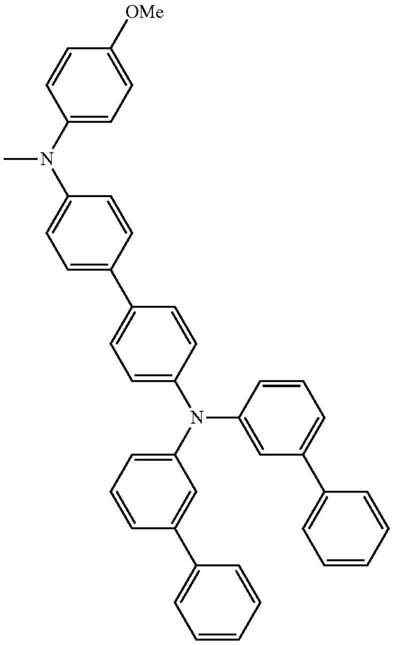
-continued
472
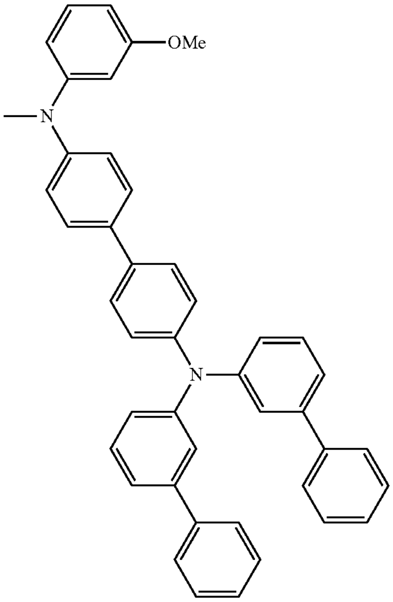
473
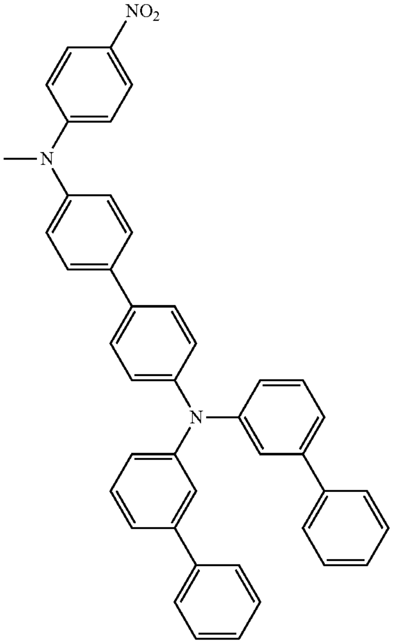

-continued

474

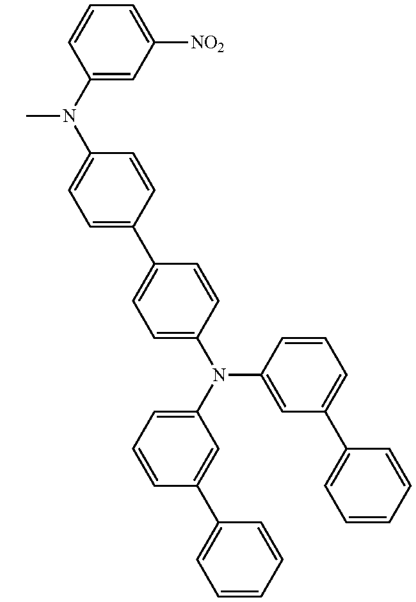

475

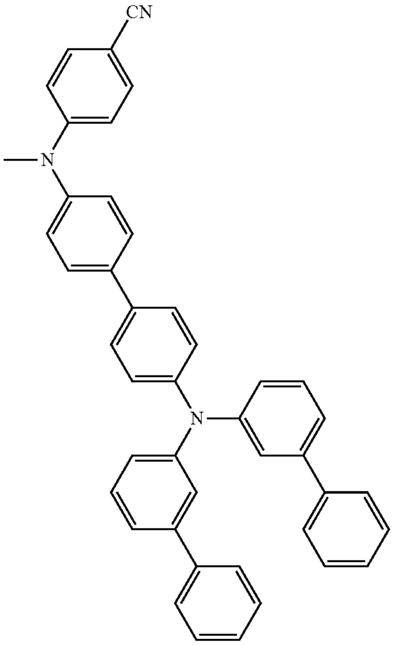

and

-continued

476

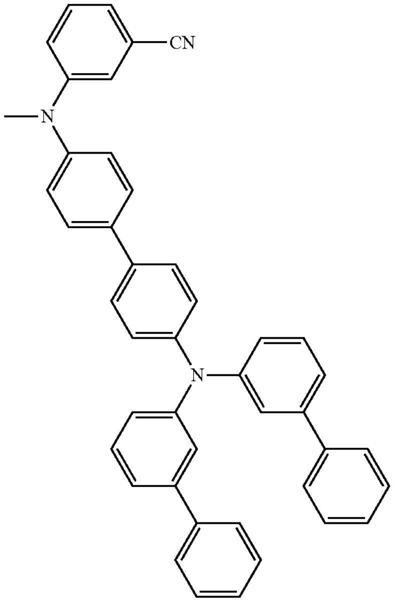

.

5. The organic light emitting device as set forth in claim 1, wherein the organic material layer(s) comprise a hole transport layer, and the hole transport layer includes the compound of Formula 1.

6. The organic light emitting device as set forth in claim 1, wherein the organic material layer(s) comprise a hole injection layer, and the hole injection layer includes the compound of Formula 1.

7. The organic light emitting device as set forth in claim 1, wherein the organic material layer(s) comprise a layer which both injects and transports holes and which includes the compound of Formula 1.

* * * * *